(12) United States Patent
Rangwala et al.

(10) Patent No.: US 12,324,841 B2
(45) Date of Patent: Jun. 10, 2025

(54) METHODS OF TREATING CANCER WITH A COMBINATION OF AN ANTI-PD-1 ANTIBODY AND AN ANTI-TISSUE FACTOR ANTIBODY-DRUG CONJUGATE

(71) Applicants: GENMAB A/S, Valby (DK); MSD International GmbH, Lucerne (CH)

(72) Inventors: Reshma Abdulla Rangwala, Philadelphia, PA (US); Esther C. W. Breij, Driebergen (NL); Sandra Verploegen, Nieuwegein (NL); Oyewale O. Abidoye, Bellevue, WA (US); Leonardo Viana Nicacio, Redmond, WA (US); Anthony Cao, Sammamish, WA (US); Shyra Gardai, Bothell, WA (US)

(73) Assignees: GENMAB A/S, Valby (DK); MSD INTERNATIONAL GMBH, Luzerne (CH)

( * ) Notice: Subject to any disclaimer, the term of this patent is extended or adjusted under 35 U.S.C. 154(b) by 641 days.

(21) Appl. No.: 17/053,753

(22) PCT Filed: May 7, 2019

(86) PCT No.: PCT/US2019/031166
§ 371 (c)(1),
(2) Date: Nov. 6, 2020

(87) PCT Pub. No.: WO2019/217455
PCT Pub. Date: Nov. 14, 2019

(65) Prior Publication Data
US 2022/0088191 A1    Mar. 24, 2022

Related U.S. Application Data

(60) Provisional application No. 62/753,725, filed on Oct. 31, 2018, provisional application No. 62/668,088, filed on May 7, 2018.

(51) Int. Cl.
| | |
|---|---|
| *A61K 47/68* | (2017.01) |
| *A61K 39/00* | (2006.01) |
| *A61K 39/395* | (2006.01) |
| *A61P 35/00* | (2006.01) |

(52) U.S. Cl.
CPC ...... *A61K 47/6849* (2017.08); *A61K 39/3955* (2013.01); *A61K 47/68031* (2023.08); *A61K 47/6817* (2017.08); *A61K 47/6845* (2017.08); *A61K 47/6889* (2017.08); *A61P 35/00* (2018.01); *A61K 2039/545* (2013.01)

(58) Field of Classification Search
CPC ............ A61K 39/3955; A61K 47/6817; A61K 47/6845; A61K 47/6889; A61K 2039/545; A61K 47/6849; A61K 47/6803; A61K 2039/507; A61K 38/05; A61K 39/395; A61K 47/65; A61K 2300/00; A61P 35/00; C07K 16/2818; C07K 16/36
See application file for complete search history.

(56) References Cited

U.S. PATENT DOCUMENTS

| | | |
|---|---|---|
| 4,474,893 A | 10/1984 | Reading |
| 4,714,681 A | 12/1987 | Reading |
| 4,925,648 A | 5/1990 | Hansen et al. |
| 5,223,427 A | 6/1993 | Edgington et al. |
| 5,545,806 A | 8/1996 | Lonberg et al. |
| 5,545,807 A | 8/1996 | Surani et al. |
| 5,569,825 A | 10/1996 | Lonberg et al. |
| 5,573,920 A | 11/1996 | Randle |
| 5,591,639 A | 1/1997 | Bebbington |
| 5,601,819 A | 2/1997 | Wong et al. |
| 5,625,126 A | 4/1997 | Lonberg et al. |
| 5,633,425 A | 5/1997 | Lonberg et al. |
| 5,635,483 A | 6/1997 | Pettit et al. |
| 5,658,759 A | 8/1997 | Bebbington |

(Continued)

FOREIGN PATENT DOCUMENTS

| | | |
|---|---|---|
| CN | 1303431 A | 7/2001 |
| CN | 1575302 A | 2/2005 |

(Continued)

OTHER PUBLICATIONS

Almagro et al. Progress and Challenges in the Design and Clinical Development of Antibodies for Cancer Therapy. Front. Immunol. 2018; 8:1751 (Year: 2018).*

(Continued)

*Primary Examiner* — Karen A. Canella
*Assistant Examiner* — John J Skoko, III
(74) *Attorney, Agent, or Firm* — MARSHALL, GERSTEIN & BORUN LLP

(57) ABSTRACT

The invention provides an anti-PD-1 antibody comprising the complementary determining regions (CDRs) of pembrolizumab in combination with an antibody-drug conjugate that binds to tissue factor (TF) comprising monomethyl auristatin E and the CDRs of tisotumab (e.g., tisotumab vedotin) and their use in methods of treating cancer, such as breast cancer and cervical cancer. The invention also provides compositions and kits comprising the anti-PD-1 antibody comprising the CDRs of pembrolizumab and the antibody-drug conjugate that binds to TF comprising monomethyl auristatin E and the CDRs of tisotumab (e.g., tisotumab vedotin) for use in treating cancer, such as breast cancer and cervical cancer.

28 Claims, 12 Drawing Sheets
Specification includes a Sequence Listing.

(56) References Cited

U.S. PATENT DOCUMENTS

| | | |
|---|---|---|
| 5,661,016 A | 8/1997 | Lonberg et al. |
| 5,663,149 A | 9/1997 | Pettit et al. |
| 5,733,743 A | 3/1998 | Johnson et al. |
| 5,741,957 A | 4/1998 | Deboer et al. |
| 5,750,172 A | 5/1998 | Meade et al. |
| 5,756,687 A | 5/1998 | Denman et al. |
| 5,770,429 A | 6/1998 | Lonberg et al. |
| 5,780,588 A | 7/1998 | Pettit et al. |
| 5,789,650 A | 8/1998 | Lonberg et al. |
| 5,814,318 A | 9/1998 | Lonberg et al. |
| 5,821,337 A | 10/1998 | Carter et al. |
| 5,827,690 A | 10/1998 | Meade et al. |
| 5,874,299 A | 2/1999 | Lonberg et al. |
| 5,877,397 A | 3/1999 | Lonberg et al. |
| 5,879,677 A | 3/1999 | del Zoppo |
| 5,879,936 A | 3/1999 | Bebbington et al. |
| 5,891,693 A | 4/1999 | Bebbington et al. |
| 5,981,216 A | 11/1999 | Kenten et al. |
| 6,214,345 B1 | 4/2001 | Firestone et al. |
| 6,274,142 B1 | 8/2001 | O'Brien et al. |
| 6,884,879 B1 | 4/2005 | Baca et al. |
| 7,115,717 B2 | 10/2006 | Mori et al. |
| 7,326,414 B2 | 2/2008 | Bedian et al. |
| 7,329,745 B2 | 2/2008 | Fujita-Yamaguchi |
| 7,405,227 B2 | 7/2008 | Kun et al. |
| 7,425,328 B2 | 9/2008 | Wang |
| 7,498,298 B2 | 3/2009 | Doronina et al. |
| 7,605,235 B2 | 10/2009 | Anderson et al. |
| 7,659,241 B2 | 2/2010 | Senter et al. |
| 7,824,677 B2 | 11/2010 | Wong et al. |
| 7,829,531 B2 | 11/2010 | Senter et al. |
| 7,851,437 B2 | 12/2010 | Senter et al. |
| 8,008,449 B2 | 8/2011 | Korman et al. |
| 8,354,509 B2 | 1/2013 | Carven et al. |
| 8,372,396 B2 | 2/2013 | Andya et al. |
| 8,900,587 B2 | 12/2014 | Carven et al. |
| 9,068,011 B2 | 6/2015 | Neijssen et al. |
| 9,150,658 B2 | 10/2015 | Verploegen et al. |
| 9,168,314 B2 | 10/2015 | Satijn et al. |
| 9,492,565 B2 | 11/2016 | Satijn et al. |
| 9,657,107 B2 | 5/2017 | Neijssen et al. |
| 9,714,297 B2 | 7/2017 | Verploegen et al. |
| 9,834,606 B2 | 12/2017 | Li et al. |
| 10,501,550 B2 | 12/2019 | Wang et al. |
| 10,617,764 B2 | 4/2020 | Valbjørn et al. |
| 2003/0017664 A1 | 1/2003 | Pnueli et al. |
| 2003/0176664 A1 | 9/2003 | Jiao et al. |
| 2004/0044187 A1 | 3/2004 | Sato et al. |
| 2005/0028649 A1 | 2/2005 | Settanni |
| 2005/0096289 A1 | 5/2005 | Prydz et al. |
| 2005/0106139 A1 | 5/2005 | Svendsen et al. |
| 2005/0169927 A1 | 8/2005 | Freskgaard et al. |
| 2005/0220793 A1 | 10/2005 | Anderson et al. |
| 2005/0276812 A1 | 12/2005 | Ebens et al. |
| 2006/0018910 A1 | 1/2006 | Gualberto et al. |
| 2006/0034846 A1 | 2/2006 | Ezban et al. |
| 2007/0014724 A1 | 1/2007 | Witte et al. |
| 2007/0031402 A1 | 2/2007 | Zhang et al. |
| 2007/0110812 A1 | 5/2007 | Xia et al. |
| 2007/0166309 A1 | 7/2007 | Lazar et al. |
| 2007/0196364 A1 | 8/2007 | Krishnamurthy et al. |
| 2008/0267968 A1 | 10/2008 | Fyfe et al. |
| 2008/0305044 A1 | 12/2008 | McDonagh et al. |
| 2009/0217401 A1 | 8/2009 | Korman et al. |
| 2009/0232734 A1 | 9/2009 | Anderson et al. |
| 2009/0280056 A1 | 11/2009 | Dennis et al. |
| 2010/0077497 A1 | 3/2010 | Deshpande et al. |
| 2011/0104184 A1 | 5/2011 | Jiao et al. |
| 2011/0268751 A1 | 11/2011 | Sievers et al. |
| 2011/0300156 A1 | 12/2011 | Verploegen et al. |
| 2013/0101608 A1* | 4/2013 | Satijn ............... A61K 45/06 424/178.1 |
| 2013/0216548 A1 | 8/2013 | Neijssen et al. |
| 2014/0341902 A1 | 11/2014 | Maecker et al. |
| 2015/0329642 A1 | 11/2015 | Neijssen et al. |
| 2016/0053020 A1 | 2/2016 | Verploegen et al. |
| 2016/0067349 A1 | 3/2016 | Satijn et al. |
| 2016/0120976 A1 | 5/2016 | Goldenberg et al. |
| 2016/0272708 A1 | 9/2016 | Chen |
| 2016/0279258 A1* | 9/2016 | Valbjørn ............ A61K 47/6843 |
| 2016/0303231 A1* | 10/2016 | Iannone ............... A61K 47/26 |
| 2016/0376367 A1 | 12/2016 | Yuan et al. |
| 2017/0080103 A1 | 3/2017 | Ariaans et al. |
| 2017/0136130 A1 | 5/2017 | Satijn et al. |
| 2017/0181988 A1 | 6/2017 | Malhotra et al. |
| 2017/0210806 A1 | 7/2017 | Liu |
| 2017/0253933 A1 | 9/2017 | Wang |
| 2017/0275375 A1 | 9/2017 | Rossi et al. |
| 2017/0285037 A1 | 10/2017 | Kulangara et al. |
| 2017/0313782 A1 | 11/2017 | Neijssen et al. |
| 2017/0320962 A1 | 11/2017 | Neijssen et al. |
| 2017/0334995 A1 | 11/2017 | Zettl et al. |
| 2018/0044431 A1 | 2/2018 | Verploegen et al. |
| 2018/0051085 A1 | 2/2018 | Chang et al. |
| 2019/0030178 A1 | 1/2019 | Lisby et al. |
| 2019/0169311 A1 | 6/2019 | Verploegen et al. |
| 2019/0201543 A1 | 7/2019 | Yu et al. |
| 2019/0315880 A1 | 10/2019 | Satijn et al. |
| 2020/0079872 A1 | 3/2020 | Neijssen et al. |
| 2020/0246477 A1 | 8/2020 | Valbjørn et al. |
| 2021/0015939 A1 | 1/2021 | Rangwala et al. |
| 2021/0019595 A1 | 1/2021 | Konisho et al. |
| 2021/0030888 A1 | 2/2021 | Rangwala et al. |
| 2021/0107980 A1 | 4/2021 | Rangwala et al. |
| 2021/0171657 A1 | 6/2021 | Verploegen et al. |
| 2021/0177987 A1 | 6/2021 | Rangwala et al. |
| 2021/0308208 A1 | 10/2021 | Rangwala et al. |
| 2021/0395384 A1 | 12/2021 | Satijn et al. |
| 2021/0402003 A1 | 12/2021 | Rangwala et al. |
| 2022/0088191 A1 | 3/2022 | Rangwala et al. |
| 2022/0265844 A1 | 8/2022 | Lisby et al. |
| 2022/0387485 A1 | 12/2022 | Rangwala et al. |
| 2023/0027495 A1 | 1/2023 | Rangwala et al. |
| 2023/0263902 A1 | 8/2023 | Rangwala |
| 2023/0416403 A1 | 12/2023 | Verploegen et al. |
| 2024/0091373 A1 | 3/2024 | Valbjørn et al. |
| 2024/0294661 A1 | 9/2024 | Satijn et al. |

FOREIGN PATENT DOCUMENTS

| | | |
|---|---|---|
| CN | 101237881 A | 8/2008 |
| CN | 101652389 A | 2/2010 |
| CN | 101677987 A | 3/2010 |
| CN | 102119065 A | 7/2011 |
| CN | 102317319 A | 1/2012 |
| CN | 103119065 A | 5/2013 |
| CN | 103124564 A | 5/2013 |
| CN | 103842030 A | 6/2014 |
| CN | 106938051 A | 7/2017 |
| CN | 107840887 A | 3/2018 |
| EP | 216846 A1 | 4/1987 |
| EP | 323997 A1 | 7/1989 |
| EP | 338841 A1 | 10/1989 |
| EP | 0216846 B1 | 1/1990 |
| EP | 0323997 B1 | 4/1993 |
| EP | 0629240 A1 | 12/1994 |
| EP | 0216846 B2 | 4/1995 |
| EP | 1069185 A1 | 1/2001 |
| EP | 0629240 B1 | 5/2002 |
| EP | 1374896 A1 | 1/2004 |
| EP | 1676574 A2 | 7/2006 |
| EP | 2991683 A1 | 3/2016 |
| JP | H09302000 A | 11/1997 |
| JP | 2001-213804 A | 8/2001 |
| JP | 2005512970 A | 5/2005 |
| JP | 2007-196364 A | 8/2007 |
| JP | 2009503105 A | 1/2009 |
| JP | 2009-185261 A | 8/2009 |
| JP | 2010530872 A | 9/2010 |
| JP | 5172811 B2 | 3/2013 |
| JP | 5244988 B1 | 7/2013 |
| JP | 2013527832 A | 7/2013 |
| JP | 2013-532148 A | 8/2013 |
| JP | 6236056 B2 | 11/2017 |

(56) References Cited

FOREIGN PATENT DOCUMENTS

| | | |
|---|---|---|
| JP | 2021513366 A | 5/2021 |
| JP | 2021523158 A | 9/2021 |
| TW | 202003046 A | 1/2020 |
| TW | 202034958 A | 10/2020 |
| WO | WO-8605807 A1 | 10/1986 |
| WO | WO-8704462 A1 | 7/1987 |
| WO | WO-8807543 A1 | 10/1988 |
| WO | WO-8901036 A1 | 2/1989 |
| WO | WO-1989/011297 A1 | 11/1989 |
| WO | WO-8911297 A1 | 11/1989 |
| WO | WO-8912463 A1 | 12/1989 |
| WO | WO-91/00360 A1 | 1/1991 |
| WO | WO-9203918 A1 | 3/1992 |
| WO | WO-92/05793 A1 | 4/1992 |
| WO | WO-9206711 A1 | 4/1992 |
| WO | WO-92/08802 A1 | 5/1992 |
| WO | WO-92/22645 A1 | 12/1992 |
| WO | WO-92/22653 A1 | 12/1992 |
| WO | WO-93/1227 A1 | 1/1993 |
| WO | WO-199301227 A1 | 1/1993 |
| WO | WO-1993/11227 A1 | 6/1993 |
| WO | WO-9311227 A1 | 6/1993 |
| WO | WO-9312227 A1 | 6/1993 |
| WO | WO-93/17715 A1 | 9/1993 |
| WO | WO-9317105 A1 | 9/1993 |
| WO | WO-9405328 A1 | 3/1994 |
| WO | WO-9411029 A1 | 5/1994 |
| WO | WO-9425585 A1 | 11/1994 |
| WO | WO-9601653 A1 | 1/1996 |
| WO | WO-9640921 A1 | 12/1996 |
| WO | WO-1997/04801 A1 | 2/1997 |
| WO | WO-9704801 A1 | 2/1997 |
| WO | WO-98/24884 A1 | 6/1998 |
| WO | WO-9840408 A1 | 9/1998 |
| WO | WO-1998/56418 A1 | 12/1998 |
| WO | WO-9856418 A1 | 12/1998 |
| WO | WO-9951743 A1 | 10/1999 |
| WO | WO-0100237 A1 | 1/2001 |
| WO | WO-2001/09187 A2 | 2/2001 |
| WO | WO-2001009187 A2 | 2/2001 |
| WO | WO-01/14424 A2 | 3/2001 |
| WO | WO-0127079 A2 | 4/2001 |
| WO | WO-0170984 A2 | 9/2001 |
| WO | WO-2002/11753 A1 | 2/2002 |
| WO | WO-0211753 A1 | 2/2002 |
| WO | WO-2002/43478 A2 | 6/2002 |
| WO | WO-2002/088172 A2 | 11/2002 |
| WO | WO-2002/096457 A2 | 12/2002 |
| WO | WO-02096457 A2 | 12/2002 |
| WO | WO-2002/096457 A3 | 2/2003 |
| WO | WO-2003/009817 A2 | 2/2003 |
| WO | WO-2002088172 A3 | 2/2003 |
| WO | WO-2003/020111 A2 | 3/2003 |
| WO | WO-03020111 A2 | 3/2003 |
| WO | WO-03029295 A1 | 4/2003 |
| WO | WO-2003026577 A2 | 4/2003 |
| WO | WO-2003/037911 A2 | 5/2003 |
| WO | WO-2003/039485 A2 | 5/2003 |
| WO | WO-03037361 A2 | 5/2003 |
| WO | WO-03037911 A2 | 5/2003 |
| WO | WO-03039485 A2 | 5/2003 |
| WO | WO-2003/070275 A1 | 8/2003 |
| WO | WO-03070275 A1 | 8/2003 |
| WO | WO-2003/009817 A3 | 11/2003 |
| WO | WO-03093422 A2 | 11/2003 |
| WO | WO-2004004639 A2 | 1/2004 |
| WO | WO-2004007557 A2 | 1/2004 |
| WO | WO-2003/039485 A3 | 2/2004 |
| WO | WO-2004010957 A2 | 2/2004 |
| WO | WO-2004016286 A2 | 2/2004 |
| WO | WO-2004/004639 A3 | 4/2004 |
| WO | WO-2004039842 A2 | 5/2004 |
| WO | WO-2004041296 A2 | 5/2004 |
| WO | WO-2004041302 A1 | 5/2004 |
| WO | WO-2004/016286 A3 | 7/2004 |
| WO | WO-2004055164 A2 | 7/2004 |
| WO | WO-2004064870 A2 | 8/2004 |
| WO | WO-2004071439 A2 | 8/2004 |
| WO | WO-2003/026577 A3 | 9/2004 |
| WO | WO-04/094475 A2 | 11/2004 |
| WO | WO-2004094475 A2 | 11/2004 |
| WO | WO-2004110363 A2 | 12/2004 |
| WO | WO-2005000896 A2 | 1/2005 |
| WO | WO-2005001038 A2 | 1/2005 |
| WO | WO-2005004793 A2 | 1/2005 |
| WO | WO-2005012360 A2 | 2/2005 |
| WO | WO-2005/25623 A2 | 3/2005 |
| WO | WO-2005020927 A2 | 3/2005 |
| WO | WO-2005025623 A2 | 3/2005 |
| WO | WO-2004/071439 A3 | 7/2005 |
| WO | WO-2005072126 A2 | 8/2005 |
| WO | WO-2005079766 A2 | 9/2005 |
| WO | WO-2005081711 A2 | 9/2005 |
| WO | WO-2005082023 A2 | 9/2005 |
| WO | WO-2005084390 A2 | 9/2005 |
| WO | WO-2005/082023 A3 | 12/2005 |
| WO | WO-2005118646 A2 | 12/2005 |
| WO | WO-2006014965 A2 | 2/2006 |
| WO | WO-2006029879 A2 | 3/2006 |
| WO | WO-2006044908 A2 | 4/2006 |
| WO | WO-2006065533 A2 | 6/2006 |
| WO | WO-2006/044908 A3 | 8/2006 |
| WO | WO-2005/084390 A3 | 10/2006 |
| WO | WO-06/121168 A1 | 11/2006 |
| WO | WO-2006121168 A1 | 11/2006 |
| WO | WO-2006130374 A2 | 12/2006 |
| WO | WO-2006132670 A2 | 12/2006 |
| WO | WO-200700860 A1 | 1/2007 |
| WO | WO-2007008600 A1 | 1/2007 |
| WO | WO-2007011968 A2 | 1/2007 |
| WO | WO-2007019232 A2 | 2/2007 |
| WO | WO-2006/014965 A3 | 3/2007 |
| WO | WO-2007056352 A2 | 5/2007 |
| WO | WO-2007059782 A1 | 5/2007 |
| WO | WO-2006/065533 A3 | 6/2007 |
| WO | WO-2006/132670 A3 | 7/2007 |
| WO | WO-2007076091 A2 | 7/2007 |
| WO | WO-2007097810 A2 | 8/2007 |
| WO | WO-2007/011968 A3 | 10/2007 |
| WO | WO-2008030260 A2 | 3/2008 |
| WO | WO-2008076379 A2 | 6/2008 |
| WO | WO-2008100805 A2 | 8/2008 |
| WO | WO-2008100805 A3 | 10/2008 |
| WO | WO-2008137382 A1 | 11/2008 |
| WO | WO-2009002425 A2 | 12/2008 |
| WO | WO-2009048967 A1 | 4/2009 |
| WO | WO-2004/055164 A3 | 7/2009 |
| WO | WO-2009097006 A2 | 8/2009 |
| WO | WO-2009/097006 A3 | 1/2010 |
| WO | WO-2010018782 A1 | 2/2010 |
| WO | WO-2010059787 A1 | 5/2010 |
| WO | WO-2010/066803 A2 | 6/2010 |
| WO | WO-2010081004 A1 | 7/2010 |
| WO | WO-2011119487 A2 | 9/2011 |
| WO | WO-2011157741 A2 | 12/2011 |
| WO | WO-2012135408 A1 * | 10/2012 | ............ A61K 39/00 |
| WO | WO-2013019906 A1 | 2/2013 |
| WO | WO-2013125148 A1 | 8/2013 |
| WO | WO-13/173223 A1 | 11/2013 |
| WO | WO-2013173337 A2 | 11/2013 |
| WO | WO-2014047221 A1 | 3/2014 |
| WO | WO-2014177771 A1 | 11/2014 |
| WO | WO-2015075201 A1 | 5/2015 |
| WO | WO-2015075477 A1 | 5/2015 |
| WO | WO-2015088847 A1 | 6/2015 |
| WO | WO-2015126903 A1 * | 8/2015 | ............ A61K 31/44 |
| WO | WO-2015/177360 | 11/2015 |
| WO | WO-2016032927 A1 * | 3/2016 | ......... A61K 31/4545 |
| WO | WO-2017019846 A1 | 2/2017 |
| WO | WO-2017024465 A1 | 2/2017 |
| WO | WO-2017025051 A1 | 2/2017 |
| WO | WO-2017040790 A1 | 3/2017 |
| WO | WO-2017042352 A1 * | 3/2017 | ............ A61K 38/07 |
| WO | WO-2017055547 A1 | 4/2017 |

(56) References Cited

FOREIGN PATENT DOCUMENTS

| WO | WO-2017071625 A1 | 5/2017 | |
| WO | WO-2017087280 A1 * | 5/2017 | ......... A61K 31/5365 |
| WO | WO-2017106656 A1 | 6/2017 | |
| WO | WO-2017133540 A1 | 8/2017 | |
| WO | WO-2017166804 A1 | 10/2017 | |
| WO | WO-2017210473 A1 * | 12/2017 | ....... A61K 47/68031 |
| WO | WO-2018036243 A1 | 3/2018 | |
| WO | WO-2018036472 A1 | 3/2018 | |
| WO | WO-2018103017 A1 | 6/2018 | |
| WO | WO-2019089973 A1 | 5/2019 | |
| WO | WO-2019136309 A1 | 7/2019 | |
| WO | WO-2019173523 A1 | 9/2019 | |
| WO | WO-2019183253 A1 | 9/2019 | |
| WO | WO-2019217455 A1 | 11/2019 | |
| WO | WO-2019217457 A1 | 11/2019 | |
| WO | WO-2020037024 A1 | 2/2020 | |
| WO | WO-2020092210 A1 | 5/2020 | |
| WO | WO-2021089794 A1 | 5/2021 | |
| WO | WO-2021090721 A1 | 5/2021 | |

OTHER PUBLICATIONS

Brown et al. Tolerance of single, but not multiple, amino acid replacements in antibody Vh Cdr 2: a means of minimizing B cell wastage from somatic hypermutation? J. Immunol., 1996 156(9):3285-91 (Year: 1996).*

Rentero et al. Screening of Large Molecule Diversities by Phage Display Chimia, 2011 65: 843-845 (Year: 2011).*

Borcoman E et al. Pembrolizumab in cervical cancer: latest evidence and clinical usefulness. Ther Adv Med Oncol. 2017 9(6): 431-439 (Year: 2017).*

Nair AB et al. A simple practice guide for dose conversion between animals and human. J Basic Clin Pharma 2016;7:27-31 (Year: 2016).*

Requirements on Content and Format of Labeling for Human Prescription Drug and Biological Products Final Rule and Notices. (Federal Register 2006 71 (15) 3922-3997) (FDA Fed Reg). (Year: 2006).*

Breij ECW et al. Use of an antibody-drug conjugate targeting tissue factor to induce complete tumor regression in xenograft models with heterogenous target expression. J Clin Oncol 2013 31 (suppl; abstract 3066) (Year: 2013).*

ADC Review Tisotumab Vedotin 2016 (https://www.adcreview.com/drugmap/tisotumab-vedotin-humax-tf-adc-humax-tf-adc-tf-011-mmae/) (ADC Review Tisotumab) (Year: 2016).*

Ilie M et al. Assessment of the PD-L1 status by immunohistochemistry: challenges and perspectives for therapeutic strategies in lung cancer patients. (Virchows Archiv 2016 468 511-525) (Year: 2016).*

Linardou H et al. Toxicity management of immunotherapy for patients with metastatic melanoma. (Ann Transl Med. Jul. 2016; 4(14): 272) (Year: 2016).*

Lo C. Conjunctivitis (https://www.drclementlo.com/health-update/72-conjunctivitis.html published Oct. 26, 2017) (Year: 2017).*

Tear Film & Ocular Surface Society A Patient's Guide to Artificial Tears (https://www.tearfilm.org/dettnews-a_patients_guide_to_artificial_tears/5523_5519/eng/) Aug. 3, 2017 (Year: 2017).*

Fessas P et al. A molecular and preclinical comparison of the PD-1-targeted T-cell checkpoint inhibitors nivolumab and pembrolizumab (Semin Oncol. Apr. 2017; 44(2): 136-140) (Year: 2017).*

Lambert JM et al. Antibody-Drug Conjugates (ADCs) for Personalized Treatment of Solid Tumors: A Review (Adv Ther (2017) 34: 1015-1035) (Year: 2017).*

Lassen et al., "A phase I, First-in-Human Study to Evaluate the Tolerability, Pharmacokinetics and Preliminary Efficacy of HuMax-TF-ADC in Patients with Solid Tumors", Abstract No. 2570, Poster, Oct. 28, 2021, p. 1.

Lassen et al., "A phase I, first-in-human study to evaluate the tolerability, pharmacokinetics and preliminary efficacy of HuMax-tissue factor-ADC (TF-ADC) in patients with solid tumors", J. Clin. Oncol. 33, (suppl. abstract 2570) 2015, 6 pages.

Lee. E.K. et al., "Antibody-drug conjugates in gynecologic malignancies," Gynecologic Oncology, vol. 153, 2019, pp. 694-702.

Mackman. N. et al., "Role of the Extrinsic Pathway of Blood Coagulation in Hemostasis and Thrombosis," Arterioscler Thromb Vasc Biol, vol. 27, 2007, pp. 1687-1693.

Mahdi, H. et al., "Phase 2 Trial of Tisotumab Vedotin in Platinum-Resistant Ovarian Cancer (innovaTV 208)," Poster 421A, Presented at the 2019 ASCO(American Society of Clinical Oncology) Annual Meeting, May 31-Jun. 4, 2019, p. 1.

Mahdi. H. et al., "Phase 2 trial of tisotumab vedotin in platinum-resistant ovarian cancer (innovaTV 208).," Journal of Clinical Oncology, vol. 37, Issue 15, 2019, pp. 5.

Mandal. S. K. et al., "Cellular localization and trafficking of tissue factor," Blood, vol. 107, No. 12, Jun. 15, 2006, pp. 4746-4753.

Marquina. G. et al., "Targeted Agents in Cervical Cancer: Beyond Bevacizumab," Current Oncology Reports, vol. 20, Issue 40, 2018, pp. 10.

McDonagh. C.F. et al., "Engineered antibody-drug conjugates with defined sites and stoichiometries of drug attachment," Protein Engineering, Design & Selection, vol. 19, No. 7, 2006, pp. 299-307.

Milsom. C.C. et al., "Tissue Factor Regulation by Epidermal Growth Factor Receptor and Epithelial-to-Mesenchymal Transitions: Effect on Tumor Initiation and Angiogenesis," Cancer Res, vol. 68, Issue 24, 2008, pp. 10068-10076.

Monk. B. et al., "Tisotumab Vedotin (TV) + Bevacizumab or Pembrolizumab or Carboplatin in Recurrent/Metastatic Cervical Cancer (r/mCC): Phase 1b/2 ENGOT-Cx8/GOG-3024/innovaTV 205 Study Dose-Escalation Results," 2021, pp. 4.

Monk. B. et al., "Tisotumab Vedotin + Bevacizumab or Pembrolizumab or Carboplatin in Recurrent/Metastatic Cervical Cancer: Phase 1b/2 ENGOT Cx8/GOG 3024/ innovaTV 205 Study Dose Escalation Results," IGCS, 2021, pp. 12.

Moore. D. H. et al., "Phase III Study of Cisplatin With or Without Paclitaxel in Stage IVB, Recurrent, or Persistent Squamous Cell Carcinoma of the Cervix: A Gynecologic Oncology Group Study," Journal of Clinical Oncology, vol. 22, No. 15, 2004, pp. 3113-3119.

Moore. K. N. et al., "Safety and Activity of Mirvetuximab Soravtansine (IMGN853), a Folate Receptor Alpha-Targeting Antibody-Drug Conjugate, in Platinum-Resistant Ovarian, Fallopian Tube, or Primary Peritoneal Cancer: A Phase I Expansion Study," Journal of Clinical Oncology, vol. 35, No. 10, 2017, pp. 1112-1118.

Morrisey. J.H. et al., "Monoclonal Antibody Analysis of Purified and Cell-Associated Tissue Factor," Thrombosis Research, vol. 52, 1988, pp. 247-261.

Myers. E. W. et al., "Optimal alignments in linear space," Cabios, vol. 4, Issue 1, 1988, pp. 11-17.

Naing. A. et al., "A Phase 1 first-in-human study of MEDI0680, an anti-PD-1 monoclonal antibody (mAb) in adult patients (pts) with advanced tumors," Annals of Oncology, vol. 27, 2016.

Needleman. S. B. et al., "A General Method Applicable to the Search for Similarities in the Amino Acid Sequence of Two Proteins," J. Mol. Biol., vol. 48, 1970, pp. 443-453.

Ngo. C. V. et al., "CNTO 859, a humanized anti-tissue factor monoclonal antibody, is a potent inhibitor of breast cancer metastasis and tumor growth in xenograft models," Int. J. Cancer, vol. 120, 2007, pp. 1261-1267.

Nooij. R.P. et al., "Functional MRI for Treatment Evaluation in Patients with Head and Neck Squamous Cell Carcinoma: A Review of the Literature from a Radiologist Perspective," Curr Radiol Rep, vol. 6, Issue 2, 2018, pp. 15.

Nyen. T.V. et al., "Modeling Endometrial Cancer: Past, Present, and Future," Int. J. Mol. Sci, vol. 19, Issue 2348, 2018, pp. 18.

Oflazoglu, E. et al., "Combination of the anti-CD30-auristatin-E antibody-drug conjugate (SGN-35) with chemotherapy improves antitumour activity in Hodgkin lymphoma," British Journal of Haematology, vol. 142, 2008, pp. 69-73.

Okeley, N. M. et al., "Specific Tumor Targeting and Potent Bystander Killing with SGN-35, an Anti-CD30 Antibody Drug Conjugate," Blood, vol. 108, Issue 11, Nov. 16, 2006, pp. 1-2.

Park, I.-H. et al., "Surveillance or resection after chemoradiation in esophageal cancer," Ann. Transl. Med., vol. 6, Issue 4, 2018, pp. 1-7.

(56) References Cited

OTHER PUBLICATIONS

Parren, "Building a novel portfolio of ADCs", European Antibody Congress, Nov. 28, 2012, pp. 1-31.
Parren, "Companion diagnostics (CDx) in antibody-drug conjugate development", 2015, 1 page.
Parren, P., "Developing antibody drug conjugates for the treatment of solid cancers", Innovating Antibodies Improving Lives, Apr. 6, 2016, 32 pages.
Parren, P., "Progressing ADCs for the treatment of solid cancers", World ADC, Oct. 28, 2014, 28 pages.
Parren, P.W.H.I., "Development of an auristatin-conjugated therapeutic antibody against Tissue Factor for the treatment of solid tumors," 3rd Annual Meeting—World ADC, Oct. 24, 2012, pp. 29.
Parrens, "Current and future trends in antibody therapeutics", 2015, 1 page.
Paul, W. E., "Fundamental Immunology," 1993, Chapter 8, pp. 242-247.
Paul, W. E., "Fundamental Immunology," Second Edition, Chap 12, Raven press, New York, 1989, pp. 1-8.
Phillips. G. D. et al., "Targeting HER2-Positive Breast Cancer with Trastuzumab-DM1, an Antibody-Cytotoxic Drug Conjugate ," Cancer Res, vol. 68, Issue 22, 2008, pp. 9280-9290.
Polson. A.G. et al., "Anti-CD22-MCC-DM1: an antibody-drug conjugate with a stable linker for the treatment of non-Hodgkin's lymphoma," Leukemia, vol. 24, 2010, pp. 1566-1573.
Portolano, S., et al., "Lack of promiscuity in autoantigen-specific H and L chain combinations as revealed by human H and L chain "roulette"," J. Immonol, vol. 150, 1993, pp. 880-887.
Presta, L., et al., "Generation of a Humanized, High Affinity Anti-tissue Factor Antibody for Use as a Novel Antithrombotic Therapeutic," Thromb Haemost, vol. 85, 2001, pp. 379-389.
Presta, L.G. et al., "Humanization of an Anti-Vascular Endothelial Growth Factor Monoclonal Antibody for the Therapy of Solid Tumors and Other Disorders," Cancer Research, vol. 57, Oct. 15, 1997, pp. 4593-4599.
Revets, H. et al., "Nanobodies as novel agents for cancer therapy," Expert Opinion on Biological Therapy, vol. 5, Apr. 20, 2005, pp. 111-124.
Rice, P. et al., "EMBOSS: The European Molecular Biology Open Software Suite," Trends Genet., vol. 16, Issue 6, Jun. 2000, pp. 276-277.
Roberts, J.T., et al., "Long-term survival results of a randomized trial comparing gemcitabine/cisplatin and methotrexate/vinblastine/doxorubicin/cisplatin in patients with locally advanced and metastatic bladder cancer," Annals of Oncology, vol. 17, 2006, pp. v118-v122.
Robinson, J R., et al., "Sustained and Controlled Release Drug Delivery Systems," Marcel dekker inc., New York, 1978, pp. 1.
Roy, M. L., at al., "The Effects of Formulation and Moisture on the Stability of a Freez-Dried Monoclonal Antibody-Vinca Conjugate: A Test of the Wlc Glass Transition Theory," Develop. Boil. Standard., vol. 74, 1990, pp. 323-340.
Rudikoff, S., et al., "Single amino acid substitution altering antigen-binding specificity," Proc. Natl. Acad., vol. 79, 1982, pp. 1979-1983.
Rustin, G. J., et al., "Definitions for Response and Progression in Ovarian Cancer Clinical Trials Incorporating RECIST 1.1 and CA 125 Agreed by the Gynecological Cancer Intergroup (GCIG)" International Journal of Gynecological Cancer, vol. 21, Issue 2, Feb. 2011, pp. 419-423.
Ryan, M. C., et al., "Targeting pancreatic and ovarian carcinomas using the auristatin-based anti-CD70 antibody-drug conjugate SGN-75," British Journal of Cancer, vol. 103, 2010, pp. 676-684.
Sanderson, R.J., et al., "In vivo Drug-Linker Stability of an Anti-CD30 Dipeptide-Linked Auristatin Immunoconjugate," Clinical Cancer Research, vol. 11, Jan. 15, 2005, pp. 843-852.
Satijn, D., "Development of ADCs against Tissue Factor for the treatment of Solid Tumors", Informa Oncology Drug Discovery, Mar. 20-21, 2011, 23 pages.
Satijn, D., "Development of an auristatin-conjugated therapeutic antibody against Tissue Factor for the treatment of solid tumors", Empowered Antibodies, ADCs-2013, 30 pages.
Satijn, D., "Targeting solid cancers using antibody-drug conjugate against the novel ADC target Tissue Factor, a preclinical and FIH study", Empowered antibodies, Jun. 17-18, 2015, 38 pages.
Scher, H.I., et al., "Design and End Points of Clinical Trials for Patients with Progressive Prostate Cancer and Castrate Levels of Testosterone: Recommendations of the Prostate Cancer Clinical Trials Working Group," Journal of Clinical Oncology, vol. 26, Issue 7, Mar. 1, 2008, pp. 1148-1159.
International Search Report and Written Opinion mailed Aug. 19, 2019 for PCT/US19/31166.
"Clinical Progress of Antibody-Drug Conjugates," The Essential Protein Engineering Summit, 15th Annual PEGS Boston, Apr. 11-12, 2019, pp. 77-78.
"Development of ADCs against Tissue Factor for the treatment of Solid Tumors", World ADC Summit, Oct. 25-28, 2011, 24 pages.
"Mylotargtm (gemtuzumab ozogamicin) for injection, for intravenous use," Highlights of Prescribing Information, Sep. 2017, pp. 19.
"Scientific Plenary I: Snap, Crackle, PARP," Abstracts Presented for the 50th Annual Meeting of the Society of Gynecologic Oncology, Mar. 16, 2019, pp. 478.
"Female Breast Cancer (Invasive," Table IV-1 Trends in Seer Incidence and U.S. Mortality Using the Jointpoint Regression Program, With up to three Joinpoints by Race and Age, SEER Cancer Statistics Review 1973-1998 National Cancer Institute, pp. 23.
Amirkhosravi. A. et al., "The Importance of Platelets in the Expression of Monocyte Tissue Factor Antigen Measured by a New Whole Blood Flow Cytometric Assay," Thromb Haemost, vol. 75, Issue 1, 1996, pp. 87-95.
Aras. O. et al., "Induction of microparticle- and cell-associated intravascular tissue factor in human endotoxemia," Blood, vol. 103, No. 12, Jun. 2004, pp. 4545-4553.
Bartlett et al., "Complete remissions with weekly dosing of SGN-35, a novel antibody-drug conjugate (ADC) targeting CD30, in a phase I dose-escalation study in patients with relapsed or refractory Hodgkin lymphoma (HL) or systemic anaplastic large cell lymphoma (sALCL)," Journal of Clinical Oncology, vol. 27, Issue 15, 3 pages.
Bauer, M. K., "Clinical Perspective of ADC Development", A case study of HuMax TF-ADC (Registered), May 8, 2015, 27 pages.
Bauer, M.K., "Transitioning HuMax-TF-ADC® Into The Clinic—Maximizing The Clinical Knowledge In Early Stage Development," World ADC, Genmab, Feb. 25, 2015, pp. 27.
Blank et al., "innovaTV 208: New Weekly Dosing Cohort in the Phase 2 Study of Tisotumab Vedotin in Platinum-Resistant Ovarian Cancer (Trial in Progress)", Society of Gynecologic Oncology Virtual Congress; Mar. 19-25, 2021, 1 page.
Breij, E. "Development of an auristatin-conjugated therapeutic antibody against Tissue Factor for the treatment of solid tumors", World ADC summit—Frankfurt, 2013, pp. 1-33.
Breij, E. C. W. et al., "Pre-Clinical Development of a Therapeutic Antibody-Drug Conjugate Targeting Tissue Factor", GTC Antibody and Protein Therapeutics Conference, Oct. 25, 2013, 47 pages.
Breij, E. C. W. et al., "Pre-Clinical Development of a Therapeutic Antibody-Drug Conjugate Targeting Tissue Factor", Informa Antibody Drug Conjugates Conference, May 17-19, 2014, 46 pages.
Breij, E., et al., "An Antibody-Drug Conjugate Targeting Tissue Factor with Broad Anti-Tumor Activity in Xenograft Models with Heterogeneous Tissue Factor Expression," Genmab, Poster, Apr. 2, 2013, p. 1.
Breij, E.C.W., et al., "Use of an antibody-drug conjugate targeting tissue factor to induce complete tumor regression in xenograft models with heterogeneous target expression," Developmental Therapeutics—Immunotherapy, Journal of Clinical Oncology vol. 31, Issue 15, Suppl 3066, May 20, 2013.
Brown. L., "SGN-30: a basis for the effective treatment of CD30 positive hematopoietic malignancies," Expert Opinion on Investigational Drugs, vol. 17, Issue 12, 2008, pp. 1883-1887.
Bueren, J, L. V. et al., "Alignmentof AntibodyDrug Conjugate-CDxCo-Development", World CDx, Mar. 18, 2015, 24 pages.

(56) References Cited

OTHER PUBLICATIONS

Carayannopoulos. L. et al., "Immunoglobulins structure and function," Fundamental immunology, 3rd edition, Chapter 9, Paul. W.E., 1993, pp. 283-314.
Casterman-Hamers. C. et al., "Naturally occurring antibodies devoid of light chains," Nature, vol. 363, 1993, pp. 446-448.
Chenard-Poirier. M. et al., "A phase I/II safety study of tisotumab vedotin (HuMAX-TF-ADC) in patients with solid tumours," Poster presented at ESMO, Sep. 2017, Poster No. 1148, p. 1.
Coleman, R. et al., "Tisotumab Vedotin in Previously Treated Recurrent or Metastatic Cervical Cancer: Results From the Phase 2 innovaTV 204/ GOG-3023/ENGOT-cx6 Study", ESMO Congress, 2020, 17 pages.
Concin, N., et al., "A phase IIa study of tisotumab vedotin in patients with previously treated recurrent or metastatic cervical cancer: updated analysis of full cervical expansion cohort," Poster 963, Presented at the Ruropean Society for Medical Onocology, Oct. 19-23, 2018, p. 1.
Gerritsen, "Bioanalysisof antibody-auristatin auristatin conjugatesin non human primate studies", Global Bioconference: Jun. 29-3, 2015, 28 pages.
Gerritsen, "Bioanalysisof antibody-auristatin conjugates in primatestudies", Innovating Antibodies Improving Lives, 2013, 28 pages.
Gerritsen, "In vitro screening approaches for antibody drug conjugates", 2 nd Annual Antibody Drug Conugates, Jun. 13-14, 2012, pp. 1-29.
Gray, E. et al., "Tisotumab Vedotin Shows Immunomodulatory Activity Through Induction of Immunogenic Cell Death", Society for Immunotherapy of Cancer, Nov. 9-14, 2020, 1 page.
Hemmingsen, P. H., "Overcoming the Challenges of your supply chain", Empoered Ab Congress, Jun. 2015, 30 pages.
Henderson. C., "Breast Cancer," clinical oncology, 1995, pp. 198-219.
Hjortoe. G.M. et al., "Tissue factor-factor VIIa-specific up-regulation of IL-8 expression in MDA-MB-231 cells is mediated by PAR-2 and results in increased cell migration," Blood, vol. 103, No. 8, Apr. 2004, pp. 3029-3037.
Ho. W.L. et al., "The ophthalmological complications of targeted agents in cancer therapy: what do we need to know as ophthalmologists?," Acta Ophthalmologica, 2012, pp. 6.
Holden. S.N. et al., "A phase I study of weekly dosing of trastuzumab-DM1 (T-DM1) in patients (pts) with advanced HER2+ breast cancer (BC)," journal of clinical oncology, vol. 26, Issue 15, 2008, pp. 1029.
Hollebecque. A. et al., "An open-label, multicohort, phase I/II study of nivolumab in patients with virus-associated tumors (CheckMate 358): Efficacy and safety in recurrent or metastatic (R/M) cervical, vaginal, and vulvar cancers.," Journal of Clinical Oncology, vol. 35, Issue 15, 2017.
Holt. L.J. et al., "Domain antibodies: proteins for therapy," Trends in Biotechnology, vol. 21, No. 11, Nov. 2003, pp. 484-490.
Hong, D. S. et al., "InnovaTV 207: Open Label Phase 2 Study of Tisotumab Vedotin for Locally Advanced or Metastatic Disease in Solid Tumors", Abstract TPS3160_ASCO_Poster, 2019, 1 page.
Hong. D. et al., "Tisotumab Vedotin in Previously Treated Recurrent or Metastatic Cervical Cancer," Clin Cancer Res, vol. 26, Issue 6, Mar. 15, 2020, pp. 1220-1228.
Hong. D.S. et al., "Efficacy and Safety of Tisotumab Vedotin in Patients with Head and Neck Squamous Cell Carcinoma: Results from a Phase II Cohort," Multidisciplinary Thoracic Cancers Symposium, 2021, pp. 2.
Hong. D.S. et al., "innovaTV 207: New Dosing Cohort in the Open Label Phase 2 Study of Tisotumab Vedotin in Solid Tumors," European Society of Medical Oncology, 2021.
Houtkamp, M., "Pre-clinical efficacy of an antibody-drug conjugate targeting TF in solid tumor PDX models", CrownBio meeting, Feb. 11, 2015, 20 pages.

Houtkamp, M., "Target expression correlates to ADC efficacy in mouse tumor models", Definiens symposium, Apr. 25, 2017, 29 pages.
Huang. J. et al., "Safety, Activity, and Biomarkers of SHR-1210, an Anti-PD-1 Antibody, for Patients with Advanced Esophageal Carcinoma," Clin Cancer Res, vol. 24, Issue 6, Mar. 15, 2018, pp. 1296-1304.
Huang. X. et al., "Tumor Infarction in Mice by Antibody-Directed Targeting of Tissue Factor to Tumor Vasculature," Science, vol. 275, 1997, pp. 547-550.
Huston. J. S. et al., "Protein engineering of antibody binding sites: Recovery of specific activity in an anti-digoxin single-chain Fv analogue produced in *Escherichia coli*," Proc. Natl. Acad. Sci. USA, vol. 85, 1988, pp. 5879-5883.
Jackson. D. et al., "A Human Antibody-Drug Conjugate Targeting EphA2 Inhibits Tumor Growth In vivo," Cancer Research, vol. 68, Issue 22, 2008, pp. 9367-9374.
Janeway. C.A. et al., "Antigen recognition by B-cell and T-cell receptors," Immuno biology, chapter 3, Austin et al., 1997, pp. 94-106.
Johnson. G. et al., "The Kabat Database and a Bioinformatics Example," Methods in Molecular Biology, vol. 248, 2003, pp. 11-25.
Johnson. M. L. et al., "Phase I trial of the programmed death receptor 1 (PD-1) inhibitor, BI 754091, in patients (pts) with advanced solid tumors.," Journal of Clinical Oncology, vol. 36, Issue 5, 2018.
Kerwin. B.A., "Polysorbates 20 and 80 Used in the Formulation of Protein Biotherapeutics: Structure and Degradation Pathways," Journal of Pharmaceutical Sciences, vol. 97, Issue 8, Aug. 2008, pp. 2924-2935.
Kirchhofer. D. et al., "Epitope Location on Tissue Factor Determines the Anticoagulant Potency of Monoclonal Anti-tissue Factor Antibodies," Thromb Haemost, vol. 84, 2000, pp. 1072-1081.
Kitagawa. R. et al., "Paclitaxel Plus Carboplatin Versus Paclitaxel Plus Cisplatin in Metastatic or Recurrent Cervical Cancer: The Open-Label Randomized Phase III Trial JCOG0505," Journal of Clinical Oncology, vol. 33, No. 19, Jul. 2015, pp. 2129-2135.
U.S. Appl. No. 17/198,1999, Satjin et al.
Vergote et al., 2017, A phase IIA Study of Tisotumab Vedotin (Humax-TF-ADC) in Patients with Relapsed, Recurrent Metastatic Cancer. (online) Annals of Oncology. 2017; vol. 28 (suppl 5) p. 331; ESMO Madrid conference Sep. 8, 2017.
Philips et al, 2014, "Therapeutic uses of anti-PD-1 and anti-PD-L1 antibodies," International Immunology 27(1) 39-46.
Vergote et al., 2019, "1064TIP—Phase I/II trial of tisotumab vedotin plus bevacizumab, pembrolizumab, or carboplatin in recurrent or metastatic cervical cancer (innovaTV 205/ENGOT-cx8)," Annals of Oncology, vol. 30, Supplement 5, pp. v433-v434.
Calvert et al., "Carboplatin Dosage: Prospective Evaluation of a Simple Formula Based on Renal Function," Journal of Clinical Oncology, vol. 7, No. 11, pp. 1748-1756, 1989.
Seattlegenetics, "SGN-35: Antibody-Drug Conjugate," 2008, p. 1.
Seattlegenetics., "Seattle genetics reports positive data from phase I weekly-dosing clinical trial of brentuximab vedotin (SGN-35) in lymphoma," retrieved at https://investor.seagen.com/press-releases/news-details/2009/Seattle-Genetics-Reports-Positive-Data-from-Phase-I-Weekly-Dosing-Clinical-Trial-of-Brentuximab-Vedotin-SGN-35-in-Lymphoma/default.aspx, Dec. 7, 2009, pp. 5.
Selva, C., et al., "Trehalose Preserves the Integrity of Lyophilized Phycoerythrin-AntiHuman CD8 Antibody Conjugates and Enhances their Thermal Stability in Flow Cytometric Assays," journal of pharmaceutical sciences, vol. 102, Issue 2, Feb. 2013, pp. 649-659.
Senter, P, et al., "Immunoconjugates comprised of drugs with impaired cellular permeability: A new approach to targeted therapy" Proc Amer Assoc Cancer Res, vol. 45, Abs 623, 2004, pp. 1-2.
Sheriff, S. et al., "Redefining the minimal antigen-binding fragment," nature structural biology, vol. 3, No. 9, Sep. 1996, pp. 733-736.
Singh, S.R. et al., "Effect of Polysorbate 80 Quality on Photostability of a Monoclonal Antibody," AAPS PharmSciTech, vol. 13, Issue 2, Jun. 2012, pp. 422-430.

(56) References Cited

OTHER PUBLICATIONS

Slaughter, K., et al., "Primary and acquired platinum-resistance among women with high grade serous ovarian cancer," 2016, Gynecologic Oncology, vol. 142, Issue 2, pp. 225-230.
Stephan, J.P. et al., "Challenges in developing bioanalytical assays for characterization of antibody-drug conjugates," Bioanalysis, vol. 3, Issue 6, 2011, pp. 677-700.
Sun, M et al., "Reduction-Alkylation Strategies for the Modification of Specific Monoclonal Antibody Disulfides," Bioconjugate chem., vol. 16, 2005, pp. 1282-1290.
Topalian, S.L. et al., "Safety, Activity, and Immune Correlates of Anti-PD-1 Antibody in Cancer," N. Engl. J. Med., vol. 366, 2012, pp. 2443-2454.
Topalian, S.L. et al., "Survival, Durable Tumor Remission, and Long-Term Safety in Patients with Advanced Melanoma Receiving Nivolumab," Journal of clinical oncology, vol. 32, 2014, pp. 1020-1030.
Topalian, S.L. et al., "Targeting the PD-1/B7-H1(PD-L1) pathway to activate anti-tumor immunity," Current Opinion Immunology, vol. 24, 2012, pp. 207-212.
Vasquez-Rey, M., et al., "Aggregates in Monoclonal Antibody Manufacturing Processes," Biotech, Bioeng., vol. 108, Issue 7, 2011, pp. 1494-1508.
Vergote, I. et al., Phase 1/2 Trial of Tisotumab Vedotin Plus Bevacizumab, Pembrolizumab, or Carboplatin in Recurrent or Metastatic Cervical Cancer (innovaTV 205/ENGOT-cx8/GOG-3024), 2019, 1 page.
Vergote, I., et al., "Phase Ib/II trial of tisotumab vedotin (TV) +-bevacizumab (BEV), pembrolizumab (PEM), or carboplatin (CBP) in recurrent or metastatic cervical cancer (innovaTV 205/ENGOT-cx8/ GOG-3024)," J. Clin. Oncol., 2020, vol. 38, Issue 15, pp. 1-3.
Vergote, I., et al., "Phase Ib/II Trial of Tisotumab Vedotin +- Bevacizumab, Pembrolizumab, or Carboplatin in Recurrent or Metastatic Cervical Cancer (innovaTV 205/ENGOT-cx8/GOG-3024)," Poster266, Presented at ASCO20 Virtual Scientific Program, May 29-31, 2020, p. 1.
Vergote. I. et al., "Tisotumab Vedotin (TV) + Carboplatin (Carbo) in First-line (1L) or + Pembrolizumab (Pembro) in Previously Treated (2L/3L) Recurrent or Metastatic Cervical Cancer (r/mCC): Interim Results of ENGOT-Cx8/GOG-3024/innovaTV 205 Study," 2021, pp. 4.
Vergote. I. et al., "Tisotumab Vedotin + Carboplatin in First Line or + Pembrolizumab in Previously Treated Recurrent/Metastatic Cervical Cancer: Interim Results of ENGOT Cx8/GOG 3024/innovaTV 205," ESMO, 2021, pp. 9.
Vergote. I. et al., "Tisotumab Vedotin Vs Investigator's Choice Chemotherapy in Second- or Third-Line Recurrent or Metastatic Cervical Cancer (innovaTV 301/ENGOT CX12/GOG 3057, Trial in Progress)," Poster, American Society of Clinical Oncology, 2021.
Vergote. I. et al., "Tisotumab Vedotin vs Investigator's Choice Chemotherapy in Second- or Third-Line Recurrent or Metastatic Cervical Cancer (innovaTV 301/ENGOT-cx12/GOG 3057, Trial in Progress)," Journal of Clinical Oncology, vol. 39, Issue 15, 2021, pp. 2.
Verma, S., et al., "Trastuzumab Emtansine for HER2-Positive Advanced Breast Cancer," The New England journ. of medicine, vol. 367, Issue 19, Nov. 8, 2012, pp. 1783-1791.
Versteeg, H. H. et al., "Inhibition of tissue factor signaling suppresses tumor growth," Blood, vol. 111, Issue 1, Jan. 1, 2008, pp. 190-199.
Vine, A. K., et al., "Recent Advances in Haemostasis and Thrombosis," Retina, The journal of retinal and vitreous diseases, vol. 29, Issue 1, 2009, pp. 1-7.
Vlachostergios, P.J. et al., "Antibody-Drug Conjugates in Bladder Cancer," Bladder Cancer, vol. 4., 2018, pp. 247-259.
Wahl, A. F., et al., "The Anti-CD30 Monoclonal Antibody SGN-30 Promotes Growth Arrest and DNA Fragmentation in Vitro and Affects Antitumor Activity in Models of Hodgkin's Disease," Cancer Research, vol. 62., Jul. 1, 2002, pp. 3736-3742.

Wakankar, A. A., et al., "Physicochemical Stability of the Antibody-Drug Conjugate Trastuzumab-DM1: Changes due to Modification and Conjugation Processes," Bioconjugate Chemistry, vol. 21, Issue 9, 2010, pp. 1588-1595.
Wakankar, A. et al., "Analytical methods for physicochemical characterization of antibody drug conjugates," MAbs, vol. 3, Issue 2, Mar. 1, 2011, pp. 161-172.
Wang, B, et al., "Radiotherapy of Human Xenograft NSCLC Tumors in Nude Mice with a 90Y-Labeled Anti-Tissue Factor Antibody," Cancer biother. & radiopharm., vol. 20, Issue 3, 2005, pp. 300-309.
Weiss, G.R., et al., "A Phase II Trial of Carboplatin for Recurrent or Metastatic Squamous Carcinoma of the Uterine Cervix: A Southwest Oncology Group Study," Gynecol. Oncol. vol, vol. 39, Issue 3, 1990, pp. 332-336.
Winkel, J. V. D., "Pre-clinical Pipeline & Technology", Innovating Antibodies Improving Lives, 2012, pp. 1-11.
Wolfgang, C. L. et al., "Recent Progress in Pancreatic Cancer," CA Cancer J. Clin., vol. 63, 2013, pp. 318-348.
Xu, J. L., et al., "Diversity in the CDR3 Region of VH Is Sufficient for Most Antibody Specificities," Immunity, vol. 13, 2000, pp. 37-45.
Yonemori et al., "Tisotumab Vedotin in Japanese Patients With Recurrent or Metastatic Cervical Cancer: Results From the Phase 1/2 innovaTV 206 Study", Japan Society of Gynecologic Oncology, 2021, 10 pages.
Younes, A. et al., "Brentuximab Vedotin (SGN-35) for Relapsed CD30-Positive Lymphomas," New England Journal of Medicine, vol. 363, Issue 19, Nov. 4, 2010, pp. 1812-1821.
Younes, A. et al., "Brentuximab vedotin combined with ABVD or AVD for patients with newly diagnosed Hodgkin's lymphoma: a phase 1, open-label, dose-escalation study," Lancet Oncol., vol. 14, 2013, pp. 1348-1356.
Younes, A. et al., "Multiple complete responses in a phase 1 dose-escalation study of the antibody drug-conjugate SGN-35 in patients with relapsed or refractory CD30-positive lymphomas," Blood, ASH Annual Meeting, vol. 112, Issue 11, Abstract 1006, Nov. 16, 2008, pp. 1-6.
Youssef, S., et al., "Abstract 2667: In vitro properties and pre-clinical activity of PF-06801591, a high affinity engineered anti-human PD-1," Cancer Research communications, vol. 77, Issue 13, Abstract 2667, Jul. 2017, pp. 1-4.
Yu, J. L., et al., "Oncogenic events regulate tissue factor expression in colorectal cancer cells: implications for tumor progression and angiogenesis," Blood, vol. 105, Issue 4, Feb. 15, 2005, pp. 1734-1741.
Zhang, Z., et al., "Pharmaceutics," Pharmacy, Higher Education Press, pp. 173-174.
Zou, Y. R., et al. "Gene targeting in the lgx locus: efficient generation of ? chain-expressing B cells, independent of gene rearrangements in Igx" the EMBO journal, vol. 12, Issue 3, 1993, pp. 811-820.
Abdulkadir, Sarki a. et al., 2020, Tissue factor expression and angiogenesis in human prostate carcinoma, Apr. 2000, Human Pathology, vol. 31, No., 4; pp. 443-447.
ADCETRIS. (Nov. 2018). "Highlights of Prescribing Information. ADCETRIS® (Brentuximab Vedotin) For Injection, for Intravenous Use Initial U.S. Approval: 2011," ADCETRIS 42 pages.
Alley SC. et al. "Abstract 221: Tisotumab vedotin induces antitumor activity through MMAE-mediated, Fc-mediated, and Fab-mediated effector functions in vitro" AACR (2019) American Association for Cancer Research—110th Annual Meeting.
Alley, S.C. et al. (Jun. 2013, e-pub. Apr. 6, 2013)., Current Opinion in Chemical Biology 17(3):406-411.
Alley, SC et al., 2008, Contribution of Linker Stability to the Activities of Anticancer Immunoconjugates; Bioconjugate Chem: 19; pp. 759-765.
Anonymous (Sep. 19, 2017). "ENGOT-cx8: Randomized Phase II of paclitaxel-carboplatin +/-Nintedanib Ongoing Trials—Status Update," 12 pages.

(56) References Cited

OTHER PUBLICATIONS

Anonymous, 2021 "NCT03786081 Safety and Efficacy of Tisotumab vedotin in combination with other cancer agents in subjects with cervical cancer (Study record versions history of changes for study)".
Aydin, F. et al., (2013). Diagn. Interv. Radiol. 19(4):271-278.
Bartlett, N et al. (2009). ASCO Abstract No. 8500, J. Clin. Oncol. 27:15S, 3 pages.
Bartlett, N.L. et al., 2008, "A phase 1 multidose study of SGN-30 immunotherapy in patients with refractory or recurrent CD30+ hematologic malignancies," Blood 111(4), pp. 1848-1854.
Bird, R.E. et al. (1988). Single-Chain Antigen-Binding Proteins, Science 242(4877):423-426.
Bizzarri, M. et al. (2016). "Pharmacodynamics and Pharmacokinetics of Inositol(s) In Health and Disease," Expert Opin. Biol Ther. 12(10):1181-1196.
Breen, et al., "Effect of Moisture on the Stability of a Lyophilized Humanized Monoclonal Antibody Formulation", vol. 18, 9, Sep. 2001.
Breij, Esther Abstract 1234: "An antibody-drug conjugate targeting tissue factor with broad anti-tumor efficacy in xenograft models with heterogeneous tissue factor expression" Dutch Society for Immunology Annual Meeting, 2013.
Burova, E. et al. (May 2017). "Characterization of the Anti-PD-1 Antibody REGN2810 and Its Antitumor Activity in Human PD-1 Knock-In Mice," Mol Cancer Ther. 16(5):861-870.
Calvo et al. (Feb. 2018). Journal of Clinical Oncology 36(5 suppl.):58-58.
Carter, MC et al.; Instability of Succinyl Ester Linkages in 0<2'>-monosuccinyl cyclic AMP-protein Conjugates of Neutral pH; Journal of Immunological Methods, vol. 81; No. 2; Aug. 2, 1985 pp. 245-257.
Chen T et al.; Development of a Stable Lyophilized Formulation for a Monoclonal Antibody-Doxorubicin Conjugate; Pharmaceutical Research; vol. 10, No. 10 1993; p. 90.
Chen, C. et al.; Characterization of Human Tissue Factor (TF)-Specific Monoclonal Antibodies Prepared Using a Rapid Immunization Protocol; Hybridoma, vol. 24(2), pp. 78-85; 2005.
Chen, Z et al., "Differential Expression of Human Tissue Factor in Normal Mammary; Epithelial Cells and in Carcinomas," Molecular Medicine, vol. 1, No. 2, Jan. 1995, pp. 153-160.
Chothia, C. et al. (1989). "Conformations of Immunoglobulin Hypervariable Regions," Nature 342(6252): 877-883.
Chothia, C. et al. (Oct. 5, 1992). Structural Repertoire of The Human VH Segments, J Mol Biol 227(3):799-817.
ClinicalTrial NCT02001623 "Tisotumab Vedotin (HuMax®-TF-ADC) Safety Study in Patients with Solid Tumors," retreived from <https://clinicaltrials.gov/ct2/show/NCT02001623>, 2021, 8 pages.
ClinicalTrials.gov. (Jul. 11, 2011). "A Phase I Dose Escalation Study of SGN-35 Alone and In Combination with Gemcitabine for CD30-Postive Malignancies," Clinical Trials NCT00649584, 4 pages.
Coleman et al. "A Single arm, Phase 2, Multicenter, International Trial of Tisotumab Vedotin (HuMax® TF ADC) in Previously Treated, Recurrent or Metastatic Cervical Cancer" ASCO 2018.
Coleman, R et al. The Lancet, vol. 22, pp. 609-6019, May 2021.
Colman, PM. Research in Immunology, Elsevier, NY, 145(1):33-36, 1994.
Connors, J. M. et al. (Jan. 25, 2018). Brentuximabl Vedotin With Chemotherapy for Stage III or IV Hodgkin's Lymphoma, N. Eng. J. Med. 378(4):331-344.
Cwirla, S.E. et al. (Aug. 1990). "Peptides On phage: A Vast Library of Peptides for Identifying Ligands," PNAS USA 87:6378-6382.
Das, C.J. et al., (Jul.-Sep. 2018). Positron Emission Tomography in Prostate Cancer: An Update On State Of The Art, Indian J. Urol. 34(3):172-179.
David K Gaffney et al. "Too many women are dying from cervix cancer: Problems and solutions" Gynecologic Oncology, vol. 151(3) pp. 547-554 2018.

De Bono JS et al."Tisotumab vedotin in patients with advanced or metastatic solid tumours(InnovaTV 201): a first-in-human, multicentre phase 1-2 trial" Lancet Oncology 2019 vol. 20: 383-93.
De Goeij, B.E.C.G et al., 2015, "High turnover of tissue factor enables efficient intracellular delivery of antibody-drug conjugates" Molecular cancer therapy, vol. 14(5), pp. 1130-1140.
Doronina, S.O. et al. (Oct. 2008, e-pub. Sep. 20, 2008). Novel Peptide Linkers for Highly Potent Antibody Auristain Conjugate, Bioconjugate Chem. 19:1960-1963.
Doronina, Svetlana O. Et al.; Development of potent monoclonal antibody auristatin conjugates for cancer therapy; Nature Biotechnology 21; 7; 778-784; 2003.
Doronina, Svetlana O. Et al:; Enhanced Activity of Monomethylauristatin F through Monoclonal Antibody Delivery: Effects of Linker Technology on Efficacy and Toxicity; Bioconjugate Chem. 17; 114-124; 2006.
Drake, Thomas A. et al., 1989; Selective Cellular Expression of Tissue Factor in Human Tissues; American Journal of Pathology, vol. 134(5), May 1989.
drugs.com. (Jun. 2008). "Seattle Genetics Reports Multiple Complete and Partial Responses With SGN-35 in Patients with Lymphoma," Drugs.Com, 3 pages.
Dubowchik, GM et al., 1999, "Receptor-mediated and enzyme-dependent targeting of cytotoxic anticancer drugs" Pharm. Therapeutics, vol. 83(2), pp. 67-123.
Egorina, Elena M. et al., 2005, Intracellular and Surface Distribution of Monocyte Tissue Factor : Application to Intersubject ariability; Arteriosclerosis, Thrombosis and Vascular Biology; vol. 25, pp. 1493-1498.
Fanale, M. et al. (2009). "The Antibody-Drug Conjugate Brentuximab Vedotin (SGN-35) Induced Multiple Objective Responses in Patients with Relapsed or Refractory CD30-Positive Lymphomas in a Phase 1 Weekly Dosing Study," Blood 114:2731, 5 pages.
Fleck, Rebecca et al., "Localization of Human Tissue Factor Antigen by Immunostaining with Monospecific, Polyclonal Anti-Human Tissue Factor Antibody," Thrombosis Research, 59, 1990, pp. 421-437.
Forero, A. et al. (2005). "Leukemia, Lymphoma, Myeloma, and Transplantation (Adult). Initial Phase II Results of SGN-30 (Anti-CD30 Monoclonal Antibody) In Patients with Refractory or Recurrent Systemic Anaplastic Large Cell Lymphoma (ALCL)," Journal of Clinical Oncology Abstract No. 6601, 1 page.
Francisco, J.A. et al. (Aug. 15, 2003, e-pub. May 8, 2003). "cAC10-vcMMAE, An Anti-CD30-Monomethyl Auristatin E Conjugate with Potent and Selective Antitumor Activity," Blood 102:1458-1465.
Förster et al.; Tissue factor and tumor: Clinical and laboratory aspects; Clinica Chimica Acta 364, 12-21; 2006.
Gessler, F. et al., Inhibition of Tissue Factor/Protease-Activated Receptor-2 Signaling Limits Proliferation, Migration and Invasion of Malignant Glioma Cells; Neuroscience 165; 1312-1322; 2010.
Goh, V. et al. (2014). "Perfusion CT Imaging of Colorectal Cancer," British Journ Radiol. vol. 87(1034), pp. 20130811.
Goldberg, R.M. et al. (Jan. 2007). "The Continuum of Care: A Paradigm for The Management of Metastatic Colorectal Cancer," Oncologist 12(1):38-50.
Haeuw, J-F. et al. (Dec. 2009). "Immunoconjugates, Drug-Armed Antibodies to Fight Against Cancer," Med. Sci. 25:1046-1052 (with machine translation).
Hamblett, K.J. et al. (2005). "SGN-35, An Anti-CD30 Antibody-Drug Conjugate, Exhibits Potent Antitumor Activity for the Treatment of CD30+ Malignancies," Blood 106:610. (Abstract Only).
Hamblett, Kevin J. et al.; Effects of Drug Loading on the Antitumor Activity of a Monoclonal Antibody Drug Conjugate; Clinical Cancer Research, 10; 7063-7070; 2004.
Hamid, O. et al. (Jul. 11, 2013, e-pub. Jun. 2, 2013). "Safety and Tumor Responses with Lambrolizumab (Anti-PD-1) In Melanoma," N. Engl. J. Med. 369(2):134-144, 18 pages.
Hanes, J. et al. (1997). "In vitro Selection and Evolution of Functional Proteins by Using Ribosome Display," PNAS USA 94:4937-4942.

(56) References Cited

OTHER PUBLICATIONS

Hanker, L.C. et al. (Oct. 2012, e-pub. Aug. 21, 2012). "The Impact of Second to Sixth Line Therapy on Surviaval of Relapsed Ovarian Cancer After Primary Taxane/Platinum-Based Therapy," Ann. Oncol. 23(10):2605-2612.
Harris, R.E. et al. (Apr. 2005). "Aspirin, Ibuprofen, and Other Non-Steroidal Anti-Inflammatory Drugs in Cancer Prevention: A Critical Review of Non-Selective COX-2 Blockade (Review)," Oncol. Rep. 3(4):559-583.
Hermsen, M.A. et al (Jan. 1996). "Centromeric Breakage as a Major Cause Of Cytogenetic Abnormalities In Oral Squamous Cell Carcinoma," Genes Chromosomes Cancer 15(1):1-9.
Younes, A. et al. (2008). "Objective Responses in a Phase l Dose-Escalation Study of SGN-35, A Novel Antibody-Drug Conjugate (ADC) Targeting CD30, in Patients with Relapsed or Refractory Hodgkin Lymphoma," Abstract No. 8526, 44th ASCO Annual Meeting, May 30-Jun. 3, 2008, 1 page.
Younes, A. et al. (2007). "A Novel Antibody-Drug Conjugate, SGN-35 (AntiCD30-Auristatin), Induces Objective Responses in Patients with Relapsed or Refractory Hodgkin Lymphoma Preliminary Results of a Phase I Tolerability Study," 7th International Symposium on Hodgkin Lymphoma, Cologne, Nov. 4-7, 2007, 1 page.
Yu, et al., 2017, Immunotherapy in urothelial cancer, part 1: T-cell checkpoint inhibition in advanced or metastatic disease. Clin Adv Hematol Oncol. vol. 15(6), pp. 466-477.
Jiang, et al, 2019, PD-1 and PD-L1 in cancer immunotherapy: clinical implications and future considerations, Hum Vaccin Immunother. Epub, vol. 15(5), pp. 1111-1122.
Breij et al, 2013, "An Antibody-Drug Conjugate That Targets Tissue Factor Exhibits Potent Therapeutic Activity against a Broad Range of Solid Tumors" Cancer Research. 74. 10.1158/0008-5472.CAN-13-2440.
Zou, Y. R., et al. "Gene targeting in the lgx locus: efficient generation of ? chain-expressing B cells, independent of gene rearrangements in lgx" the EMBO journal, vol. 12, Issue 3, 1993, pp. 811-820.
Al-Lazikani et al., 1997, JMB 273,927-948 ("Chothia" numbering scheme).
Breij EC et al. 2014, Cancer Res. 74(4):1214-1226.
Burotto et al., 2015, Oncologist 20:725-726.
Candelaria et al., 2009, Int. J. Gynecol. Cancer. 19:1632-1637.
Carter D. "New global survey shows an increasing cancer burden". Am J Nurs. Mar. 2014; 114(3):17).
Chen et al, 1993, EMBO J. 12:811-820.
Chen, J. et al., 1993, International Immunology. 5:647-656.
Chiswell and McCafferty, 1992, Tibtech, 10:80-84.
Choi et al., 2008, J. Gynecol. Oncol. 19(3):205.
Chothia and Lesk, 1987, J. Mol. Biol., 195, 901-917.
Chu AJ, 2011, Tissue Factor, Blood Coagulation, and Beyond: An Overview, International Journal of Inflammation, Article ID 367284, 30 pages. https://doi.org/10.4061/2011/367284.
Clackson et al., 1991, Nature, 352, 624-628.
Cocco E et al. BMC Cancer. 2011;11:263.
Coronel et al., 2009, Med. Oncol. 26:210-214.
Cwirla et al.,1990, PNAS USA, 87:6378-6382.
De la Cruz Edmunds et al., 2006, Molecular Biotechnology 34; 179-190.
Fiorica et al., 2009, Gynecol. Oncol. 115:285-289.
Fishwild et al., 1996, Nature Biotechnology, 14:845-851.
Förster Y et al., 2006, Clin Chim Acta. 364(1-2):12-21.
Garcia et al., 2007, Am. J. Clin. Oncol. 30-428-431.
Goncalves et al., 2008, Gynecol. Oncol. 108:42-46.
Gruber et al., 2013, BMC Cancer. 13:328.
Hamid and Carvajal, 2013, Expert Opin Biol Ther 13(6):847-61.
Hanes and Plucthau, 1997, PNAS USA 94:4937-4942.
Harding, F. and Lonberg, N. Ann, N. Y. Acad. Sci 764:536-546 (1995)).
Harlow et al. Antibodies: A Laboratory Manual. Ch.14 (Cold Spring Harbor Laboratory, Cold Spring Harbor, NY, 1988).
Hillemanns et al., 2016, Oncol. Res. Treat. 39:501-506.
Hobbs et al., 2007, Thrombosis Res. 120(2):S13-S21.
Hodi et al., 2010, N Engl J Med 363:711-723.
Hoogenboom et al., 1992, Building antibodies from their genes. Immunol. Reviews, 130:43-68.
Homesley et al., 2008, Int. J. Clin. Oncol. 13:62-65.
Honegger A and Plückthun A, 2001, "Yet another numbering scheme for immunoglobulin variable domains: an automatic modeling and analysis tool," J Mol Biol 8;309(3):657-70.
Hoogenboom et al., 1992, By-passing immunisation. Human antibodies from synthetic repertoires of germline VH gene segments rearranged in vitro. J. Mol, Biol. 227(2):381-388.
Jefferis and Lefranc, 2009, mAbs vol. 1 Issue 4 1-7.
Kohler et al., 1975, Nature, 256, 495.
Kostelny et al., 1992, J. Immunol. 148:1547 1553.
Lefranc MP et al., 2003, "IMGT unique numbering for immunoglobulin and T cell receptor variable domains and Ig superfamily V-like domains," Dev Comp Immunol. 27(1):55-77.
Lonberg, N. and Huszar. D., 1995, Intern. Rev. Immunol, vol. 13 65-93.
Lonberg, N. et al., 1994, Nature, 368, 856-859.
Lonberg, N. Handbook of Experimental Pharmacology 113, 49-101 (1994).
MacCallum et al., J. Mol. Biol. 262:732-745 (1996), "Antibody-antigen interactions: Contact analysis and binding site topography," J. Mol. Biol. 262, 732-745. ("Contact" numbering scheme).
Marks et al., 1991, J. Mol. Biol., 222(3):581-597.
Martin et al., 1989, "Modeling antibody hypervariable loops: a combined algorithm," PNAS 86(23):9268-9272.
McDermott and Atkins, 2013, Cancer Med 2(5):662-73.
McLachlan et al., 2017, Clin. Oncol. (R. Coll. Radiol.) 29:153-160.
Miller et al., 2008, Gynecol. Oncol. 110:65-70.
Monk et al., 2009, J. Clin. Oncol. 27:1069-1074.
Muggia et al., 2004, Gynecol. Oncol. 92:639-643.
Ouyang, J., 2013, Antibody-Drug Conjugates, Methods in Molecular Biology (Methods and Protocols).
Parmley and Smith, 1988, Gene, 73:305-318.
Pettit et al., 1998, Antimicrob. Agents and Chemother. 42: 2961-2965.
Rose et al., 2006, Gynecol. Oncol. 102:210-213.
Russel et al., 1993, Nucl. Acids Research, 21:1081-4085.
Sambrook et al., 1989, Molecular Cloning: A laboratory Manual, New York: Cold Spring Harbor Laboratory Press, Ch. 15.
Santin et al., 2011, Gynecol. Oncol. 122:495-500.
Schellens J.H.M, et al., J Clin Oncol, 2017, 35. (Suppl.): abstr 5514. A Phase I/II trial demonstrated a robust efficacy and manageable safety profile for 2.0 mg/kg tisotumab vedotin administered to subjects with relapsed, recurrent, and/or metastatic cervical cancer (NCT02001623).
Schilder et al., 2005, Gynecol. Oncol. 96:103-107.
Scott, 1992, TIBS. 17:241-245.
Sjoblom et al., 2006, Science 314:268-74).
Taylor, L. et al.,1994, International Immunology, 6:579-591.
Taylor, L. et al., 1992, Nucleic Acids Research. 20:6287-6295.
Tempfer et al., 2016, Oncol. Res. Treat. 39:525-533.
Tewari et al., 2014, N Engl J Med., 370:734-743.
Torfs et al., 2012, Eur. J. Cancer. 48:1332-1340.
Tuaillon et al., 194, J. Immunol, 152:2912-2920.
Tutt, et al., 1991, J. Immunol. 147:60-69.
U.S. General Accounting Office. Breast Cancer, 1971-1991: Prevention, Treatment and Research. GAO/PEMD-92-12; 1991.
Vaughan et al., 1996, Nature Biotech, 14:309.
Woyke et al., 2001, Antimicrob. Agents and Chemother. 45(12): 3580-3584.
Zhu et al., 2016, Drug Des. Devel. Ther. 10:1885-1895.
De Bono et al., Tisotumab vedotin in patients with advanced or metastatic solid tumours (InnovaTV 201): a first-in-human, multicentre, phase 1-2 trial, Lancet Oncol., 20: 383-393, (2019).
Sun et al., Reduction-Alkylation Strategies for the Modification of Specific Monoclonal Antibody Disulfides, Bioconjug. Chem., 16(5): 1282-1290, (2005).
Gaffney et al., Too many women are dying from cervix cancer: Problems and solution, Gynecol. Oncol., 151: 547-554, (2018).

(56) References Cited

OTHER PUBLICATIONS

Prat, Staging classification for cancer of the ovary, fallopian tube, and peritoneum, Int. J. Gynecol. Obst., 124: 1-5, (2014).
Rowland et al., "Preclinical investigation of the antitumour effects of anti-CD19-idarubicin immunoconjugates", Cancer Immunol. Immunother., 37:195-202 (1993).
Thomas et al., "Antibody-drug conjugates for cancer therapy", Lancet Oncol., 17(6):e254-e262 (2016).
A Phase 1b/2 Open-Label Trial of Tisotumab Vedotin (HuMax®-TF-ADC) Monotherapy and in Combination With Other Agents in Subjects With Recurrent or Stage IVB Cervical Cancer, National Library of Medicine, ClinicalTrials.gov, 17 pages (Dec. 13, 2018).
Abdulkadir et al., Tissue Factor Expression and Angiogenesis in Human Prostate Carcinoma, Human Pathology, 31(4):443-447(2000).
Adcetris, Highlights of Prescribing Information. ADCETRIS® (Brentuximab Vedotin) For Injection, for Intravenous Use, US approval, 42 pages (Nov. 2018).
Alley et al., Analytical and Bioanalytical Technologies for Characterizing Antibody-Drug Conjugates, Curr Opin in Chem Biology, 17(3):406-411 (Jun. 2013).
Alley et al., Contribution of Linker Stability to the Activities of Anticancer Immunoconjugates, Bioconjugate Chem., 19(3):759-795 (Mar. 2008).
Alley et al., Tisotumab Vedotin Induces Anti-Tumor Activity Through MMAE-Mediated, Fc-Mediated, and Fab-Mediated Effector Functions in Vitro, AACR Annual Meeting, 79(13), Abst. 221, 4 pages (July 1019).
Amirkhosravi et al., The Importance of Platelets in the Expression of Monocyte Tissue Factor Antigen Measured by a New Whole Blood Flow Cytometric Assay, Thrombosis and Haemostasis, 75(1):87-95 (1996).
Anonymous—NCT03786081, Safety and Efficacy of Tisotumab Vedotin Monotherapy & in Combination With Other Cancer Agents in Subjects With Cervical Cancer, National Library of Medicine, ClinicalTrials.gov, 14 pages (Feb. 27, 2019).
Aras et al., Induction and microparticle- and cell-associated intravascular tissue factor in human endotoxemia, Blood, vol. 103(12), 4545-4553, 2004.
AYD56882, SEQID 5, Score Search Result Details, pp. 1-2, Aug. 19, 2010.
AYD56926, SEQ ID 49, Score Search Result Details, pp. 1-2, Aug. 19, 2010.
AYD56930, SEQ ID 53, Score Search Result Details, pp. 1-2, Aug. 19, 2010.
AYD56938, SEQ ID 61, Score Search Result Details, pp. 1-2, Aug. 19, 2010.
AYD56982, SEQ ID 105, Score Search Result Details, pp. 1-2, Aug. 19, 2010.
Aydin et al., Measurements of tumor size using CT and PET compared to histopathological size in non-small cell lung cancer, Diagn Interv Radiol, 19:271-278 (2013).
Bartlett et al., Abstract 8500—Complete Remissions With Weekly Dosing of SGN-35, A Novel Antibody-Drug Conjugate (ADC) Targeting CD30 in a Phase I Dose-Escalation Study in Patients With Relapsed or Refractory Hodgkin Lymphoma (HL) or Systemic Anaplastic Large Cell Lymphoma (sALCL), J. Clin. Oncol, 27, 2 pages (2009).
Bartlett et al., A phase 1 multidose study of SGN-30 immunotherapy in patients with refractory or recurrent CD30 hematologic malignancies, Blood, 111(4):1848-1854 (Feb. 15, 2008).
Bauer M.K., Transitioning HuMax-TF-ADC Into the Clinic—Maximizing Clinical Knowledge in Early Stage Development, World ADC, Genmab, 27 pages (2015).
Bauer M.K., Clinical Perspective of ADC Development, PEGS, Boston, Genmab, 27 pages (May 8, 2015).
Beck A., Biosimilar, biobetter and next generation therapeutic antibodies, mAbs, 3(2):107-110 (2011).

Bhatt et al., Role of antibodies in diagnosis and treatment of ovarian cancer: Basic approach and clinical status, Journal of Controlled Release, 226:148-167 (Mar. 28, 2016).
Bird et al., Single-Chain Antigen-Binding Proteins, Science, 242:423-426 (1988).
Bizzarri et al., Pharmacodynamics and pharmacokinetics of inositol(s) in health and disease, Expert Opinion on Drug Metabolism & Toxicology, 12(10):1181-1196 (Jul. 12, 2016).
Blank et al., Abstract No. 882TIP-innovaTV 208: New Weekly Dosing Cohort in the Phase 2 Study of Tisotumab Vedotin in Platinum-Resistant Ovarian Cancer, ESMO Poster, Genmab (Sep. 19, 2020).
Blank et al., Abstract No. 10862-innovaTV 208: New Weekly Dosing Cohort in the Phase 2 Study of Tisotumab Vedotin in Platinum-Resistant Ovarian Cancer, SGO, Seagen, Inc., (Sep. 19, 2021).
Breen et al., Effect of moisture on the stability of a lyophilized humanized monoclonal antibody formulation, Pharmaceutical Research, 18(9):1345-1353 (2001).
Breij E., Pre-Clinical Development of a Therapeutic Antibody-Drug Conjugate Targeting Tissue Factor, Informa Empowered Antibodies Congress, Antibody-Drug Conjugates, Barcelona, Genmab Presentation Slides, 46 pages (May 17-19, 2014).
Breij et al., An Antibody-Drug Conjugate Targeting Tissue Factor With Broad Anti-Tumor Efficacy in Xenograft Models With Heterogeneous Tissue Factor Expression, Cancer Res, 2013, 73(8_Supplement):1234.
Breij E., Development of an Auristatin-Conjugated Therapeutic Antibody Against Tissue Factor for the Treatment of Solid Tumors, World ADC Summit Frankfurt, Genmab Presentation Slides, 33 pages (2013).
Breij E., An antibody-drug conjugate targeting tissue factor for the treatment of solid cancers, Dutch Society for Immunology, Annual Meeting 2013, Genmab Presentation Slides, 16 pages (Dec. 17, 2013).
Breij E.C.W., Pre-Clinical Development of a Therapeutic Antibody-Drug Conjugate Targeting Tissue Factor, GTC Antibody & Protein Therapeutics Conference, San Diego, Genmab Presentation Slides, 47 pages (Oct. 25, 2013).
Breij E., Targeting Solid Cancers Using Antibody-Drug Conjugates Against the Novel ADC Targets Tissue Factor and AXL, World ADC Summit, London, Genmab Presentation Slides, 41 pages (May 18-19, 2015).
Burova et al., Characterization of the Anti-PD-1 Antibody REGN2810 and Its Antitumor Activity in Human PD-1 Knock-In Mice, American Association for Cancer Research, Molecular Cancer Therapeutics, 16(5):861-870 (May 2017).
Calvo et al., Interim results of a phase 1/2 study of JNJ-63723283, an anti-PD-1 monoclonal antibody, in patients with advanced cancers, Journal of Clinical Oncology, 36(Suppl. 5), Abstract 58, 2 pages (2018).
Cao et al., Rational design of lyophilized high concentration protein formulations-mitigating the challenge of slow reconstitution with multidisciplinary strategies, European Journal of Pharmaceutics and Biopharmaceutics, 85:287-293 (2013).
Carter et al., Instability of succinyl ester linkages in $O^{2'}$-monosuccinyl cyclic AMP-protein conjugates at neutral pH, Journal of Immunological Methods, 81(2):245-257 (Aug. 1985).
Champiat et al., Management of immune checkpoint blockade dysimmune toxicities: a collaborative position paper, Ann Oncol, 24(4):559-574 (Apr. 2016).
Chen et al., Characterization of Human Tissue Factor (TF)-Specific Monoclonal Antibodies Prepared Using a Rapid Immunization Protocol, Hybridoma, 24(2):78-85 (2005).
Chen et al., B cell development in mice that lack one or both immunoglobulin kappa light chain genes, The EMBO Journal, Oxford University Press, 12(3):821-830 (Mar. 1, 1993).
Chen et al., Differential Expression of Human Tissue Factor in Normal Mammary Epithelial Cells and in Carcinomas, Molecular Medicine, 1(2):153-160 (Jan. 1, 1995).
Chenard-Poirier et al., A phase I/II safety study of tisotumab vedotin (HuMax-TF-ADC) in patients with solid tumors, ESMO, Spain, Poster (2017).

(56) References Cited

OTHER PUBLICATIONS

Chothia et al., Conformations of immunoglobulin hypervariable regions, Nature, 342:877-883 (Dec. 21/28, 1989).
Chothia et al., Structural Repertoire of the Human VH Segments, J. Mol. Biol, 227:799-817 (1992).
Chu et al., Tissue factor mediates inflammation, Archives of Biochemistry and Biophysics, 440:123-132 (2005).
Clinical Trials NCT00649584, A Phase I Dose Escalation Study of SGN-35 Alone and In Combination with Gemcitabine for CD30-Postive Malignancies, ClinicalTrials.gov, 4 pages (Jul. 11, 2011).
Clinical Trials NCT02001623, Tisotumab Vedotin (HuMax®-TF-ADC) Safety Study in Patients With Solid Tumors, ClinicalTrials.gov, 8 pages (Dec. 31, 2019).
Clinical Trials NCT02552121, Tisotumab Vedotin (HuMax®-TF-ADC) Safety Study in Patients With Solid Tumors, ClinicalTrials.gov, 37 pages (Nov. 30, 2015).
Cohen et al., Evaluation of venous thrombosis and tissue factor in epithelial ovarian cancer, Gynecologic Oncology, 146(1):146-152 (Jul. 2017).
Coleman et al., Abstract TPS5601—A Single Arm, Phase 2, Multicenter, International Trial of Tisotumab Vedotin (Hu Max® TF ADC) in Previously Treated, Recurrent or Metastatic Cervical Cancer, Poster 327b, ASCO (2018).
Coleman et al., Tisotumab Vedotin (TV) in Previously Treated Recurrent or Metastatic Cervical Cancer (r/mCC): Results From the Phase 2 InnovaTV 204/GOG-3023/ENGOT-cx6 Study, ESMO Congress, 17 pages (2020).
Coleman et al., Efficacy and safety of tisotumab vedotin in previously treated recurrent or metastatic cervical cancer (innovaTV 204/GOG-3023/ENGOT-cx6): a multicentre, open-label, single-arm, phase 2 study, The Lancet Oncology, 22:609-619 (2021).
Colman P.M., Effects of amino acid sequence changes on antibody-antigen interactions, $55^{th}$ Forum in Immunology, 145(1):33-36 (1994).
Concin et al., A Phase IIA Study OF Tisotumab Vedotin (HuMax®-TF-ADC) in Patients with Relapsed, Recurrent and/or Metastatic Cervical Cancer: Updated Safety and Efficacy, 27(4):1971(2017).
Concin et al., A Phase IIa Study of Tisotumab Vedotin (HuMax®-TF-ADC) in Patients With Relapsed, Recurrent and or Metastatic Cervical Cancer, European Gynecological Oncology Congress, ESGO Poster (Nov. 4-7, 2017).
Concin, N., A Phase IIa Study of Tisotumab Vedotin in Patients With Previously Treated Recurrent or Metastatic Cervical Cancer: Updated Analysis of Full Cervical Expansion Cohort, Annals of Oncology, Abstract 963P, 29(Supplement 8), 1 page (2018).
Connors et al., Brentuximab Vedotin With Chemotherapy for Stage III or IV Hodgkin's Lymphoma, The New England Journal of Medicine, 378(4):331-344 (2018).
Das et al., Positron emission tomography in prostate cancer: An update on state of the art, Indian Journal of Urology, 34(3):172-179 (2018).
De Goeij et al., High Turnover of Tissue Factor Enables Efficient Intracellular Delivery of Antibody-Drug Conjugates, AACR, Molecular Cancer Therapeutics, 14(5):1130-1140 (2015).
De Goeij B., Targeting solid cancers using antibody-drug conjugate against the novel ADC target tissue factor. HuMax®-TF-ADC, a preclinical and FIH study, IBC Antibody Eng & Therapeutics, Genmab Presentation Slides, 23 pages (Dec. 8, 2015).
De Goeij B., High Turnover of Tissue Factor Enables Efficient Intracellular Delivery of Antibody-Drug Conjugates, Mykonos Conference, Abstract for Mykonos, 1 page (2014).
De Goeij B., High Turnover of Tissue Factor Enables Efficient Intracellular Delivery of Antibody- Drug Conjugates, Mykonos Conference, Genmab Presentation Slides, 38 pages (2014).
Doronina et al., Enhanced Activity of Monomethylauristatin F through Monoclonal Antibody Delivery: Effects of Linker Technology on Efficacy and Toxicity, Bioconjugate Chem., 17(1):114-124 (2006).
Doronina et al., Novel Peptide Linkers for Highly Potent Antibody-Auristatin Conjugate, Bioconjugate Chem., 19(10):1960-1963 (2008).
Doronina et al., Development of potent monoclonal antibody auristatin conjugates for cancer therapy, Nature Biotechnology, 21(7):778-784;941 (Jul. 2003).
Drake et al., Selective Cellular Expression of Tissue Factor in Human Tissues, American Journal of Pathology, 134(5):1087-1097 (May 1989).
Dubowchik et al., Receptor-mediated and enzyme-dependent targeting of cytotoxic anticancer drugs, Pharmacology & Therapeutics, 83(2):67-123 (1999).
Eaton et al., Ocular Adverse Events Associated with Antibody-Drug Conjugates in Human Clinical Trials, Journal of Ocular Pharmacology and Therapeutics, 31(10):589-604 (2015).
Edwards et al., The Remarkable Flexibility of the Human Antibody Repertoire; Isolation of Over One Thousand Different Antibodies to a Single Protein, BLyS, J. Mol. Biol., 334:103-118 (2003).
Egorina, E. M. et al., Intracellular and Surface Distribution of Monocyte Tissue Factor, Application to Intersubject Variability, Arteriosclerosis, Thrombosis, and Vascular Biology—Journal of the American Heart Association, 25:1493-1498 (2005).
Engot, Engot-cx1 Randomized Phase II of paclitaxel-carboplatin +/− Nintedanib, Gynecologic Cancer Intergroup (2017).
Fanale et al., The Antibody-Drug Conjugate Brentuximab Vedotin (SGN-35) Induced Multiple Objective Responses in Patients with Relapsed or Refractory CD30-Positive Lymphomas in a Phase 1 Weekly Dosing Study, Blood, Abstract 2731, 114(220), 3 pages (2009).
Fishwild et al., High-avidity human IgGk monoclonal antibodies from a novel strain of minilocus transgenic mice, Nature Biotechnology, 14:845-851 (1996).
Fleck et al., Localization of Human Tissue Factor Antigen By Immunostaining with Monospecific, Polyclonal Anti-Human Tissue Factor Antibody, Thrombosis Research, 59:421-437 (1990).
Forero et al., Initial phase II results of SGN-30 (anti-CD30 monoclonal antibody) in patients with refractory or recurrent systemic anaplastic large cell lymphoma (ALCL), Journal of Clinical Oncology, Abstract 6601, 1 page (2005).
Francisco et al., cAC10-vcMMAE, an anti-CD30-monomethyl auristatin E conjugate with potent and selective antitumor activity, Blood, 102(4):1458-1465 (Aug. 15, 2003).
Garcia et al., Phase II Clinical Trial of Docetaxel in Refractory Squamous Cell Carcinoma of the Cervix, American Journal of Clinical Oncology, 30(4):428-431 (Aug. 2007).
Genbank, F3 coagulation factor III, tissue factor [Homo sapiens (human)], NCBI, NP 001984, 11 pages (Oct. 18, 2021).
Gencore Version 6.4.3, OM Protein—Protein Search, Using SW Model, Perfect Score 556, Biocceleration Ltd., 2 pages (Jun. 28, 2023).
Gencore Version 6.4.3, OM Protein—Protein Search, Using SW Model, Perfect Score 616, Biocceleration Ltd., 2 pages (Jun. 28, 2023).
Genmab Announcement, Genmab Announces Preliminary Cervical Cancer Data from Tisotumab Vedotin Phase I/II Study, Genmab A/S, Company Announcement No. 22, 2 pages (Jun. 16, 2017).
Genmab Presentation, Development of ADCs against Tissue Factor for the treatment of Solid Tumors, World ADC Summit, 24 pages (Oct. 25-28, 2011).
Gerritsen A., Bioanalysis of Antibody-Auristatin Conjugates in Primate Studies, Basel, Genmab Presentation Slides, 28 pages (2013).
Gerritsen A., In vitro screening approaches for antibody drug conjugates, 2nd Annual Antibody Drug Conjugates, Berlin, Genmab Powerpoint Presentation, 29 pages (Jun. 13-14, 2012).
Gerritsen A., BioAnalysis in ADC development, Genmab Global Bioconference, Incheon Korea, 1 page (Jun. 29-Jul. 3, 2015).
Gessler et al., Inhibition of Tissue Factor/Protease-Activated Receptor-2 Signaling Limits Proliferation, Migration, and Invasion of Malignant Glioma Cells, Neuroscience, 165:1312-1322 (2010).
Goel et al., Plasticity within the Antigen-Comb Site May Manifest as Molecular Mimicry in the Humoral Immune Response, The Journal of Immunology, 173(12):7358-7367 (Dec. 15, 2004).
Goh et al., Perfusion CT imaging of colorectal cancer, British Institute of Radiology 87:20130811, 9 pages (2013).

(56) References Cited

OTHER PUBLICATIONS

Goldberg et al., The Continuum of Care: A Paradigm for the Management of Metastatic Colorectal Cancer, The Oncologist-Gastrointestinal Cancer, 12:38-50 (2007).

Gonzalez-Rodriguez et al., Immune Checkpoint Inhibitors: Review and Management of Endocrine Adverse Events, The Oncologist, 21(7):1-13 (2016).

Gray et al., Tisotumab Vedotin Shows Immunomodulatory Activity Through Induction of Immunogenic Cell Death, Society for Immunotherapy of Cancer, Poster No. 617, 2 pages (Nov. 9-14, 2020).

Gruber et al., Measurement of tumour size with mammography, sonography and magnetic resonance imaging as compared to histological tumour size in primary breast cancer, BMC Cancer, 13(328), 8 pages (Jul. 2013).

Haeuw et al., Les immunoconjugues, anticorps « armés » pour combattre le cancer, Medecine/Sciences, 25:1046-1052 (2009).

Hamblett et al., Effects of Drug Loading on the Antitumor Activity of a Monoclonal Antibody Drug Conjugate, Clinical Cancer Research, 10:7063-7070 (2004).

Hamblett et al., SGN-35, an Anti-CD30 Antibody-Drug Conjugate, Exhibits Potent Antitumor Activity for the Treatment of CD30+ Malignancies, Blood, 106(11):610 (Nov. 16, 2005).

Hamers-Casterman et al., Naturally occurring antibodies devoid of light chains, Nature, 363(6428):446-448 (Jun. 3, 1993).

Hamid et al., Safety and Tumor Responses With Lambrolizumab (Anti-PD-1) In Melanoma, The New England Journal of Medicine, 369(2):134-144 (2013).

Hanker et al., The Impact of Second to Sixth Line Therapy on Survival of Relapsed Ovarian Cancer After Primary Taxane/Platinum-Based Therapy, Annals of Oncology, 23:2605-2612 (Aug. 21, 2012).

Harlow et al., Antibodies, A Laboratory Manual (Second Edition), Table of contents, Cold Spring Harbor Laboratory Press, 8 pages (1988).

Harris J.R., Tisotumab Vedotin—A Novel Tissue Factor-Targeting Antibody-Drug Conjugate for the Treatment of Advanced Solid Tumors, PEGS Boston, Genmab Presentation Slides, 32 pages (2019).

Harris J.R., Tisotumab Vedotin—A Novel Tissue Factor-Targeting Antibody-Drug Conjugate for the Treatment of Advanced Solid Tumors, PEGS Boston, Abstract, 1 page (2019).

Harris et al., Aspirin, Ibuprofen, and Other Non-Steroidal Anti-Inflammatory Drugs in Cancer Prevention: A Critical Review of Non-Selective COX-2 Blockade, Oncology Reports, 13:559-583(2005).

Hemmingsen P., Overcoming the challenges of your supply chain, Empowered Antibodies Congress, Barcelona, Genmab Presentation Slides, 30 pages (Jun. 2015).

Henderson I.C., Breast Cancer, Textbook of clinical oncology, American Cancer Society, pp. 198-219(1995).

Hermsen et al., Centromeric Breakage as a Major Cause of Cytogenetic Abnormalities in Oral Squamous Cell Carcinoma, Genes, Chromosomes Cancer, 15(1):1-9(1996).

Hjortoe et al., Tissue factor-factor VIIa-specific up-regulation of IL-8 expression in MDA-MB- 231 cells is mediated by PAR-2 and results in increases cell migration, Blood, 103(8):3029-3037(2004).

Ho et al., The ophthalmological complications of targeted agents in cancer therapy: what do we need to know as ophthalmologists?, Acta Ophthalmologica, 91(7):604-609(2013).

Holden et al., Phase I Study of Weekly Dosing of Trastuzumab-DM1 (T-DM1) in Patients With Advanced, Meeting Abstract, ASCO Poster 1029, 1 page (2008).

Hollebecque, A et al., An Open-Label, Multicohort, Phase I/II Study of Nivolumab in Patients With Virus-Associated Tumors (Checkmate 358: Efficacy and Safety in Recurrent or Metastatic Cervical, Vaginal and Vulvar Cancers, 2, Jun. 2-6, 2017, ASCO Annual Meeting Chicago.

Holt, L. J. et al., Domain antibodies: proteins for therapy, Trends in Biotechnology, 21(11), 484-490, 2003.

Hong D.S. et al., InnovaTV 207: Open Label Phase 2 Study of Tisotumab Vedotin for Locally Advanced or Metastatic Disease in Solid Tumors-TIP, Abstract No. TPS3160, 1, May 31 to Jun. 4, 2019, ASCO.

Hong D.S. et al., innova TV 207: New Dosing Cohort in The Open Label Phase 2 Study of Tisotumab Vedotin In Solid Tumors, Abstract 646, 1, Sep. 16-21, 2021, European Society of Medical Oncology 2021, Virtual Congress.

Hong DS. et al., Efficacy and Safety of Tisotumab Vedotin in Patients With Head and Neck Squamous Cell Carcinoma: Resulats From a Phase II Cohort, 2, Dec. 2 to 4, 2021, Multidisciplinary Thoracic Cancers Symposium.

Hong, D S et al., Tisotumab Vedotin in Patients With Previously Treated Recurrent or Metastatic Cervical Cancer, Updated Safety and Efficacy Results From the Full Cervical Cohort of the Phase II innovaTV 201 Study, SGO Society of Gynecologic Oncology, 1-2, 2019.

Hong, D.S. et al., Tisotumab Vedotin in Patients With Previously Treated Recurrent or Metastatic Cervical Cancer: Updated Safety and Efficacy Results From the Full Cervical Cohort of the Phase II innovaTV 201 Study, SGO Society of Gynecologic Oncology, 1-18, 2019.

Hong, D.S. et al., Tisotumab Vedotin in Previously Treated Recurrent or Metastatic Cervical Cancer, Clinical Cancer Research, vol. 26, No. 6, p. 1220-1228, Mar. 15, 2020.

Hoogenboom, H. et al., By-passing immunisation: Human antibodies from synthetic repertoires of germline VH gene segments rearranged in vitro, Journal of Molecular Biology, 227(2), pp. 381-388, Sep. 1992.

Houtkamp, M, Target Expression Correlates to ADC Efficacy in Mouse Tumor Models, Definiens Symposium, International Symposium for Tissue Phenomics, 1-29, Apr. 25, 2017.

Houtkamp, M., Pre-Clinical Efficacy of an Antibody-Drug Conjugate Targeting TF in Solid Tumor PDX Models, 1-20, Feb. 11, 2015, CrownBio Meeting.

Howard, D. G., et al., Antibody-drug conjugates and other nanomedicines: the frontier of gynaecological cancer treatment, Interface Focus, 6(6), pp. 1-13, 2016.

Huang, J. et al., Safety, Activity, and Biomarkers of SHR-1210, an Anti-PD-1 Antibody, for Patients with Advanced Esophageal Carcinoma, Clinical Cancer Research, 24(6), pp. 1296-1304, Mar. 15, 2018.

Huang, L. et al., Abstract 4608: A 5T4 x CD3 bispecific DART® molecule with extended half-life for T-cell immunotherapy of cancers, vol. 77(13), pp. 4608-4608, Jul. 1, 2017, AACR.

Huang, X. et al., Tumor Infarction in Mice by Antibody-Directed Targeting of Tissue Factor to Tumor Vasculature, Science, 275(5299), 547550, 1997.

Huston, J. et al., Protein engineering of antibody binding sites: recovery of specific activity in an anti-digoxin single-chain Fv analogue produced in Escherichia coli, PNAS, 85(16), pp. 5879-5883, 1988.

International Application No. PCT/EP2011/059917, International Preliminary Report on Patentability, mailed on Dec. 19, 2012.

International Preliminary Report on Patentability PCT/EP2014/075326, May 24, 2016.

International Preliminary Report on Patentability PCT/EP2020/081314, May 10, 2022.

International Preliminary Report on Patentability PCT/US2018/058771, May 5, 2020.

International Preliminary Report on Patentability PCT/US2019/031166, Nov. 10, 2020.

International Preliminary Report on Patentability PCT/US2019/031168, Nov. 10, 2020.

International Preliminary Report on Patentability PCT/US2019/046467, Feb. 16, 2021.

International Preliminary Report On Patentability PCT/US2019/058300, Apr. 27, 2021.

International Preliminary Report on Patentability PCTUS2010020504, pp. 1-6, Jul. 21, 2011.

International Search Report and Written Opinion PCT/EP2009/066755, pp. 1-31, Jun. 28, 2010.

(56) References Cited

OTHER PUBLICATIONS

International Search Report and Written Opinion PCT/EP2011/059917, pp. 1-19, Dec. 23, 2011.
International Search Report and Written Opinion PCT/EP2014/075326, pp. 1-13, Mar. 10, 2015.
International Search Report and Written Opinion PCT/EP2020/081314, pp. 1-12, Feb. 16, 2021.
International Search Report and Written Opinion PCT/US2018/058771, pp. 1-4, Feb. 1, 2019.
International Search Report and Written Opinion PCT/US2019/023218, pp. 1-8, Jun. 25, 2019.
International Search Report and Written Opinion PCT/US2019/031166, pp. 1-9, Aug. 19, 2019.
International Search Report and Written Opinion PCT/US2019/031168, pp. 1-11, Sep. 24, 2019.
International Search Report and Written Opinion PCT/US2019/046467, pp. 1-9, Nov. 22, 2019.
International Search Report and Written Opinion PCTUS2010020504, pp. 1-8, Mar. 9, 2010.
International Search Report PCT/US2019/058300, pp. 1-13, Feb. 10, 2020.
International Search Report and Written Opinion PCT/IB2020/060485, Nov. 6, 2020.
Jackson, Dowdy et al., A Human Antibody-Drug Conjugate Targeting EphA2 Inhibits Tumor Growth in vivo, Cancer Res, 68(22), 9367-9374, 2008.
Jacobs, B. et al., Association of tissue factor expression in squamous cell head and neck carcinomas with well-differentiated tumors, Journal of Clinical Oncology, vol. 30, No. 15 supplement, May 20, 2012.
Janeway et al., Structure of the Antibody Molecule and Immunoglobulin Genes, 3:1-3:11, 1997.
Jefferis and Lefranc, Human immunoglobulin allotypes, Mabs, 1(4), pp. 1-7, 2009.
Johnson, G., et al., The Kabat Database and a Bioinformatics Example, Methods in biology, 248, pp. 11-25, 2004.
Johnson, M.L. et al., Phase I trial of the programmed death receptor 1 (PD-1) inhibitor, BI 754091, in patients (pts) with advanced solid tumors, Journal of Clinical Oncology, 36(5), Abstract 212, 2018.
Kabat, E. A., et al., Sequences of proteins of Immunological Interest, 5th Ed—extract, pp. 680+718, 1991.
Kabat, E. et al., Sequences of proteins of Immunological interest, 1991, US Department of Health and Human Services.
Kanyavuz, A., et al., Breaking the law—unconventional strategies for antibody diversification, Nat. Rev. Immunol., vol. 19(6), pp. 355-358, Jun. 2019.
Kerwin, B.A., Polysorbates 20 and 80 Used In The Formulation Of Protein Biotherapeutics: Structure and Degradation Pathways, Journal of Pharmaceutical Sciences, 97(8), pp. 2924-2935, 2008.
Killmurray C., TV Shows Promising Efficacy and Manageable Toxicity Profile in Phase 2 Study of Schn, XP093067583, Mar. 2, 2022, Internet.
Kirchhofer, Daniel et al., Epitope Location on Tissue Factor Determines the Anticoagulant Potency of Monoclonal Anti-tissue Factor Antibodies, Thromb Haemost, 84, 1072-1081, 2000.
Kitagawa, R. et al., Paclitaxel Plus Carboplatin Versus Paclitaxel Plus Cisplatin in Metastatic or Recurrent Cervical Cancer: The Open-Label Randomized Phase III Trial JCOG0505, J. Clin. Oncol., 33(19), pp. 2129-2135, 2015.
Kobayashi-Kato et al., Platinum-free interval affects efficacy of following treatment for platinum-refractory or -resistant ovarian cancer, Cancer Chemother Pharmacol, 84(1), pp. 33-39, Jul. 1, 2019.
Lassen, U et al., Phase I, First-in-Human Study to Evaluate the Tolerability, Pharmacokinetics and Preliminary Efficacy of HuMax®-Tissue Factor-ADC (TF-ADC) in Patients with Solid Tumors, 1-6, 2015, ASCO Annual Meeting.
Lassen, U., et al., A phase I, first in human . . . , Journ of Clin Oncol, vol. 33(15), Abstract No. 2570, 2015.
Lee, E.K. et al., Antibody-Drug Conjugates in Gynecologic Malignancies, Gynecologic Oncology, 153, pp. 694-702, 2019.
Lescar, J., et al., Crystal Structure of a Crossreaction Complex between Fab F9.13.7 and Guinea Fowl Lysozyme, vol. 270(30), Journ Biol Chem, pp. 18067-18076, Jul. 28, 1995.
Lewis Phillips, G.D. et al., Targeting HER2-Positive Breast Cancer with Trastuzumab-DM1, an Antibody-Cytotoxic Drug Conjugate, Cancer Research, 68, 9280-9290, 2008.
Lin et al., Head and neck squamous cell carcinoma cell lines: Established models and rationale for selection, Head Neck, 29(2), pp. 163-188, Jan. 6, 2007.
Lloyd, C. et al., Modelling the Human Immune Response: Performance of a 1011 Human Antibody Repertoire Against a Broad Panel of Therapeutically Relevant Antigens, Protein Eng Des Sel, 22(3), pp. 159-168, 2009.
Lo, C., Conjunctivitis, 2017, https://www.drclementlo.com/health-update/72-conjunctivitis.
Mackman, Nigel et al., Role of the Extrinsic Pathway of Blood Coagulation in Hemostasis and Thrombosis, Arterioscler Thromb Vasc Biol, 27, 1687-1693, 2007.
Mahdi, H. et al., Phase 2 Trial of Tisotumab Vedotin In Platinum-Resistant Ovarian Cancer (innovaTV 208), 37, Abstract TPS5602, Journal of Clinical Oncology, pp. 1-4, May 20, 2019.
Mahdi, H. et al., Phase 2 trial of tisotumab vedotin in platinum-resistant ovarian cancer (innovaTV 208), 37(15), Poster 421A, 1 page, May 2019, American Society of Clinical Oncology.
Mandal, Samir K. et al., Cellular localization and trafficking of tissue factor, Blood, 107, 4746-4753, 2006.
Marquina, G., et al., Targeted Agents in Cervical Cancer—Beyond Bevacizumab, Curr Oncol Reports, vol. 20(5), pp. 1-10, Apr. 2, 2018.
McDonagh, Charlotte F. et al., Engineered antibody-drug conjugates with defined sites and stoichiometries of drug attachment, Protein Engineering, Design and Selection, 19(7), 299-307, 2006.
Milsom, Chloe C. et al., Tissue Factor Regulation by Epidermal Growth Factor Receptor and Epithelial-to-Mesenchymal Transitions: Effect on Tumor Initiation and Angiogenesis, Cancer Res. 68(24), 10068-10076, 2008.
Monk, B.J et al., Tisotumab Vedotin TVplus Bevacizumab or Pembrolizumab or Carboplatin in Recurrent or Metastatic Cervical Cancer r-mCC—Phase 1 b-2 ENGOT, 1-12, Aug. 30-Sep. 2, 2021, International Gynecologic Cancer Society.
Monk, B.J. et al., Tisotumab Vedotin TVplus Bevacizumab or Pembrolizumab or Caboplatin in Recurrent or Metastatic Cervical Cancer r-mCC, 1-4, 2021, International Gynecologic Cancer Society.
Moore, D.H. et al., Phase III Study of Cisplatin With or Without Paclitaxel in Stage IVB, Recurrent, or Persistent Squamous Cell Carcinoma of the Cervix: A Gynecologic Oncology Group Study, Journal of Clinical Oncology, 22(15), pp. 3113-3119, Aug. 1, 2004.
Moore, K.N., et al. Safety and Activity . . . Journ of Clin oncology, pp. 1112-1119, vol. 35(10), Apr. 1, 2017.
Morris, G.E., Epitope Mapping Protocol, Methods in Molecular Biology 66, 1-12, 1996.
Morrissey, James H. et al., Monoclonal Antibody Analysis of Purified and Cell-associated Tissue Factor, Thromb Res, 52, 247-261, 1988.
Myers and Miller, Optimal alignments in linear space, Cabios, vol. 4(1), pp. 11-17, 1988.
Mylotarg, Mylotarg gemtuzumab ozgamicin for injection. For intravenous use only, 1-19, Aug. 2017, Wyeth Pharmaceuticals Inc.
Nagayama, A., et al., Antibody-Drug Conjugates for the Treatment of Solid Tumors: Clinical Experience and Latest Developments, Targeted Oncology, vol. 12(6), pp. 719-739, Dec. 2017.
Naing, A et al., A first-in-human phase I study of the anti-PD-1 antibody PDR001 in patients with advanced solid tumors, Journal of Clinical Oncology, 34 (Suppl 15), p. 3060 (Abstract 3060), 2016.
Naing, A. et al., A Phase 1 first-in-human study of MEDI0680, an anti-PD-1 monoclonal antibody (mAb) in adult patients (pts) with advanced tumors, Annals of Oncology, 27(Suppl. 6), 1072, 1 page, 2016.
NCI Surveillance, Epidemiology and end results program, SEER Cancer Statistics Review, pp. 1-2, 1973-1997.

(56) References Cited

OTHER PUBLICATIONS

Needleman, S. et al., A general method applicable to the search for similarities in the amino acid sequence of two proteins, J Mol Biol, 48(3), pp. 443-453, Mar. 1970.
Ngo, Cam V. et al., CNTO 859, a humanized anti-tissue factor monoclonal antibody, is a potent inhibitor of breast cancer metastasis and tumor growth in xenograft models, Tumor Immunology, 120, 1261-1267, 2007.
Nooij, R.P. et al., Functional MRI for Treatment Evaluation in Patients with Head and Neck Squamous Cell Carcinoma: A Review of the Literature from a Radiologist Perspective, Curr Radiol Rep, 6(2), pp. 1-15, 2018.
Nyen, T.V. et al., Modeling Endometrial Cancer: Past, Present, and Future, Int. J. Mol. Sci., 19, pp. 2348, 2018.
Oflazoglu, E. et al., Combination of the Anti-CD30-Auristatin-E Antibody-Drug Conjugate (SGN-35) With Chemotherapy Improves Antitumour Activity in Hodgkin Lymphoma, British Journal of Haematology, 142, pp. 67-73, 2008.
Okeley, N.M. et al., Specific Tumor Targeting and Potent Bystander Killing With SG-35, An Anti-CD30 Antibody Drug Conjugate, Blood, 108(11), pp. 231, Nov. 16, 2006.
Park, I-H. and Kim, J.Y., Surveillance or Resection After Chemoradiation In Esophageal Cancer, Annals of Translational Medicine, 6(4), pp. 82, 2018.
Parren, P, Building a Novel Portfolio of ADCs, 1-31, Nov. 28, 2012, 8th Annual European Antibody Congress.
Parren, Paul W, Companion Diagnostics (CDx) in Antibody-Drug Conjugate Development, 1, 2015, CTMM-TI Pharma Launch Event.
Parren, Paul W., Development of an auristatin-conjugated therapeutic antibody against Tissue Factor for the treatment of solid tumors, 1-29, Oct. 24, 2012, 3rd Annual Meeting—World ADC, San F, USA.
Parren, Paul WH, Progressing ADCs for the Treatment of Solid Cancers, 1-28, Oct. 28, 2014, World ADC.
Parren, Paul WH., Current and Future Trends in Antibody Therapeutics, PEGS EU, 1, 2015.
Parren, Paul WHI, Developing Antibody Drug Conjugates for the Treatment of Solid Cancers, 1-32, Apr. 6, 2016, PEGS Shanghai China.
Parren, Paul WHI., Pre-Clinical Development of a Therapeutic ADC Targeting Tissue Factor, 1-34, 2013, World ADC San F, USA.
Paul, W. E., Fundamental Immunology, Third Edition, Chapter 9, pp. 292-295, 1993, Raven Press, New York.
Paul, W., Fundamental Immunology, Chap. 8, 1993, Raven Press, NY.
Paul, WE, Fundamental Immunology, 3rd Edition, 242, 1993, Raven Press.
Perkins, V. et al., Incorporation of whole pelvic radiation into treatment of stage IVB cervical cancer; a novel treatment strategy, Gynecol Oncol, vol. 156. No. 1, pp. 100-106, Jan. 2020.
Philips, G.K, et al., Therapeutic uses of anti-PD-1 and anti-PD-L 1 antibodies, The Japanese Soc for Immunology, vol. 27(1), pp. 39-46, 2014.
Pinter-Brown, L.C., SGN-30: A Basis for the Effective Treatment of CD30 Positive Hematopoietic Malignancies, Expert Opinion on Investigational Drugs, 17(12), pp. 18331887, 2008.
Polson, A.G. et al., Anti-CD22-MCC-DM1: an antibody-drug conjugate with a stable linker for the treatment of non-Hodgkin's lymphoma, Leukemia, 24, pp. 1566-1573, 2010.
Portolano, S. et al., Lack of promiscuity in autoantigen-specific H and L chain combinations as revealed by human H and L chain "roulette", J Immunol, 150(3), 880-887, 1993.
Presta, L. et al., Generation of a Humanized, High Affinity Antitissue Factor Antibody for Use as a Novel Antithrombotic Therapeutic, Thromb Haemost, pp. 379-389, 2001.
Presta, L.G. et al., Humanization of an Anti-Vascular Endothelial Growth Factor Monoclonal Antibody for the Therapy of Solid Tumors and Other Disorders, Cancer Research, 57, pp. 4593-4599, Oct. 15, 1997.
Prevention, Treatment and Research, GAO/PEMD-92-12, pp. 1-52, Dec. 1991, US General Accounting Office.
Pujade-Lauraine et al., Update of randomized trials in recurrent disease, Annals of Oncology 22 (Supplement 8), viii61-viii64, 1-4, 2011, ESMO.
Pujade-Lauraine, E. et al., Bevacizumab Combined With Chemotherapy for Platinum-Resistant Recurrent Ovarian Cancer: The AURELIA Open-Label Randomized Phase III Tria, Journal of Clinical Oncology, 32(13), pp. 1302-1308, May 1, 2014.
Raaphorst, F.M., et al., Restricted utilization of germ-line VH3 genes and short diverse third complementarity-determining regions (CDR3) in human fetal B lymphocyte immunoglobulin heavy chain rearrangements, Eur. J. Immunol., vol. 22, pp. 247-251, 1992.
Revets, H. et al., Nanobodies as novel agents for cancer therapy, Expert Opinion on Biological Therapy 5(1), 111-124, 2005.
Rice et al., EMBOSS: The European Molecular Biology Open Software Suite, 16(6), pp. 276-277, Jun. 1, 2000, Elsevier Current Trends.
Roberts, J.T. et al., Long-Term Survival Results of a Randomized Trial Comparing Gemcitabine/ Cisplatin and MethotrexateNinblastine/ doxorubicin/Cisplatin in Patients With Locally Advanced and Metastatic Bladder Cancer, Annals of Oncology, 17(Supplement 5), pp. 118-v122, 2006—Retracted.
Rudikoff, S. et al., Single amino acid substitution altering antigenbinding specificity, Proc. Natl. Acad. Sci. USA, vol. 79, pp. 1979-1983, 1982.
Rustin, G.J.S. et al., Definitions for Response and Progression in Ovarian Cancer Clinical Trials Incorporating RECIST 1.1 and CA 125 Agreed by the Gynecological Cancer Intergroup (GCIG), International Journal of Gynecological Cancer, 21(2), pp. 419-423, Feb. 2011.
Ryan, M.C. et al., Targeting pancreatic and ovarian carcinomas using the auristatin-based anti-CD70 antibody-drug conjugate SGN-75, British Journal of Cancer, 103, pp. 676-684, 2010.
Sabbatini, P.J. et al., Pilot Study of a Heptavalent Vaccine-Keyhole Limpet Hemocyanin Conjugate plus QS21 in Patients with Epithelial Ovarian, Fallopian Tube, or Peritoneal Cancer, Clin Cancer Res, 13(14), pp. 4170-4177, Jul. 15, 2007.
Sambrook, J. et al., Molecular Cloning: A laboratory Manual, Ch. 15, 1989, Cold Spring Harbor Laboratory Press.
Sanderson, R.J. et al., In vivo Drug-Linker Stability of an Anti-CD30 Dipeptide-Linked Auristatin Immunoconjugate, Clinical Cancer Research, 11, pp. 843852, Jan. 15, 2005.
Satijn, D, Targeting solid cancers using antibody-drug conjugate against the novel ADC target Tissue Factor, a preclinical and FIH study, 1-38, Jun. 17-18, 2015, ADCs Antibodies, Barcelona.
Satijn, D., Development of an Auristatin-Conjugated Therapeutic Antibody Against Tissue Factor for the Treatment of Solid Tumors, 130, 2013, ADCs, Barcelona.
Satijn, David, Development of an Auristatin-Conjugated Therapeutic Antibody Against Tissue Factor for the Treatment of Solid Tumors, 3rd Annual World ADC series, 1-29, 2012, ADCs.
Scher, H.I., et al., Design and End Points of Clinical Trials for Patients With Progressive Prostate Cancer and Castrate Levels of Testosterone: Recommendations of the Prostate Cancer Clinical Trials Working Group, Journal of Clinical Oncology, 26(7), pp. 1148-1159, Mar. 1, 2008.
Seattle Genetics—Press Release, Seattle Genetics Highlights Promising Data with Tisotumab Vedotin in Cervical Cancer, Sep. 8, 2017, ESMO 2017 Congress.
Seattle Genetics Inc., Seattle Genetics Reports Positive Data From Phase I Weekly-Dosing Clinical Trial of Brentuximab Vedotin SGN-35 in Lymphoma, 1-2, 2009, Seattle Genetics.
Seattle Genetics, Inc, SGN-35, Antibody-Drug Conjugate, 1, 2008, Seattle Genetics.
Seattle Genetics, Inc., Seattle Genetics Reports Multiple Complete and Partial Responses With SGN-35 in Patients With Lymphoma, Jun. 2008, Drugs.com.
Seer—US National Cancer Institute Nci, Cancer Statistics Review, pp. 1-7, 1975-2011, NCI.
Senter, P. et al., Immunoconjugates comprised of drugs with impaired cellular permeability: A new approach to targeted therapy, Proc. Amer. Assoc. Cancer Res, 45, 2 pages, 2004.

(56) References Cited

OTHER PUBLICATIONS

Serio, R., Toward an Integrative Analysis of the Tumor Microenvironment in Ovarian Epithelial Carcinom, Cancer Microenvironment, vol. 5(2), pp. 173-183, 2012.
Sherrif, S. and Constantine, K.L., Redefining the minimal antigen binding fragment, Nature Structural Biology, 3(9), pp. 733-736, Sep. 9, 1996.
Shriner, A.K., et al., Analysis of the young and elderly variable gene repertoire in response to pneumococcal polysaccharides using a reconstituted SCID mouse model, Vaccine, vol. 24(49-50), pp. 7159-7166, Nov. 30, 2006.
Singh, S.R. et al., Effect of Polysorbate 80 Quality on Photostability of a Monoclonal Antibody, AAPS PharmSciTech, 13(2), pp. 422-430, Jun. 2012.
Slaughter, K. et al., Primary and acquired platinum-resistance among women with high grade serous ovarian cancer, Gynecologic Oncology, 142(2), pp. 225-230, Aug. 2016.
Smeets, S. et al., A novel algorithm for reliable detection of human papillomavirus in paraffin embedded head and neck cancer specimen, Int J Cancer, 121(11), pp. 2465-2472, Sep. 25, 2007.
Soubeyran, P. et al., Predictors of Early Death Risk in Older Patients Treated With First-Line Chemotherapy for Cancer, American Society of Clinical Oncology, 30(15), pp. 1829-1834, May 20, 2012.
Stephan, J.P. et al., Challenges in Developing Bioanalytical Assays for Characterization of Antibody-Drug Conjugates, Bioanalysis, 3(6), pp. 677-700, 2011.
TFOS, A Patient's Guide to Artificial Tears, 2017, https://www.tearfilm.org/ dettnews-a_patients_guide_to_artificial_tears/5523_5519/eng, TFOS.
Topalian, S. et al., Safety, Activity, and Immune Correlates of Anti-PD-1 Antibody in Cancer, The new england journal of medicine, 366(26), pp. 2443-2454, Jun. 28, 2012.
Topalian, S.L. et al., Survival, Durable Tumor Remission, and Long-Term Safety in Patients With Advanced Melanoma Receiving Nivolumab, Journal of Clinical Oncology, 32(2), pp. 1020-1030, Apr. 1, 2014.
Topalian, S.L. et al., Targeting the PD-1/B7-H1(PD-L1) pathway to activate anti-tumor immunity, Current Opinion in Immunology, 24(2), pp. 207-212, Apr. 2012.
Traynor, K., Pharmacy News. Gemtuzumab Withdrawn From U.S. Market, 1-2, Jun. 22, 2010, ASHP.
US Allowance May 22, 2015, U.S. Appl. No. 13/133,811, pp. 1-19.
US OA Oct. 17, 2014, U.S. Appl. No. 13/133,811, pp. 1-14.
US OA Jun. 20, 2014, U.S. Appl. No. 13/133,811, pp. 1-6.
US OA Feb. 3, 2015, U.S. Appl. No. 13/133,811, pp. 1-6.
Vaede, D. et al., Preservatives in eye drops: Toward awareness of their toxicity, Journal Français d'Ophtalmologie, 33(7), pp. 505-524, Sep. 2010.
Van Bueren, J.L., Alignment of Antibody Drug Conjugate—CDx Co-Development, 1-24, Mar. 18, 2015, Word CDx Meeting, Berlin, Germany.
Van De Winkel, Jan, Pre-clinical Pipeline and Technology, HuMax-TF-ADC Aimed at the Clinic Post ASH, 1-11, Jan. 23, 2012, Post ASH Seminar.
Van Zeeburg et al., Generation and Molecular Characterization of Head and Neck Squamous Cell Lines of Fanconi Anemia Patients, American Association for Cancer Research, 65(4), pp. 1271-1276, Feb. 15, 2005.
Vanderstraeten, A. et al., Mapping the immunosuppressive environment in uterine tumors: implications for immunotherapy, Cancer Immunol Immunotherapy, 63, pp. 545-557, 2014.
Vazquez-Rey, M. and Lang, D.A., Aggregates in monoclonal antibody manufacturing processes, Biotechnology and Bioengineering, 108(7), pp. 1494-1508, May 16, 2011.
Vergote et al., Phase I/II trial of tisotumab vedotin plus bevacizumab, pembrolizumab, or carboplatin in recurrent or metastatic cervical cancer (innovaTV 205/ENGOT-cx8), Annals of Oncology, vol. 30(5), pp. 433-434, Oct. 2019.
Vergote I et al, Tisotumab Vedotin plus Carboplatin in First-Line or-plus Pembrolizumab in Previously Treated Recurrent or Metastatic Cervical Cancer, Interim Results of ENGOT-Cx8 GOG-3024 innovaTV, ESMO 205, 1-4, Jul. 26, 2021.
Vergote, I et al, Tisotumab Vedotin vs Investigator's Choice Chemotherapy in Second-or Third-Line Recurrent or Metastatic Cervical Cancer innovaTV 301,ENGOT CX12,GOG 3057, Abstract, 1-2, 2021, American Society of Clinical Onocology.
Vergote, I. et al., Phase Ib/II Trial of Tisotumab Vedotin ± Bevacizumab, Pembrolizumab, or Carboplatin in Recurrent or Metastatic Cervical Cancer (innovaTV 205/ENGOT-cx8/GOG-3024), 38(15), pp. TPS6095-TPS6095, 2020, ENGOT.
Vergote et al., A phase IIa study of TV (HuMaxVR-TF-ADC) in patients with relaps, recurrent and/or metastic cervical cancer, Abstr 9310, ESMO Congress, Madrid, 16 pages (2017).
Vergote et al., Phase 1/2 Trial of TV Plus Bevacizumab, Pembrolizumab, or Carboplatin in Recurrent or Metastatic Cervical Cancer (innovaTV 205/ENGOT-cx8/GOG-3024), ESMO Poster (Sep. 6, 2019).
Vergote et al., A Phase IIA study of TV (Humax-TF ADC) in patients with relapsed, recurrent and/or metastatic cervical cancer, Annals of Oncology, 28(5):1-16 (2017).
Vergote et al., Tisotumab Vedotin plus Carboplatin in First-Line or plus Pembrolizumab in Previously Treated Recurrent or Metastatic Cervical Cancer, Interim Results of ENGOT-Cx8 GOG-3024 innovaTV 205, Annals of Oncology, 32(55), 2 pages (2021).
Verma et al., Trastuzumab Emtansine for HER2-Positive Advanced Breast Cancer, New England Journal of Medicine, 367(19):1783-1791 (2012).
Versteeg et al., Inhibition of tissue factor signaling suppresses tumor growth, Blood, 111:190-199 (2008).
Vine A., Recent Advances in Haemostasis and Thrombosis, Retina, the Journal of Retinal and Vitreous Diseases, 29(1), 7 pages (2009).
Vlachostergios et al., Antibody-Drug Conjugates in Bladder Cancer, Bladder Cancer, 4(3):247-259 (Jul. 30, 2018).
Wahl et al., The Anti-CD30 Monoclonal Antibody SGN-30 Promotes Growth Arrest and DNA Fragmentation in Vitro and Affects Antitumor Activity in Models of Hodgkin's Disease, Cancer Research, 62:3736-3742 (Jul. 1, 2002).
Wakankar et al., Physicochemical Stability of the Antibody-5 Drug Conjugate Trastuzumab-DM1: Changes due to Modification and Conjugation Processes, Bioconjugate Chem, 21(9):1588-1595 (2010).
Wakankar et al., Analytical methods for physicochemical characterization of antibody drug conjugates, mAbs, 3(2):161-172 (2011).
Wang et al., Radiotherapy of Human Xenograft NSCLC Tumors in Nude Mice with a 90Y-Labeled Anti-Tissue Factor Antibody, Cancer Biotherapy & Radiopharmaceuticals, 20(3):300-309 (2005).
Ward et al., Binding activities of a repertoire of single immunoglobulin variable domains secreted from *Escherichia coli*, Nature, 341:544-546 (1989).
Weiss et al., A Phase II Trial of Carboplatin for Recurrent or Metastatic Squamous Carcinoma of the Uterine Cervix: A Southwest Oncology Group Study, Gynecologic Oncology, 39(2):332-336 (1990).
Wolfgang et al., Recent Progress in Pancreatic Cancer, CA Cancer J Clin., 63(3):318-348 (2013).
Xu et al., Diversity in the CDR3 Region of VH Is Sufficient for Most Antibody Specificities, Immunity, 13(1):37-45 (2000).
Yang et al., Increased expression of programmed death (PD)-1 and its ligand PD-L1 correlates with impaired cell-mediated immunity in high-risk human papillomavirus-related cervical intraepithelial neoplasia, Immunology, 139(4):513-522 (Aug. 2013).
Yonemori et al., Tisotumab Vedotin in Japanese Patients With Recurrent or Metastatic Cervical Cancer, Results From the Phase 1,2 innovaTV 206 Study, Cancer Science, 113:2788-2797 (Mar. 24, 2021).
Younes et al., Multiple Complete Responses in a Phase 1 Dose-Escalation Study of the Antibody-Drug Conjugate SGN-35 in Patients with Relapsed or Refractory CD30-Positive Lymphomas, Blood, 112(11), 1006 (2008).
Younes et al., Brentuximab vedotin (SGN-35) for relapsed CD30-positive lymphomas, The New England Journal of Medicine, 363(19):1812-1821(2010).
Younes et al., A Novel Antibody-Drug Conjugate, SGN-35 AntiCD30-Auristatin, Induces Objective Responses in Patients With Relapsed or Refractory Hodgkin Lymphoma Preliminary Results of a Phase

(56) References Cited

OTHER PUBLICATIONS

I Tolerability Study, The International Symposium on Hodgkin Lymphoma, Cologne, Germany, P099bis, 1 page (Nov. 2007).
Younes et al., Objective Responses in a Phase I Dose-Escalation Study of SGN-35, A Novel Antibody-Drug Conjugate ADC Targeting CD30, in Patients With Relapsed or Refractory Hodgkin Lymphoma, Journal of Clinical Oncology, vol. 26(15), Supplement 8526 (May 1, 2008).
Younes et al., Brentuximab vedotin combined with ABVD or AVD for patients with newly diagnosed Hodgkin's lymphoma: a phase 1, open-label, dose-escalation study, The Lancet Oncology, 14:1348-1356, (2013).
Youssef et al., Abstract 2667: In vitro properties and pre-clinical activity of PF-06801591, a high-affinity engineered anti-human PD-1, Cancer Res, 33(Suppl 13):2667 (2017).
Yu et al., Oncogenic events regulate tissue factor expression in colorectal cancer cells: implications for tumor progression and angiogenesis, Blood, 105(4):1734-1741 (2005).
Zhang et al., Reduced expression of tissue factor pathway inhibitor-2 contributes to apoptosis and angiogenesis in cervical cancer, Journal of Experimental & Clinical Cancer Research, 31(1):1-9 (Jan. 2, 2012).
Zhang Z., Pharmaceutics, 2. Principle, pp. 1-5 (Dec. 2017).
Zhao et al., Preparation and identification of anti-human recombinant soluble tissue factor monoclonal antibody, Chinese Journal of Hematology, 23(9):489-491 (Sep. 30, 2022).
Zou et al., Gene targeting in the Ig kappa locus: efficient generation of lambda chain expressing B cells, independent of gene rearrangements in Ig kappa., The EMBO Journal, 12:811-820 (1993).

\* cited by examiner

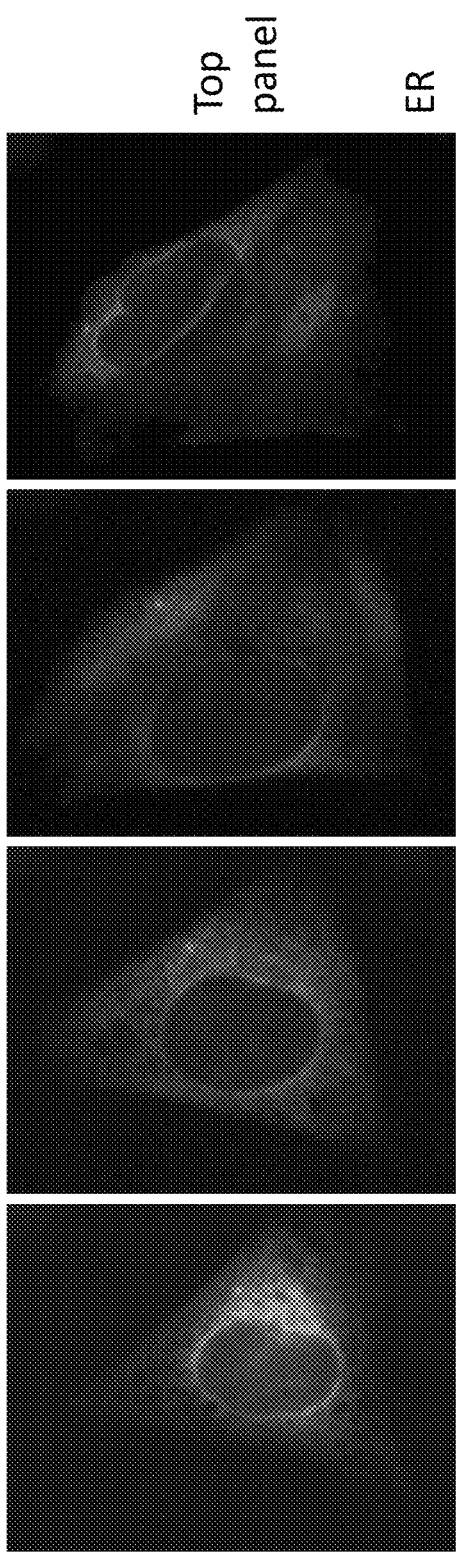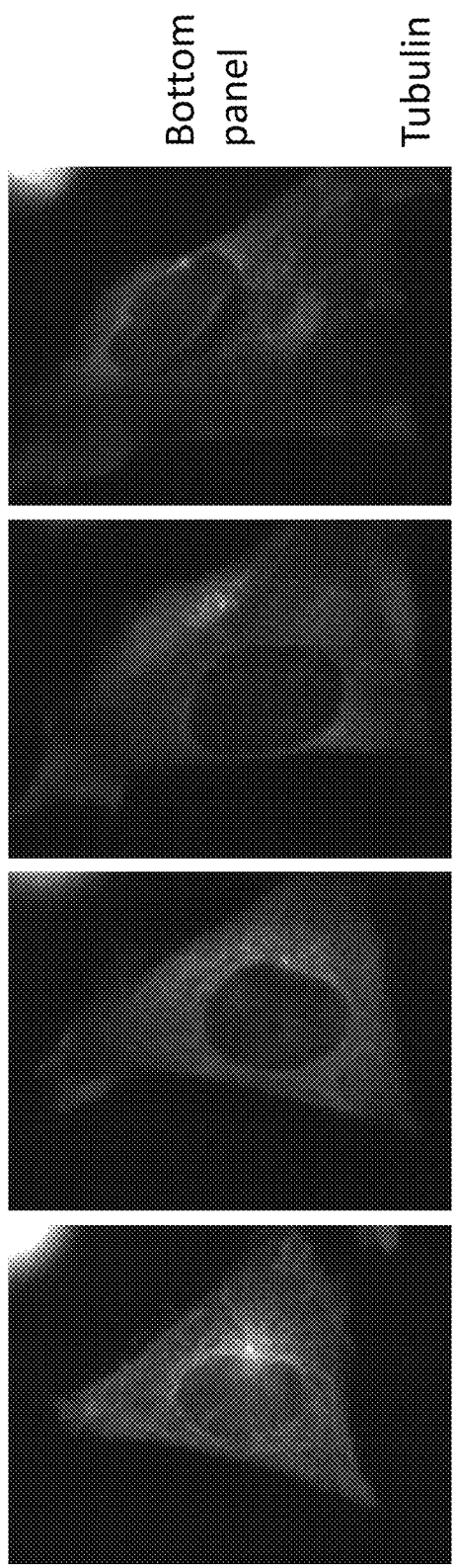

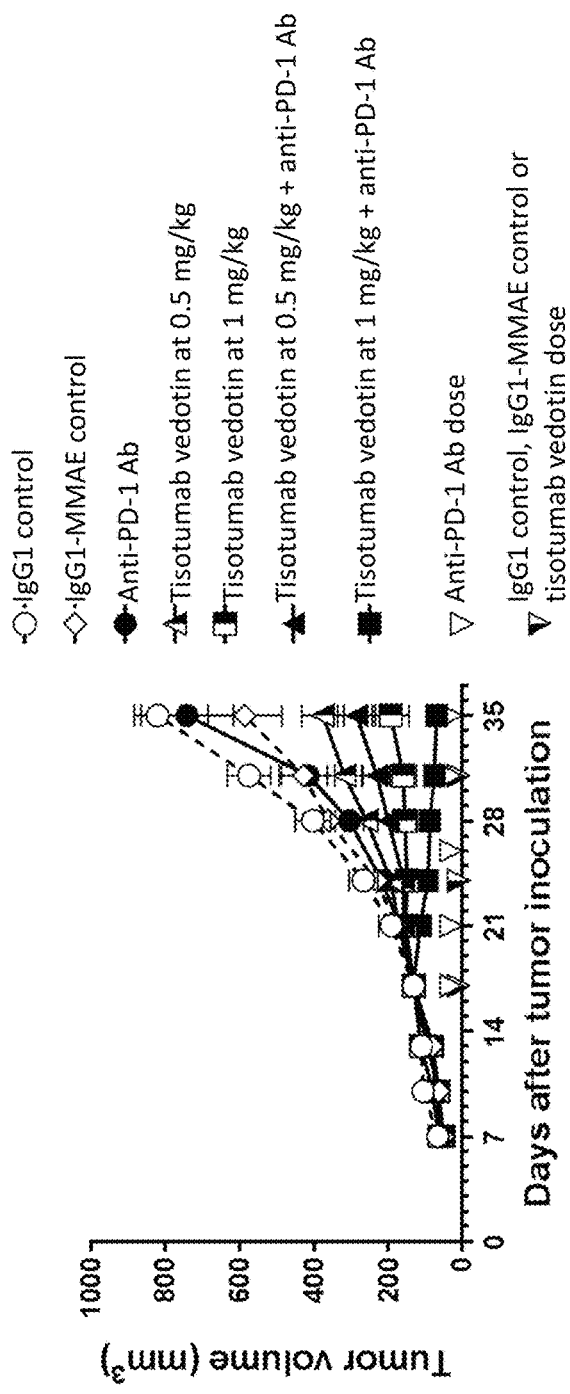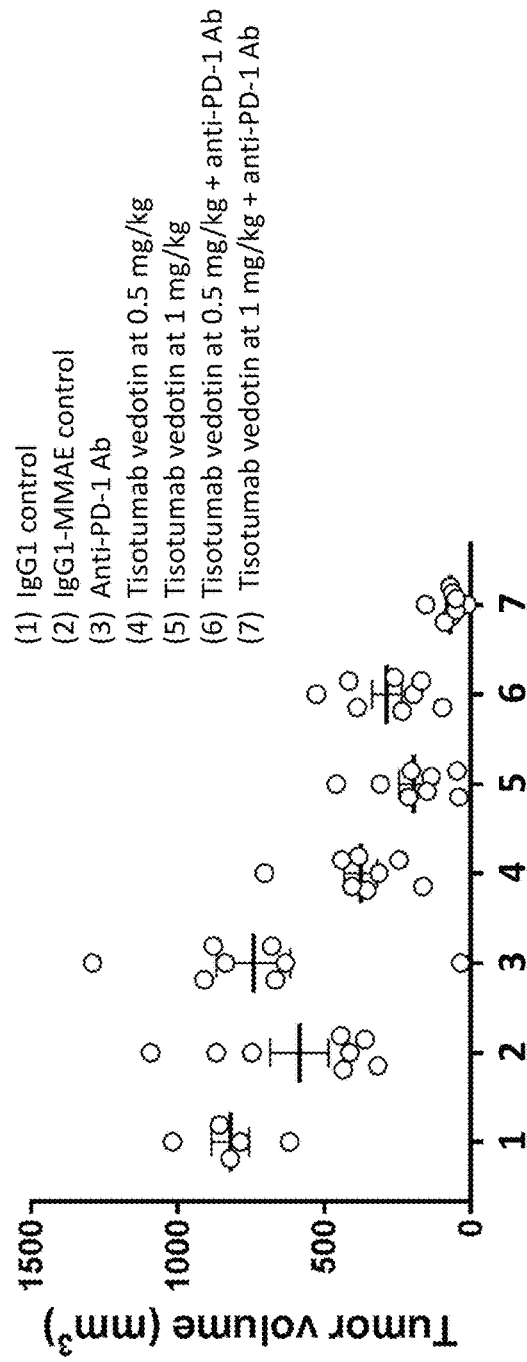
FIG. 4A
FIG. 4B

METHODS OF TREATING CANCER WITH A COMBINATION OF AN ANTI-PD-1 ANTIBODY AND AN ANTI-TISSUE FACTOR ANTIBODY-DRUG CONJUGATE

CROSS-REFERENCE TO RELATED APPLICATIONS

This application is the National Stage of International Application No. PCT/US2019/031166, filed May 7, 2019, and claims priority to U.S. Provisional Application 62/668,088 filed May 7, 2018 and U.S. Provisional Application 62/753,725 filed Oct. 31, 2018 the contents of each of which are incorporated herein by reference in their entirety.

SUBMISSION OF SEQUENCE LISTING ON ASCII TEXT FILE

This application contains a sequence listing that has been submitted in ASCII format via EFS-Web and is incorporated herein by reference in its entirety. Said ASCII copy, created on Oct. 31, 2020, is named 220847_0001_US.txt and is 17,819 bytes in size.

TECHNICAL FIELD

The present invention relates to methods of treating cancer, such as breast cancer and cervical cancer, with a combination of an anti-PD-1 antibody comprising the complementary determining regions (CDRs) of pembrolizumab and an anti-Tissue Factor (anti-TF) antibody-drug conjugate, wherein the antibody-drug conjugate comprises an anti-TF antibody or an antigen-binding fragment thereof comprising the CDRs of tisotumab conjugated to monomethyl auristatin E (MMAE).

BACKGROUND

Tissue factor (TF), also called thromboplastin, factor III or CD142 is a protein present in subendothelial tissue, platelets, and leukocytes necessary for the initiation of thrombin formation from the zymogen prothrombin. Thrombin formation ultimately leads to the coagulation of blood. TF enables cells to initiate the blood coagulation cascades, and it functions as the high-affinity receptor for the coagulation factor VII (FVII), a serine protease. The resulting complex provides a catalytic event that is responsible for initiation of the coagulation protease cascades by specific limited proteolysis. Unlike the other cofactors of these protease cascades, which circulate as nonfunctional precursors, TF is a potent initiator that is fully functional when expressed on cell surfaces.

TF is the cell surface receptor for the serine protease factor VIIa (FVIIa). Binding of FVIIa to TF starts signaling processes inside the cell, said signaling function playing a role in angiogenesis. Whereas angiogenesis is a normal process in growth and development, as well as in wound healing, it is also a fundamental step in the transition of tumors from a dormant state to a malignant state. When cancer cells gain the ability to produce proteins that participate in angiogenesis (i.e., angiogenic growth factors), these proteins are released by the tumor into nearby tissues, thereby stimulating new blood vessels to sprout from existing healthy blood vessels toward and into the tumor. Once new blood vessels enter the tumor, the tumor can rapidly expand its size and invade local tissue and organs. Through the new blood vessels, cancer cells may further escape into the circulation and lodge in other organs to form new tumors, also known as metastasis.

TF expression is observed in many types of cancer, including cervical cancer, and is associated with more aggressive disease. Furthermore, human TF also exists in a soluble alternatively-spliced form, asHTF. It has recently been found that asHTF promotes tumor growth (Hobbs et al., 2007, *Thrombosis Res.* 120(2):S13-S21).

Human cancers harbor numerous genetic and epigenetic alterations, generating neoantigens potentially recognizable by the immune system (Sjoblom et al., 2006, *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities. Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of an antibody, ipilimumab (YERVOY®), that binds to and inhibits CTLA-4 for the treatment of patients with advanced melanoma (Hodi et al., 2010, *N Engl J Med* 363:711-23) and the development of an antibody, pembrolizumab (formerly lambrolizumab; USAN Council Statement, 2013), that binds specifically to the Programmed Death-1 (PD-1) receptor and block the inhibitory PD-1/PD-1 ligand pathway (Hamid and Carvajal, *Expert Opin Biol Ther* 13(6):847-61 (2013); and McDermott and Atkins, *Cancer Med* 2(5):662-73 (2013)).

Breast cancer is by far the most common cancer among women. Each year, more than 180,000 and 1 million women in the U.S. and worldwide, respectively, are diagnosed with breast cancer. Breast cancer is the leading cause of death for women between ages 50-55, and is the most common non-preventable malignancy in women in the Western Hemisphere. An estimated 2,167,000 women in the United States are currently living with the disease (National Cancer Institute, Surveillance Epidemiology and End Results (NCI SEER) program, *Cancer Statistics Review* (CSR), www-seer.ims.nci.nih.gov/Publications/CSR1973 (1998)). Based on cancer rates from 1995 through 1997, a report from the National Cancer Institute (NCI) estimates that about 1 in 8 women in the United States (approximately 12.8 percent) will develop breast cancer during her lifetime (NCI's Surveillance, Epidemiology, and End Results Program (SEER) publication *SEER Cancer Statistics Review* 1973-1997). Breast cancer is the second most common form of cancer, after skin cancer, among women in the United States. An estimated 250,100 new cases of breast cancer are expected to be diagnosed in the United States in 2001. Of these, 192,200 new cases of more advanced (invasive) breast cancer are expected to occur among women (an increase of 5% over last year), 46,400 new cases of early stage (in situ) breast cancer are expected to occur among women (up 9% from last year), and about 1,500 new cases of breast cancer are expected to be diagnosed in men (Cancer Facts & FIGS. 2001 American Cancer Society). An estimated 40,600 deaths (40,300 women, 400 men) from breast cancer are expected in 2001. Breast cancer ranks second only to lung cancer among causes of cancer deaths in women. Nearly 86% of women who are diagnosed with breast cancer are likely to still be alive five years later, though 24% of them will die of breast cancer after 10 years, and nearly half (47%) will die of breast cancer after 20 years.

Every woman is at risk for breast cancer. Over 70 percent of breast cancers occur in women who have no identifiable risk factors other than age (U.S. General Accounting Office. Breast Cancer, 1971-1991: Prevention, Treatment and Research. GAO/PEMD-92-12; 1991). Only 5 to 10% of breast cancers are linked to a family history of breast cancer (Henderson I C, Breast Cancer. In: Murphy G P, Lawrence W L, Lenhard R E (eds). *Clinical Oncology.* Atlanta, Ga.: American Cancer Society; 1995:198-219).

Cervical cancer poses a significant medical problem worldwide with an estimated incidence of more than 500,000 new cases and 250,000 deaths annually. See Tewari et al., 2014, *N Engl J Med.,* 370:734-743. In the Europe Union, approximately 34,000 new cases of cervical cancer and 13,000 deaths occur annually. See Hillemanns et al., 2016, *Oncol. Res. Treat.* 39:501-506. The main types of cervical cancer are squamous cell carcinoma and adenocarcinoma. Long-lasting infections with human papillomavirus (HPV) type 16 and 18 cause most cases of cervical cancer. The standard for first-line therapy of cervical cancer was a platinum-based therapy plus a taxane-based therapy. Bevacizumab, an anti-VEGF antibody, was approved by the U.S. Food and Drug Administration for use in combination with chemotherapy for the treatment of cervical cancer, which had improved overall survival in clinical trials. First-line (1L) treatment for advanced cervical cancer is comprised of bevacizumab combined with paclitaxel plus a platinum (e.g., cisplatin or carboplatin) or paclitaxel plus topotecan. Despite a 48% objective response rate (ORR) and a median overall survival (OS) of approximately 18 months, unfortunately almost all patients relapse after this 1L treatment. See Tewari et al., 2014, *N Engl J Med.,* 370:734-743. For second-line (2L) treatment, no approved therapy is available and patients are often treated with single agent modalities including, but not limited to: pemetrexed, topotecan, docetaxel, nab-paclitaxel, vinorelbine and in some cases bevacizumab. A meta-analysis of single agent treatment demonstrates a modest response rate of only 10.9% (i.e., 60 responders out of 552 patients) and median overall survivals (OS) of approximately 7 months. See e.g., Burotto et al., 2015, *Oncologist* 20:725-726; Candelaria et al., 2009, *Int. J. Gynecol. Cancer.* 19:1632-1637; Coronel et al., 2009, *Med. Oncol.* 26:210-214; Fiorica et al., 2009, *Gynecol. Oncol.* 115:285-289; Garcia et. al., 2007, *Am. J. Clin. Oncol.* 30-428-431; Goncalves et al., 2008, *Gynecol. Oncol.* 108: 42-46; Homesley et al., 2008, *Int. J. Clin. Oncol.* 13:62-65; McLachlan et al., 2017, *Clin. Oncol.* (R. Coll. Radiol.) 29:153-160; Miller et al., 2008, *Gynecol. Oncol.* 110:65-70; Monk et al., 2009, *J. Clin. Oncol.* 27:1069-1074; Muggia et al., 2004, *Gynecol. Oncol.* 92:639-643; Rose et al., 2006, *Gynecol. Oncol.* 102:210-213; Santin et al., 2011, *Gynecol. Oncol.* 122:495-500; Schilder et al., 2005, *Gynecol. Oncol.* 96:103-107; and Torfs et al., 2012, *Eur. J. Cancer.* 48:1332-1340. The five year relative survival for stage IV cervical cancer is only 15%, demonstrating a high need for improved therapy against cervical cancer.

Targeted therapy of multiple non-redundant molecular pathways regulating immune responses can enhance antitumor immunotherapy. However, not all combinations have acceptable safety and/or efficacy. There remains a need for combination therapies with an acceptable safety profile and high efficacy for the treatment of cancer, in particular for the treatment of breast cancer and cervical cancer.

All references cited herein, including patent applications, patent publications, and scientific literature, are herein incorporated by reference in their entirety, as if each individual reference were specifically and individually indicated to be incorporated by reference.

SUMMARY

Provided herein are methods of treating cancer in a subject comprising administering to the subject an antibody or an antigen-binding fragment thereof, wherein the antibody binds to Programmed Death-1 (PD-1) and inhibits PD-1 activity, and an antibody-drug conjugate that binds to tissue factor (TF), wherein the antibody-drug conjugate comprises an anti-TF antibody or an antigen-binding fragment thereof conjugated to monomethyl auristatin E, wherein the anti-PD-1 antibody or antigen-binding fragment thereof comprises a heavy chain variable region and a light chain variable region, wherein the heavy chain variable region comprises:
  (i) a CDR-H1 comprising the amino acid sequence of SEQ ID NO:17;
  (ii) a CDR-H2 comprising the amino acid sequence of SEQ ID NO:18; and
  (iii) a CDR-H3 comprising the amino acid sequence of SEQ ID NO:19; and
wherein the light chain variable region comprises:
  (i) a CDR-L1 comprising the amino acid sequence of SEQ ID NO:20;
  (ii) a CDR-L2 comprising the amino acid sequence of SEQ ID NO:21; and
  (iii) a CDR-L3 comprising the amino acid sequence of SEQ ID NO:22, wherein the CDRs of the anti-PD-1 antibody or antigen-binding fragment thereof are generally defined by the Kabat numbering scheme,
and wherein the anti-TF antibody or antigen-binding fragment thereof comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6, wherein the CDRs of the anti-TF antibody or antigen-binding fragment thereof are defined by the IMGT numbering scheme. In some embodiments, the antibody-drug conjugate is administered at a dose ranging from about 0.9 mg/kg to about 2.1 mg/kg. In some embodiments, the antibody-drug conjugate is administered at a dose of about 1.3 mg/kg. In some embodiments, the antibody-drug conjugate is administered at a dose of 1.3 mg/kg. In some embodiments, the antibody-drug conjugate is administered at a dose of about 2.0 mg/kg. In some embodiments, the antibody-drug conjugate is administered at a dose of 2.0 mg/kg. In some of any of the embodiments herein, the antibody-drug conjugate is administered once about every 1 week, once about every 2 weeks, once about every 3 weeks or once about every 4 weeks. In some of any of the embodiments herein, the antibody-drug conjugate is administered once about every 3 weeks. In some of any of the embodiments herein, the antibody-drug conjugate is administered once every 3 weeks. In some of any of the embodiments herein, the anti-PD-1 antibody or antigen-binding fragment thereof is administered at a flat dose ranging from about 50 mg to about 500 mg. In some of any of the embodiments herein, the anti-PD-1 antibody or antigen-binding fragment thereof is administered at a flat dose of about 200 mg. In some of any of the embodiments herein, the anti-PD-1 antibody or antigen-binding fragment thereof is administered at a flat dose of 200 mg. In some of any of the embodiments herein, the anti-PD-1 antibody or antigen-binding fragment thereof is administered at a flat dose of about 400 mg. In some of any of the embodiments herein, the anti-PD-1 antibody or antigen-binding fragment thereof is administered at a flat dose of 400 mg. In some of any of the embodiments herein, the anti-PD-1 antibody or antigen-binding fragment thereof is administered once about every 1 week, once about every 2 weeks, once about every 3 weeks, once about every 4 weeks, once about every 5 weeks, or once about every 6 weeks. In some of any of the embodiments herein, the anti-PD-1 antibody or antigen-binding fragment thereof is administered once about every 3 weeks. In some of any of the embodiments herein, the anti-PD-1 antibody or antigen-binding fragment thereof is administered once every 3 weeks. In some of any of the embodiments herein, the anti-PD-1 antibody or antigen-binding fragment thereof is administered once about every 6 weeks. In some of any of the embodiments herein, the anti-PD-1 antibody or antigen-binding fragment thereof is administered once every 6 weeks. In some of any of the embodiments herein, the cancer is breast cancer. In some of any of the embodiments herein, the cancer is cervical cancer. In some of any of the embodiments herein, the subject is not a candidate for curative therapy. In some of any of the embodiments herein, the curative therapy comprises radiotherapy and/or exenterative surgery. In some of any of the embodiments herein, the subject has not received prior systemic therapy for the cervical cancer. In some of any of the embodiments herein, the cervical cancer is an adenocarcinoma, an adenosquamous carcinoma or a squamous cell carcinoma. In some of any of the embodiments herein, the cervical cancer is an advanced stage cervical cancer. In some of any of the embodiments herein, the advanced stage cervical cancer is a stage 3 or stage 4 cervical cancer. In some of any of the embodiments herein, the advanced stage cervical cancer is metastatic cervical cancer. In some of any of the embodiments herein, the cervical cancer is recurrent cervical cancer. In some of any of the embodiments herein, the anti-TF antibody or antigen-binding fragment thereof of the antibody-drug conjugate is a monoclonal antibody or a monoclonal antigen-binding fragment thereof. In some of any of the embodiments herein, the anti-TF antibody or antigen-binding fragment thereof of the antibody-drug conjugate comprises a heavy chain variable region comprising an amino acid sequence having at least 85% sequence identity to the amino acid sequence of SEQ ID NO:7 and a light chain variable region comprising an amino acid sequence having at least 85% sequence identity to the amino acid sequence of SEQ ID NO:8. In some of any of the embodiments herein, the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8. In some of any of the embodiments herein, the anti-TF antibody of the antibody-drug conjugate is tisotumab. In some of any of the embodiments herein, the antibody-drug conjugate further comprises a linker between the anti-TF antibody or antigen-binding fragment thereof and the monomethyl auristatin E. In some of any of the embodiments herein, the linker is a cleavable peptide linker. In some of any of the embodiments herein, the cleavable peptide linker has a formula: -MC-vc-PAB-, wherein:

a) MC is:

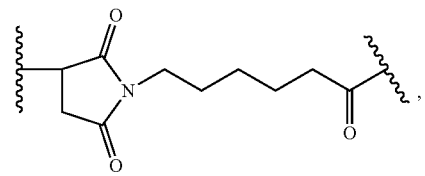 [SMILES: *C(=O)CCCCCN1C(=O)CC(*)C1=O]

b) vc is the dipeptide valine-citrulline, and c) PAB is:

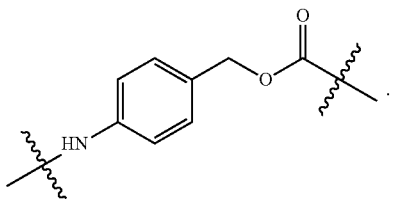 [SMILES: *Nc1ccc(COC(*)=O)cc1]

In some of any of the embodiments herein, the linker is attached to sulphydryl residues of the anti-TF antibody or antigen-binding fragment thereof obtained by partial reduction or full reduction of the anti-TF antibody or antigen-binding fragment thereof. In some of any of the embodiments herein, the linker is attached to MMAE, wherein the antibody-drug conjugate has the following structure:

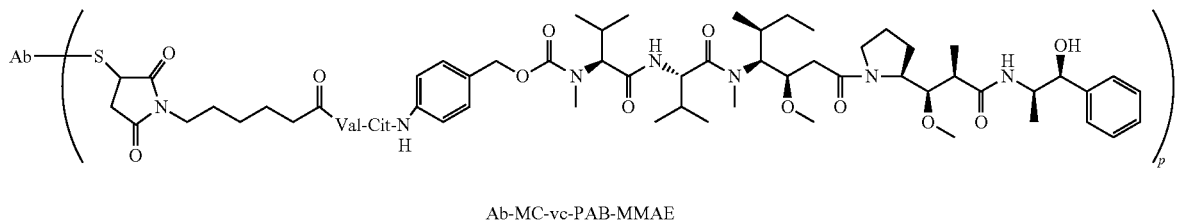

Ab-MC-vc-PAB-MMAE wherein p denotes a number from 1 to 8, S represents a sulphydryl residue of the anti-TF antibody, and Ab designates the anti-TF antibody or antigen-binding fragment thereof. In some of any of the embodiments herein, the average value of p in a population of the antibody-drug conjugates is about 4. In some of any of the embodiments herein, the antibody-drug conjugate is tisotumab vedotin. In some of any of the embodiments herein, the route of administration for the antibody-drug conjugate is intravenous. In some of any of the embodiments herein, the anti-PD-1 antibody or antigen-binding fragment thereof comprises a heavy chain variable region comprising an amino acid sequence having at least 85% sequence identity to the amino acid sequence of SEQ ID NO:31 and a light chain variable region comprising an amino acid sequence having at least 85% sequence identity to the amino acid sequence of SEQ ID NO:32. In some of any of the embodiments herein, the anti-PD-1 antibody comprises a heavy chain variable region comprising the amino acid sequence of SEQ ID NO:31 and a light chain variable region comprising the amino acid sequence of SEQ ID NO:32. In some of any of the embodiments herein, the anti-PD-1 antibody comprises a heavy chain comprising the amino acid sequence of SEQ ID NO:33 and a light chain comprising the amino acid sequence of SEQ ID NO:34. In some of any of the embodiments herein the anti-PD-1 antibody is pembrolizumab. In some of any of the embodiments herein, the route of administration for the anti-PD-1 antibody or antigen-binding fragment thereof is intravenous. In some of any of the embodiments herein, the route of administration for the anti-PD-1 antibody or antigen-binding fragment thereof is subcutaneous. In some of any of the embodiments herein, the anti-PD-1 antibody or antigen-binding fragment thereof and the antibody-drug conjugate are administered sequentially. In some of any of the embodiments herein, the anti-PD-1 antibody or antigen-binding fragment thereof and the antibody-drug conjugate are administered simultaneously. In some of any of the embodiments herein, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express TF. In some of any of the embodiments herein, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express PD-L1. In some of any of the embodiments herein, the subject's tumor expresses PD-L1 with a tumor proportion score (TPS)≥1%. In some of any of the embodiments herein, the subject's tumor has high PD-L1 expression (TPS≥50%). In some of any of the embodiments herein, the subject's tumor expresses PD-L1 with a combined positive score (CPS)≥1%. In some of any of the embodiments herein, the subject's tumor expresses PD-L1 with a combined positive score (CPS)≥10%. In some of any of the embodiments herein, a tumor derived from the cancer comprises one or more cells that express PD-L1, PD-L2, or both PD-L1 and PD-L2. In some of any of the embodiments herein, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1. In some of any of the embodiments herein, one or more therapeutic effects in the subject is improved after administration of the antibody-drug conjugate and the anti-PD-1 antibody or antigen-binding fragment thereof relative to a baseline. In some of any of the embodiments herein, the one or more therapeutic effects is selected from the group consisting of: size of a tumor derived from the cancer, objective response rate, duration of response, time to response, progression free survival, and overall survival. In some of any of the embodiments herein, the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the antibody-drug conjugate and the anti-PD-1 antibody or antigen-binding fragment thereof. In some of any of the embodiments herein, the objective response rate is at least about 20%, at least about 25%, at least about 30%, at least about 35%, at least about 40%, at least about 45%, at least about 50%, at least about 60%, at least about 70%, or at least about 80%. In some of any of the embodiments herein, the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof. In some of any of the embodiments herein, the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof. In some of any of the embodiments herein, the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof. In some of any of the embodiments herein, the subject has one or more adverse events and is further administered an additional therapeutic agent to eliminate or reduce the severity of the one or more adverse events. In some of any of the embodiments herein, the subject is at risk of developing one or more adverse events and is further administered an additional therapeutic agent to prevent or reduce the severity of the one or more adverse events. In some of any of the embodiments herein, the one or more adverse events is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration. In some of any of the embodiments herein, the one or more adverse events is a grade 3 or greater adverse event. In some of any of the embodiments herein, the one or more adverse events is a serious adverse event. In some of any of the embodiments herein, the one or more adverse events is conjunctivitis, conjunctival ulceration, and/or keratitis and the additional agent is a preservative-free lubricating eye drop, an ocular vasoconstrictor, antibiotic, and/or a steroid eye drop. In some of any of the embodiments herein, the subject is a human. In some of any of the embodiments herein, the antibody-drug conjugate is in a pharmaceutical composition comprising the antibody-drug conjugate and a pharmaceutical acceptable carrier. In some of any of the embodiments herein, the anti-PD-1 antibody or antigen-binding fragment thereof is in a pharmaceutical composition comprising the anti-PD-1 antibody or antigen-binding fragment thereof and a pharmaceutical acceptable carrier.

Also provided herein are kits comprising:
(a) a dosage ranging from about 50 mg to about 500 mg of an antibody or an antigen-binding fragment thereof, wherein the antibody binds to Programmed Death-1 (PD-1) and inhibits PD-1 activity, wherein the antibody or antigen-binding fragment thereof comprises a heavy chain variable region and a light chain variable region, wherein the heavy chain variable region comprises:
  (i) a CDR-H1 comprising the amino acid sequence of SEQ ID NO:17;
  (ii) a CDR-H2 comprising the amino acid sequence of SEQ ID NO:18; and
  (iii) a CDR-H3 comprising the amino acid sequence of SEQ ID NO:19; and
wherein the light chain variable region comprises:
  (i) a CDR-L1 comprising the amino acid sequence of SEQ ID NO:20;
  (ii) a CDR-L2 comprising the amino acid sequence of SEQ ID NO:21; and
  (iii) a CDR-L3 comprising the amino acid sequence of SEQ ID NO:22, wherein the CDRs of the anti-PD-1 antibody or antigen-binding fragment thereof are generally defined by the Kabat numbering scheme;
(b) a dosage ranging from about 0.9 mg/kg to about 2.1 mg/kg of an antibody-drug conjugate that binds to tissue factor (TF), wherein the antibody-drug conjugate comprises an anti-TF antibody or an antigen-binding fragment thereof conjugated to monomethyl auristatin E, wherein the anti-TF antibody or antigen-binding fragment thereof comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6, wherein the CDRs of the anti-TF antibody or antigen-binding fragment thereof are defined by the IMGT numbering scheme; and
(c) instructions for use of the anti-PD-1 antibody or antigen-binding fragment thereof and the antibody drug conjugate according to some of any of the embodiments herein. In some of any of the embodiments herein, the anti-PD-1 antibody or antigen-binding fragment thereof is pembrolizumab. In some of any of the embodiments herein, the dose of the pembrolizumab is 200 mg. In some of any of the embodiments herein, the dose of the pembrolizumab is 400 mg. In some of any of the embodiments herein, the antibody-drug conjugate is tisotumab vedotin. In some of any of the embodiments herein, the dose of the tisotumab vedotin is 1.3 mg/kg. In some of any of the embodiments herein, the dose of the tisotumab vedotin is 2.0 mg/kg.

BRIEF DESCRIPTION OF THE DRAWINGS

FIGS. 2A and 2B are immunofluorescent images of HeLa cells treated with 100 nM MMAE and imaged at the indicated time points in the presence of MMAE. A) Top panel shows staining for the ER with the ER-binding dye ER-ID Green and B) the lower panel shows RFP-labeled tubulin expressed by the cells

FIGS. 4A and 4B is a series of graphs showing the anti-tumor activity of the combination of tisotumab vedotin and pembrolizumab in an MDA-MB-231 xenograft model in humanized mice. A) Average tumor size in the MDA-MB-231 xenograft model in NSG mice after treatment with IgG1 control (empty circle), IgG1-MMAE control (empty diamond), pembrolizumab (filled circle), tisotumab vedotin at a concentration of 0.5 mg/kg (half-filled triangle) or 1 mg/kg (half-filled square), or tisotumab vedotin at a concentration of 0.5 mg/kg (filled triangle) or 1 mg/kg (filled square) combined with pembrolizumab. Inverted empty triangle indicates day of administration of pembrolizumab dose. Inverted half-filled triangle indicates day of administration of IgG1 control, IgG1-MMAE control or tisotumab vedotin dose. Tumor burden was assessed by caliper measurements. Error bars indicate standard error of the mean. B) Tumor burden in individual mice within the different treatment groups at day 35. Each dot represents one mouse. Anti-PD-1 Ab indicates pembrolizumab.

DETAILED DESCRIPTION

I. Definitions

Figure 1:
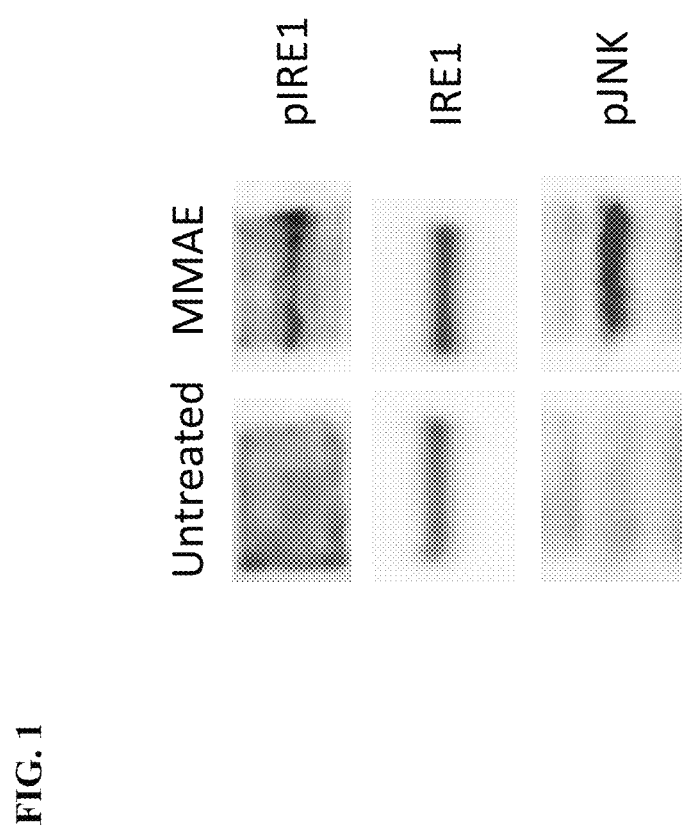
FIG. 1 is an image of a Western blot showing phosphorylation of IRE1 and JNK in cell lysates of HeLa cells treated with MMAE (right lane) as compared to HeLa cells not treated with MMAE (left lane). Treatment with MMAE led to phosphorylation of both IRE1 and JNK. pIRE1 indicates phosphorylated IRE1 protein; IRE1 indicated total IRE1 protein; and pJNK indicates phosphorylated JNK protein.

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that aspects and embodiments of the invention described herein include "comprising," "consisting," and "consisting essentially of" aspects and embodiments.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "tissue factor", "TF", "CD142", "tissue factor antigen", "TF antigen" and "CD142 antigen" are used interchangeably herein, and, unless specified otherwise, include any variants, isoforms and species homologs of human tissue factor which are naturally expressed by cells or are expressed on cells transfected with the tissue factor gene. In some embodiments, tissue factor comprises the amino acid sequence found under Genbank accession NP_001984.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region ($C_H$ or CH). The heavy chain constant region typically is comprised of three domains, $C_H1$, $C_H2$, and $C_H3$. The heavy chains are generally inter-connected via disulfide bonds in the so-called "hinge region." Each light chain typically is comprised of a light chain variable region (abbreviated herein as $V_L$ or VL) and a light chain constant region ($C_L$ or CL). The light chain constant region typically is comprised of one domain, $C_L$. The CL can be of κ (kappa) or λ (lambda) isotype. The terms "constant domain" and "constant region" are used interchangeably herein. Unless stated otherwise, the numbering of amino acid residues in the constant region is according to the EU-index as described in Kabat et al., Sequences of Proteins of Immunological Interest, 5th Ed. Public Health Service, National Institutes of Health, Bethesda, MD. (1991). An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody may be further subdivided into regions of hypervariability (or hypervariable regions, which may be hypervariable in sequence and/or form of structurally defined loops), also termed complementarity-determining regions (CDRs), interspersed with regions that are more conserved, termed framework regions (FRs). The terms "complementarity determining regions" and "CDRs," synonymous with "hypervariable regions" or "HVRs" are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). Within each $V_H$ and $V_L$, three CDRs and four FRs are typically arranged from amino-terminus to carboxy-terminus in the following order: FR1, CDR1, FR2, CDR2, FR3, CDR3, FR4 (See also Chothia and Lesk *J. Mot. Biol.*, 195, 901-917 (1987)).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, multispecific antibody or similar molecule.

The term "monoclonal antibody" as used herein refers to a preparation of antibody molecules that are recombinantly produced with a single primary amino acid sequence. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

An "isolated antibody" refers to an antibody that is substantially free of other antibodies having different antigenic specificities (e.g., an isolated antibody that binds specifically to TF is substantially free of antibodies that bind specifically to antigens other than TF). An isolated antibody that binds specifically to TF can, however, have cross-reactivity to other antigens, such as TF molecules from different species. Moreover, an isolated antibody can be substantially free of other cellular material and/or chemicals. In one embodiment, an isolated antibody includes an antibody conjugate attached to another agent (e.g., small molecule drug). In some embodiments, an isolated anti-TF antibody includes a conjugate of an anti-TF antibody with a small molecule drug (e.g., MMAE or MMAF).

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

An "anti-antigen antibody" refers to an antibody that binds to the antigen. For example, an anti-TF antibody is an antibody that binds to the antigen TF. In another example, an anti-PD-1 antibody is an antibody that binds to the antigen PD-1.

An "antigen-binding portion" or antigen-binding fragment" of an antibody refers to one or more fragments of an antibody that retain the ability to bind specifically to the antigen bound by the whole antibody. Examples of antibody fragments (e.g., antigen-binding fragment) include but are not limited to Fv, Fab, Fab', Fab'-SH, F(ab')$_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Percent (%) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % sequence identity of a given amino acid sequence A to, with, or against a given amino acid sequence B (which can alternatively be phrased as a given amino acid sequence A that has or comprises a certain % sequence identity to, with, or against a given amino acid sequence B) is calculated as follows:

$$100 \text{ times the fraction } X/Y$$

where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % sequence identity of A to B will not equal the % sequence identity of B to A.

As used herein, the terms "binding", "binds" or "specifically binds" in the context of the binding of an antibody to a pre-determined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

The term "ADC" refers to an antibody-drug conjugate, which in the context of the present invention refers to an anti-TF antibody comprising the CDRs of tisotumab, which is coupled to monomethyl auristatin E (MMAE) as described in the present application.

The abbreviations "vc" and "val-cit" refer to the dipeptide valine-citrulline.

The abbreviation "PAB" refers to the self-immolative spacer:

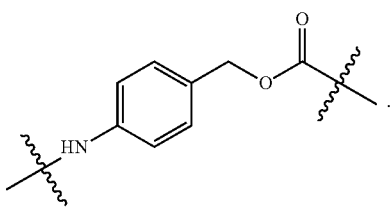 [SMILES: *Nc1ccc(COC(*)=O)cc1]

The abbreviation "MC" refers to the stretcher maleimidocaproyl:

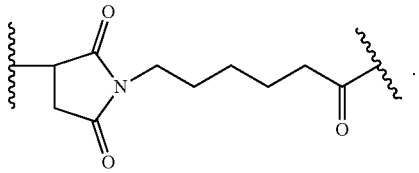 [SMILES: *C(=O)CCCCCN1C(=O)CC(*)C1=O]

The term "Ab-MC-vc-PAB-MMAE" refers to an antibody conjugated to the drug MMAE through a MC-vc-PAB linker.

"Programmed Death-1" (PD-1) refers to an immunoinhibitory receptor belonging to the CD28 family. PD-1 is expressed predominantly on previously activated T-cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. In some embodiments, hPD-1 comprises the amino acid sequence found under GenBank Accession No. U64863.

"Programmed Death Ligand-1" (PD-L1) is one of two cell surface glycoprotein ligands for PD-1 (the other being PD-L2) that downregulate T-cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. In some embodiments, hPD-L1 comprises the amino acid sequence found under GenBank Accession No. Q9NZQ7.

"Combined positive score" or "CPS" is the ratio of the number of PD-L1 positive tumor cells and PD-L1 positive mononuclear inflammatory cells (MIC) within the tumor nests and the adjacent supporting stroma (numerator) compared to the total number of tumor cells (denominator, i.e. the number of PD-L1 positive and PD-L1 negative tumor cells).

"Tumor proportion score" or "TPS" is the percentage of viable tumor cells showing partial or complete PD-L1 membrane staining in an immunohistochemical assay at any intensity.

A "cancer" refers to a broad group of various diseases characterized by the uncontrolled growth of abnormal cells in the body. A "cancer" or "cancer tissue" can include a tumor. Unregulated cell division and growth results in the formation of malignant tumors that invade neighboring tissues and can also metastasize to distant parts of the body through the lymphatic system or bloodstream. Following metastasis, the distal tumors can be said to be "derived from" the pre-metastasis tumor. For example, a "tumor derived from" a cervical cancer refers to a tumor that is the result of a metastasized cervical cancer.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease. In some embodiments, the disease is cancer.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human. The terms "subject" and "patient" and "individual" are used interchangeably herein.

An "effective amount" or "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount of an anti-cancer agent inhibits cell growth or tumor growth by at least about 10%, by at least about 20%, by at least about 30%, by at least about 40%, by at least about 50%, by at least about 60%, by at least about 70%, or by at least about 80%, by at least about 90%, by at least about 95%, by at least about 96%, by at least about 97%, by at least about 98%, or by at least about 99% in a treated subject(s) (e.g., one or more treated subjects) relative to an untreated subject(s) (e.g., one or more untreated subjects). In some embodiments, a therapeutically effective amount of an anti-cancer agent inhibits cell growth or tumor growth by 100% in a treated subject(s) (e.g., one or more treated subjects) relative to an untreated subject(s) (e.g., one or more untreated subjects).

In other embodiments of the disclosure, tumor regression can be observed and continue for a period of at least about 20 days, at least about 30 days, at least about 40 days, at least about 50 days, or at least about 60 days. Notwithstanding these ultimate measurements of therapeutic effectiveness, evaluation of immunotherapeutic drugs must also make allowance for "immune-related response patterns".

A therapeutically effective amount of a drug (e.g., anti-TF antibody-drug conjugate comprising MMAE and the CDRs of tisotumab or anti-PD-1 antibody comprising the CDRs of pembrolizumab) includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

As used herein, "subtherapeutic dose" means a dose of a therapeutic compound (e.g., an anti-TF antibody-drug conjugate comprising MMAE and the CDRs of tisotumab or anti-PD-1 antibody comprising the CDRs of pembrolizumab) that is lower than the usual or typical dose of the therapeutic compound when administered alone for the treatment of a hyperproliferative disease (e.g., cancer).

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity or other adverse physiological effects at the cellular, organ and/or organism level (adverse effects) resulting from administration of the drug.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration that is at least the same as the treatment duration, or at least 1.5, 2.0, 2.5, or 3 times longer than the treatment duration.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progression free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" or "ORR" refers to the sum of complete response (CR) rate and partial response (PR) rate.

As used herein, "overall survival" or "OS" refers to the percentage of individuals in a group who are likely to be alive after a particular duration of time.

The term "weight-based dose", as referred to herein, means that a dose administered to a subject is calculated based on the weight of the subject. For example, when a subject with 60 kg body weight requires 2.0 mg/kg of an anti-PD-1 antibody comprising the CDRs of pembrolizumab or an anti-TF antibody-drug conjugate comprising MMAE and the CDRs of tisotumab, one can calculate and use the appropriate amount of the anti-PD-1 antibody comprising the CDRs of pembrolizumab or anti-TF antibody-drug conjugate comprising MMAE and the CDRs of tisotumab (i.e., 120 mg) for administration to said subject.

The use of the term "fixed dose" with regard to a method of the disclosure means that two or more different antibodies (e.g., anti-PD-1 antibody comprising the CDRs of pembrolizumab and anti-TF antibody-drug conjugate comprising MMAE and the CDRs of tisotumab) are administered to a subject in particular (fixed) ratios with each other. In some embodiments, the fixed dose is based on the amount (e.g., mg) of the antibodies. In certain embodiments, the fixed dose is based on the concentration (e.g., mg/ml) of the antibodies. For example, a 3:1 ratio of an anti-PD-1 antibody comprising the CDRs of pembrolizumab to an anti-TF antibody-drug conjugate comprising MMAE and the CDRs of tisotumab administered to a subject can mean about 240 mg of the anti-PD-1 antibody comprising the CDRs of pembrolizumab and about 80 mg of the anti-TF antibody-drug conjugate comprising MMAE and the CDRs of tisotumab or about 3 mg/ml of the anti-PD-1 antibody comprising the CDRs of pembrolizumab and about 1 mg/ml of the anti-TF antibody-drug conjugate comprising MMAE and the CDRs of tisotumab are administered to the subject.

The use of the term "flat dose" with regard to the methods and dosages of the disclosure means a dose that is administered to a subject without regard for the weight or body surface area (BSA) of the subject. The flat dose is therefore not provided as a mg/kg dose, but rather as an absolute amount of the agent (e.g., the anti-TF antibody-drug conjugate comprising MMAE and the CDRs of tisotumab and/or anti-PD-1 antibody comprising the CDRs of pembrolizumab). For example, a subject with 60 kg body weight and a subject with 100 kg body weight would receive the same dose of an antibody or an antibody-drug conjugate (e.g., 240 mg of an anti-TF antibody-drug conjugate comprising MMAE and the CDRs of tisotumab or e.g. 200 mg of an anti-PD-1 antibody comprising the CDRs of pembrolizumab).

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 4,4'-methylenebis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Administering" or "administration" refer to the physical introduction of a therapeutic agent to a subject, using any of the various methods and delivery systems known to those skilled in the art. Exemplary routes of administration for the anti-TF antibody-drug conjugate comprising MMAE and the CDRs of tisotumab and/or anti-PD-1 antibody comprising the CDRs of pembrolizumab include intravenous, intramuscular, subcutaneous, intraperitoneal, spinal or other parenteral routes of administration, for example by injection or infusion (e.g., intravenous infusion). The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent can be administered via a non-parenteral route, or orally. Other non-parenteral routes include a topical, epidermal or mucosal route of administration, for example, intranasally, vaginally, rectally, sublingually or topically. Administration can also be performed, for example, once, a plurality of times, and/or over one or more extended periods.

The terms "baseline" or "baseline value" used interchangeably herein can refer to a measurement or characterization of a symptom before the administration of the therapy (e.g., an anti-TF antibody-drug conjugate as described herein and/or an anti-PD-1 antibody as described herein) or at the beginning of administration of the therapy. The baseline value can be compared to a reference value in order to determine the reduction or improvement of a symptom of a TF-associated disease and/or PD-1 associated disease contemplated herein (e.g., breast cancer or cervical cancer). The terms "reference" or "reference value" used interchangeably herein can refer to a measurement or characterization of a symptom after administration of the therapy (e.g., an anti-TF antibody-drug conjugate as described herein and/or an anti-PD-1 antibody as described herein). The reference value can be measured one or more times during a dosage regimen or treatment cycle or at the completion of the dosage regimen or treatment cycle. A "reference value" can be an absolute value; a relative value; a value that has an upper and/or lower limit; a range of values; an average value; a median value: a mean value; or a value as compared to a baseline value.

Similarly, a "baseline value" can be an absolute value; a relative value; a value that has an upper and/or lower limit; a range of values; an average value; a median value; a mean value; or a value as compared to a reference value. The reference value and/or baseline value can be obtained from one individual, from two different individuals or from a group of individuals (e.g., a group of two, three, four, five or more individuals).

The term "monotherapy" as used herein means that the anti-TF antibody-drug conjugate comprising MMAE and the CDRs of tisotumab or anti-PD-1 antibody comprising the CDRs of pembrolizumab is the only anti-cancer agent administered to the subject during the treatment cycle. Other therapeutic agents, however, can be administered to the subject. For example, anti-inflammatory agents or other agents administered to a subject with cancer to treat symptoms associated with cancer, but not the underlying cancer itself, including, for example inflammation, pain, weight loss, and general malaise, can be administered during the period of monotherapy.

An "adverse event" (AE) as used herein is any unfavorable and generally unintended or undesirable sign (including an abnormal laboratory finding), symptom, or disease associated with the use of a medical treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

A "serious adverse event" or "SAE" as used herein is an adverse event that meets one of the following criteria:
Is fatal or life-threatening (as used in the definition of a serious adverse event, "life-threatening" refers to an event in which the patient was at risk of death at the time of the event; it does not refer to an event which hypothetically might have caused death if it was more severe.
Results in persistent or significant disability/incapacity
Constitutes a congenital anomaly/birth defect
Is medically significant, i.e., defined as an event that jeopardizes the patient or may require medical or surgical intervention to prevent one of the outcomes listed above. Medical and scientific judgment must be exercised in deciding whether an AE is "medically significant"
Requires inpatient hospitalization or prolongation of existing hospitalization, excluding the following: 1) routine treatment or monitoring of the underlying disease, not associated with any deterioration in condition; 2) elective or pre-planned treatment for a pre-existing condition that is unrelated to the indication under study and has not worsened since signing the informed consent; and 3) social reasons and respite care in the absence of any deterioration in the patient's general condition.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days t one day, i.e., every six days to every eight days. "Once about every two weeks" can include every fourteen days t two days, i.e., every twelve days to every sixteen days. "Once about every three weeks" can include every twenty-one days t three days, i.e., every eighteen days to every twenty-four days. Similar approximations apply, for example, to once about every four weeks, once about every five weeks, once about every six weeks, and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. Combination Therapy

One aspect of the invention provides anti-TF antibody-drug conjugates that binds to TF for use in the treatment of cancer wherein the antibody-drug conjugate is for administration, or to be administered in combination with an anti-PD-1 antibody or an antigen-binding fragment thereof wherein the antibody-drug conjugate comprises an anti-TF antibody or an antigen-binding fragment thereof conjugated to monomethyl auristatin E, and wherein the anti-PD-1 antibody or the antigen-binding fragment thereof inhibits PD-1 activity, wherein the anti-PD-1 antibody or antigen-binding fragment thereof comprises a heavy chain variable region and a light chain variable region, wherein the heavy chain variable region comprises:
 (i) a CDR-H1 comprising the amino acid sequence of SEQ ID NO:17;
 (ii) a CDR-H2 comprising the amino acid sequence of SEQ ID NO:18; and
 (iii) a CDR-H3 comprising the amino acid sequence of SEQ ID NO:19; and
wherein the light chain variable region comprises:
 (i) a CDR-L1 comprising the amino acid sequence of SEQ ID NO:20;
 (ii) a CDR-L2 comprising the amino acid sequence of SEQ ID NO:21; and
 (iii) a CDR-L3 comprising the amino acid sequence of SEQ ID NO:22, wherein the CDRs of the anti-PD-1 antibody or antigen-binding fragment thereof are generally defined by the Kabat numbering scheme,
and wherein the anti-TF antibody or antigen-binding fragment thereof comprises a heavy chain variable region and a light chain variable region, wherein the heavy chain variable region comprises:
 (i) a CDR-H1 comprising the amino acid sequence of SEQ ID NO:1;
 (ii) a CDR-H2 comprising the amino acid sequence of SEQ ID NO:2; and
 (iii) a CDR-H3 comprising the amino acid sequence of SEQ ID NO:3; and
wherein the light chain variable region comprises:
 (i) a CDR-L1 comprising the amino acid sequence of SEQ ID NO:4;
 (ii) a CDR-L2 comprising the amino acid sequence of SEQ ID NO:5; and
 (iii) a CDR-L3 comprising the amino acid sequence of SEQ ID NO:6, wherein the CDRs of the anti-TF antibody or antigen-binding fragment thereof are defined by the IMGT numbering scheme. In another aspect the invention provides an anti-PD-1 antibody comprising the CDRs of pembrolizumab or an antigen-binding fragment thereof for use in the treatment of cancer wherein the anti-PD-1 antibody is for administration, or to be administered in combination with an antibody-drug conjugate that binds to TF wherein the antibody-drug conjugate comprises an anti-TF antibody or an antigen-binding fragment thereof comprising the CDRs of tisotumab conjugated to monomethyl auristatin E, and wherein the anti-PD-1 antibody or the antigen-binding fragment thereof inhibits PD-1 activity. In some embodiments, the cancer is breast cancer. In some embodiments, the breast cancer is ER+/HER2− breast cancer. In some embodiments, the breast cancer is triple negative breast cancer. In some embodiments, the cancer is cervical cancer. In some embodiments, the cervical cancer is an advanced stage cervical cancer (e.g., stage 3 cervical cancer or stage 4 cervical cancer or metastatic cervical cancer). In some embodiments, the advanced cervical cancer is a metastatic cancer. In some embodiments, the subject has relapsed, recurrent and/or metastatic cervical cancer.

A. Anti-TF Antibody

Generally, anti-TF antibodies of the disclosure bind TF, e.g., human TF, and exert cytostatic and cytotoxic effects on malignant cells, such as breast cancer cells or cervical cancer cells, wherein the anti-TF antibody or antigen binding fragment thereof comprises a heavy chain variable region and a light chain variable region, wherein the heavy chain variable region comprises:
 (i) a CDR-H1 comprising the amino acid sequence of SEQ ID NO:1;
 (ii) a CDR-H2 comprising the amino acid sequence of SEQ ID NO:2; and
 (iii) a CDR-H3 comprising the amino acid sequence of SEQ ID NO:3; and
wherein the light chain variable region comprises:
 (i) a CDR-L1 comprising the amino acid sequence of SEQ ID NO:4;
 (ii) a CDR-L2 comprising the amino acid sequence of SEQ ID NO:5; and
 (iii) a CDR-L3 comprising the amino acid sequence of SEQ ID NO:6, wherein the CDRs of the anti-TF antibody or antigen-binding fragment thereof are defined by the IMGT numbering scheme. Anti-TF antibodies of the disclosure comprise the CDRs of tisotumab and are preferably monoclonal, and may be multispecific, human, humanized or chimeric antibodies, single chain antibodies, Fab fragments, F(ab') fragments, fragments produced by a Fab expression library, and TF binding fragments of any of the above. In some embodiments, the anti-TF antibodies of the disclosure comprise the CDRs of tisotumab and specifically bind TF. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the anti-TF antibodies comprise the CDRs of tisotumab and are antigen-binding fragments (e.g., human antigen-binding fragments) as described herein and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. In some embodiments, the anti-TF antibodies or antigen-binding fragments thereof are human, murine (e.g., mouse and rat), donkey, sheep, rabbit, goat, guinea pig, camelid, horse, or chicken and comprise the CDRs of tisotumab.

The anti-TF antibodies of the present disclosure comprise the CDRs of tisotumab and may be monospecific, bispecific, trispecific or of greater multi specificity. Multispecific antibodies may be specific for different epitopes of TF or may be specific for both TF as well as for a heterologous protein. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553.

Anti-TF antibodies of the present disclosure may be described or specified in terms of the particular CDRs they comprise. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme). The boundaries of a given CDR may vary depending on the scheme used for identification. In some embodiments, a "CDR" or "complementary determining region," or individual specified CDRs (e.g., CDR-H1, CDR-H2, CDR-H3), of a given antibody or region thereof (e.g., variable region thereof) should be understood to encompass a (or the specific) CDR as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. The scheme for identification of a particular CDR or CDRs may be specified, such as the CDR as defined by the Kabat, Chothia, AbM or IMGT method.

Numbering of amino acid residues in CDR sequences of the anti-TF antibodies of the anti-TF antibody-drug conjugate provided herein are according to the IMGT numbering scheme as described in Lefranc, M. P. et al., Dev. Comp. Immunol., 2003, 27, 55-77. CDR sequences provided herein for the anti-TF antibodies of the anti-TF antibody-drug conjugate are according to the IMGT method as described in Lefranc, M. P. et al., Dev. Comp. Immunol., 2003, 27, 55-77.

The anti-TF antibodies of the disclosure comprise the CDRs of the antibody 011. See WO 2011/157741 and WO 2010/066803. The disclosure encompasses an antibody or derivative thereof comprising a heavy or light chain variable domain, said variable domain comprising (a) a set of three CDRs, in which said set of CDRs are from monoclonal antibody 011, and (b) a set of four framework regions, in which said set of framework regions differs from the set of framework regions in monoclonal antibody 011, and in which said antibody or derivative thereof binds to TF. In some embodiments, said antibody or derivative thereof specifically binds to TF. In certain embodiments, the anti-TF antibody is 011. The antibody 011 is also known as tisotumab.

In one aspect, provided herein is an anti-TF antibody comprising a heavy chain variable region and a light chain variable region, wherein the heavy chain variable region comprises (i) CDR-H1 comprising the amino acid sequence of SEQ ID NO:1, (ii) CDR-H2 comprising the amino acid sequence of SEQ ID NO:2, and (iii) CDR-H3 comprising the amino acid sequence of SEQ ID NO:3; and wherein the light chain variable region comprises (i) CDR-L1 comprising the amino acid sequence of SEQ ID NO:4, (ii) CDR-L2 comprising the amino acid sequence of SEQ ID NO:5, and (iii) CDR-L3 comprising the amino acid sequence of SEQ ID NO:6, wherein the CDRs of the anti-TF antibody are defined by the IMGT numbering scheme.

An anti-TF antibody described herein may comprise any suitable framework variable domain sequence, provided that the antibody retains the ability to bind TF (e.g., human TF). As used herein, heavy chain framework regions are designated "HC-FR1-FR4," and light chain framework regions are designated "LC-FR1-FR4." In some embodiments, the anti-TF antibody comprises a heavy chain variable domain framework sequence of SEQ ID NO:9, 10, 11, and 12 (HC-FR1, HC-FR2, HC-FR3, and HC-FR4, respectively). In some embodiments, the anti-TF antibody comprises a light chain variable domain framework sequence of SEQ ID NO:13, 14, 15, and 16 (LC-FR1, LC-FR2, LC-FR3, and LC-FR4, respectively).

In some embodiments of the anti-TF antibodies described herein, the heavy chain variable domain comprises the amino acid sequence of

```
                                         (SEQ ID NO: 7)
EVQLLESGGGLVQPGGSLRLSCAASGFTFSNYAMSWVRQAPGK

GLEWVSSISGSGDYTYYTDSVKGRFTISRDNSKNTLYLQMNSL

RAEDTAVYYCARSPWGYYLDSWGQGTLVTVSS
and the light chain variable domain comprises
the amino acid sequence of
                                         (SEQ ID NO: 8)
DIQMTQSPPSLSASAGDRVTITCRASQGISSRLAWYQQKPEK

APKSLIYAASSLQSGVPSRFSGSGSGTDFTLTISSLQPEDFA

TYYCQQYNSYPYTFGQGTKLEIK.
```

In some embodiments of the anti-TF antibodies described herein, the heavy chain CDR sequences comprise the following:

```
    a) CDR-H1
    (GFTFSNYA (SEQ ID NO: 1));

b) CDR-H2
    (ISGSGDYT (SEQ ID NO: 2));
```

-continued and c) CDR-H3
(ARSPWGYYLDS (SEQ ID NO: 3)).

In some embodiments of the anti-TF antibodies described herein, the heavy chain FR sequences comprise the following:

a) HC-FR1
(EVQLLESGGGLVQPGGSLRLS

CAAS (SEQ ID NO: 9));

b) HC-FR2
(MSWVRQAPGKGLEWVSS (SEQ ID NO: 10));

c) HC-FR3
(YYTDSVKGRFTISRDNSKNTLYLQMNSLR

AEDTAVYYC (SEQ ID NO: 11));
and d) HC-FR4
(WGQGTLVTVSS (SEQ ID NO: 12)).

In some embodiments of the anti-TF antibodies described herein, the light chain CDR sequences comprise the following:

a) CDR-L1
(QGISSR (SEQ ID NO: 4));

b) CDR-L2
(AAS (SEQ ID NO: 5));
and c) CDR-L3
(QQYNSYPYT (SEQ ID NO: 6)).

In some embodiments of the anti-TF antibodies described herein, the light chain FR sequences comprise the following:

a) LC-FR1
(DIQMTQSPPSLSASAGDRVTITC

RAS (SEQ ID NO: 13));

b) LC-FR2
(LAWYQQKPEKAPK

SLIY (SEQ ID NO: 14));

c) LC-FR3
(SLQSGVPSRFSGSGSGTDFTLTISS

LQPEDFATYYC (SEQ ID NO: 15));
and d) LC-FR4
(FGQGTKLEIK (SEQ ID NO: 16)).

In some embodiments, provided herein is an anti-TF antibody that binds to TF (e.g., human TF), wherein the antibody comprises a heavy chain variable region and a light chain variable region, wherein the antibody comprises:
(a) heavy chain variable domain comprising:
(1) an HC-FR1 comprising the amino acid sequence of SEQ ID NO:9;
(2) an CDR-H1 comprising the amino acid sequence of SEQ ID NO:1;
(3) an HC-FR2 comprising the amino acid sequence of SEQ ID NO:10;
(4) an CDR-H2 comprising the amino acid sequence of SEQ ID NO:2;
(5) an HC-FR3 comprising the amino acid sequence of SEQ ID NO:11;
(6) an CDR-H3 comprising the amino acid sequence of SEQ ID NO:3; and
(7) an HC-FR4 comprising the amino acid sequence of SEQ ID NO:12, and/or
(b) a light chain variable domain comprising:
(1) an LC-FR1 comprising the amino acid sequence of SEQ ID NO:13;
(2) an CDR-L1 comprising the amino acid sequence of SEQ ID NO:4;
(3) an LC-FR2 comprising the amino acid sequence of SEQ ID NO:14;
(4) an CDR-L2 comprising the amino acid sequence of SEQ ID NO:5;
(5) an LC-FR3 comprising the amino acid sequence of SEQ ID NO:15;
(6) an CDR-L3 comprising the amino acid sequence of SEQ ID NO:6; and
(7) an LC-FR4 comprising the amino acid sequence of SEQ ID NO:16.

In one aspect, provided herein is an anti-TF antibody comprising a heavy chain variable domain comprising the amino acid sequence of SEQ ID NO:7 or comprising a light chain variable domain comprising the amino acid sequence of SEQ ID NO:8. In one aspect, provided herein is an anti-TF antibody comprising a heavy chain variable domain comprising the amino acid sequence of SEQ ID NO:7 and comprising a light chain variable domain comprising the amino acid sequence of SEQ ID NO:8. In one aspect, provided herein is an anti-TF antibody comprising the CDRs of the heavy chain variable domain comprising the amino acid sequence of SEQ ID NO:7 and comprising the CDRs of the light chain variable domain comprising the amino acid sequence of SEQ ID NO:8.

In some embodiments, provided herein is an anti-TF antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:7. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:7 contains substitutions (e.g., conservative substitutions), insertions, or deletions relative to the reference sequence and retains the ability to bind to a TF (e.g., human TF). In certain embodiments, a total of 1 to 10 amino acids have been substituted, inserted and/or deleted in SEQ ID NO:7. In certain embodiments, substitutions, insertions, or deletions (e.g., 1, 2, 3, 4, or 5 amino acids) occur in regions outside the CDRs (i.e., in the FRs). In some embodiments, the anti-TF antibody comprises a heavy chain variable domain sequence of SEQ ID NO:7 including post-translational modifications of that sequence. In a particular embodiment, the heavy chain variable domain comprises: (a) CDR-H1 comprising the amino acid sequence of SEQ ID NO:1, (b) CDR-H2 comprising the amino acid sequence of SEQ ID NO:2, and (c) CDR-H3 comprising the amino acid sequence of SEQ ID NO:3.

In some embodiments, provided herein is an anti-TF antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:8. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:8 contains substitutions (e.g., conservative substitutions), insertions, or deletions relative to the reference sequence and retains the ability to bind to a TF (e.g., human TF). In certain embodiments, a total of 1 to 10 amino acids have been substituted, inserted and/or deleted in SEQ ID NO:8. In certain embodiments, substitutions, insertions, or deletions (e.g., 1, 2, 3, 4, or 5 amino acids) occur in regions outside the CDRs (i.e., in the FRs). In some embodiments, the anti-TF antibody comprises a light chain variable domain sequence of SEQ ID NO:8 including post-translational modifications of that sequence. In a particular embodiment, the light chain variable domain comprises: (a) CDR-L1 comprising the amino acid sequence of SEQ ID NO:4, (b) CDR-L2 comprising the amino acid sequence of SEQ ID NO:5, and (c) CDR-L3 comprising the amino acid sequence of SEQ ID NO:6.

In some embodiments, the anti-TF antibody comprises a heavy chain variable domain as in any of the embodiments provided above, and a light chain variable domain as in any of the embodiments provided above. In one embodiment, the antibody comprises the heavy chain variable domain sequence of SEQ ID NO:7 and the light chain variable domain sequence of SEQ ID NO:8, including post-translational modifications of those sequences.

In some embodiments, the anti-TF antibody of the anti-TF antibody-drug conjugate comprises: i) a heavy chain CDR1 comprising the amino acid sequence of SEQ ID NO: 1, a heavy chain CDR2 comprising the amino acid sequence of SEQ ID NO: 2, a heavy chain CDR3 comprising the amino acid sequence of SEQ ID NO: 3; and ii) a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6, wherein the CDRs of the anti-TF antibody are defined by the IMGT numbering scheme.

In some embodiments, the anti-TF antibody of the anti-TF antibody-drug conjugate comprises: i) an amino acid sequence having at least 85% sequence identity to a heavy chain variable region comprising the amino acid sequence of SEQ ID NO: 7, and ii) an amino acid sequence having at least 85% sequence identity to a light chain variable region comprising the amino acid sequence of SEQ ID NO: 8.

In some embodiments, the anti-TF antibody of the anti-TF antibody-drug conjugate comprise the CDRs of tisotumab and is a monoclonal antibody.

In some embodiments, the anti-TF antibody of the anti-TF antibody-drug conjugate is tisotumab, which is also known as antibody 011 as described in WO 2011/157741 and WO 2010/066803.

Anti-TF antibodies of the invention comprising the CDRs of tisotumab may also be described or specified in terms of their binding affinity to TF (e.g., human TF). Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

There are five classes of immunoglobulins: IgA, IgD, IgE, IgG and IgM, having heavy chains designated α, δ, ε, γ and µ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. *mAbs* Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

The antibodies also include derivatives that are modified, i.e., by the covalent attachment of any type of molecule to the antibody such that covalent attachment does not prevent the antibody from binding to TF or from exerting a cytostatic or cytotoxic effect on HD cells. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

B. Antibody-Drug Conjugate Structure

In some aspects, the anti-TF antibody-drug conjugates described herein comprise a linker between an anti-TF antibody or antigen-binding fragment thereof as described herein and monomethyl auristatin E (MMAE). In some embodiments the linker is a non-cleavable linker. In some embodiments the linker is a cleavable linker.

In some embodiments, the linker is a cleavable peptide linker comprising maleimido caproyl (MC), the dipeptide valine-citrulline (vc) and p-aminobenzylcarbamate (PAB). In some embodiments, the cleavable peptide linker has the formula: MC-vc-PAB-, wherein:

a) MC is:

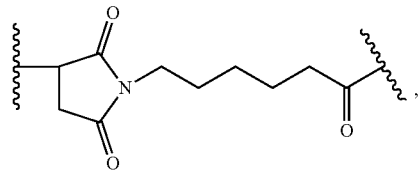 [SMILES: *C(=O)CCCCCN1C(=O)CC(*)C1=O]

b) vc is the dipeptide valine-citrulline, and
c) PAB is:

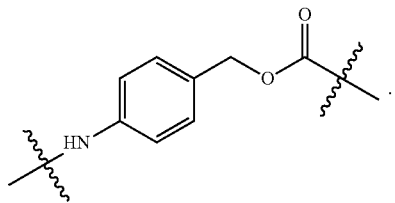 [SMILES: *Nc1ccc(COC(*)=O)cc1]

In some embodiments, the linker is a cleavable peptide linker comprising maleimido caproyl (MC). In some embodiments, the cleavable peptide linker has the formula: MC-, wherein:

a) MC is:

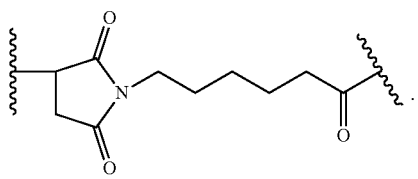

In some embodiments, the linker is attached to sulphydryl residues of the anti-TF antibody or antigen-binding fragment thereof comprising the CDRs of tisotumab obtained by partial or full reduction of the anti-TF antibody or antigen-binding fragment thereof. In some embodiments, the linker is attached to sulphydryl residues of the anti-TF antibody or antigen-binding fragment thereof comprising the CDRs of tisotumab obtained by partial reduction of the anti-TF antibody or antigen-binding fragment thereof. In some embodiments, the linker is attached to sulphydryl residues of the anti-TF antibody or antigen-binding fragment thereof comprising the CDRs of tisotumab obtained by full reduction of the anti-TF antibody or antigen-binding fragment thereof.

In some aspects, the anti-TF antibody-drug conjugates described herein comprise a linker as described herein between an anti-TF antibody or antigen-binding fragment thereof as described herein and monomethyl auristatin E (MMAE). Auristatins, such as MMAE, have been shown to interfere with microtubule dynamics, GTP hydrolysis and nuclear and cellular division (See Woyke et al (2001) *Antimicrob. Agents and Chemother.* 45(12): 3580-3584) and have anti-cancer (See U.S. Pat. No. 5,663,149) and antifungal activity (See Pettit et al., (1998) *Antimicrob. Agents and Chemother.* 42: 2961-2965. MMAE, as well as suitable linkers for conjugation of MMAE to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023. The anti-TF antibody-drug conjugates described herein comprise MMAE and the CDRs of tisotumab Monomethyl auristatin E (MMAE) has the following structure:

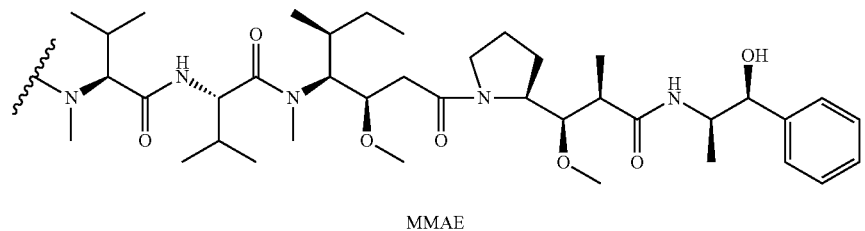 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE wherein the wavy line indicates the attachment site for the linker.

In one embodiment, the cleavable peptide linker has the formula: MC-vc-PAB-, and is attached to MMAE. The resulting linker-auristatin, MC-vc-PAB-MMAE is also designated vcMMAE. The vcMMAE drug linker moiety and conjugation methods are disclosed in WO2004010957, U.S. Pat. Nos. 7,659,241, 7,829,531 and 7,851,437. When vcMMAE is attached to an anti-TF antibody or antigen-binding fragment thereof comprising the CDRs of tisotumab as described herein, the resulting structure is:

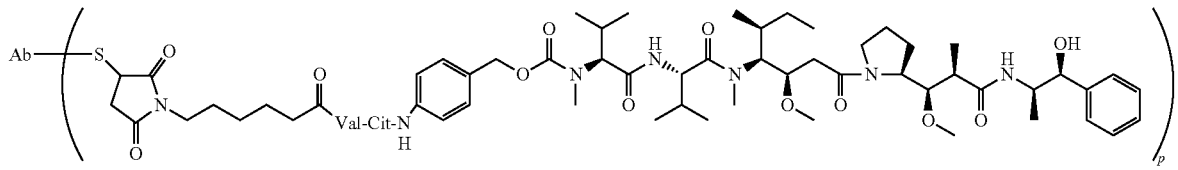

Ab-MC-vc-PAB-MMAE wherein p denotes a number from 1 to 8, e.g., 1, 2, 3, 4, 5, 6, 7 or 8, e.g., p may be from 3-5, S represents a sulphydryl residue of the anti-TF antibody and Ab designates an anti-TF antibody or antigen-binding fragment thereof as described herein. In one embodiment, the average value of p in a population of antibody-drug conjugates is about 4. In some embodiments, p is measured by hydrophobic interaction chromatography (HIC), for example by resolving drug-loaded species based on the increasing hydrophobicity with the least hydrophobic, unconjugated form eluting first and the most hydrophobic, 8-drug form eluting last with the area percentage of a peak representing the relative distribution of the particular drug-loaded antibody-drug conjugate species. See Ouyang, J., 2013, Antibody-Drug Conjugates, Methods in Molecular Biology (Methods and Protocols). In some embodiments, p is measured by reversed phase high-performance liquid chromatography (RP-HPLC), for example by first performing a reduction reaction to completely dissociate the heavy and light chains of the ADC, then separating the light and heavy chains and their corresponding drug-loaded forms on an RP column, where the percentage peak are from integration of the light chain and heavy chain peaks, combined with the assigned drug load for each peak, is used to calculate the weighted average drug to antibody ration. See Ouyang, J., 2013, Antibody-Drug Conjugates, Methods in Molecular Biology (Methods and Protocols).

In one embodiment, the antibody-drug conjugate is tisotumab vedotin.

C. Anti-PD-1 Antibody

Generally, anti-PD-1 antibodies or antigen-binding fragments thereof of the disclosure bind to PD-1, e.g., human PD-1, wherein the anti-PD-1 antibody or antigen-binding fragment thereof comprises a heavy chain variable region and a light chain variable region, wherein the heavy chain variable region comprises:
  (i) a CDR-H1 comprising the amino acid sequence of SEQ ID NO:17;
  (ii) a CDR-H2 comprising the amino acid sequence of SEQ ID NO:18; and
  (iii) a CDR-H3 comprising the amino acid sequence of SEQ ID NO:19; and
wherein the light chain variable region comprises:
  (i) a CDR-L1 comprising the amino acid sequence of SEQ ID NO:20;
  (ii) a CDR-L2 comprising the amino acid sequence of SEQ ID NO:21; and
  (iii) a CDR-L3 comprising the amino acid sequence of SEQ ID NO:22, wherein the CDRs of the anti-PD-1 antibody or antigen-binding fragment thereof are generally defined by the Kabat numbering scheme. Anti-PD-1 antibodies of the disclosure comprise the CDRs of pembrolizumab and are preferably monoclonal, and may be multispecific, human, humanized or chimeric antibodies, single chain antibodies, Fab fragments, F(ab') fragments, fragments produced by a Fab expression library, and PD-1 binding fragments of any of the above. In some embodiments, an anti-PD-1 antibody described herein comprises the CDRs of pembrolizumab and binds specifically to PD-1 (e.g., human PD-1). The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the antibodies are antigen-binding fragments (e.g., human antigen-binding fragments) as described herein and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. In some embodiments, the anti-PD-1 antibodies or antigen-binding fragments thereof are human, murine (e.g., mouse and rat), donkey, sheep, rabbit, goat, guinea pig, camelid, horse, or chicken and comprise the CDRs of pembrolizumab.

The anti-PD-1 antibodies of the present disclosure comprise the CDRs of pembrolizumab and may be monospecific, bispecific, trispecific or of greater multi specificity. Multispecific antibodies may be specific for different epitopes of PD-1 or may be specific for both PD-1 as well as for a heterologous protein. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553.

Anti-PD-1 antibodies of the present disclosure may be described or specified in terms of the particular CDRs they comprise. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme). The boundaries of a given CDR may vary depending on the scheme used for identification. In some embodiments, a "CDR" or "complementary determining region," or individual specified CDRs (e.g., CDR-H1, CDR-H2, CDR-H3), of a given antibody or region thereof (e.g., variable region thereof) should be understood to encompass a (or the specific) CDR as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. The scheme for identification of a particular CDR or CDRs may be specified, such as the CDR as defined by the Kabat, Chothia, AbM or IMGT method.

Numbering of amino acid residues in CDR sequences of the anti-PD-1 antibodies and antigen-binging fragments provided herein are generally according to the Kabat numbering scheme as described in Kabat E. A., et al., 1991, Sequences of proteins of Immunological interest, In: NIH Publication No. 91-3242, US Department of Health and Human Services, Bethesda, MD.

The anti-PD-1 antibodies of the present disclosure comprise the CDRs of the antibody pembrolizumab. See U.S. Pat. Nos. 8,354,509 and 8,900,587. The present disclosure encompasses an anti-PD-1 antibody or derivative thereof comprising a heavy or light chain variable domain, said variable domain comprising (a) a set of three CDRs, in which said set of CDRs are from the monoclonal antibody pembrolizumab, and (b) a set of four framework regions, in which said set of framework regions differs from the set of framework regions in the monoclonal antibody pembrolizumab, and in which said anti-PD-1 antibody or derivative thereof binds to PD-1. In certain embodiments, the anti-PD-1 antibody is pembrolizumab. The antibody pembrolizumab is also known as KEYTRUDA®. (Merck & Co., Inc., Kenilworth, NJ, USA).

In one aspect, provided herein is an anti-PD-1 antibody comprising a heavy chain variable region and a light chain variable region, wherein the heavy chain variable region comprises (i) CDR-H1 comprising the amino acid sequence of SEQ ID NO:17, (ii) CDR-H2 comprising the amino acid sequence of SEQ ID NO:18, and (iii) CDR-H3 comprising the amino acid sequence of SEQ ID NO:19; and wherein the light chain variable region comprises (i) CDR-L1 comprising the amino acid sequence of SEQ ID NO:20, (ii) CDR-L2 comprising the amino acid sequence of SEQ ID NO:21, and (iii) CDR-L3 comprising the amino acid sequence of SEQ ID NO:22, wherein the CDRs of the anti-PD-1 antibody are generally defined by the Kabat numbering scheme.

In one embodiment, an anti-PD-1 antibody comprises a light chain variable domain comprising a framework sequence and hypervariable regions, wherein the framework sequence comprises the LC-FR1-LC-FR4 amino acid sequences of SEQ ID NO:27 (LC-FR1), SEQ ID NO:28 (LC-FR2), SEQ ID NO:29 (LC-FR3), and SEQ ID NO:30 (LC-FR4), respectively; the CDR-L 1 comprises the amino acid sequence of SEQ ID NO:20; the CDR-L2 comprises the amino acid sequence of SEQ ID NO:21; and the CDR-L3 comprises the amino acid sequence of SEQ ID NO:22.

In some embodiments of the anti-PD-1 antibodies described herein, the heavy chain variable domain comprises the amino acid sequence of

```
                                       (SEQ ID NO: 31)
QVQLVQSGVEVKKPGASVKVSCKASGYTFTNYYMYWVRQA

PGQGLEWMGGINPSNGGTNFNEKFKNRVTLTTDSSTTTAY

MELKSLQFDDTAVYYCARRDYRFDMGFDYWGQGTTVTVSS
and the light chain variable domain
comprises the amino acid sequence of
                                       (SEQ ID NO: 32)
EIVLTQSPATLSLSPGERATLSCRASKGVSTSGYSYLHW

YQQKPGQAPRLLIYLASYLESGVPARFSGSGSGTDFTLT

ISSLEPEDFAVYYCQHSRDLPLTFGGGTKVEIK.
```

In some embodiments of the anti-PD-1 antibodies described herein, the heavy chain CDR sequences comprise the following:

```
a) CDR-H1
(NYYMY (SEQ ID NO: 17));

b) CDR-H2
(GINPSNGGTNFNEKFKN (SEQ ID NO: 18));
and c) CDR-H3
(RDYRFDMGFDY (SEQ ID NO: 19)).
```

In some embodiments of the anti-PD-1 antibodies described herein, the heavy chain FR sequences comprise the following:

```
a) HC-FR1
(QVQLVQSGVEVKKPGASVKV

SCKASGYTFT (SEQ ID NO: 23));

b) HC-FR2
(WVRQAPGQGLEWMG (SEQ ID NO: 24));

c) HC-FR3
(RVTLTTDSSTTTAYMELKS

LQFDDTAVYYCAR (SEQ ID NO: 25));
and d) HC-FR4
(WGQGTTVTVSS (SEQ ID NO: 26)).
```

In some embodiments of the anti-PD-1 antibodies described herein, the light chain CDR sequences comprise the following:

```
a) CDR-L1
(RASKGVSTSGYSYLH (SEQ ID NO: 20));

b) CDR-L2
(LASYLES (SEQ ID NO: 21));
and c) CDR-L3
(QHSRDLPLT (SEQ ID NO: 22)).
```

In some embodiments of the anti-PD-1 antibodies described herein, the light chain FR sequences comprise the following:

```
a) LC-FR1
(EIVLTQSPATLSLSPGERA

TLSC (SEQ ID NO: 27));

b) LC-FR2
(WYQQKPGQAPRLLIY (SEQ ID NO: 28));

c) LC-FR3
(GVPARFSGSGSGTDFTLTISSLEP

EDFAVYYC (SEQ ID NO: 29));
and d) LC-FR4
(FGGGTKVEIK (SEQ ID NO: 30)).
```

In some embodiments, provided herein is an anti-PD-1 antibody that binds to PD-1 (e.g., human PD-1), wherein the antibody comprises a heavy chain variable region and a light chain variable region, wherein the antibody comprises:

(a) heavy chain variable domain comprising:
(1) an HC-FR1 comprising the amino acid sequence of SEQ ID NO:23;
(2) an CDR-H1 comprising the amino acid sequence of SEQ ID NO:17;
(3) an HC-FR2 comprising the amino acid sequence of SEQ ID NO:24;
(4) an CDR-H2 comprising the amino acid sequence of SEQ ID NO:18;
(5) an HC-FR3 comprising the amino acid sequence of SEQ ID NO:25;
(6) an CDR-H3 comprising the amino acid sequence of SEQ ID NO:19; and
(7) an HC-FR4 comprising the amino acid sequence of SEQ ID NO:26,
and/or
(b) a light chain variable domain comprising:
(1) an LC-FR1 comprising the amino acid sequence of SEQ ID NO:27;
(2) an CDR-L1 comprising the amino acid sequence of SEQ ID NO:20;
(3) an LC-FR2 comprising the amino acid sequence of SEQ ID NO:28;
(4) an CDR-L2 comprising the amino acid sequence of SEQ ID NO:21;
(5) an LC-FR3 comprising the amino acid sequence of SEQ ID NO:29;
(6) an CDR-L3 comprising the amino acid sequence of SEQ ID NO:22; and
(7) an LC-FR4 comprising the amino acid sequence of SEQ ID NO:30.

In one aspect, provided herein is an anti-PD-1 antibody comprising a heavy chain variable domain comprising the amino acid sequence of SEQ ID NO:31 or comprising a light chain variable domain comprising the amino acid sequence of SEQ ID NO:32. In one aspect, provided herein is an anti-PD-1 antibody comprising a heavy chain variable domain comprising the amino acid sequence of SEQ ID NO:31 and comprising a light chain variable domain comprising the amino acid sequence of SEQ ID NO:32. In one aspect, provided herein is an anti-PD-1 antibody comprising the CDRs of the heavy chain variable domain comprising the amino acid sequence of SEQ ID NO:31 and comprising the CDRs of the light chain variable domain comprising the amino acid sequence of SEQ ID NO:32.

In some embodiments, provided herein is an anti-PD-1 antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:31. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:31 contains substitutions (e.g., conservative substitutions), insertions, or deletions relative to the reference sequence and retains the ability to bind to a PD-1 (e.g., human PD-1). In certain embodiments, a total of 1 to 10 amino acids have been substituted, inserted and/or deleted in SEQ ID NO:31. In certain embodiments, substitutions, insertions, or deletions (e.g., 1, 2, 3, 4, or 5 amino acids) occur in regions outside the CDRs (i.e., in the FRs). In some embodiments, the anti-PD-1 antibody comprises a heavy chain variable domain sequence of SEQ ID NO:31 including post-translational modifications of that sequence. In a particular embodiment, the heavy chain variable domain comprises: (a) CDR-H1 comprising the amino acid sequence of SEQ ID NO:17, (b) CDR-H2 comprising the amino acid sequence of SEQ ID NO:18, and (c) CDR-H3 comprising the amino acid sequence of SEQ ID NO:19.

In some embodiments, provided herein is an anti-PD-1 antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:32. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:32 contains substitutions (e.g., conservative substitutions), insertions, or deletions relative to the reference sequence and retains the ability to bind to a PD-1 (e.g., human PD-1). In certain embodiments, a total of 1 to 10 amino acids have been substituted, inserted and/or deleted in SEQ ID NO:32. In certain embodiments, substitutions, insertions, or deletions (e.g., 1, 2, 3, 4, or 5 amino acids) occur in regions outside the CDRs (i.e., in the FRs). In some embodiments, the anti-PD-1 antibody comprises a light chain variable domain sequence of SEQ ID NO:32 including post-translational modifications of that sequence. In a particular embodiment, the light chain variable domain comprises: (a) CDR-L1 comprising the amino acid sequence of SEQ ID NO:20, (b) CDR-L2 comprising the amino acid sequence of SEQ ID NO:21, and (c) CDR-L3 comprising the amino acid sequence of SEQ ID NO:22.

In some embodiments, the anti-PD-1 antibody comprises a heavy chain variable domain as in any of the embodiments provided above, and a light chain variable domain as in any of the embodiments provided above. In one embodiment, the antibody comprises the heavy chain variable domain sequence of SEQ ID NO:31 and the light chain variable domain sequence of SEQ ID NO:32, including post-translational modifications of those sequences.

In some embodiments, the anti-PD-1 antibody comprises: i) a heavy chain CDR1 comprising the amino acid sequence of SEQ ID NO: 17, a heavy chain CDR2 comprising the amino acid sequence of SEQ ID NO: 18, a heavy chain CDR3 comprising the amino acid sequence of SEQ ID NO: 19; and ii) a light chain CDR1 comprising the amino acid sequence of SEQ ID NO: 20, a light chain CDR2 comprising the amino acid sequence of SEQ ID NO: 21, and a light chain CDR3 comprising the amino acid sequence of SEQ ID NO: 22, wherein the CDRs of the anti-PD-1 antibody are generally defined by the Kabat numbering scheme.

In some embodiments, the anti-PD-1 antibody comprises: i) an amino acid sequence having at least 85% sequence identity to a heavy chain variable region comprising the amino acid sequence of SEQ ID NO: 31, and ii) an amino acid sequence having at least 85% sequence identity to a light chain variable region comprising the amino acid sequence of SEQ ID NO: 32.

In some embodiments, the anti-PD-1 antibody comprises a heavy chain comprising the amino acid sequence of (SEQ ID NO: 33)
QVQLVQSGVEVKKPGASVKVSCKASGYTFTNYYMY

WVRQAPGQGLEWMGGINPSNGGTNFNEKFKNRVTL

TTDSSTTTAYMELKSLQFDDTAVYYCARRDYRFDM

```
                                   -continued
    GFDYWGQGTTVTVSSASTKGPSVFPLAPCSRSTSE

STAALGCLVKDYFPEPVTVSWNSGALTSGVHTFPA

VLQSSGLYSLSSVVTVPSSSLGTKTYTCNVDHKPS

NTKVDKRVESKYGPPCPPCPAPEFLGGPSVFLFPP

KPKDTLMISRTPEVTCVVVDVSQEDPEVQFNWYVD

GVEVHNAKTKPREEQFNSTYRVVSVLTVLHQDWLN

GKEYKCKVSNKGLPSSIEKTISKAKGQPREPQVYT

LPPSQEEMTKNQVSLTCLVKGFYPSDIAVEWESNG

QPENNYKTTPPVLDSDGSFFLYSRLTVDKSRWQEG

NVFSCSVMHEALHNHYTQKSLSLSLG
    and a light chain comprising the amino
    acid sequence of
                                     (SEQ ID NO: 34)
    EIVLTQSPATLSLSPGERATLSCRASKGVSTSGYS

YLHWYQQKPGQAPRLLIYLASYLESGVPARFSGSG

SGTDFTLTISSLEPEDFAVYYCQHSRDLPLTFGGG

TKVEIKRTVAAPSVFIFPPSDEQLKSGTASVVCLL

NNFYPREAKVQWKVDNALQSGNSOESVTEQDSKDS

TYSLSSTLTLSKADYEKHKVYACEVTHQGLSSPVT

KSFNRGEC.
```

In some embodiments, provided herein is an anti-PD-1 antibody comprising a heavy chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:33. In certain embodiments, a heavy chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:33 contains substitutions (e.g., conservative substitutions), insertions, or deletions relative to the reference sequence and retains the ability to bind to a PD-1 (e.g., human PD-1). In certain embodiments, a total of 1 to 10 amino acids have been substituted, inserted and/or deleted in SEQ ID NO:33. In certain embodiments, substitutions, insertions, or deletions (e.g., 1, 2, 3, 4, or 5 amino acids) occur in regions outside the CDRs (i.e., in the FRs). In some embodiments, the anti-PD-1 antibody comprises a heavy chain sequence of SEQ ID NO:33 including post-translational modifications of that sequence. In a particular embodiment, the heavy chain comprises: (a) CDR-H1 comprising the amino acid sequence of SEQ ID NO:17, (b) CDR-H2 comprising the amino acid sequence of SEQ ID NO:18, and (c) CDR-H3 comprising the amino acid sequence of SEQ ID NO:19.

In some embodiments, provided herein is an anti-PD-1 antibody comprising a light chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:34. In certain embodiments, a light chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:34 contains substitutions (e.g., conservative substitutions), insertions, or deletions relative to the reference sequence and retains the ability to bind to a PD-1 (e.g., human PD-1). In certain embodiments, a total of 1 to 10 amino acids have been substituted, inserted and/or deleted in SEQ ID NO:34. In certain embodiments, substitutions, insertions, or deletions (e.g., 1, 2, 3, 4, or 5 amino acids) occur in regions outside the CDRs (i.e., in the FRs). In some embodiments, the anti-PD-1 antibody comprises a light chain sequence of SEQ ID NO:34 including post-translational modifications of that sequence. In a particular embodiment, the light chain comprises: (a) CDR-L1 comprising the amino acid sequence of SEQ ID NO:20, (b) CDR-L2 comprising the amino acid sequence of SEQ ID NO:21, and (c) CDR-L3 comprising the amino acid sequence of SEQ ID NO:22.

In some embodiments, the anti-PD-1 antibody comprises the CDRs of pembrolizumab and is a monoclonal antibody.

In some embodiments, the anti-PD-1 antibody is pembrolizumab, which is also known as antibody KEYTRUDA® as described in U.S. Pat. Nos. 8,354,509 and 8,900,587.

Anti-PD-1 antibodies of the invention comprising the CDRs of pembrolizumab may also be described or specified in terms of their binding affinity to PD-1 (e.g., human PD-1). Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

There are five classes of immunoglobulins: IgA, IgD, IgE, IgG and IgM, having heavy chains designated α, δ, ε, γ and μ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. *mAbs* Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

The antibodies also include derivatives that are modified, i.e., by the covalent attachment of any type of molecule to the antibody such that covalent attachment does not prevent the antibody from binding to PD-1. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

D. Nucleic Acids, Host Cells and Methods of Production

In some aspects, also provided herein are nucleic acids encoding an anti-TF antibody or antigen-binding fragment thereof as described herein or an anti-PD-1 antibody or antigen-binding fragment thereof as described herein. Further provided herein are vectors comprising the nucleic acids encoding an anti-TF antibody or antigen-binding fragment thereof as described herein or an anti-PD-1 antibody or antigen-binding fragment thereof as described herein. Further provided herein are host cells expressing the nucleic acids encoding an anti-TF antibody or antigen-binding fragment thereof as described herein or an anti-PD-1 antibody or antigen-binding fragment thereof as described herein. Further provided herein are host cells comprising the vectors comprising the nucleic acids encoding an anti-TF antibody or antigen-binding fragment thereof as described herein or an anti-PD-1 antibody or antigen-binding fragment thereof as described herein. Methods of producing an anti-TF antibody, linker and anti-TF antibody-drug conjugate are described in U.S. Pat. No. 9,168,314.

The anti-TF antibodies described herein or anti-PD-1 antibodies described herein may be prepared by well-known recombinant techniques using well known expression vector systems and host cells. In one embodiment, the antibodies are prepared in a CHO cell using the GS expression vector system as disclosed in De la Cruz Edmunds et al., 2006, *Molecular Biotechnology* 34; 179-190, EP216846, U.S. Pat. No. 5,981,216, WO 87/04462, EP323997, U.S. Pat. Nos. 5,591,639, 5,658,759, EP338841, U.S. Pat. Nos. 5,879,936, and 5,891,693.

After isolating and purifying the anti-TF antibodies from the cell media using well known techniques in the art, they are conjugated with monomethyl auristatin E via a linker as described in U.S. Pat. No. 9,168,314.

Monoclonal anti-TF antibodies described herein or anti-PD-1 antibodies described herein may e.g. be produced by the hybridoma method first described by Kohler et al., *Nature*, 256, 495 (1975), or may be produced by recombinant DNA methods. Monoclonal antibodies may also be isolated from phage antibody libraries using the techniques described in, for example, Clackson et al., *Nature*, 352, 624-628 (1991) and Marks et al., *J. Mol. Biol.*, 222(3):581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody (e.g., anti-TF antibody comprising the CDRs of tisotumab or anti-PD-1 antibody comprising the CDRs of pembrolizumab) of the invention is a human antibody. Human monoclonal antibodies directed against TF or PD-1 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci (Lonberg, N. et al., *Nature*, 368, 856-859 (1994)). Accordingly, the mice exhibit reduced expression of mouse IgM or K and in response to immunization, the introduced human heavy and light chain transgenes undergo class switching and somatic mutation to generate high affinity human IgG,κ monoclonal antibodies (Lonberg, N. et al. (1994). supra; reviewed in Lonberg, N. *Handbook of Experimental Pharmacology* 113, 49-101 (1994), Lonberg, N. and Huszar. D., *Intern. Rev. Immunol*, Vol. 13 65-93 (1995) and Harding, F. and Lonberg, N. *Ann, N.Y. Acad. Sci* 764:536-546 (1995)). The preparation of HuMAb mice is described in detail in Taylor, L. et al., *Nucleic Acids Research*. 20:6287-6295 (1992), Chen, J. et al., *International Immunology*. 5:647-656 (1993), Tuaillon at al., *J. Immunol*, 152:2912-2920 (1994), Taylor, L. et al., *International Immunology*, 6:579-591 (1994), Fishwild, D. et al., *Nature Biotechnology*, 14:845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al, *EMBO J*. 12:821-830 (1993)), a CMD disruption in their endogenous heavy chain genes (as described in Example 1 of WO 01/14424), a KCo5 human kappa light chain transgene (as described in Fishwild et al., *Nature Biotechnology*, 14:845-851 (1996)), and a HCo7 human heavy chain transgene (as described in U.S. Pat. No. 5,770,429).

The HCo12 mice have a JKD disruption in their endogenous light chain (kappa) genes (as described in Chen et al., *EMBO J*. 12:821-830 (1993)), a CMD disruption in their endogenous heavy chain genes (as described in Example 1 of WO 01/14424), a KCo5 human kappa light chain transgene (as described in Fishwild et al., *Nature Biotechnology*, 14:845-851 (1996)), and a HCo12 human heavy chain transgene (as described in Example 2 of WO 01/14424).

The HCo17 transgenic mouse strain (see also US 2010/0077497) was generated by coinjection of the 80 kb insert of pHC2 (Taylor et al. (1994) *Int. Immunol.*, 6:579-591), the Kb insert of pVX6, and a ~460 kb yeast artificial chromosome fragment of the yIgH24 chromosome. This line was designated (HCo17) 25950. The (HCo17) 25950 line was then bred with mice comprising the CMD mutation (described in Example 1 of PCT Publication WO 01109187), the JKD mutation (Chen et al, (1993) *EMBO J*. 12:811-820), and the (KC05) 9272 transgene (Fishwild et al. (1996) *Nature Biotechnology*, 14:845-851). The resulting mice express human immunoglobulin heavy and kappa light chain trans genes in a background homozygous for disruption of the endogenous mouse heavy and kappa light chain loci.

The HCo20 transgenic mouse strain is the result of a co-injection of minilocus 30 heavy chain transgene pHC2, the germline variable region (Vh)-containing YAC yIgH10, and the minilocus construct pVx6 (described in WO09097006). The (HCo20) line was then bred with mice comprising the CMD mutation (described in Example 1 of PCT Publication WO 01/09187), the JKD mutation (Chen et al. (1993) *EMBO J*. 12:811-820), and the (KC05) 9272 trans gene (Fishwild eta). (1996) *Nature Biotechnology*, 14:845-851). The resulting mice express human 10 immunoglobulin heavy and kappa light chain transgenes in a background homozygous for disruption of the endogenous mouse heavy and kappa light chain loci.

In order to generate HuMab mice with the salutary effects of the Balb/c strain, HuMab mice were crossed with KCO05 [MIK](Balb) mice which were generated by backcrossing the KC05 strain (as described in Fishwild et (1996) *Nature Biotechnology*, 14:845-851) to wild-type Balb/c mice to generate mice as described in WO09097006. Using this crossing Balb/c hybrids were created for HCo12, HCo17, and HCo20 strains.

In the KM mouse strain, the endogenous mouse kappa light chain gene has been homozygously disrupted as described in Chen et al, *EMBO J*. 12:811-820 (1993) and the endogenous mouse heavy chain gene has been homozygously disrupted as described in Example 1 of WO 01/09187, This mouse strain carries a human kappa light chain transgene, KCo5, as described in Fishwild et al., *Nature Biotechnology*, 14:845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well-known techniques. Human monoclonal or polyclonal antibodies of the invention, or antibodies of the invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

Further, human antibodies of the invention or antibodies of the invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (See for instance Hoogenboom et al., *J. Mol, Biol*. 227(2):381-388 (1992) (phage display), Vaughan et al., *Nature Biotech*, 14:309 (1996) (phage display), Hanes and Plucthau, *PNAS USA* 94:4937-4942 (1997) (ribosomal display), Parmley and Smith, *Gene*, 73:305-318 (1988) (phage display), Scott, *TIBS*. 17:241-245 (1992), Cwirla et al., *PNAS USA,* 87:6378-6382 (1990), Russel et al., *Nucl. Acids Research,* 21:1081-4085 (1993), Hogenboom et al., *Immunol, Reviews,* 130:43-68 (1992), Chiswell and McCafferty, TIBTECH, 10:80-84 (1992), and U.S. Pat. No. 5,733,743). If display technologies are utilized to produce antibodies that are not human, such antibodies may be humanized.

III. Binding Assays and Other Assays

In one aspect, an antibody of the invention is tested for its antigen binding activity, for example, by known methods such as Enzyme-Linked Immunosorbant Assay (ELISA), immunoblotting (e.g., Western blotting), flow cytometry (e.g., FACS™), immunohistochemistry, immunofluorescence, etc.

In another aspect, competition assays may be used to identify an antibody that competes with any one of the antibodies described herein for binding to TF (e.g., tisotumab) or PD-1 (e.g., pembrolizumab). Cross-competing antibodies can be readily identified based on their ability to cross-compete in standard TF or PD-1 binding assays such as Biacore analysis, ELISA assays or flow cytometry (See, e.g., WO 2013/173223). In certain embodiments, such a competing antibody binds to the same epitope (e.g., a linear or a conformational epitope) that is bound by any one of the antibodies disclosed herein (e.g., tisotumab or pembrolizumab,). Detailed exemplary methods for mapping an epitope to which an antibody binds are provided in Morris "Epitope Mapping Protocols," in Methods in Molecular Biology Vol. 66 (Humana Press, Totowa, NJ, 1996).

In an exemplary competition assay, immobilized PD-1 is incubated in a solution comprising a first labeled antibody that binds to PD-1 (e.g., pembrolizumab) and a second unlabeled antibody that is being tested for its ability to compete with the first antibody for binding to PD-1. The second antibody may be present in a hybridoma supernatant. As a control, immobilized PD-1 is incubated in a solution comprising the first labeled antibody but not the second unlabeled antibody. After incubation under conditions permissive for binding of the first antibody to PD-1, excess unbound antibody is removed, and the amount of label associated with immobilized PD-1 is measured. If the amount of label associated with immobilized PD-1 is substantially reduced in the test sample relative to the control sample, then that indicates that the second antibody is competing with the first antibody for binding to PD-1. See, e.g., Harlow et al. Antibodies: A Laboratory Manual. Ch. 14 (Cold Spring Harbor Laboratory, Cold Spring Harbor, NY, 1988). In some embodiments, an anti-PD-1 antibody competes for binding to PD-1 with another PD-1 antibody (e.g., pembrolizumab) if the antibody blocks binding of the other antibody to PD-1 in a competition assay by more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%. In some embodiments, an anti-PD-1 antibody does not compete for binding to PD-1 with another PD-1 antibody (e.g., pembrolizumab) if the antibody blocks binding of the other antibody to PD-1 in a competition assay by less than 20%, less than 15%, less than 10%, less than 9%, less than 8%, less than 7%, less than 6%, less than 5%, less than 4%, less than 3%, less than 2%, less than 1%. In some embodiments, the PD-1 is human PD-1.

Similar competition assays can be performed to determine if an anti-TF antibody competes with tisotumab for binding to TF. In some embodiments, an anti-TF antibody competes for binding to TF with another TF antibody (e.g., tisotumab) if the antibody blocks binding of the other antibody to TF in a competition assay by more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%. In some embodiments, an anti-TF antibody does not compete for binding to TF with another TF antibody (e.g., tisotumab) if the antibody blocks binding of the other antibody to TF in a competition assay by less than 20%, less than 15%, less than 10%, less than 9%, less than 8%, less than 7%, less than 6%, less than 5%, less than 4%, less than 3%, less than 2%, less than 1%. In some embodiments, the TF is human TF.

IV. Methods of Treatment

The invention provides methods for treating cancer in a subject with an anti-TF antibody-drug conjugate described herein and an anti-PD-1 antibody described herein. In one aspect, the antibody-drug conjugate is tisotumab vedotin. In one aspect, the anti-PD-1 antibody is pembrolizumab. In a particular embodiment, the subject is a human.

In another aspect the invention provides an antibody-drug conjugate that binds to TF for use in the treatment of cancer wherein the antibody-drug conjugate is for administration, or to be administered in combination with an anti-PD-1 antibody or an antigen-binding fragment thereof wherein the antibody-drug conjugate comprises an anti-TF antibody or an antigen-binding fragment thereof conjugated to monomethyl auristatin E, wherein the anti-PD-1 antibody or the antigen-binding fragment thereof inhibits PD-1 activity, wherein the anti-PD-1 antibody or antigen-binding fragment thereof comprises a heavy chain variable region and a light chain variable region, wherein the heavy chain variable region comprises:
(i) a CDR-H1 comprising the amino acid sequence of SEQ ID NO:17;
(ii) a CDR-H2 comprising the amino acid sequence of SEQ ID NO:18; and
(iii) a CDR-H3 comprising the amino acid sequence of SEQ ID NO:19; and
wherein the light chain variable region comprises:
(i) a CDR-L1 comprising the amino acid sequence of SEQ ID NO:20;
(ii) a CDR-L2 comprising the amino acid sequence of SEQ ID NO:21; and
(iii) a CDR-L3 comprising the amino acid sequence of SEQ ID NO:22, wherein the CDRs of the anti-PD-1 antibody or antigen-binding fragment thereof are generally defined by the Kabat numbering scheme,
and wherein the anti-TF antibody or antigen-binding fragment thereof comprises a heavy chain variable region and a light chain variable region, wherein the heavy chain variable region comprises:
(i) a CDR-H1 comprising the amino acid sequence of SEQ ID NO:1;
(ii) a CDR-H2 comprising the amino acid sequence of SEQ ID NO:2; and
(iii) a CDR-H3 comprising the amino acid sequence of SEQ ID NO:3; and
wherein the light chain variable region comprises:
(i) a CDR-L1 comprising the amino acid sequence of SEQ ID NO:4;
(ii) a CDR-L2 comprising the amino acid sequence of SEQ ID NO:5; and
(iii) a CDR-L3 comprising the amino acid sequence of SEQ ID NO:6, wherein the CDRs of the anti-TF antibody or antigen-binding fragment thereof are defined by the IMGT numbering scheme.

In another aspect the invention provides an anti-PD-1 antibody or an antigen-binding fragment thereof for use in the treatment of cancer wherein the anti-PD-1 antibody is for administration, or to be administered in combination with an antibody-drug conjugate that binds to TF wherein the antibody-drug conjugate comprises an anti-TF antibody or an antigen-binding fragment thereof conjugated to monomethyl auristatin E, and wherein the anti-PD-1 antibody or the antigen-binding fragment thereof inhibits PD-1 activity, wherein the anti-PD-1 antibody or antigen-binding fragment thereof comprises a heavy chain variable region and a light chain variable region, wherein the heavy chain variable region comprises:
(i) a CDR-H1 comprising the amino acid sequence of SEQ ID NO:17;
(ii) a CDR-H2 comprising the amino acid sequence of SEQ ID NO:18; and
(iii) a CDR-H3 comprising the amino acid sequence of SEQ ID NO:19; and
wherein the light chain variable region comprises:
(i) a CDR-L1 comprising the amino acid sequence of SEQ ID NO:20;
(ii) a CDR-L2 comprising the amino acid sequence of SEQ ID NO:21; and
(iii) a CDR-L3 comprising the amino acid sequence of SEQ ID NO:22, wherein the CDRs of the anti-PD-1 antibody or antigen-binding fragment thereof are generally defined by the Kabat numbering scheme,
and wherein the anti-TF antibody or antigen-binding fragment thereof comprises a heavy chain variable region and a light chain variable region, wherein the heavy chain variable region comprises:
(i) a CDR-H1 comprising the amino acid sequence of SEQ ID NO:1;
(ii) a CDR-H2 comprising the amino acid sequence of SEQ ID NO:2; and
(iii) a CDR-H3 comprising the amino acid sequence of SEQ ID NO:3; and
wherein the light chain variable region comprises:
(i) a CDR-L1 comprising the amino acid sequence of SEQ ID NO:4;
(ii) a CDR-L2 comprising the amino acid sequence of SEQ ID NO:5; and
(iii) a CDR-L3 comprising the amino acid sequence of SEQ ID NO:6, wherein the CDRs of the anti-TF antibody or antigen-binding fragment thereof are defined by the IMGT numbering scheme.

A. Breast Cancer

The 2014 World Cancer Report from WHO (The World health organization) reports that breast cancer is the second most common cancer worldwide, accounting for just over 1 million new cases annually. It states that in 2000 about 400,000 women died from breast cancer, representing 1.6 percent of all female deaths. The proportion of breast cancer deaths was far higher in the rich countries (2 percent of all female deaths) than in economically poor regions (0.5 percent). Thus, breast cancer is strongly related to the Western lifestyle. As developing countries succeed in achieving lifestyles similar to Europe, North America, Australia. New Zealand and Japan, they will also encounter much higher cancer rates, particularly cancers of the breast. Recent data supports this prediction and show a 20% increase in breast cancer from 2008 to 2012. (Carter D. "New global survey shows an increasing cancer burden". Am J Nurs. 2014 March; 114(3): 17).

In some aspects, the invention provides methods for treating breast cancer in a subject with an anti-TF antibody-drug conjugate described herein and an anti-PD-1 antibody described herein. In some embodiments, the breast cancer is ER+/HER2− breast cancer. In some embodiments, the breast cancer is triple negative breast cancer. In one aspect, the antibody-drug conjugate is tisotumab vedotin. In one aspect, the anti-PD-1 antibody is pembrolizumab. In a particular embodiment, the subject is a human.

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the breast cancer cells from the subject express TF. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of the breast cancer cells from the subject express TF. In some embodiments, the percentage of cells that express TF is determined using immunohistochemistry (IHC). In some embodiments, the percentage of cells that express TF is determined using flow cytometry. In some embodiments, the percentage of cells that express TF is determined using an enzyme-linked immunosorbent assay (ELISA).

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the breast cancer cells from the subject express PD-L1. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of the breast cancer cells from the subject express PD-L1. In some of any of the embodiments herein, the subject's tumor expresses PD-L1 with a tumor proportion score (TPS)≥1%. In some of embodiments herein, the subject's tumor has high PD-L1 expression (TPS≥50%). In some embodiments herein, the subject's tumor expresses PD-L1 with a combined positive score (CPS)≥1%. See US 2017/0285037. In some embodiments herein, the subject's tumor expresses PD-L1 with a combined positive score (CPS)≥10%. In some embodiments, the percentage of cells that express PD-L1 is determined using immunohistochemistry (IHC). In some embodiments, the percentage of cells that express PD-L1 is determined using flow cytometry. In some embodiments, the percentage of cells that express PD-L1 is determined using an enzyme-linked immunosorbent assay (ELISA).

In some embodiments, a tumor derived from the breast cancer comprises one or more cells that express PD-L1, PD-L2, or both PD-L1 and PD-L2.

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of T-cells from the subject express PD-1. In some embodiments, the percentage of cells that express PD-1 is determined using immunohistochemistry (IHC). In some embodiments, the percentage of cells that express PD-1 is determined using flow cytometry. In some embodiments, the percentage of cells that express PD-1 is determined using an enzyme-linked immunosorbent assay (ELISA).

B. Cervical Cancer

Cervical cancer remains to be one of the leading causes of cancer-related death in women despite advances in screening, diagnosis, prevention, and treatment. It accounts for ~4% of the total newly diagnosed cancer cases and 4% of the total cancer deaths. See Zhu et al., 2016, *Drug Des. Devel. Ther.* 10:1885-1895. Cervical cancer is the $7^{th}$ most common female cancer worldwide and the $16^{th}$ most common cancer in the European Union. Depending on the stage at initial presentation, cervical cancer will recur in 25-61% of women. See Tempfer et al., 2016, *Oncol. Res. Treat.* 39:525-533. In most cases, recurrent disease is diagnosed within 2 years of the initial treatment and may be observed in various sites. Chemotherapy is the standard treatment for these patients. See Zhu et al., 2016, *Drug Des. Devel. Ther.* 10:1885-1895. The median overall survival exceeds one year now, however, the five year relative survival for stage IV cervical cancer is only 15%, demonstrating the high need for improved methods of treating cervical cancer.

In some aspects, provided herein are methods for treating cervical cancer in a subject with an anti-TF antibody-drug conjugate described herein and an anti-PD-1 antibody described herein. In one aspect, the antibody-drug conjugate is tisotumab vedotin. In one aspect, the anti-PD-1 antibody is pembrolizumab. In some embodiments, the subject has not previously received prior systemic therapy for the cervical cancer. In some embodiments, chemotherapy is not considered a prior systemic therapy for the cervical cancer. In some embodiments, radiation therapy is not considered a prior systemic therapy for the cervical cancer. In some embodiments, chemotherapy in combination with radiation therapy is not considered a prior systemic therapy for the cervical cancer. In some embodiments, the subject has been previously treated with chemotherapy and/or radiation therapy. In some embodiments, the subject is not a candidate for curative therapy. In some embodiments, the curative therapy is radiotherapy and/or exenterative therapy. In some embodiments, the curative therapy is radiotherapy. In some embodiments, the curative therapy is exenterative therapy. In a particular embodiment, the subject is a human.

In some embodiments of the methods or uses or product for uses provided herein, the cervical cancer is an adenocarcinoma, an adenosquamous carcinoma, a squamous cell carcinoma, a small cell carcinoma, a neuroendocrine tumor, a glassy cell carcinoma or a villoglandular adenocarcinoma. In some embodiments, the cervical cancer is an adenocarcinoma, an adenosquamous carcinoma or a squamous cell carcinoma. In some embodiments, the cervical cancer is an adenocarcinoma. In some embodiments, the cervical cancer is an adenosquamous carcinoma. In some embodiments, the cervical cancer is a squamous cell carcinoma.

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells from the subject express TF. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of the cervical cancer cells from the subject express TF. In some embodiments, the percentage of cells that express TF is determined using immunohistochemistry (IHC). In some embodiments, the percentage of cells that express TF is determined using flow cytometry. In some embodiments, the percentage of cells that express TF is determined using an enzyme-linked immunosorbent assay (ELISA).

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells from the subject express PD-L1. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of the cervical cancer cells from the subject express PD-L1. In some of any of the embodiments herein, the subject's tumor expresses PD-L1 with a tumor proportion score (TPS)≥1%. In some embodiments herein, the subject's tumor has high PD-L1 expression (TPS≥50%). In some embodiments herein, the subject's tumor expresses PD-L1 with a combined positive score (CPS)≥1%. See US 2017/0285037. In some embodiments herein, the subject's tumor expresses PD-L1 with a combined positive score (CPS)≥10%. In some embodiments, the percentage of cells that express PD-L1 is determined using immunohistochemistry (IHC). In some embodiments, the percentage of cells that express PD-L1 is determined using flow cytometry. In some embodiments, the percentage of cells that express PD-L1 is determined using an enzyme-linked immunosorbent assay (ELISA).

In some embodiments, a tumor derived from the cervical cancer comprises one or more cells that express PD-L1, PD-L2, or both PD-L1 and PD-L2.

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of T-cells from the subject express PD-1. In some embodiments, the percentage of cells that express PD-1 is determined using immunohistochemistry (IHC). In some embodiments, the percentage of cells that express PD-1 is determined using flow cytometry. In some embodiments, the percentage of cells that express PD-1 is determined using an enzyme-linked immunosorbent assay (ELISA).

In some embodiments of the methods or uses or product for uses provided herein, the cervical cancer is a stage 0, 1, 2, 3, or 4 cervical cancer. In some embodiments, the cervical cancer is a stage 0, 1A, 1B, 2A, 2B, 3A, 3B, 4A or 4B cervical cancer. In some embodiments, the cervical cancer is staged by the International Federation of Gynecology and Obstetrics (FIGO) staging system. In some embodiments, the staging is based on clinical examination. In some embodiments, in stage 0 cervical cancer the carcinoma is confined to the surface layer (cells lining) the cervix. In some embodiments, in stage 1 cervical cancer the carcinoma has grown deeper into the cervix but has not yet spread beyond it. In some embodiments, in stage 1A cervical cancer the invasive carcinoma can be diagnosed only by microscopy and the deepest invasion is less than 5 mm and the largest extension is less than 7 mm. In some embodiments, in stage 1B cervical cancer the lesions are clinically visible and are limited to the cervix uteri. In some embodiments, in stage 2 cervical cancer the cervical carcinoma has invaded beyond the uterus, but not to the pelvic wall or to the lower third of the vagina. In some embodiments, in stage 2A cervical cancer there is no parametrial invasion. In some embodiments, in stage 2B cervical cancer there is parametrial invasion. In some embodiments, in stage 3 cervical cancer the tumor extends to the pelvic wall and/or involves the lower third of the vagina and/or causes hydronephrosis or non-functioning kidney. In some embodiments, in stage 3A cervical cancer the tumor involves the lower third of the vagina, with no extension to the pelvic wall. In some embodiments, in stage 3B cervical cancer extends to the pelvic wall and/or cause hydronephrosis or non-functioning kidney. In some embodiments, in stage 4 cervical cancer, the carcinoma has extended beyond the true pelvis or has involved the mucosa of the bladder or rectum. In some embodiments, in stage 4A cervical cancer the tumor has spread to adjacent organs. In some embodiments, in stage 4B cervical cancer the tumor has spread to distant organs. In some embodiments, the cervical cancer is an advanced stage cervical cancer. In some embodiments, the advanced stage cervical cancer is a grade 3 or grade 4 cervical cancer. In some embodiments, the advanced stage cervical cancer is metastatic cervical cancer. In some embodiments, the cervical cancer is metastatic and recurrent cervical cancer. In some embodiments, the cervical cancer is metastatic cervical cancer. In some embodiments, the cervical cancer is recurrent cervical cancer.

In some embodiments of the methods or uses or product for uses provided herein, the subject has not received prior systemic therapy for the cervical cancer. In some embodiments, chemotherapy is not considered a prior systemic therapy for the cervical cancer. In some embodiments, radiation therapy is not considered a prior systemic therapy for the cervical cancer. In some embodiments, chemotherapy in combination with radiation therapy is not considered a prior systemic therapy for the cervical cancer. In some embodiments, the subject has been previously treated with chemotherapy and/or radiation therapy. In some embodiments, the subject did not respond to the treatment with chemotherapy and radiation therapy. In some embodiments, the subject received treatment for the cervical cancer with chemotherapy and did not respond to the chemotherapy. In some embodiments, the subject received treatment for the cervical cancer with irradiation and did not respond to the irradiation. In some embodiments, the subject relapsed after treatment with chemotherapy and radiation therapy. In some embodiments, the subject received treatment for the cervical cancer with chemotherapy and relapsed after treatment with the chemotherapy. In some embodiments, the subject received treatment for the cervical cancer with irradiation and relapsed after treatment with irradiation. In some embodiments, the subject experienced disease progression after treatment with chemotherapy and/or radiation therapy. In some embodiments, the subject received treatment for the cervical cancer with chemotherapy and experienced disease progression after treatment with the chemotherapy. In some embodiments, the subject received treatment for the cervical cancer with irradiation and experienced disease progression after treatment with irradiation. In some embodiments, the subject has been previously treated for the cervical cancer with one or more therapeutic agents. In some embodiments, the subject has been previously treated with one or more therapeutic agents and did not respond to the treatment. In some embodiments, the subject has been previously treated with one or more therapeutic agents and relapsed after the treatment. In some embodiments, the subject has been previously treated with one or more therapeutic agents and experienced disease progression during treatment. In some embodiments, the one or more therapeutic agents is selected from the group consisting of a chemotherapeutic agent, pemetrexed, nab-paclitaxel, vinorelbine, bevacizumab, cisplatin, carboplatin, paclitaxel, topotecan, a combination of bevacizumab and paclitaxel, a combination of bevacizumab and cisplatin, a combination of bevacizumab and carboplatin, a combination of paclitaxel and topotecan, a combination of bevacizumab and topotecan, a combination of bevacizumab, cisplatin and paclitaxel, a combination of bevacizumab, carboplatin and paclitaxel, and a combination of bevacizumab, paclitaxel and topotecan. In some embodiments, the one or more therapeutic agents is a chemotherapeutic agent. In some embodiments, the one or more therapeutic agents is bevacizumab. In some embodiments, the one or more therapeutic agents is cisplatin, In some embodiments, the one or more therapeutic agents is carboplatin. In some embodiments, the one or more therapeutic agents is paclitaxel. In some embodiments, the one or more therapeutic agents is topotecan. In some embodiments, the one or more therapeutic agents is a combination of bevacizumab and paclitaxel. In some embodiments, the one or more therapeutic agents is a combination of bevacizumab and cisplatin. In some embodiments, the one or more therapeutic agents is a combination of bevacizumab and carboplatin. In some embodiments, the one or more therapeutic agents is a combination of paclitaxel and topotecan. In some embodiments, the one or more therapeutic agents is a combination of bevacizumab and topotecan. In some embodiments, the one or more therapeutic agents is a combination of bevacizumab, cisplatin and paclitaxel. In some embodiments, the one or more therapeutic agents is a combination of bevacizumab, carboplatin and paclitaxel. In some embodiments, the one or more therapeutic agents is a combination of bevacizumab, paclitaxel and topotecan. In some embodiments, the subject is not a candidate for curative therapy. In some embodiments, the curative therapy is radiotherapy and/or exenterative therapy. In some embodiments, the curative therapy is radiotherapy. In some embodiments, the curative therapy is exenterative therapy. In a particular embodiment, the subject is a human.

C. Routes of Administration

An anti-PD-1 antibody or antigen-binding fragment thereof described herein or anti-TF antibody-drug conjugate or antigen-binding fragment thereof described herein can be administered by any suitable route and mode. Suitable routes of administering antibodies and/or antibody-drug conjugate of the invention are well known in the art and may be selected by those of ordinary skill in the art. In one embodiment, the anti-PD-1 antibody described herein and/or anti-TF antibody-drug conjugate described herein are administered parenterally. Parenteral administration refers to modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In some embodiments, the route of administration of an anti-TF antibody-drug conjugate or antigen-binding fragment described herein is intravenous injection or infusion. In some embodiments, the route of administration of an anti-TF antibody-drug conjugate or antigen-binding fragment described herein is intravenous infusion. In some embodiments, the route of administration of an anti-PD-1 antibody or antigen-binding fragment described herein is intravenous injection or infusion. In some embodiments, the route of administration of an anti-PD-1 antibody or antigen-binding fragment described herein is intravenous infusion. In some embodiments, the route of administration of an anti-PD-1 antibody or antigen-binding fragment described herein is subcutaneous.

D. Dosage and Frequency of Administration

In one aspect, the invention provides for methods of treating a subject with cancer as described herein with a particular dose of an anti-TF antibody-drug conjugate or antigen-binding fragment thereof as described herein and an anti-PD-1 antibody or antigen-binding fragment thereof as described herein, wherein the subject is administered the antibody-drug conjugate or antigen-binding fragment thereof as described herein and the anti-PD-1 antibody or antigen-binding fragment thereof as described herein with particular frequencies.

In one embodiment of the methods or uses or product for uses provided herein, an anti-TF antibody-drug conjugate or antigen-binding fragment thereof as described herein is administered to the subject at a dose ranging from about 0.9 mg/kg to about 2.1 mg/kg of the subject's body weight. In certain embodiments, the dose is about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg or about 2.1 mg/kg. In some embodiments of the methods or uses or product for uses provided herein, an anti-TF antibody-drug conjugate or antigen-binding fragment thereof as described herein is administered to the subject at a dose ranging from 0.9 mg/kg to 2.1 mg/kg of the subject's body weight. In certain embodiments, the dose is 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg or 2.1 mg/kg. In one embodiment, the dose is about 2.0 mg/kg. In one embodiment, the dose is 2.0 mg/kg. In some embodiments, the dose is 2.0 mg/kg and the anti-TF antibody-drug conjugate is tisotumab vedotin. In one embodiment, the dose is about 1.3 mg/kg. In one embodiment, the dose is 1.3 mg/kg. In some embodiments, the dose is 1.3 mg/kg and the anti-TF antibody-drug conjugate is tisotumab vedotin. In some embodiments, for a subject weighing more than 100 kg, the dose of the anti-TF antibody-drug conjugate administered is the amount that would be administered if the subject weighed 100 kg. In some embodiments, for a subject weighing more than 100 kg, the dose of the anti-TF antibody-drug conjugate administered is 65 mg, 90 mg, 130 mg, or 200 mg.

In one embodiment of the methods or uses or product for uses provided herein, an anti-TF antibody-drug conjugate or antigen-binding fragment thereof as described herein is administered to the subject once about every 1 to 4 weeks. In certain embodiments, an anti-TF antibody-drug conjugate or antigen-binding fragment thereof as described herein is administered once about every 1 week, once about every 2 weeks, once about every 3 weeks or once about every 4 weeks. In one embodiment, an anti-TF antibody-drug conjugate or antigen-binding fragment thereof as described herein is administered once about every 3 weeks. In one embodiment, an anti-TF antibody-drug conjugate or antigen-binding fragment thereof as described herein is administered once every 3 weeks. In some embodiments, the dose is about 0.9 mg/kg and is administered once about every 1 week. In some embodiments, the dose is about 0.9 mg/kg and is administered once about every 2 weeks. In some embodiments, the dose is about 0.9 mg/kg and is administered once about every 3 weeks. In some embodiments, the dose is about 0.9 mg/kg and is administered once about every 4 weeks. In some embodiments, the dose is about 1.0 mg/kg and is administered once about every 1 week. In some embodiments, the dose is about 1.0 mg/kg and is administered once about every 2 weeks. In some embodiments, the dose is about 1.0 mg/kg and is administered once about every 3 weeks. In some embodiments, the dose is about 1.0 mg/kg and is administered once about every 4 weeks. In some embodiments, the dose is about 1.1 mg/kg and is administered once about every 1 week. In some embodiments, the dose is about 1.1 mg/kg and is administered once about every 2 weeks. In some embodiments, the dose is about 1.1 mg/kg and is administered once about every 3 weeks. In some embodiments, the dose is about 1.1 mg/kg and is administered once about every 4 weeks. In some embodiments, the dose is about 1.2 mg/kg and is administered once about every 1 week. In some embodiments, the dose is about 1.2 mg/kg and is administered once about every 2 weeks. In some embodiments, the dose is about 1.2 mg/kg and is administered once about every 3 weeks. In some embodiments, the dose is about 1.2 mg/kg and is administered once about every 4 weeks. In some embodiments, the dose is about 1.3 mg/kg and is administered once about every 1 week. In some embodiments, the dose is about 1.3 mg/kg and is administered once about every 2 weeks. In some embodiments, the dose is about 1.3 mg/kg and is administered once about every 3 weeks. In some embodiments, the dose is about 1.3 mg/kg and is administered once about every 4 weeks. In some embodiments, the dose is about 1.4 mg/kg and is administered once about every 1 week. In some embodiments, the dose is about 1.4 mg/kg and is administered once about every 2 weeks. In some embodiments, the dose is about 1.4 mg/kg and is administered once about every 3 weeks. In some embodiments, the dose is about 1.4 mg/kg and is administered once about every 4 weeks. In some embodiments, the dose is about 1.5 mg/kg and is administered once about every 1 week. In some embodiments, the dose is about 1.5 mg/kg and is administered once about every 2 weeks. In some embodiments, the dose is about 1.5 mg/kg and is administered once about every 3 weeks. In some embodiments, the dose is about 1.5 mg/kg and is administered once about every 4 weeks. In some embodiments, the dose is about 1.6 mg/kg and is administered once about every 1 week. In some embodiments, the dose is about 1.6 mg/kg and is administered once about every 2 weeks. In some embodiments, the dose is about 1.6 mg/kg and is administered once about every 3 weeks. In some embodiments, the dose is about 1.6 mg/kg and is administered once about every 4 weeks. In some embodiments, the dose is about 1.7 mg/kg and is administered once about every 1 week. In some embodiments, the dose is about 1.7 mg/kg and is administered once about every 2 weeks. In some embodiments, the dose is about 1.7 mg/kg and is administered once about every 3 weeks. In some embodiments, the dose is about 1.7 mg/kg and is administered once about every 4 weeks. In some embodiments, the dose is about 1.8 mg/kg and is administered once about every 1 week. In some embodiments, the dose is about 1.8 mg/kg and is administered once about every 2 weeks. In some embodiments, the dose is about 1.8 mg/kg and is administered once about every 3 weeks. In some embodiments, the dose is about 1.8 mg/kg and is administered once about every 4 weeks. In some embodiments, the dose is about 1.9 mg/kg and is administered once about every 1 week. In some embodiments, the dose is about 1.9 mg/kg and is administered once about every 2 weeks. In some embodiments, the dose is about 1.9 mg/kg and is administered once about every 3 weeks. In some embodiments, the dose is about 1.9 mg/kg and is administered once about every 4 weeks. In some embodiments, the dose is about 2.0 mg/kg and is administered once about every 1 week. In some embodiments, the dose is about 2.0 mg/kg and is administered once about every 2 weeks. In some embodiments, the dose is about 2.0 mg/kg and is administered once about every 3 weeks. In some embodiments, the dose is about 2.0 mg/kg and is administered once about every 4 weeks. In some embodiments, the dose is about 2.1 mg/kg and is administered once about every 1 week. In some embodiments, the dose is about 2.1 mg/kg and is administered once about every 2 weeks. In some embodiments, the dose is about 2.1 mg/kg and is administered once about every 3 weeks. In some embodiments, the dose is about 2.1 mg/kg and is administered once about every 4 weeks. In some embodiments, the dose is 0.9 mg/kg and is administered once about every 1 week. In some embodiments, the dose is 0.9 mg/kg and is administered once about every 2 weeks. In some embodiments, the dose is 0.9 mg/kg and is administered once about every 3 weeks. In some embodiments, the dose is 0.9 mg/kg and is administered once about every 4 weeks. In some embodiments, the dose is 1.0 mg/kg and is administered once about every 1 week. In some embodiments, the dose is 1.0 mg/kg and is administered once about every 2 weeks. In some embodiments, the dose is 1.0 mg/kg and is administered once about every 3 weeks. In some embodiments, the dose is 1.0 mg/kg and is administered once about every 4 weeks. In some embodiments, the dose is 1.1 mg/kg and is administered once about every 1 week. In some embodiments, the dose is 1.1 mg/kg and is administered once about every 2 weeks. In some embodiments, the dose is 1.1 mg/kg and is administered once about every 3 weeks. In some embodiments, the dose is 1.1 mg/kg and is administered once about every 4 weeks. In some embodiments, the dose is 1.2 mg/kg and is administered once about every 1 week. In some embodiments, the dose is 1.2 mg/kg and is administered once about every 2 weeks. In some embodiments, the dose is 1.2 mg/kg and is administered once about every 3 weeks. In some embodiments, the dose is 1.2 mg/kg and is administered once about every 4 weeks. In some embodiments, the dose is 1.3 mg/kg and is administered once about every 1 week. In some embodiments, the dose is 1.3 mg/kg and is administered once about every 2 weeks. In some embodiments, the dose is 1.3 mg/kg and is administered once about every 3 weeks. In some embodiments, the dose is 1.3 mg/kg and is administered once about every 4 weeks. In some embodiments, the dose is 1.4 mg/kg and is administered once about every 1 week. In some embodiments, the dose is 1.4 mg/kg and is administered once about every 2 weeks. In some embodiments, the dose is 1.4 mg/kg and is administered once about every 3 weeks. In some embodiments, the dose is 1.4 mg/kg and is administered once about every 4 weeks. In some embodiments, the dose is 1.5 mg/kg and is administered once about every 1 week. In some embodiments, the dose is 1.5 mg/kg and is administered once about every 2 weeks. In some embodiments, the dose is 1.5 mg/kg and is administered once about every 3 weeks. In some embodiments, the dose is 1.5 mg/kg and is administered once about every 4 weeks. In some embodiments, the dose is 1.6 mg/kg and is administered once about every 1 week. In some embodiments, the dose is 1.6 mg/kg and is administered once about every 2 weeks. In some embodiments, the dose is 1.6 mg/kg and is administered once about every 3 weeks. In some embodiments, the dose is 1.6 mg/kg and is administered once about every 4 weeks. In some embodiments, the dose is 1.7 mg/kg and is administered once about every 1 week. In some embodiments, the dose is 1.7 mg/kg and is administered once about every 2 weeks. In some embodiments, the dose is 1.7 mg/kg and is administered once about every 3 weeks. In some embodiments, the dose is 1.7 mg/kg and is administered once about every 4 weeks. In some embodiments, the dose is 1.8 mg/kg and is administered once about every 1 week. In some embodiments, the dose is 1.8 mg/kg and is administered once about every 2 weeks. In some embodiments, the dose is 1.8 mg/kg and is administered once about every 3 weeks. In some embodiments, the dose is 1.8 mg/kg and is administered once about every 4 weeks. In some embodiments, the dose is 1.9 mg/kg and is administered once about every 1 week. In some embodiments, the dose is 1.9 mg/kg and is administered once about every 2 weeks. In some embodiments, the dose is 1.9 mg/kg and is administered once about every 3 weeks. In some embodiments, the dose is 1.9 mg/kg and is administered once about every 4 weeks. In some embodiments, the dose is 2.0 mg/kg and is administered once about every 1 week. In some embodiments, the dose is 2.0 mg/kg and is administered once about every 2 weeks. In some embodiments, the dose is 2.0 mg/kg and is administered once about every 3 weeks. In some embodiments, the dose is 2.0 mg/kg and is administered once about every 4 weeks. In some embodiments, the dose is 2.1 mg/kg and is administered once about every 1 week. In some embodiments, the dose is 2.1 mg/kg and is administered once about every 2 weeks. In some embodiments, the dose is 2.1 mg/kg and is administered once about every 3 weeks. In some embodiments, the dose is 2.1 mg/kg and is administered once about every 4 weeks. In some embodiments, the dose is 2.0 mg/kg and is administered once about every 3 weeks (e.g., ±3 days). In some embodiments, the dose is 2.0 mg/kg and is administered once every 3 weeks. In some embodiments, the dose is 2.0 mg/kg and is administered once every 3 weeks and the antibody-drug conjugate is tisotumab vedotin. In some embodiments, the dose of the antibody-drug conjugate is modified if one or more adverse events occur. In some embodiments, the dose is 2.0 mg/kg and is administered once every 3 weeks and the antibody-drug conjugate is tisotumab vedotin and the dose is decreased to 1.3 mg/kg if one or more adverse events occur. In some embodiments, the dose is 1.3 mg/kg and is administered once every 3 weeks. In some embodiments, the dose is 1.3 mg/kg and is administered once every 3 weeks and the antibody-drug conjugate is tisotumab vedotin. In some embodiments, the dose is 1.3 mg/kg and is administered once every 3 weeks and the antibody-drug conjugate is tisotumab vedotin and the dose is decreased to 0.9 mg/kg if one or more adverse events occur.

In one embodiment of the methods or uses or product for uses provided herein, an anti-TF antibody-drug conjugate or antigen-binding fragment thereof as described herein is administered to the subject at a flat dose ranging from about 50 mg to about 200 mg such as at a flat dose of about 50 mg or a flat dose of about 60 mg or a flat dose of about 70 mg or a flat dose of about 80 mg or a flat dose of about 90 mg or a flat dose of about 100 mg or a flat dose of about 110 mg or a flat dose of about 120 mg or a flat dose of about 130 mg or a flat dose of about 140 mg or a flat dose of about 150 mg or a flat dose of about 160 mg or a flat dose of about 170 mg or a flat dose of about 180 mg or a flat dose of about 190 mg or a flat dose of about 200 mg. In some embodiments, the flat dose is administered to the subject once about every 1 to 4 weeks. In certain embodiments, the flat dose is administered to the subject once about every 1 week, once about every 2 weeks, once about every 3 weeks or once about every 4 weeks. In some embodiments, the flat dose is administered to the subject once about every 3 weeks (e.g., ±3 days). In some embodiments, the flat dose is administered to the subject once every 3 weeks. In some embodiments, the flat dose is administered to the subject once every 3 weeks and the antibody-drug conjugate is tisotumab vedotin.

In one embodiment of the methods or uses or product for uses provided herein, an anti-TF antibody-drug conjugate or antigen-binding fragment thereof as described herein is administered to the subject at a flat dose ranging from 50 mg to 200 mg such as at a flat dose of 50 mg or a flat dose of 60 mg or a flat dose of 70 mg or a flat dose of 80 mg or a flat dose of 90 mg or a flat dose of 100 mg or a flat dose of 110 mg or a flat dose of 120 mg or a flat dose of 130 mg or a flat dose of 140 mg or a flat dose of 150 mg or a flat dose of 160 mg or a flat dose of 170 mg or a flat dose of 180 mg or a flat dose of 190 mg or a flat dose of 200 mg. In some embodiments, the flat dose is administered to the subject once about every 1 to 4 weeks. In certain embodiments, the flat dose is administered to the subject once about every 1 week, once about every 2 weeks, once about every 3 weeks or once about every 4 weeks. In some embodiments, the flat dose is administered to the subject once about every 3 weeks (e.g., ±3 days). In some embodiments, the flat dose is administered to the subject once every 3 weeks. In some embodiments, the flat dose is administered to the subject once every 3 weeks and the antibody-drug conjugate is tisotumab vedotin.

In one embodiment of the methods or uses or product for uses provided herein, an anti-PD-1 antibody or antigen-binding fragment thereof as described herein is administered to the subject at flat dose ranging from about 50 mg to about 500 mg such as at a flat dose of about 50 mg or a flat dose of about 60 mg or a flat dose of about 70 mg or a flat dose of about 80 mg or a flat dose of about 90 mg or a flat dose of about 100 mg or a flat dose of about 120 mg or a flat dose of about 140 mg or a flat dose of about 160 mg or a flat dose of about 180 mg or a flat dose of about 200 mg or a flat dose of about 220 mg or a flat dose of about 240 mg or a flat dose of about 260 mg or a flat dose of about 280 mg or a flat dose of about 300 mg or a flat dose of about 320 mg or a flat dose of about 340 mg or a flat dose of about 360 mg or a flat dose of about 380 mg or a flat dose of about 400 mg or a flat dose of about 420 mg or a flat dose of about 440 mg or a flat dose of about 460 mg or a flat dose of about 480 mg or a flat dose of about 500 mg. In some embodiments, the flat dose is about 200 mg. In some embodiments of the methods or uses or product for uses provided herein, an anti-PD-1 antibody or antigen-binding fragment thereof as described herein is administered to the subject at flat dose ranging from 50 mg to 500 mg such as at a flat dose of 50 mg or a flat dose of 60 mg or a flat dose of 70 mg or a flat dose of 80 mg or a flat dose of 90 mg or a flat dose of 100 mg or a flat dose of 120 mg or a flat dose of 140 mg or a flat dose of 160 mg or a flat dose of 180 mg or a flat dose of 200 mg or a flat dose of 220 mg or a flat dose of 240 mg or a flat dose of 260 mg or a flat dose of 280 mg or a flat dose of 300 mg or a flat dose of 320 mg or a flat dose of 340 mg or a flat dose of 360 mg or a flat dose of 380 mg or a flat dose of 400 mg or a flat dose of 420 mg or a flat dose of 440 mg or a flat dose of 460 mg or a flat dose of 480 mg or a flat dose of 500 mg. In some embodiments, the flat dose is 200 mg. In some embodiments, the flat dose is 200 mg and the anti-PD-1 antibody is pembrolizumab. In some embodiments, the flat dose is 400 mg. In some embodiments, the flat dose is 400 mg and the anti-PD-1 antibody is pembrolizumab. In some embodiments, the flat dose is about 140 mg and is administered once about every 1 week. In some embodiments, the flat dose is about 140 mg and is administered once about every 2 weeks.

In some embodiments, the flat dose is about 140 mg and is administered once about every 3 weeks. In some embodiments, the flat dose is about 140 mg and is administered once about every 4 weeks. In some embodiments, the flat dose is about 160 mg and is administered once about every 1 week. In some embodiments, the flat dose is about 160 mg and is administered once about every 2 weeks. In some embodiments, the flat dose is about 160 mg and is administered once about every 3 weeks. In some embodiments, the flat dose is about 160 mg and is administered once about every 4 weeks. In some embodiments, the flat dose is about 180 mg and is administered once about every 1 week. In some embodiments, the flat dose is about 180 mg and is administered once about every 2 weeks. In some embodiments, the flat dose is about 180 mg and is administered once about every 3 weeks. In some embodiments, the flat dose is about 180 mg and is administered once about every 4 weeks. In some embodiments, the flat dose is about 200 mg and is administered once about every 1 week. In some embodiments, the flat dose is about 200 mg and is administered once about every 2 weeks. In some embodiments, the flat dose is about 200 mg and is administered once about every 3 weeks. In some embodiments, the flat dose is about 200 mg and is administered once about every 4 weeks. In some embodiments, the flat dose is about 220 mg and is administered once about every 1 week. In some embodiments, the flat dose is about 220 mg and is administered once about every 2 weeks. In some embodiments, the flat dose is about 220 mg and is administered once about every 3 weeks. In some embodiments, the flat dose is about 220 mg and is administered once about every 4 weeks. In some embodiments, the flat dose is about 240 mg and is administered once about every 1 week. In some embodiments, the dose is about 240 mg and is administered once about every 2 weeks. In some embodiments, the flat dose is about 240 mg and is administered once about every 3 weeks. In some embodiments, the flat dose is about 240 mg and is administered once about every 4 weeks. In some embodiments, the flat dose is about 260 mg and is administered once about every 1 week. In some embodiments, the flat dose is about 260 mg and is administered once about every 2 weeks. In some embodiments, the flat dose is about 260 mg and is administered once about every 3 weeks. In some embodiments, the flat dose is about 260 mg and is administered once about every 4 weeks. In some embodiments, the flat dose is about 360 mg and is administered once about every 1 week. In some embodiments, the flat dose is about 360 mg and is administered once about every 2 weeks. In some embodiments, the flat dose is about 360 mg and is administered once about every 3 weeks. In some embodiments, the flat dose is about 360 mg and is administered once about every 4 weeks. In some embodiments, the flat dose is about 360 mg and is administered once about every 5 weeks. In some embodiments, the flat dose is about 360 mg and is administered once about every 6 weeks. In some embodiments, the flat dose is about 400 mg and is administered once about every 1 week. In some embodiments, the flat dose is about 400 mg and is administered once about every 2 weeks. In some embodiments, the flat dose is about 400 mg and is administered once about every 3 weeks. In some embodiments, the flat dose is about 400 mg and is administered once about every 4 weeks. In some embodiments, the flat dose is about 400 mg and is administered once about every 5 weeks. In some embodiments, the flat dose is about 400 mg and is administered once about every 6 weeks. In some embodiments, the flat dose is about 440 mg and is administered once about every 1 week. In some embodiments, the flat dose is about 440 mg and is administered once about every 2 weeks. In some embodiments, the flat dose is about 440 mg and is administered once about every 3 weeks. In some embodiments, the flat dose is about 440 mg and is administered once about every 4 weeks. In some embodiments, the flat dose is about 440 mg and is administered once about every 5 weeks. In some embodiments, the flat dose is about 440 mg and is administered once about every 6 weeks. In some embodiments, the flat dose is 140 mg and is administered once about every 1 week. In some embodiments, the flat dose is 140 mg and is administered once about every 2 weeks. In some embodiments, the flat dose is 140 mg and is administered once about every 3 weeks. In some embodiments, the flat dose is 140 mg and is administered once about every 4 weeks. In some embodiments, the flat dose is 160 mg and is administered once about every 1 week. In some embodiments, the flat dose is 160 mg and is administered once about every 2 weeks. In some embodiments, the flat dose is 160 mg and is administered once about every 3 weeks. In some embodiments, the flat dose is 160 mg and is administered once about every 4 weeks. In some embodiments, the flat dose is 180 mg and is administered once about every 1 week. In some embodiments, the flat dose is 180 mg and is administered once about every 2 weeks. In some embodiments, the flat dose is 180 mg and is administered once about every 3 weeks. In some embodiments, the flat dose is 180 mg and is administered once about every 4 weeks. In some embodiments, the flat dose is 200 mg and is administered once about every 1 week. In some embodiments, the flat dose is 200 mg and is administered once about every 2 weeks. In some embodiments, the flat dose is 200 mg and is administered once about every 3 weeks. In some embodiments, the flat dose is 200 mg and is administered once about every 4 weeks. In some embodiments, the flat dose is 220 mg and is administered once about every 1 week. In some embodiments, the flat dose is 220 mg and is administered once about every 2 weeks. In some embodiments, the flat dose is 220 mg and is administered once about every 3 weeks. In some embodiments, the flat dose is 220 mg and is administered once about every 4 weeks. In some embodiments, the flat dose is 240 mg and is administered once about every 1 week. In some embodiments, the flat dose is 240 mg and is administered once about every 2 weeks. In some embodiments, the flat dose is 240 mg and is administered once about every 3 weeks. In some embodiments, the flat dose is 240 mg and is administered once about every 4 weeks. In some embodiments, the flat dose is 260 mg and is administered once about every 1 week. In some embodiments, the flat dose is 260 mg and is administered once about every 2 weeks. In some embodiments, the flat dose is 260 mg and is administered once about every 3 weeks. In some embodiments, the flat dose is 260 mg and is administered once about every 4 weeks. In some embodiments, the flat dose is 360 mg and is administered once about every 1 week. In some embodiments, the flat dose is 360 mg and is administered once about every 2 weeks. In some embodiments, the flat dose is 360 mg and is administered once about every 3 weeks. In some embodiments, the flat dose is 360 mg and is administered once about every 4 weeks. In some embodiments, the flat dose is 360 mg and is administered once about every 5 weeks. In some embodiments, the flat dose is 360 mg and is administered once about every 6 weeks. In some embodiments, the flat dose is 400 mg and is administered once about every 1 week. In some embodiments, the flat dose is 400 mg and is administered once about every 2 weeks. In some embodiments, the flat dose is 400 mg and is administered once about every 3 weeks. In some embodiments, the flat dose is 400 mg and is administered once about every 4 weeks. In some embodiments, the flat dose is 400 mg and is administered once about every 5 weeks. In some embodiments, the flat dose is 400 mg and is administered once about every 6 weeks. In some embodiments, the flat dose is 440 mg and is administered once about every 1 week. In some embodiments, the flat dose is 440 mg and is administered once about every 2 weeks. In some embodiments, the flat dose is 440 mg and is administered once about every 3 weeks. In some embodiments, the flat dose is 440 mg and is administered once about every 4 weeks. In some embodiments, the flat dose is 440 mg and is administered once about every 5 weeks. In some embodiments, the flat dose is 440 mg and is administered once about every 6 weeks. In some embodiments, the flat dose is 200 mg and is administered once about every 3 weeks (e.g., ±3 days). In some embodiments, the flat dose is 200 mg and is administered once every 3 weeks. In some embodiments, the flat dose is 200 mg and is administered once every 3 weeks and the antibody is pembrolizumab. In some embodiments, the flat dose is 400 mg and is administered once about every 6 weeks (e.g., ±6 days). In some embodiments, the flat dose is 400 mg and is administered once every 6 weeks. In some embodiments, the flat dose is 400 mg and is administered once every 6 weeks and the antibody is pembrolizumab.

In some embodiments of the methods or uses or product for uses provided herein, an anti-PD-1 antibody or antigen-binding fragment thereof as described herein and an anti-TF antibody-drug conjugate or antigen-binding fragment thereof as described herein are administered to the subject at a fixed dose. In some embodiments, the fixed dose is based on the amount (e.g., mg) of the antibodies. In certain embodiments, the fixed dose is based on the concentration (e.g., mg/ml) of the antibodies. In some embodiments, the ratio of the amount (e.g., mg) of the anti-PD-1 antibody or antigen-binding fragment thereof as described herein to the amount (e.g., mg) of the anti-TF antibody-drug conjugate or antigen-binding fragment thereof as described herein is about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1. In some embodiments, the ratio of the amount (e.g., mg) of the anti-PD-1 antibody or antigen-binding fragment thereof as described herein to the amount (e.g., mg) of the anti-TF antibody-drug conjugate or antigen-binding fragment thereof as described herein is 1:1, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90, 1:100, 1:120, 1:140, 1:160, 1:180, 1:200, 200:1, 180:1, 160:1, 140:1, 120:1, 100:1, 90:1, 80:1, 70:1, 60:1, 50:1, 40:1, 30:1, 20:1, 15:1, 10:1, 9:1, 8:1, 7:1, 6:1, 5:1, 4:1, 3:1, or 2:1. In some embodiments, the ratio of the concentration (e.g., mg/ml) of the anti-PD-1 antibody or antigen-binding fragment thereof as described herein to the concentration (e.g., mg/ml) of the anti-TF antibody-drug conjugate or antigen-binding fragment thereof as described herein is about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1. In some embodiments, the ratio of the concentration (e.g., mg/ml) of the anti-PD-1 antibody or antigen-binding fragment thereof described herein to the concentration (e.g., mg/ml) of the anti-TF antibody-drug conjugate or antigen-binding fragment thereof described herein is 1:1, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90, 1:100, 1:120, 1:140, 1:160, 1:180, 1:200, 200:1, 180:1, 160:1, 140:1, 120:1, 100:1, 90:1, 80:1, 70:1, 60:1, 50:1, 40:1, 30:1, 20:1, 15:1, 10:1, 9:1, 8:1, 7:1, 6:1, 5:1, 4:1, 3:1, or 2:1.

In some embodiments, the dose of the anti-TF antibody-drug conjugate described herein is 2.0 mg/kg and is administered once about every 3 weeks (e.g., ±3 days) and the dose of the anti-PD-1 antibody described herein is 200 mg and is administered once about every 3 weeks (e.g., ±3 days). In some embodiments, the dose of the anti-TF antibody-drug conjugate described herein is 2.0 mg/kg and is administered once every 3 weeks and the dose of the anti-PD-1 antibody described herein is 200 mg and is administered once every 3 weeks. In some embodiments, the dose of the anti-TF antibody-drug conjugate is 2.0 mg/kg and is administered once every 3 weeks and the antibody-drug conjugate is tisotumab vedotin and the dose of the anti-PD-1 antibody is 200 mg and is administered once every 3 weeks and the anti-PD-1 antibody is pembrolizumab.

In some embodiments, the dose of the anti-TF antibody-drug conjugate described herein is 2.0 mg/kg and is administered once about every 3 weeks (e.g., ±3 days) and the dose of the anti-PD-1 antibody described herein is 400 mg and is administered once about every 6 weeks (e.g., ±6 days). In some embodiments, the dose of the anti-TF antibody-drug conjugate described herein is 2.0 mg/kg and is administered once every 3 weeks and the dose of the anti-PD-1 antibody described herein is 400 mg and is administered once every 6 weeks. In some embodiments, the dose of the anti-TF antibody-drug conjugate is 2.0 mg/kg and is administered once every 3 weeks and the antibody-drug conjugate is tisotumab vedotin and the dose of the anti-PD-1 antibody is 400 mg and is administered once every 6 weeks and the anti-PD-1 antibody is pembrolizumab.

In some embodiments, the dose of the anti-TF antibody-drug conjugate described herein is 1.3 mg/kg and is administered once about every 3 weeks (e.g., ±3 days) and the dose of the anti-PD-1 antibody described herein is 200 mg and is administered once about every 3 weeks (e.g., ±3 days). In some embodiments, the dose of the anti-TF antibody-drug conjugate described herein is 1.3 mg/kg and is administered once every 3 weeks and the dose of the anti-PD-1 antibody described herein is 200 mg and is administered once every 3 weeks. In some embodiments, the dose of the anti-TF antibody-drug conjugate is 1.3 mg/kg and is administered once every 3 weeks and the antibody-drug conjugate is tisotumab vedotin and the dose of the anti-PD-1 antibody is 200 mg and is administered once every 3 weeks and the anti-PD-1 antibody is pembrolizumab.

In some embodiments, the dose of the anti-TF antibody-drug conjugate described herein is 1.3 mg/kg and is administered once about every 3 weeks (e.g., ±3 days) and the dose of the anti-PD-1 antibody described herein is 400 mg and is administered once about every 6 weeks (e.g., ±6 days). In some embodiments, the dose of the anti-TF antibody-drug conjugate described herein is 1.3 mg/kg and is administered once every 3 weeks and the dose of the anti-PD-1 antibody described herein is 400 mg and is administered once every 6 weeks. In some embodiments, the dose of the anti-TF antibody-drug conjugate is 1.3 mg/kg and is administered once every 3 weeks and the antibody-drug conjugate is tisotumab vedotin and the dose of the anti-PD-1 antibody is 400 mg and is administered once every 6 weeks and the anti-PD-1 antibody is pembrolizumab.

In some embodiments, an anti-TF antibody-drug conjugate or antigen-binding fragment thereof as described herein and an anti-PD-1 antibody or antigen-binding fragment thereof as described herein are coadministered. In some embodiments the coadministration is simultaneous or sequential. In some embodiments, an anti-TF antibody-drug conjugate as described herein is administered simultaneously with an anti-PD-1 antibody as described herein. In some embodiments, simultaneous means that the anti-TF antibody-drug conjugate as described herein and the anti-PD-1 antibody as described herein are administered to the subject less than about one hour apart, such as less than about 30 minutes apart, less than about 15 minutes apart, less than about 10 minutes apart or less than about 5 minutes apart. In some embodiments, simultaneous means that the anti-TF antibody-drug conjugate as described herein and the anti-PD-1 antibody as described herein are administered to the subject less than one hour apart, such as less than 30 minutes apart, less than 15 minutes apart, less than 10 minutes apart or less than 5 minutes apart. In some embodiments, an anti-TF antibody-drug conjugate as described herein is administered sequentially with an anti-PD-1 antibody as described herein. In some embodiments, sequential administration means that the anti-TF antibody-drug conjugate as described herein and the anti-PD-1 antibody as described herein are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart.

In some embodiments, a method of treatment or use described herein further comprises the administration of one or more additional therapeutic agents. In some embodiments, the one or more additional therapeutic agents are administered simultaneously with an anti-TF antibody-drug conjugate or antigen-binding fragment thereof as described herein, such as tisotumab vedotin, and an anti-PD-1 antibody or antigen-binding fragment thereof as described herein, such as pembrolizumab. In some embodiments, the one or more additional therapeutic agents and an anti-TF antibody-drug conjugate or antigen-binding fragment thereof as described herein and an anti-PD-1 antibody or antigen-binding fragment thereof as described herein are administered sequentially.

E. Treatment Outcome

In one aspect, a method of treating cancer with an anti-TF antibody-drug conjugate or antigen-binding fragment thereof as described herein and an anti-PD-1 antibody or antigen-binding fragment thereof as described herein results in an improvement in one or more therapeutic effects in the subject after administration of the antibody-drug conjugate relative to a baseline. In some embodiments, the one or more therapeutic effects is the size of the tumor derived from the cancer (e.g., breast cancer or cervical cancer), the objective response rate, the duration of response, the time to response, progression free survival, overall survival, or any combination thereof. In one embodiment, the one or more therapeutic effects is the size of the tumor derived from the cancer. In one embodiment, the one or more therapeutic effects is decreased tumor size. In one embodiment, the one or more therapeutic effects is stable disease. In one embodiment, the one or more therapeutic effects is partial response. In one embodiment, the one or more therapeutic effects is complete response. In one embodiment, the one or more therapeutic effects is the objective response rate. In one embodiment, the one or more therapeutic effects is the duration of response. In one embodiment, the one or more therapeutic effects is the time to response. In one embodiment, the one or more therapeutic effects is progression free survival. In one embodiment, the one or more therapeutic effects is overall survival. In one embodiment, the one or more therapeutic effects is cancer regression.

In one embodiment of the methods or uses or product for uses provided herein, response to treatment with an anti-TF antibody-drug conjugate or antigen-binding fragment thereof as described herein and an anti-PD-1 antibody or antigen-binding fragment thereof as described herein may include the following criteria (RECIST Criteria 1.1):

| | Category | Criteria |
|---|---|---|
| Based on target lesions | Complete Response (CR) | Disappearance of all target lesions. Any pathological lymph nodes must have reduction in short axis to <10 mm. |
| | Partial Response (PR) | >30% decrease in the sum of the longest diameter (LD) of target lesions, taking as reference the baseline sum of LDs. |
| | Stable Disease (SD) | Neither sufficient shrinkage to qualify for PR nor sufficient increase to qualify for PD, taking as reference the smallest sum of LDs while in trial. |
| | Progressive Disease (PD) | >20% (and >5 mm) increase in the sum of the LDs of target lesions, taking as reference the smallest sum of the target LDs recorded while in trial or the appearance of one or more new lesions. |
| Based on non-target lesions | CR | Disappearance of all non-target lesions and normalization of tumor marker level. All lymph nodes must be non-pathological in size (<10 mm short axis). |
| | SD | Persistence of one or more non-target lesion(s) or/and maintenance of tumor marker level above the normal limits. |
| | PD | Appearance of one or more new lesions and/or unequivocal progression of existing non-target lesions. |

In one embodiment of the methods or uses or product for uses provided herein, the effectiveness of treatment with an anti-TF antibody-drug conjugate or antigen-binding fragment thereof described herein and an anti-PD-1 antibody or antigen-binding fragment thereof described herein is assessed by measuring the objective response rate. In some embodiments, the objective response rate is the proportion of patients with tumor size reduction of a predefined amount and for a minimum period of time. In some embodiments the objective response rate is based upon RECIST v1.1. In one embodiment, the objective response rate is at least about 20%, at least about 25%, at least about 30%, at least about 35%, at least about 40%, at least about 45%, at least about 50%, at least about 60%, at least about 70%, or at least about 80%. In one embodiment, the objective response rate is at least about 20%-80%. In one embodiment, the objective response rate is at least about 30%-80%. In one embodiment, the objective response rate is at least about 40%-80%. In one embodiment, the objective response rate is at least about 50%-80%. In one embodiment, the objective response rate is at least about 60%-80%. In one embodiment, the objective response rate is at least about 70%-80%. In one embodiment, the objective response rate is at least about 80%. In one embodiment, the objective response rate is at least about 85%. In one embodiment, the objective response rate is at least about 90%. In one embodiment, the objective response rate is at least about 95%. In one embodiment, the objective response rate is at least about 98%. In one embodiment, the objective response rate is at least about 99%. In one embodiment, the objective response rate is at least 20%, at least 25%, at least 30%, at least 35%, at least 40%, at least 45%, at least 50%, at least 60%, at least 70%, or at least 80%. In one embodiment, the objective response rate is at least 20%-80%. In one embodiment, the objective response rate is at least 30%-80%. In one embodiment, the objective response rate is at least 40%-80%. In one embodiment, the objective response rate is at least 50%-80%. In one embodiment, the objective response rate is at least 60%-80%. In one embodiment, the objective response rate is at least 70%-80%. In one embodiment, the objective response rate is at least 80%. In one embodiment, the objective response rate is at least 85%. In one embodiment, the objective response rate is at least 90%. In one embodiment, the objective response rate is at least 95%. In one embodiment, the objective response rate is at least 98%. In one embodiment, the objective response rate is at least 99%. In one embodiment, the objective response rate is 100%.

In one embodiment of the methods or uses or product for uses provided herein, response to treatment with an anti-TF antibody-drug conjugate or antigen-binding fragment thereof described herein and an anti-PD-1 antibody or antigen-binding fragment thereof described herein is assessed by measuring the size of a tumor derived from the cancer (e.g., breast cancer or cervical cancer). In one embodiment, the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the anti-TF antibody-drug conjugate described herein and/or the anti-PD-1 antibody described herein. In one embodiment, the size of a tumor derived from the cancer is reduced by at least about 10%-80%. In one embodiment, the size of a tumor derived from the cancer is reduced by at least about 20%-80%. In one embodiment, the size of a tumor derived from the cancer is reduced by at least about 30%-80%. In one embodiment, the size of a tumor derived from the cancer is reduced by at least about 40%-80%. In one embodiment, the size of a tumor derived from the cancer is reduced by at least about 50%-80%. In one embodiment, the size of a tumor derived from the cancer is reduced by at least about 60%-80%. In one embodiment, the size of a tumor derived from the cancer is reduced by at least about 70%-80%. In one embodiment, the size of a tumor derived from the cancer is reduced by at least about 80%. In one embodiment, the size of a tumor derived from the cancer is reduced by at least about 85%. In one embodiment, the size of a tumor derived from the cancer is reduced by at least about 90%. In one embodiment, the size of a tumor derived from the cancer is reduced by at least about 95%. In one embodiment, the size of a tumor derived from the cancer is reduced by at least about 98%. In one embodiment, the size of a tumor derived from the cancer is reduced by at least about 99%. In one embodiment, the size of a tumor derived from the cancer is reduced by at least 10%, at least 15%, at least 20%, at least 25%, at least 30%, at least 35%, at least 40%, at least 45%, at least 50%, at least 60%, at least 70%, or at least 80% relative to the size of the tumor derived from the cancer before administration of the anti-TF antibody-drug conjugate described herein and/or the anti-PD-1 antibody described herein. In one embodiment, the size of a tumor derived from the cancer is reduced by at least 10%-80%. In one embodiment, the size of a tumor derived from the cancer is reduced by at least 20%-80%. In one embodiment, the size of a tumor derived from the cancer is reduced by at least 30%-80%. In one embodiment, the size of a tumor derived from the cancer is reduced by at least 40%-80%. In one embodiment, the size of a tumor derived from the cancer is reduced by at least 50%-80%. In one embodiment, the size of a tumor derived from the cancer is reduced by at least 60%-80%. In one embodiment, the size of a tumor derived from the cancer is reduced by at least 70%-80%. In one embodiment, the size of a tumor derived from the cancer is reduced by at least 80%. In one embodiment, the size of a tumor derived from the cancer is reduced by at least 85%. In one embodiment, the size of a tumor derived from the cancer is reduced by at least 90%. In one embodiment, the size of a tumor derived from the cancer is reduced by at least 95%. In one embodiment, the size of a tumor derived from the cancer is reduced by at least 98%. In one embodiment, the size of a tumor derived from the cancer is reduced by at least 99%. In one embodiment, the size of a tumor derived from the cancer is reduced by 100%. In one embodiment, the size of a tumor derived from the cancer is measured by magnetic resonance imaging (MRI). In one embodiment, the size of a tumor derived from the cancer is measured by computed tomography (CT). In some embodiments, the size of a tumor derived from a cervical cancer is measured by pelvic examination. See Choi et al., 2008, *J. Gynecol. Oncol.* 19(3):205. In some embodiments, the size of a tumor derived from a breast cancer is measured by mammography, sonography or magnetic resonance imaging (MRI). See Gruber et. al., 2013, *BMC Cancer.* 13:328. In some embodiments, the size of the tumor derived from the cancer is reduced relative to the size of the tumor before administration of the anti-TF antibody drug conjugate described herein and the anti-PD-1 antibody described herein. In some embodiments, the size of the tumor derived from the cancer is reduced relative to the size of the tumor before administration of the anti-TF antibody drug conjugate described herein. In some embodiments, the size of the tumor derived from the cancer is reduced relative to the size of the tumor before administration of the anti-PD-1 antibody described herein.

In one embodiment of the methods or uses or product for uses provided described herein, response to treatment with an antibody-drug conjugate or antigen-binding fragment thereof described herein, such as e.g., tisotumab vedotin, and an anti-PD-1 antibody or antigen-binding fragment thereof described herein, such as e.g., pembrolizumab, promotes regression of a tumor derived from the cancer (e.g., breast cancer or cervical cancer). In one embodiment, a tumor derived from the cancer regresses by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the anti-TF antibody-drug conjugate described herein and/or anti-PD-1 antibody described herein. In one embodiment, a tumor derived from the cancer regresses by at least about 10% to about 80%. In one embodiment, a tumor derived from the cancer regresses by at least about 20% to about 80%. In one embodiment, a tumor derived from the cancer regresses by at least about 30% to about 80%. In one embodiment, a tumor derived from the cancer regresses by at least about 40% to about 80%. In one embodiment, a tumor derived from the cancer regresses by at least about 50% to about 80%. In one embodiment, a tumor derived from the cancer regresses by at least about 60% to about 80%. In one embodiment, a tumor derived from the cancer regresses by at least about 70% to about 80%. In one embodiment, a tumor derived from the cancer regresses by at least about 80%. In one embodiment, a tumor derived from the cancer regresses by at least about 85%. In one embodiment, a tumor derived from the cancer regresses by at least about 90%. In one embodiment, a tumor derived from the cancer regresses by at least about 95%. In one embodiment, a tumor derived from the cancer regresses by at least about 98%. In one embodiment, a tumor derived from the cancer regresses by at least about 99%. In one embodiment, a tumor derived from the cancer regresses by at least 10%, at least 15%, at least 20%, at least 25%, at least 30%, at least 35%, at least 40%, at least 45%, at least 50%, at least 60%, at least 70%, or at least 80% relative to the size of the tumor derived from the cancer before administration of the anti-TF antibody-drug conjugate described herein and/or anti-PD-1 antibody described herein. In one embodiment, a tumor derived from the cancer regresses by at least 10% to 80%. In one embodiment, a tumor derived from the cancer regresses by at least 20% to 80%. In one embodiment, a tumor derived from the cancer regresses by at least 30% to 80%. In one embodiment, a tumor derived from the cancer regresses by at least 40% to 80%. In one embodiment, a tumor derived from the cancer regresses by at least 50% to 80%. In one embodiment, a tumor derived from the cancer regresses by at least 60% to 80%. In one embodiment, a tumor derived from the cancer regresses by at least 70% to 80%. In one embodiment, a tumor derived from the cancer regresses by at least 80%. In one embodiment, a tumor derived from the cancer regresses by at least 85%. In one embodiment, a tumor derived from the cancer regresses by at least 90%. In one embodiment, a tumor derived from the cancer regresses by at least 95%. In one embodiment, a tumor derived from the cancer regresses by at least 98%. In one embodiment, a tumor derived from the cancer regresses by at least 99%. In one embodiment, a tumor derived from the cancer regresses by 100%. In one embodiment, regression of a tumor is determined by measuring the size of the tumor by magnetic resonance imaging (MRI). In one embodiment, regression of a tumor is determined by measuring the size of the tumor by computed tomography (CT). In some embodiments, regression of a tumor is determined by measuring the size of the tumor by pelvic examination. See Choi et al., 2008, *J. Gynecol. Oncol.* 19(3):205. In some embodiments, regression of a tumor is determined by mammography, sonography or magnetic resonance imaging (MRI). See Gruber et. al., 2013, *BMC Cancer.* 13:328. In some embodiments, the tumor derived from the cancer regresses relative to the size of the tumor before administration of the anti-TF antibody drug conjugate described herein and the anti-PD-1 antibody described herein. In some embodiments, the tumor derived from the cancer regresses relative to the size of the tumor before administration of the anti-TF antibody drug conjugate described herein. In some embodiments, the tumor derived from the cancer regresses relative to the size of the tumor before administration of the anti-PD-1 antibody described herein.

In one embodiment of the methods or uses or product for uses described herein, response to treatment with an anti-TF antibody-drug conjugate or antigen-binding fragment thereof described herein and an anti-PD-1 antibody or antigen-binding fragment thereof described herein is assessed by measuring the time of progression free survival after administration of the anti-TF antibody-drug conjugate described herein and/or the anti-PD-1 antibody described herein. In some embodiments, the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-TF antibody-drug conjugate described herein and/or the anti-PD-1 antibody described herein. In some embodiments, the subject exhibits progression-free survival of at least about 6 months after administration of the anti-TF antibody-drug conjugate described herein and/or the anti-PD-1 antibody described herein. In some embodiments, the subject exhibits progression-free survival of at least about one year after administration of the anti-TF antibody-drug conjugate described herein and/or the anti-PD-1 antibody described herein. In some embodiments, the subject exhibits progression-free survival of at least about two years after administration of the anti-TF antibody-drug conjugate described herein and/or the anti-PD-1 antibody described herein. In some embodiments, the subject exhibits progression-free survival of at least about three years after administration of the anti-TF antibody-drug conjugate described herein and/or the anti-PD-1 antibody described herein. In some embodiments, the subject exhibits progression-free survival of at least about four years after administration of the anti-TF antibody-drug conjugate described herein and/or the anti-PD-1 antibody described herein. In some embodiments, the subject exhibits progression-free survival of at least about five years after administration of the anti-TF antibody-drug conjugate described herein and/or the anti-PD-1 antibody described herein. In some embodiments, the subject exhibits progression-free survival of at least 1 month, at least 2 months, at least 3 months, at least 4 months, at least 5 months, at least 6 months, at least 7 months, at least 8 months, at least 9 months, at least 10 months, at least 11 months, at least 12 months, at least eighteen months, at least two years, at least three years, at least four years, or at least five years after administration of the anti-TF antibody-drug conjugate described herein and/or the anti-PD-1 antibody described herein. In some embodiments, the subject exhibits progression-free survival of at least 6 months after administration of the anti-TF antibody-drug conjugate described herein and/or the anti-PD-1 antibody described herein. In some embodiments, the subject exhibits progression-free survival of at least one year after administration of the anti-TF antibody-drug conjugate described herein and/or the anti-PD-1 antibody described herein. In some embodiments, the subject exhibits progression-free survival of at least two years after administration of the anti-TF antibody-drug conjugate described herein and/or the anti-PD-1 antibody described herein. In some embodiments, the subject exhibits progression-free survival of at least three years after administration of the anti-TF antibody-drug conjugate described herein and/or the anti-PD-1 antibody described herein. In some embodiments, the subject exhibits progression-free survival of at least four years after administration of the anti-TF antibody-drug conjugate described herein and/or the anti-PD-1 antibody described herein. In some embodiments, the subject exhibits progression-free survival of at least five years after administration of the anti-TF antibody-drug conjugate described herein and/or the anti-PD-1 antibody described herein. In some embodiments, response to treatment is assessed by measuring the time of progression free survival after administration of the anti-TF antibody-drug conjugate described herein and the anti-PD-1 antibody described herein. In some embodiments, response to treatment is assessed by measuring the time of progression free survival after administration of the anti-TF antibody-drug conjugate described herein. In some embodiments, response to treatment is assessed by measuring the time of progression free survival after administration of the anti-PD-1 antibody described herein.

In one embodiment of the methods or uses or product for uses described herein, response to treatment with an anti-TF antibody-drug conjugate or antigen-binding fragment thereof described herein and an anti-PD-1 antibody or antigen-binding fragment thereof described herein is assessed by measuring the time of overall survival after administration of the anti-TF antibody-drug conjugate described herein and/or the anti-PD-1 antibody described herein. In some embodiments, the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-TF antibody-drug conjugate described herein and/or the anti-PD-1 antibody described herein. In some embodiments, the subject exhibits overall survival of at least about 6 months after administration of the anti-TF antibody-drug conjugate described herein and/or the anti-PD-1 antibody described herein. In some embodiments, the subject exhibits overall survival of at least about one year after administration of the anti-TF antibody-drug conjugate described herein and/or the anti-PD-1 antibody described herein. In some embodiments, the subject exhibits overall survival of at least about two years after administration of the anti-TF antibody-drug conjugate described herein and/or the anti-PD-1 antibody described herein. In some embodiments, the subject exhibits overall survival of at least about three years after administration of the anti-TF antibody-drug conjugate described herein and/or the anti-PD-1 antibody described herein. In some embodiments, the subject exhibits overall survival of at least about four years after administration of the anti-TF antibody-drug conjugate described herein and/or the anti-PD-1 antibody described herein. In some embodiments, the subject exhibits overall survival of at least about five years after administration of the anti-TF antibody-drug conjugate described herein and/or the anti-PD-1 antibody described herein. In some embodiments, the subject exhibits overall survival of at least 1 month, at least 2 months, at least 3 months, at least 4 months, at least 5 months, at least 6 months, at least 7 months, at least 8 months, at least 9 months, at least 10 months, at least 11 months, at least about 12 months, at least eighteen months, at least two years, at least three years, at least four years, or at least five years after administration of the anti-TF antibody-drug conjugate described herein and/or the anti-PD-1 antibody described herein. In some embodiments, the subject exhibits overall survival of at least 6 months after administration of the anti-TF antibody-drug conjugate described herein and/or the anti-PD-1 antibody described herein. In some embodiments, the subject exhibits overall survival of at least one year after administration of the anti-TF antibody-drug conjugate described herein and/or the anti-PD-1 antibody described herein. In some embodiments, the subject exhibits overall survival of at least two years after administration of the anti-TF antibody-drug conjugate described herein and/or the anti-PD-1 antibody described herein. In some embodiments, the subject exhibits overall survival of at least three years after administration of the anti-TF antibody-drug conjugate described herein and/or the anti-PD-1 antibody described herein. In some embodiments, the subject exhibits overall survival of at least four years after administration of the anti-TF antibody-drug conjugate described herein and/or the anti-PD-1 antibody described herein. In some embodiments, the subject exhibits overall survival of at least five years after administration of the anti-TF antibody-drug conjugate described herein and/or the anti-PD-1 antibody described herein. In some embodiments, response to treatment is assessed by measuring the time of overall survival after administration of the anti-TF antibody-drug conjugate described herein and the anti-PD-1 antibody described herein. In some embodiments, response to treatment is assessed by measuring the time of overall survival after administration of the anti-TF antibody-drug conjugate described herein. In some embodiments, response to treatment is assessed by measuring the time of overall survival after administration of the anti-PD-1 antibody described herein.

In one embodiment of the methods or uses or product for uses described herein, response to treatment with an anti-TF antibody-drug conjugate or antigen-binding fragment thereof described herein and an anti-PD-1 antibody or antigen-binding fragment thereof described herein is assessed by measuring the duration of response to the anti-TF antibody-drug conjugate described herein and the anti-PD-1 antibody described herein after administration of the anti-TF antibody-drug conjugate described herein and/or the anti-PD-1 antibody described herein. In some embodiments, the duration of response to the anti-TF antibody-drug conjugate described herein and the anti-PD-1 antibody described herein is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-TF antibody-drug conjugate described herein and/or the anti-PD-1 antibody described herein. In some embodiments, the duration of response to the anti-TF antibody-drug conjugate described herein and the anti-PD-1 antibody described herein is at least about 6 months after administration of the antibody-drug conjugate described herein and/or the anti-PD-1 antibody described herein. In some embodiments, the duration of response to the anti-TF antibody-drug conjugate described herein and the anti-PD-1 antibody described herein is at least about one year after administration of the antibody-drug conjugate described herein and/or the anti-PD-1 antibody described herein. In some embodiments, the duration of response to the anti-TF antibody-drug conjugate described herein and the anti-PD-1 antibody described herein is at least about two years after administration of the antibody-drug conjugate described herein and/or the anti-PD-1 antibody described herein. In some embodiments, the duration of response to the anti-TF antibody-drug conjugate described herein and the anti-PD-1 antibody described herein is at least about three years after administration of the antibody-drug conjugate described herein and/or the anti-PD-1 antibody described herein. In some embodiments, the duration of response to the anti-TF antibody-drug conjugate described herein and the anti-PD-1 antibody described herein is at least about four years after administration of the antibody-drug conjugate described herein and/or the anti-PD-1 antibody described herein. In some embodiments, the duration of response to the anti-TF antibody-drug conjugate described herein and the anti-PD-1 antibody described herein is at least about five years after administration of the antibody-drug conjugate described herein and/or the anti-PD-1 antibody described herein. In some embodiments, the duration of response to the anti-TF antibody-drug conjugate described herein and the anti-PD-1 antibody described herein is at least 1 month, at least 2 months, at least 3 months, at least 4 months, at least 5 months, at least 6 months, at least 7 months, at least 8 months, at least 9 months, at least 10 months, at least 11 months, at least 12 months, at least eighteen months, at least two years, at least three years, at least four years, or at least five years after administration of the anti-TF antibody-drug conjugate described herein and/or the anti-PD-1 antibody described herein. In some embodiments, the duration of response to the anti-TF antibody-drug conjugate described herein and the anti-PD-1 antibody described herein is at least 6 months after administration of the antibody-drug conjugate described herein and/or the anti-PD-1 antibody described herein. In some embodiments, the duration of response to the anti-TF antibody-drug conjugate described herein and the anti-PD-1 antibody described herein is at least one year after administration of the antibody-drug conjugate described herein and/or the anti-PD-1 antibody described herein. In some embodiments, the duration of response to the anti-TF antibody-drug conjugate described herein and the anti-PD-1 antibody described herein is at least two years after administration of the antibody-drug conjugate described herein and/or the anti-PD-1 antibody described herein. In some embodiments, the duration of response to the anti-TF antibody-drug conjugate described herein and the anti-PD-1 antibody described herein is at least three years after administration of the antibody-drug conjugate described herein and/or the anti-PD-1 antibody described herein. In some embodiments, the duration of response to the anti-TF antibody-drug conjugate described herein and the anti-PD-1 antibody described herein is at least four years after administration of the antibody-drug conjugate described herein and/or the anti-PD-1 antibody described herein. In some embodiments, the duration of response to the anti-TF antibody-drug conjugate described herein and the anti-PD-1 antibody described herein is at least five years after administration of the antibody-drug conjugate described herein and/or the anti-PD-1 antibody described herein. In some embodiments, the duration of response is measured after administration of the anti-TF antibody drug conjugate described herein and the anti-PD-1 antibody described herein. In some embodiments, the duration of response is measured after administration of the anti-TF antibody drug conjugate described herein. In some embodiments, the duration of response is measured after administration of the anti-PD-1 antibody described herein.

F. Adverse Events

In one aspect, a method of treating cancer (e.g., breast cancer or cervical cancer) with an anti-TF antibody-drug conjugates or antigen-binding fragments thereof described herein and an anti-PD-1 antibody or antigen-binding fragment thereof described herein results in the subject developing one or more adverse events. In some embodiments, the subject is administered an additional therapeutic agent to eliminate or reduce the severity of the adverse event. In some embodiments, the one or more adverse events the subject develops is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration, or any combination thereof. In some embodiments, the one or more adverse events is a grade 1 or greater adverse event. In some embodiments, the one or more adverse events is a grade 2 or greater adverse event. In some embodiments, the one or more adverse events is a grade 3 or greater adverse event. In some embodiments, the one or more adverse events is a grade 1 adverse event. In some embodiments, the one or more adverse events is a grade 2 adverse event. In some embodiments, the one or more adverse events is a grade 3 adverse event. In some embodiments, the one or more adverse events is a grade 4 adverse event. In some embodiments, the one or more adverse events is a serious adverse event. In some embodiments, the one or more adverse events is conjunctivitis, conjunctival ulceration, and/or keratitis and the additional therapeutic agent is a preservative-free lubricating eye drop, an ocular vasoconstrictor, antibiotic, a steroid eye drop, or any combination thereof. In some embodiments, the one or more adverse events is conjunctivitis, conjunctival ulceration, and keratitis and the additional therapeutic agent is a preservative-free lubricating eye drop, an ocular vasoconstrictor, antibiotic, a steroid eye drop, or any combination thereof. In some embodiments, the one or more adverse events is conjunctivitis and keratitis and the additional therapeutic agent is a preservative-free lubricating eye drop, an ocular vasoconstrictor, antibiotic, a steroid eye drop, or any combination thereof. In some embodiments, the one or more adverse events is conjunctivitis and the additional therapeutic agent is a preservative-free lubricating eye drop, an ocular vasoconstrictor, antibiotic, a steroid eye drop, or any combination thereof. In some embodiments, the one or more adverse events is keratitis and the additional therapeutic agent is a preservative-free lubricating eye drop, an ocular vasoconstrictor, antibiotic, a steroid eye drop, or any combination thereof. In some of any of the embodiments herein, the subject is administered a treatment with the additional therapeutic agent to eliminate or reduce the severity of the adverse event (e.g., conjunctivitis, conjunctival ulceration, and/or keratitis). In some embodiments, the treatment is eye cooling pads (e.g. THERA PEARL Eye Mask or similar). In some embodiments, the one or more adverse events is a recurrent infusion related reaction and the additional therapeutic agent is an antihistamine, acetaminophen and/or a corticosteroid. In some embodiments, the one or more adverse events is neutropenia and the additional therapeutic agent is growth factor support (G-CSF). In some embodiments, the one or more adverse events is hyperthyroidism and the additional agent is a non-selective beta-blockers (e.g., propranolol) or thionamides. In some embodiments, the one or more adverse events is hypothyroidism and the additional agent is a thyroid replacement hormone (e.g., levothyroxine or liothyroinine).

In one aspect, the subject treated with an anti-TF antibody-drug conjugates or antigen-binding fragments thereof described herein and an anti-PD-1 antibody or antigen-binding fragment thereof described herein is at risk of developing one or more adverse events. In some embodiments, the subject is administered an additional therapeutic agent to prevent the development of the adverse event or to reduce the severity of the adverse event. In some embodiments, the one or more adverse events the subject is at risk of developing is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration, or any combination thereof. In some embodiments, the one or more adverse events is a grade 1 or greater adverse event. In some embodiments, the one or more adverse events is a grade 2 or greater adverse event. In some embodiments, the one or more adverse events is a grade 3 or greater adverse event. In some embodiments, the one or more adverse events is a grade 1 adverse event. In some embodiments, the one or more adverse events is a grade 2 adverse event. In some embodiments, the one or more adverse events is a grade 3 adverse event. In some embodiments, the one or more adverse events is a grade 4 adverse event. In some embodiments, the one or more adverse events is a serious adverse event. In some embodiments, the one or more adverse events is conjunctivitis, conjunctival ulceration, and/or keratitis and the additional agent is a preservative-free lubricating eye drop, an ocular vasoconstrictor, antibiotic, a steroid eye drop, or any combination thereof. In some embodiments, the one or more adverse events is conjunctivitis and keratitis and the additional agent is a preservative-free lubricating eye drop, an ocular vasoconstrictor, antibiotic, a steroid eye drop, or any combination thereof. In some embodiments, the one or more adverse events is conjunctivitis and the additional agent is a preservative-free lubricating eye drop, an ocular vasoconstrictor, antibiotic, a steroid eye drop, or any combination thereof. In some embodiments, the one or more adverse events is keratitis and the additional agent is a preservative-free lubricating eye drop, an ocular vasoconstrictor, antibiotic, a steroid eye drop, or any combination thereof. In some of any of the embodiments herein, the subject is administered a treatment with the additional therapeutic agent to prevent the development of the adverse event or to reduce the severity of the adverse event (e.g., conjunctivitis, conjunctival ulceration, and/or keratitis). In some embodiments, the treatment is eye cooling pads (e.g. THERA PEARL Eye Mask or similar). In some embodiments, the one or more adverse events is a recurrent infusion related reaction and the additional agent is an antihistamine, acetaminophen and/or a corticosteroid. In some embodiments, the one or more adverse events is neutropenia and the additional agent is growth factor support (G-CSF). In some embodiments, the one or more adverse events is hyperthyroidism and the additional agent is a non-selective beta-blockers (e.g., propranolol) or thionamides. In some embodiments, the one or more adverse events is hypothyroidism and the additional agent is a thyroid replacement hormone (e.g., levothyroxine or liothyroinine).

V. Compositions

In some aspects, also provided herein are compositions (e.g., pharmaceutical compositions and therapeutic formulations) comprising any of the anti-TF antibody-drug conjugates or antigen-binding fragments thereof described herein and/or the anti-PD-1 antibody or antigen-binding fragments thereof described herein.

Therapeutic formulations are prepared for storage by mixing the active ingredient having the desired degree of purity with optional pharmaceutically acceptable carriers, excipients or stabilizers (Remington: The Science and Practice of Pharmacy, 20th Ed., Lippincott Williams & Wilkins, Pub., Gennaro Ed., Philadelphia, Pa. 2000).

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers can be used to control the pH in a range which optimizes the therapeutic effectiveness, especially if stability is pH dependent. Buffers can be present at concentrations ranging from about 50 mM to about 250 mM. Suitable buffering agents for use with the invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intramolecular interactions. Tonicity agents can be present in any amount between about 0.1% to about 25% by weight or between about 1% to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, a-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001% to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

Formulations comprising an anti-TF antibody-conjugate described herein for use in methods of treatment provided herein are described in WO2015/075201. In some embodiments, an anti-TF antibody-drug conjugate described herein is in a formulation comprising the anti-TF antibody drug conjugate, histidine, sucrose, and D-mannitol, wherein the formulation has a pH of about 6.0. In some embodiments, an anti-TF antibody-drug conjugate described herein is in a formulation comprising the anti-TF antibody drug conjugate at a concentration of about 10 mg/ml, histidine at a concentration of about 30 mM, sucrose at a concentration of about 88 mM, D-mannitol at a concentration of about 165 mM, wherein the formulation has a pH of about 6.0. In some embodiments, an anti-TF antibody-drug conjugate described herein is in a formulation comprising the anti-TF antibody drug conjugate at a concentration of 10 mg/ml, histidine at a concentration of 30 mM, sucrose at a concentration of 88 mM, D-mannitol at a concentration of 165 mM, wherein the formulation has a pH of 6.0. In some embodiments, the formulation comprises tisotumab vedotin at a concentration of 10 mg/ml, histidine at a concentration of 30 mM, sucrose at a concentration of 88 mM, D-mannitol at a concentration of 165 mM, wherein the formulation has a pH of 6.0.

In some embodiments provided herein, a formulation comprising the anti-TF antibody-conjugate described herein does not comprise a surfactant (i.e., is free of surfactant).

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The invention provides compositions comprising a population of anti-TF antibody-drug conjugates or antigen-binding fragments thereof as described herein for use in a method of treating cervical cancer as described herein. In some aspects, provided herein are compositions comprising a population of antibody-drug conjugates, wherein the antibody-drug conjugates comprise a linker attached to MMAE, wherein the antibody-drug conjugate has the following structure:

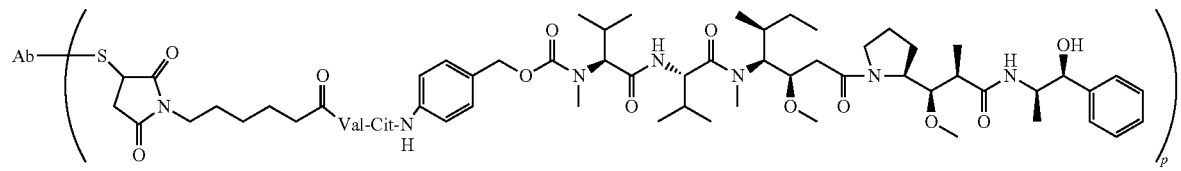

Ab-MC-vc-PAB-MMAE wherein p denotes a number from 1 to 8, e.g., 1, 2, 3, 4, 5, 6, 7 or 8, S represents a sulphydryl residue of the anti-TF antibody or antigen-binding fragment thereof, and Ab designates the anti-TF antibody or antigen-binding fragment thereof as described herein, such as tisotumab. In some embodiments, p denotes a number from 3 to 5. In some embodiments, the average value of p in the composition is about 4. In some embodiments, the population is a mixed population of antibody-drug conjugates in which p varies from 1 to 8 for each antibody-drug conjugate. In some embodiments, the population is a homogenous population of antibody-drug conjugates with each antibody-drug conjugate having the same value for p.

In some embodiments, a composition comprising an anti-TF antibody-drug conjugate or antigen-binding fragment thereof as described herein is coadministered with a composition comprising an anti-PD-1 antibody or antigen-binding fragment thereof as described herein. In some embodiments the coadministration is simultaneous or sequential. In some embodiments, the anti-TF antibody-drug conjugate as described herein is administered simultaneously with the anti-PD-1 antibody as described herein. In some embodiments, simultaneous means that the anti-TF antibody-drug conjugate described herein and the anti-PD-1 antibody described herein are administered to the subject less than about one hour apart, such as less than about 30 minutes apart, less than about 15 minutes apart, less than about 10 minutes apart or less than about 5 minutes apart. In some embodiments, simultaneous means that the anti-TF antibody-drug conjugate described herein and the anti-PD-1 antibody described herein are administered to the subject less than one hour apart, such as less than 30 minutes apart, less than 15 minutes apart, less than 10 minutes apart or less than 5 minutes apart. In some embodiments, the anti-TF antibody-drug conjugate described herein is administered sequentially with the anti-PD-1 antibody described herein. In some embodiments, sequential administration means that the anti-TF antibody-drug conjugate described herein and the anti-PD-1 antibody described herein are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart. In some embodiments, a composition comprising an anti-TF antibody-drug conjugate as described herein and/or an anti-PD-1 antibody as described herein is coadministered with one or more therapeutic agents to eliminate or reduce the severity of one or more adverse events. In some embodiments, a composition comprising an anti-TF antibody-drug conjugate as described herein and/or an anti-PD-1 antibody as described herein is coadministered with one or more therapeutic agents to prevent the development of the adverse event or to reduce the severity of the adverse event.

In some embodiments, a composition comprising an anti-TF antibody-drug conjugate as described herein and/or anti-PD-1 antibody as described herein is coadministered with one or additional therapeutic agents. In some embodiments the coadministration is simultaneous or sequential. In some embodiments, the anti-TF antibody-drug conjugate as described herein and/or anti-PD-1 antibody as described herein is administered simultaneously with the one or more additional therapeutic agents. In some embodiments, simultaneous means that the anti-TF antibody-drug conjugate described herein and/or anti-PD-1 antibody described herein and the one or more therapeutic agents are administered to the subject less than about one hour apart, such as less than about 30 minutes apart, less than about 15 minutes apart, less than about 10 minutes apart or less than about 5 minutes apart. In some embodiments, simultaneous means that the anti-TF antibody-drug conjugate described herein and/or anti-PD-1 antibody described herein and the one or more therapeutic agents are administered to the subject less than one hour apart, such as less than 30 minutes apart, less than 15 minutes apart, less than 10 minutes apart or less than 5 minutes apart. In some embodiments, the anti-TF antibody-drug conjugate described herein and/or anti-PD-1 antibody described herein is administered sequentially with the one or more additional therapeutic agents. In some embodiments, sequential administration means that the anti-TF antibody-drug conjugate described herein and/or anti-PD-1 antibody described herein and the one or more additional therapeutic agents are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart.

In some embodiments, a composition comprising an anti-TF antibody-drug conjugate as described herein and/or anti-PD-1 antibody as described herein is coadministered with one or more therapeutic agents to eliminate or reduce the severity of one or more adverse events. In some embodiments the coadministration is simultaneous or sequential. In some embodiments, the anti-TF antibody-drug conjugate described herein and/or anti-PD-1 antibody described herein is administered simultaneously with the one or more therapeutic agents to eliminate or reduce the severity of one or more adverse events. In some embodiments, simultaneous means that the anti-TF antibody-drug conjugate described herein and/or anti-PD-1 antibody described herein and the one or more therapeutic agents to eliminate or reduce the severity of one or more adverse events are administered to the subject less than about one hour apart, such as less than about 30 minutes apart, less than about 15 minutes apart, less than about 10 minutes apart or less than about 5 minutes apart. In some embodiments, simultaneous means that the anti-TF antibody-drug conjugate described herein and/or anti-PD-1 antibody described herein and the one or more therapeutic agents to eliminate or reduce the severity of one or more adverse events are administered to the subject less than one hour apart, such as less than 30 minutes apart, less than 15 minutes apart, less than 10 minutes apart or less than 5 minutes apart. In some embodiments, the anti-TF antibody-drug conjugate described herein and/or anti-PD-1 antibody described herein is administered sequentially with the one or more therapeutic agents to eliminate or reduce the severity of one or more adverse events. In some embodiments, sequential administration means that the anti-TF antibody-drug conjugate described herein and/or anti-PD-1 antibody described herein and the one or more additional therapeutic agents are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart. In some embodiments, the anti-TF antibody-drug conjugate described herein and/or anti-PD-1 antibody described herein is administered prior to the one or more therapeutic agents to eliminate or reduce the severity of one or more adverse events. In some embodiments, the one or more therapeutic agents to eliminate or reduce the severity of one or more adverse events is administered prior to the anti-TF antibody-drug conjugate described herein and/or anti-PD-1 antibody described herein.

VI. Articles of Manufacture and Kits

In another aspect, an article of manufacture or kit is provided which comprises an anti-TF antibody-drug conjugate described herein and/or an anti-PD-1 antibody described herein. The article of manufacture or kit may further comprise instructions for use of the anti-TF antibody-drug conjugate described herein and/or anti-PD-1 antibody described herein in the methods of the invention. Thus, in certain embodiments, the article of manufacture or kit comprises instructions for the use of an anti-TF antibody-drug conjugate described herein and/or an anti-PD-1 antibody described herein in methods for treating cancer (e.g., breast cancer or cervical cancer) in a subject comprising administering to the subject an effective amount of an anti-TF antibody-drug conjugate described herein and/or anti-PD-1 antibody described herein. In some embodiments, the cancer is breast cancer. In some embodiments, the breast cancer is ER+/HER2– breast cancer. In some embodiments, the breast cancer is triple negative breast cancer. In some embodiments, the cancer is cervical cancer. In some embodiments, the cervical cancer is advanced stage cervical cancer. In some embodiments, the advanced stage cervical cancer is metastatic cervical cancer. In some embodiments, the advanced stage cervical cancer is a stage 3 or stage 4 cervical cancer. In some embodiments, the cervical cancer is metastatic cancer and recurrent cancer. In some embodiments the cervical cancer is recurrent cancer. In some embodiments, the subject is not a candidate for curative therapy. In some embodiments, the subject has not received prior systemic therapy for the cervical cancer. In some embodiments, the subject is a human.

The article of manufacture or kit may further comprise a container. Suitable containers include, for example, bottles, vials (e.g., dual chamber vials), syringes (such as single or dual chamber syringes) and test tubes. In some embodiments, the container is a vial. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous (e.g., intravenous infusion), or other modes of administration for treating cancer in a subject such as breast cancer or cervical cancer described herein (e.g., advanced cervical cancer such as grade 3 or grade 4 or metastatic cervical cancer). The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the anti-TF antibody-drug conjugate described herein is a first medicament, and which article or kit further comprises instructions on the label or package insert for treating the subject with the second medicament, in an effective amount. In some embodiments, the second medicament is an anti-PD-1 antibody as described herein. In some embodiments, the label or package insert indicates that the first and second medicaments are to be administered sequentially or simultaneously, as described herein.

The article of manufacture or kit herein optionally further comprises a container comprising a third medicament, wherein the third medicament is for eliminating or reducing the severity of one or more adverse events, wherein the anti-TF antibody-drug conjugate described herein is a first medicament, the anti-PD-1 antibody described herein is a second medicament, and which article or kit further comprises instructions on the label or package insert for treating the subject with the third medicament, in an effective amount. In some embodiments, the label or package insert indicates that the first, second and third medicaments are to be administered sequentially or simultaneously, as described herein, for example wherein the label or package insert indicates that the anti-TF antibody-drug conjugate described herein is to be administered first, followed by administration of the anti-PD-1 antibody described herein, followed by administration of the third medicament.

In some embodiments, the anti-TF antibody-drug conjugate described herein and/or anti-PD-1 antibody described herein is present in the container as a lyophilized powder. In some embodiments, the lyophilized powder is in a hermetically sealed container, such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components can also be included in the kit.

VII. Exemplary Embodiments

Among the embodiments provided herein are:

1. A method of treating cancer in a subject, the method comprising administering to the subject an antibody or an antigen-binding fragment thereof, wherein the antibody binds to Programmed Death-1 (PD-1) and inhibits PD-1 activity, and an antibody-drug conjugate that binds to tissue factor (TF), wherein the antibody-drug conjugate comprises an anti-TF antibody or an antigen-binding fragment thereof conjugated to monomethyl auristatin E, wherein the anti-PD-1 antibody or antigen-binding fragment thereof comprises a heavy chain variable region and a light chain variable region, wherein the heavy chain variable region comprises:
   (i) a CDR-H1 comprising the amino acid sequence of SEQ ID NO:17;
   (ii) a CDR-H2 comprising the amino acid sequence of SEQ ID NO:18; and
   (iii) a CDR-H3 comprising the amino acid sequence of SEQ ID NO:19; and
wherein the light chain variable region comprises:
   (i) a CDR-L1 comprising the amino acid sequence of SEQ ID NO:20;
   (ii) a CDR-L2 comprising the amino acid sequence of SEQ ID NO:21; and
   (iii) a CDR-L3 comprising the amino acid sequence of SEQ ID NO:22;

and wherein the anti-TF antibody or antigen-binding fragment thereof comprises a heavy chain variable region and a light chain variable region, wherein the heavy chain variable region comprises:
- (i) a CDR-H1 comprising the amino acid sequence of SEQ ID NO:1;
- (ii) a CDR-H2 comprising the amino acid sequence of SEQ ID NO:2; and
- (iii) a CDR-H3 comprising the amino acid sequence of SEQ ID NO:3; and wherein the light chain variable region comprises:
- (i) a CDR-L1 comprising the amino acid sequence of SEQ ID NO:4;
- (ii) a CDR-L2 comprising the amino acid sequence of SEQ ID NO:5; and
- (iii) a CDR-L3 comprising the amino acid sequence of SEQ ID NO:6, wherein the CDRs of the anti-TF antibody or antigen-binding fragment thereof are defined by the IMGT numbering scheme.

2. The method of embodiment 1, wherein the antibody-drug conjugate is administered at a dose ranging from about 0.9 mg/kg to about 2.1 mg/kg, such as about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg or about 2.1 mg/kg.

3. The method of any one of embodiments 1-2, wherein the antibody-drug conjugate is administered at a dose of about 1.3 mg/kg.

4. The method of any one of embodiments 1-2, wherein the antibody-drug conjugate is administered at a dose of 1.3 mg/kg.

5. The method of any one of embodiments 1-2, wherein the antibody-drug conjugate is administered at a dose of about 2.0 mg/kg.

6. The method of any one of embodiments 1-2, wherein the antibody-drug conjugate is administered at a dose of 2.0 mg/kg.

7. The method of any one of embodiments 1-6, wherein the antibody-drug conjugate is administered once about every 1 week, once about every 2 weeks, once about every 3 weeks or once about every 4 weeks.

8. The method of embodiment 7, wherein the antibody-drug conjugate is administered once about every 3 weeks.

9. The method of embodiment 7, wherein the antibody-drug conjugate is administered once every 3 weeks.

10. The method of any one of embodiments 1-9, wherein the anti-PD-1 antibody or antigen-binding fragment thereof is administered at a flat dose ranging from about 50 mg to about 500 mg.

11. The method of any one of embodiments 1-10, wherein the anti-PD-1 antibody or antigen-binding fragment thereof is administered at a flat dose of about 200 mg.

12. The method of any one of embodiments 1-10, wherein the anti-PD-1 antibody or antigen-binding fragment thereof is administered at a flat dose of 200 mg.

13. The method of any one of embodiments 1-12, wherein the anti-PD-1 antibody or antigen-binding fragment thereof is administered once about every 1 week, once about every 2 weeks, once about every 3 weeks or once about every 4 weeks.

14. The method of embodiment 13, wherein the anti-PD-1 antibody or antigen-binding fragment thereof is administered once about every 3 weeks.

15. The method of embodiment 13, wherein the anti-PD-1 antibody or antigen-binding fragment thereof is administered once every 3 weeks.

16. The method of any one of embodiments 1-15, wherein the cancer is breast cancer.

17. The method of embodiment 16, wherein the breast cancer is ER+/HER2− breast cancer or triple negative breast cancer.

18. The method of any one of embodiments 1-15, wherein the cancer is cervical cancer.

19. The method of embodiment 18, wherein the subject is not a candidate for curative therapy.

20. The method of embodiment 19, wherein curative therapy comprises radiotherapy and/or exenterative surgery.

21. The method of embodiment 18, wherein the subject has not received prior systemic therapy for the cervical cancer.

22. The method of any one of embodiments 18-21, wherein the cervical cancer is an adenocarcinoma, an adenosquamous carcinoma or a squamous cell carcinoma.

23. The method of any one of embodiments 18-22, wherein the cervical cancer is an advanced stage cervical cancer.

24. The method of embodiment 23, wherein the advanced stage cervical cancer is a stage 3 or stage 4 cervical cancer.

25. The method of embodiment 23 or 24, wherein the advanced stage cervical cancer is metastatic cervical cancer.

26. The method of any one of embodiments 18-25, wherein the cervical cancer is recurrent cervical cancer.

27. The method of any one of embodiments 1-26, wherein the anti-TF antibody or antigen-binding fragment thereof of the antibody-drug conjugate is a monoclonal antibody or a monoclonal antigen-binding fragment thereof.

28. The method of any one of embodiments 1-27, wherein the anti-TF antibody or antigen-binding fragment thereof of the antibody-drug conjugate comprises a heavy chain variable region comprising an amino acid sequence having at least 85% sequence identity to the amino acid sequence of SEQ ID NO:7 and a light chain variable region comprising an amino acid sequence having at least 85% sequence identity to the amino acid sequence of SEQ ID NO:8.

29. The method of any one of embodiments 1-28, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

30. The method of any one of embodiments 1-29, wherein the anti-TF antibody of the antibody-drug conjugate is tisotumab.

31. The method of any one of embodiments 1-30, wherein the antibody-drug conjugate further comprises a linker between the anti-TF antibody or antigen-binding fragment thereof and the monomethyl auristatin E.

32. The method of embodiment 31, wherein the linker is a cleavable peptide linker.

33. The method of embodiment 32, wherein the cleavable peptide linker has a formula: -MC-vc-PAB-, wherein:
a) MC is:

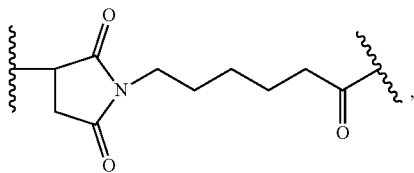 [SMILES: *C(=O)CCCCCN1C(=O)CC(*)C1=O]

b) vc is the dipeptide valine-citrulline, and
c) PAB is:

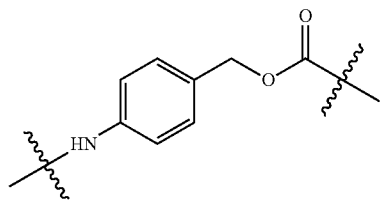

34. The method of any one of embodiments 31-33, wherein the linker is attached to sulphydryl residues of the anti-TF antibody or antigen-binding fragment thereof obtained by partial reduction or full reduction of the anti-TF antibody or antigen-binding fragment thereof.

35. The method of embodiment 34, wherein the linker is attached to MMAE, wherein the antibody-drug conjugate has the following structure:

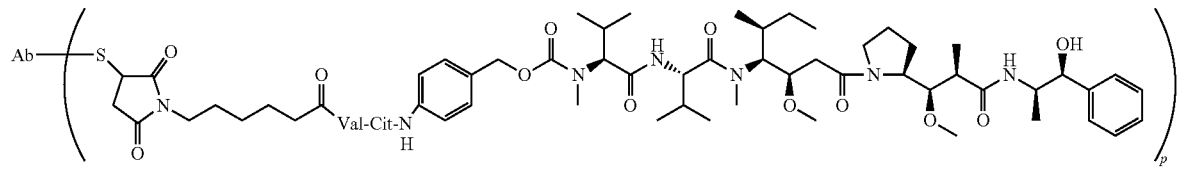

Ab-MC-vc-PAB-MMAE wherein p denotes a number from 1 to 8, S represents a sulphydryl residue of the anti-TF antibody, and Ab designates the anti-TF antibody or antigen-binding fragment thereof.

36. The method of embodiment 35, wherein the average value of p in a population of the antibody-drug conjugates is about 4.

37. The method of any one of embodiments 1-36, wherein the antibody-drug conjugate is tisotumab vedotin.

38. The method of any one of embodiments 1-37, wherein the route of administration for the antibody-drug conjugate is intravenous.

39. The method of any one of embodiments 1-38, wherein the anti-PD-1 antibody or antigen-binding fragment thereof comprises a heavy chain variable region comprising an amino acid sequence having at least 85% sequence identity to the amino acid sequence of SEQ ID NO:31 and a light chain variable region comprising an amino acid sequence having at least 85% sequence identity to the amino acid sequence of SEQ ID NO:32.

40. The method of any one of embodiments 1-39, wherein the anti-PD-1 antibody comprises a heavy chain variable region comprising the amino acid sequence of SEQ ID NO:31 and a light chain variable region comprising the amino acid sequence of SEQ ID NO:32.

41. The method of any one of embodiments 1-40, wherein the anti-PD-1 antibody comprises a heavy chain comprising the amino acid sequence of SEQ ID NO:33 and a light chain comprising the amino acid sequence of SEQ ID NO:34.

42. The method of any one of embodiments 1-41, wherein the anti-PD-1 antibody is pembrolizumab.

43. The method of any one of embodiments 1-42, wherein the route of administration for the anti-PD-1 antibody or antigen-binding fragment thereof is intravenous or subcutaneous.

44. The method any one of embodiments 1-42, wherein the route of administration for the anti-PD-1 antibody or antigen-binding fragment thereof is intravenous.

45. The method of any one of embodiments 1-44, wherein the anti-PD-1 antibody or antigen-binding fragment thereof and the antibody-drug conjugate are administered sequentially.

46. The method of any one of embodiments 1-44, wherein the anti-PD-1 antibody or antigen-binding fragment thereof and the antibody-drug conjugate are administered simultaneously.

47. The method of any one of embodiments 1-46, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express TF.

48. The method of any one of embodiments 1-47, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express PD-L1.

49. The method of any one of embodiments 1-48, wherein the subject has a tumor that expresses PD-L1 (TPS≥1).

50. The method of any one of embodiments 1-48, wherein the subject has a tumor that has high PD-L1 expression (TPS≥50).

51. The method of any one of embodiments 1-48, wherein the subject has a tumor that expresses PD-L1 (CPS≥1).

52. The method of any one of embodiments 1-51, wherein a tumor derived from the cancer comprises one or more cells that express PD-L1, PD-L2, or both PD-L1 and PD-L2.

53. The method of any one of embodiments 1-52, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1.

54. The method of any one of embodiments 1-53, wherein one or more therapeutic effects in the subject is improved after administration of the antibody-drug conjugate and the anti-PD-1 antibody or antigen-binding fragment thereof relative to a baseline.

55. The method of embodiment 54, wherein the one or more therapeutic effects is selected from the group consisting of: size of a tumor derived from the cancer, objective response rate, duration of response, time to response, progression free survival, and overall survival.

56. The method of any one of embodiments 1-55, wherein the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the antibody-drug conjugate and the anti-PD-1 antibody or antigen-binding fragment thereof.

57. The method of any one of embodiments 1-56, wherein the objective response rate is at least about 20%, at least about 25%, at least about 30%, at least about 35%, at least about 40%, at least about 45%, at least about 50%, at least about 60%, at least about 70%, or at least about 80%.

58. The method of any one of embodiments 1-57, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

59. The method of any one of embodiments 1-58, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

60. The method of any one of embodiments 1-59, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

61. The method of any one of embodiments 1-60, wherein the subject has one or more adverse events and is further administered an additional therapeutic agent to eliminate or reduce the severity of the one or more adverse events.

62. The method of any one of embodiments 1-61, wherein the subject is at risk of developing one or more adverse events and is further administered an additional therapeutic agent to prevent or reduce the severity of the one or more adverse events.

63. The method of embodiment 61 or embodiment 62, wherein the one or more adverse events is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration.

64. The method of any one of embodiments 61-63, wherein the one or more adverse events is a grade 3 or greater adverse event.

65. The method of any one of embodiments 61-63, wherein the one or more adverse events is a serious adverse event.

66. The method of embodiment 61 or embodiment 62, wherein the one or more adverse events is conjunctivitis, conjunctival ulceration, and/or keratitis and the additional agent is a preservative-free lubricating eye drop, an ocular vasoconstrictor, antibiotic, and/or a steroid eye drop.

67. The method of any one of embodiments 1-66, wherein the subject is a human.

68. The method of any one of embodiments 1-67, wherein the antibody-drug conjugate is in a pharmaceutical composition comprising the antibody-drug conjugate and a pharmaceutical acceptable carrier.

69. The method of any one of embodiments 1-68, wherein the anti-PD-1 antibody or antigen-binding fragment thereof is in a pharmaceutical composition comprising the anti-PD-1 antibody or antigen-binding fragment thereof and a pharmaceutical acceptable carrier.

70. An antibody-drug conjugate that binds to TF for use in the treatment of cancer in a subject, wherein the antibody-drug conjugate is for administration, or to be administered in combination with an anti-PD-1 antibody or an antigen-binding fragment thereof, wherein the antibody-drug conjugate comprises an anti-TF antibody or an antigen-binding fragment thereof conjugated to monomethyl auristatin E, wherein the anti-PD-1 antibody or the antigen-binding fragment thereof inhibits PD-1 activity, wherein the anti-PD-1 antibody or antigen-binding fragment thereof comprises a heavy chain variable region and a light chain variable region, wherein the heavy chain variable region comprises:
  (i) a CDR-H1 comprising the amino acid sequence of SEQ ID NO:17;
  (ii) a CDR-H2 comprising the amino acid sequence of SEQ ID NO:18; and
  (iii) a CDR-H3 comprising the amino acid sequence of SEQ ID NO:19; and
wherein the light chain variable region comprises:
  (i) a CDR-L1 comprising the amino acid sequence of SEQ ID NO:20;
  (ii) a CDR-L2 comprising the amino acid sequence of SEQ ID NO:21; and
  (iii) a CDR-L3 comprising the amino acid sequence of SEQ ID NO:22;
and wherein the anti-TF antibody or antigen-binding fragment thereof comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and (iii) a CDR-L3 comprising the amino acid sequence of SEQ ID NO:6, wherein the CDRs of the anti-TF antibody or antigen-binding fragment thereof are defined by the IMGT numbering scheme.

71. The antibody-drug conjugate for use of embodiment 70, wherein the antibody-drug conjugate is administered at a dose ranging from about 0.9 mg/kg to about 2.1 mg/kg, such as about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg or about 2.1 mg/kg.

72. The antibody-drug conjugate for use of any one of embodiments 70-71, wherein the antibody-drug conjugate is administered at a dose of about 1.3 mg/kg.

73. The antibody-drug conjugate for use of any one of embodiments 70-71, wherein the antibody-drug conjugate is administered at a dose of 1.3 mg/kg.

74. The antibody-drug conjugate for use of any one of embodiments 70-71, wherein the antibody-drug conjugate is administered at a dose of about 2.0 mg/kg.

75. The antibody-drug conjugate for use of any one of embodiments 70-71, wherein the antibody-drug conjugate is administered at a dose of 2.0 mg/kg.

76. The antibody-drug conjugate for use of any one of embodiments 70-75, wherein the antibody-drug conjugate is administered once about every 1 week, once about every 2 weeks, once about every 3 weeks or once about every 4 weeks.

77. The antibody-drug conjugate for use of embodiment 76, wherein the antibody-drug conjugate is administered once about every 3 weeks.

78. The antibody-drug conjugate for use of embodiment 76, wherein the antibody-drug conjugate is administered once every 3 weeks.

79. The antibody-drug conjugate for use of any one of embodiments 70-78, wherein the anti-PD-1 antibody or antigen-binding fragment thereof is administered at a flat dose ranging from about 50 mg to about 500 mg.

80. The antibody-drug conjugate for use of any one of embodiments 70-79, wherein the anti-PD-1 antibody or antigen-binding fragment thereof is administered at a flat dose of about 200 mg.

81. The antibody-drug conjugate for use of any one of embodiments 70-79, wherein the anti-PD-1 antibody or antigen-binding fragment thereof is administered at a flat dose of 200 mg.

82. The antibody-drug conjugate for use of any one of embodiments 70-79, wherein the anti-PD-1 antibody or antigen-binding fragment thereof is administered at a flat dose of about 400 mg.

83. The antibody-drug conjugate for use of any one of embodiments 70-79, wherein the anti-PD-1 antibody or antigen-binding fragment thereof is administered at a flat dose of 400 mg.

84. The antibody-drug conjugate for use of any one of embodiments 70-83, wherein the anti-PD-1 antibody or antigen-binding fragment thereof is administered once about every 1 week, once about every 2 weeks, once about every 3 weeks, once about every 4 weeks, once about every 5 weeks, or once about every 6 weeks.

85. The antibody-drug conjugate for use of embodiment 84, wherein the anti-PD-1 antibody or antigen-binding fragment thereof is administered once about every 3 weeks.

86. The antibody-drug conjugate for use of embodiment 84, wherein the anti-PD-1 antibody or antigen-binding fragment thereof is administered once every 3 weeks.

87. The antibody-drug conjugate for use of embodiment 84, wherein the anti-PD-1 antibody or antigen-binding fragment thereof is administered once about every 6 weeks.

88. The antibody-drug conjugate for use of embodiment 84, wherein the anti-PD-1 antibody or antigen-binding fragment thereof is administered once every 6 weeks.

89. The antibody-drug conjugate for use of any one of embodiments 70-88, wherein the cancer is breast cancer.

90. The antibody-drug conjugate for use of embodiment 89, wherein the breast cancer is ER+/HER2− breast cancer or triple negative breast cancer.

91. The antibody-drug conjugate for use of any one of embodiments 70-88, wherein the cancer is cervical cancer.

92. The antibody-drug conjugate for use of embodiment 91, wherein the subject is not a candidate for curative therapy.

93. The antibody-drug conjugate for use of embodiment 92, wherein curative therapy comprises radiotherapy and/or exenterative surgery.

94. The antibody-drug conjugate for use of embodiment 91, wherein the subject has not received prior systemic therapy for the cervical cancer.

95. The antibody-drug conjugate for use of any one of embodiments 91-94, wherein the cervical cancer is an adenocarcinoma, an adenosquamous carcinoma or a squamous cell carcinoma.

96. The antibody-drug conjugate for use of any one of embodiments 91-95, wherein the cervical cancer is an advanced stage cervical cancer.

97. The antibody-drug conjugate for use of embodiment 96, wherein the advanced stage cervical cancer is a stage 3 or stage 4 cervical cancer.

98. The antibody-drug conjugate for use of embodiment 96 or 97, wherein the advanced stage cervical cancer is metastatic cervical cancer.

99. The antibody-drug conjugate for use of any one of embodiments 91-98, wherein the cervical cancer is recurrent cervical cancer.

100. The antibody-drug conjugate for use of any one of embodiments 70-99, wherein the anti-TF antibody or antigen-binding fragment thereof of the antibody-drug conjugate is a monoclonal antibody or a monoclonal antigen-binding fragment thereof.

101. The antibody-drug conjugate for use of any one of embodiments 70-100, wherein the anti-TF antibody or antigen-binding fragment thereof of the antibody-drug conjugate comprises a heavy chain variable region comprising an amino acid sequence having at least 85% sequence identity to the amino acid sequence of SEQ ID NO:7 and a light chain variable region comprising an amino acid sequence having at least 85% sequence identity to the amino acid sequence of SEQ ID NO:8.

102. The antibody-drug conjugate for use of any one of embodiments 70-101, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

103. The antibody-drug conjugate for use of any one of embodiments 70-102, wherein the anti-TF antibody of the antibody-drug conjugate is tisotumab.

104. The antibody-drug conjugate for use of any one of embodiments 70-103, wherein the antibody-drug conjugate further comprises a linker between the anti-TF antibody or antigen-binding fragment thereof and the monomethyl auristatin E.

105. The antibody-drug conjugate for use of embodiment 104, wherein the linker is a cleavable peptide linker.

106. The antibody-drug conjugate for use of embodiment 105, wherein the cleavable peptide linker has a formula: -MC-vc-PAB-, wherein:
a) MC is:

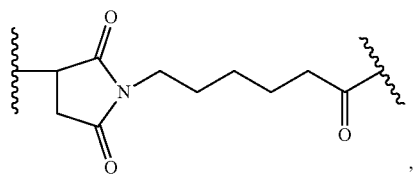 [SMILES: *C(=O)CCCCCN1C(=O)CC(*)C1=O]
, b) vc is the dipeptide valine-citrulline, and
c) PAB is:

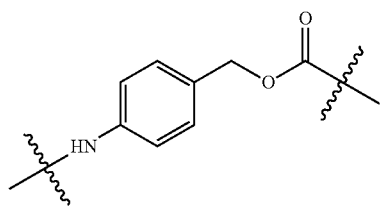
.

107. The antibody-drug conjugate for use of any one of embodiments 104-106, wherein the linker is attached to sulphydryl residues of the anti-TF antibody or antigen-binding fragment thereof obtained by partial reduction or full reduction of the anti-TF antibody or antigen-binding fragment thereof.

108. The antibody-drug conjugate for use of embodiment 107, wherein the linker is attached to MMAE, wherein the antibody-drug conjugate has the following structure:

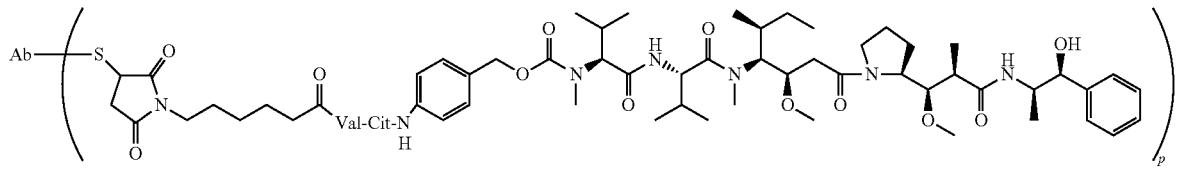

Ab-MC-vc-PAB-MMAE wherein p denotes a number from 1 to 8, S represents a sulphydryl residue of the anti-TF antibody, and Ab designates the anti-TF antibody or antigen-binding fragment thereof.

109. The antibody-drug conjugate for use of embodiment 108, wherein the average value of p in a population of the antibody-drug conjugates is about 4.

110. The antibody-drug conjugate for use of any one of embodiments 70-109, wherein the antibody-drug conjugate is tisotumab vedotin.

111. The antibody-drug conjugate for use of any one of embodiments 70-110, wherein the route of administration for the antibody-drug conjugate is intravenous.

112. The antibody-drug conjugate for use of any one of embodiments 70-111, wherein the anti-PD-1 antibody or antigen-binding fragment thereof comprises a heavy chain variable region comprising an amino acid sequence having at least 85% sequence identity to the amino acid sequence of SEQ ID NO:31 and a light chain variable region comprising an amino acid sequence having at least 85% sequence identity to the amino acid sequence of SEQ ID NO:32.

113. The antibody-drug conjugate for use of any one of embodiments 70-112, wherein the anti-PD-1 antibody comprises a heavy chain variable region comprising the amino acid sequence of SEQ ID NO:31 and a light chain variable region comprising the amino acid sequence of SEQ ID NO:32.

114. The antibody-drug conjugate for use of any one of embodiments 70-113, wherein the anti-PD-1 antibody comprises a heavy chain comprising the amino acid sequence of SEQ ID NO:33 and a light chain comprising the amino acid sequence of SEQ ID NO:34.

115. The antibody-drug conjugate for use of any one of embodiments 70-114, wherein the anti-PD-1 antibody is pembrolizumab.

116. The antibody-drug conjugate for use of any one of embodiments 70-115, wherein the route of administration for the anti-PD-1 antibody or antigen-binding fragment thereof is intravenous or subcutaneous.

117. The antibody-drug conjugate for use of any one of embodiments 70-115, wherein the route of administration for the anti-PD-1 antibody or antigen-binding fragment thereof is intravenous.

118. The antibody-drug conjugate for use of any one of embodiments 70-115, wherein the route of administration for the anti-PD-1 antibody or antigen-binding fragment thereof is subcutaneous.

119. The antibody-drug conjugate for use of any one of embodiments 70-118, wherein the anti-PD-1 antibody or antigen-binding fragment thereof and the antibody-drug conjugate are administered sequentially.

120. The antibody-drug conjugate for use of any one of embodiments 70-118, wherein the anti-PD-1 antibody or antigen-binding fragment thereof and the antibody-drug conjugate are administered simultaneously.

121. The antibody-drug conjugate for use of any one of embodiments 70-120, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express TF.

122. The antibody-drug conjugate for use of any one of embodiments 70-121, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express PD-L1.

123. The antibody-drug conjugate for use of any one of embodiments 70-122, wherein the subject has a tumor that expresses PD-L1 (TPS≥1).

124. The antibody-drug conjugate for use of any one of embodiments 70-122, wherein the subject has a tumor that has high PD-L1 expression (TPS≥50).

125. The antibody-drug conjugate for use of any one of embodiments 70-122, wherein the subject has a tumor that expresses PD-L1 (CPS≥1).

126. The antibody-drug conjugate for use of any one of embodiments 70-125, wherein a tumor derived from the cancer comprises one or more cells that express PD-L1, PD-L2, or both PD-L1 and PD-L2.

127. The antibody-drug conjugate for use of any one of embodiments 70-126, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1.

128. The antibody-drug conjugate for use of any one of embodiments 70-127, wherein one or more therapeutic effects in the subject is improved after administration of the antibody-drug conjugate and the anti-PD-1 antibody or antigen-binding fragment thereof relative to a baseline.

129. The antibody-drug conjugate for use of embodiment 128, wherein the one or more therapeutic effects is selected from the group consisting of: size of a tumor derived from the cancer, objective response rate, duration of response, time to response, progression free survival, and overall survival.

130. The antibody-drug conjugate for use of any one of embodiments 70-129, wherein the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the antibody-drug conjugate and the anti-PD-1 antibody or antigen-binding fragment thereof.

131. The antibody-drug conjugate for use of any one of embodiments 70-130, wherein the objective response rate is at least about 20%, at least about 25%, at least about 30%, at least about 35%, at least about 40%, at least about 45%, at least about 50%, at least about 60%, at least about 70%, or at least about 80%.

132. The antibody-drug conjugate for use of any one of embodiments 70-131, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

133. The antibody-drug conjugate for use of any one of embodiments 70-132, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

134. The antibody-drug conjugate for use of any one of embodiments 70-133, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

135. The antibody-drug conjugate for use of any one of embodiments 70-134, wherein the subject has one or more adverse events and is further administered an additional therapeutic agent to eliminate or reduce the severity of the one or more adverse events.

136. The antibody-drug conjugate for use of any one of embodiments 70-135, wherein the subject is at risk of developing one or more adverse events and is further administered an additional therapeutic agent to prevent or reduce the severity of the one or more adverse events.

137. The antibody-drug conjugate for use of embodiment 135 or embodiment 136, wherein the one or more adverse events is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration.

138. The antibody-drug conjugate for use of any one of embodiments 135-137, wherein the one or more adverse events is a grade 3 or greater adverse event.

139. The antibody-drug conjugate for use of any one of embodiments 135-137, wherein the one or more adverse events is a serious adverse event.

140. The antibody-drug conjugate for use of embodiment 135 or embodiment 136, wherein the one or more adverse events is conjunctivitis, conjunctival ulceration, and/or keratitis and the additional agent is a preservative-free lubricating eye drop, an ocular vasoconstrictor, antibiotic, and/or a steroid eye drop.

141. The antibody-drug conjugate for use of any one of embodiments 70-140, wherein the subject is a human.

142. The antibody-drug conjugate for use of any one of embodiments 70-141, wherein the antibody-drug conjugate is in a pharmaceutical composition comprising the antibody-drug conjugate and a pharmaceutical acceptable carrier.

143. The antibody-drug conjugate for use of any one of embodiments 70-142, wherein the anti-PD-1 antibody or antigen-binding fragment thereof is in a pharmaceutical composition comprising the anti-PD-1 antibody or antigen-binding fragment thereof and a pharmaceutical acceptable carrier.

144. Use of an antibody-drug conjugate that binds to TF for the manufacture of a medicament for treating cancer in a subject, wherein the medicament is for use in combination with an anti-PD-1 antibody or an antigen-binding fragment thereof, wherein the antibody-drug conjugate comprises an anti-TF antibody or an antigen-binding fragment thereof conjugated to monomethyl auristatin E, wherein the anti-PD-1 antibody or the antigen-binding fragment thereof inhibits PD-1 activity, wherein the anti-PD-1 antibody or antigen-binding fragment thereof comprises a heavy chain variable region and a light chain variable region, wherein the heavy chain variable region comprises:

(i) a CDR-H1 comprising the amino acid sequence of SEQ ID NO:17;
(ii) a CDR-H2 comprising the amino acid sequence of SEQ ID NO:18; and
(iii) a CDR-H3 comprising the amino acid sequence of SEQ ID NO:19; and wherein the light chain variable region comprises:

(i) a CDR-L1 comprising the amino acid sequence of SEQ ID NO:20;
(ii) a CDR-L2 comprising the amino acid sequence of SEQ ID NO:21; and
(iii) a CDR-L3 comprising the amino acid sequence of SEQ ID NO:22;

and wherein the anti-TF antibody or antigen-binding fragment thereof comprises a heavy chain variable region and a light chain variable region, wherein the heavy chain variable region comprises:

(i) a CDR-H1 comprising the amino acid sequence of SEQ ID NO:1;
(ii) a CDR-H2 comprising the amino acid sequence of SEQ ID NO:2; and
(iii) a CDR-H3 comprising the amino acid sequence of SEQ ID NO:3; and wherein the light chain variable region comprises:

(i) a CDR-L1 comprising the amino acid sequence of SEQ ID NO:4;
(ii) a CDR-L2 comprising the amino acid sequence of SEQ ID NO:5; and
(iii) a CDR-L3 comprising the amino acid sequence of SEQ ID NO:6, wherein the CDRs of the anti-TF antibody or antigen-binding fragment thereof are defined by the IMGT numbering scheme.

145. The use of embodiment 144, wherein the antibody-drug conjugate is administered at a dose ranging from about 0.9 mg/kg to about 2.1 mg/kg, such as about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg or about 2.1 mg/kg.

146. The use of any one of embodiments 144-145, wherein the antibody-drug conjugate is administered at a dose of about 1.3 mg/kg.

147. The use of any one of embodiments 144-145, wherein the antibody-drug conjugate is administered at a dose of 1.3 mg/kg.

148. The use of any one of embodiments 144-145, wherein the antibody-drug conjugate is administered at a dose of about 2.0 mg/kg.

149. The use of any one of embodiments 144-145, wherein the antibody-drug conjugate is administered at a dose of 2.0 mg/kg.

150. The use of any one of embodiments 144-149, wherein the antibody-drug conjugate is administered once about every 1 week, once about every 2 weeks, once about every 3 weeks or once about every 4 weeks.

151. The use of embodiment 150, wherein the antibody-drug conjugate is administered once about every 3 weeks.

152. The use of embodiment 150, wherein the antibody-drug conjugate is administered once every 3 weeks.

153. The use of any one of embodiments 144-152, wherein the anti-PD-1 antibody or antigen-binding fragment thereof is administered at a flat dose ranging from about 50 mg to about 500 mg.

154. The use of any one of embodiments 144-153, wherein the anti-PD-1 antibody or antigen-binding fragment thereof is administered at a flat dose of about 200 mg.

155. The use of any one of embodiments 144-153, wherein the anti-PD-1 antibody or antigen-binding fragment thereof is administered at a flat dose of 200 mg.

156. The use of any one of embodiments 144-153, wherein the anti-PD-1 antibody or antigen-binding fragment thereof is administered at a flat dose of about 400 mg.

157. The use of any one of embodiments 144-153, wherein the anti-PD-1 antibody or antigen-binding fragment thereof is administered at a flat dose of 400 mg.

158. The use of any one of embodiments 144-157, wherein the anti-PD-1 antibody or antigen-binding fragment thereof is administered once about every 1 week, once about every 2 weeks, once about every 3 weeks, once about every 4 weeks, once about every 5 weeks, or once about every 6 weeks.

159. The use of embodiment 158, wherein the anti-PD-1 antibody or antigen-binding fragment thereof is administered once about every 3 weeks.

160. The use of embodiment 158, wherein the anti-PD-1 antibody or antigen-binding fragment thereof is administered once every 3 weeks.

161. The use of embodiment 158, wherein the anti-PD-1 antibody or antigen-binding fragment thereof is administered once about every 6 weeks.

162. The use of embodiment 158, wherein the anti-PD-1 antibody or antigen-binding fragment thereof is administered once every 6 weeks.

163. The use of any one of embodiments 144-162, wherein the cancer is breast cancer.

164. The use of embodiment 163, wherein the breast cancer is ER+/HER2− breast cancer or triple negative breast cancer.

165. The use of any one of embodiments 144-162, wherein the cancer is cervical cancer.

166. The use of embodiment 165, wherein the subject is not a candidate for curative therapy.

167. The use of embodiment 166, wherein curative therapy comprises radiotherapy and/or exenterative surgery.

168. The use of embodiment 165, wherein the subject has not received prior systemic therapy for the cervical cancer.

169. The use of any one of embodiments 165-168, wherein the cervical cancer is an adenocarcinoma, an adenosquamous carcinoma or a squamous cell carcinoma.

170. The use of any one of embodiments 165-169, wherein the cervical cancer is an advanced stage cervical cancer.

171. The use of embodiment 170, wherein the advanced stage cervical cancer is a stage 3 or stage 4 cervical cancer.

172. The use of embodiment 170 or 171, wherein the advanced stage cervical cancer is metastatic cervical cancer.

173. The use of any one of embodiments 165-172, wherein the cervical cancer is recurrent cervical cancer.

174. The use of any one of embodiments 144-173, wherein the anti-TF antibody or antigen-binding fragment thereof of the antibody-drug conjugate is a monoclonal antibody or a monoclonal antigen-binding fragment thereof.

175. The use of any one of embodiments 144-174, wherein the anti-TF antibody or antigen-binding fragment thereof of the antibody-drug conjugate comprises a heavy chain variable region comprising an amino acid sequence having at least 85% sequence identity to the amino acid sequence of SEQ ID NO:7 and a light chain variable region comprising an amino acid sequence having at least 85% sequence identity to the amino acid sequence of SEQ ID NO:8.

176. The use of any one of embodiments 144-175, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

177. The use of any one of embodiments 144-176, wherein the anti-TF antibody of the antibody-drug conjugate is tisotumab.

178. The use of any one of embodiments 144-177, wherein the antibody-drug conjugate further comprises a linker between the anti-TF antibody or antigen-binding fragment thereof and the monomethyl auristatin E.

179. The use of embodiment 178, wherein the linker is a cleavable peptide linker.

180. The use of embodiment 179, wherein the cleavable peptide linker has a formula: -MC-vc-PAB-, wherein:
a) MC is:

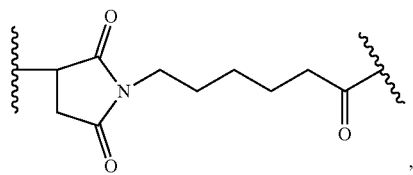 [SMILES: *C(=O)CCCCCN1C(=O)CC(*)C1=O]

b) vc is the dipeptide valine-citrulline, and
c) PAB is:

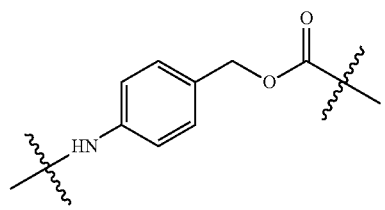

181. The use of any one of embodiments 178-180, wherein the linker is attached to sulphydryl residues of the anti-TF antibody or antigen-binding fragment thereof obtained by partial reduction or full reduction of the anti-TF antibody or antigen-binding fragment thereof.

182. The use of embodiment 181, wherein the linker is attached to MMAE, wherein the antibody-drug conjugate has the following structure:

wherein p denotes a number from 1 to 8, S represents a sulphydryl residue of the anti-TF antibody, and Ab designates the anti-TF antibody or antigen-binding fragment thereof.

183. The use of embodiment 182, wherein the average value of p in a population of the antibody-drug conjugates is about 4.

184. The use of any one of embodiments 144-183, wherein the antibody-drug conjugate is tisotumab vedotin.

185. The use of any one of embodiments 144-184, wherein the route of administration for the antibody-drug conjugate is intravenous.

186. The use of any one of embodiments 144-185, wherein the anti-PD-1 antibody or antigen-binding fragment thereof comprises a heavy chain variable region comprising an amino acid sequence having at least 85% sequence identity to the amino acid sequence of SEQ ID NO:31 and a light chain variable region comprising an amino acid sequence having at least 85% sequence identity to the amino acid sequence of SEQ ID NO:32.

187. The use of any one of embodiments 144-186, wherein the anti-PD-1 antibody comprises a heavy chain variable region comprising the amino acid sequence of SEQ ID NO:31 and a light chain variable region comprising the amino acid sequence of SEQ ID NO:32.

188. The use of any one of embodiments 144-187, wherein the anti-PD-1 antibody comprises a heavy chain comprising the amino acid sequence of SEQ ID NO:33 and a light chain comprising the amino acid sequence of SEQ ID NO:34.

189. The use of any one of embodiments 144-188, wherein the anti-PD-1 antibody is pembrolizumab.

190. The use of any one of embodiments 144-189, wherein the route of administration for the anti-PD-1 antibody or antigen-binding fragment thereof is intravenous or subcutaneous.

191. The use of any one of embodiments 144-189, wherein the route of administration for the anti-PD-1 antibody or antigen-binding fragment thereof is intravenous.

192. The use of any one of embodiments 144-189, wherein the route of administration for the anti-PD-1 antibody or antigen-binding fragment thereof is subcutaneous.

193. The use of any one of embodiments 144-192, wherein the anti-PD-1 antibody or antigen-binding fragment thereof and the antibody-drug conjugate are administered sequentially.

194. The use of any one of embodiments 144-192, wherein the anti-PD-1 antibody or antigen-binding fragment thereof and the antibody-drug conjugate are administered simultaneously.

195. The use of any one of embodiments 144-194, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at

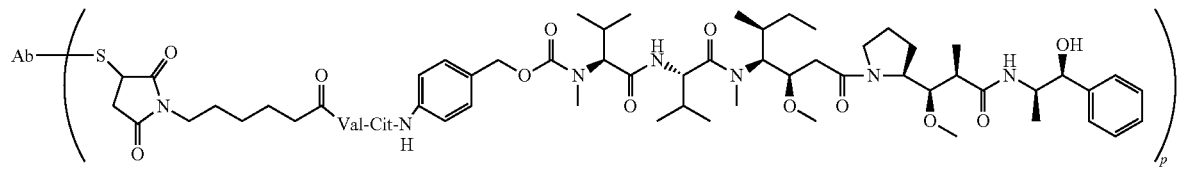

Ab-MC-vc-PAB-MMAE least about 20%, at least about 25%, at least about 30%, at least about 35%, at least about 40%, at least about 45%, at least about 50%, at least about 60%, at least about 70%, or at least about 80% of cancer cells from the subject express TF.

196. The use of any one of embodiments 144-195, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express PD-L1.

197. The use of any one of embodiments 144-196, wherein the subject has a tumor that expresses PD-L1 (TPS≥1).

198. The use of any one of embodiments 144-196, wherein the subject has a tumor that has high PD-L1 expression (TPS≥50).

199. The use of any one of embodiments 144-196, wherein the subject has a tumor that expresses PD-L1 (CPS≥1).

200. The use of any one of embodiments 144-199, wherein a tumor derived from the cancer comprises one or more cells that express PD-L1, PD-L2, or both PD-L1 and PD-L2.

201. The use of any one of embodiments 144-200, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1.

202. The use of any one of embodiments 144-201, wherein one or more therapeutic effects in the subject is improved after administration of the antibody-drug conjugate and the anti-PD-1 antibody or antigen-binding fragment thereof relative to a baseline.

203. The use of embodiment 202, wherein the one or more therapeutic effects is selected from the group consisting of: size of a tumor derived from the cancer, objective response rate, duration of response, time to response, progression free survival, and overall survival.

204. The use of any one of embodiments 144-203, wherein the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the antibody-drug conjugate and the anti-PD-1 antibody or antigen-binding fragment thereof.

205. The use of any one of embodiments 144-204, wherein the objective response rate is at least about 20%, at least about 25%, at least about 30%, at least about 35%, at least about 40%, at least about 45%, at least about 50%, at least about 60%, at least about 70%, or at least about 80%.

206. The use of any one of embodiments 144-205, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

207. The use of any one of embodiments 144-206, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

208. The use of any one of embodiments 144-207, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

209. The use of any one of embodiments 144-208, wherein the subject has one or more adverse events and is further administered an additional therapeutic agent to eliminate or reduce the severity of the one or more adverse events.

210. The use of any one of embodiments 144-209, wherein the subject is at risk of developing one or more adverse events and is further administered an additional therapeutic agent to prevent or reduce the severity of the one or more adverse events.

211. The use of embodiment 209 or embodiment 210, wherein the one or more adverse events is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration.

212. The use of any one of embodiments 209-211, wherein the one or more adverse events is a grade 3 or greater adverse event.

213. The use of any one of embodiments 209-211, wherein the one or more adverse events is a serious adverse event.

214. The use of embodiment 209 or embodiment 210, wherein the one or more adverse events is conjunctivitis, conjunctival ulceration, and/or keratitis and the additional agent is a preservative-free lubricating eye drop, an ocular vasoconstrictor, antibiotic, and/or a steroid eye drop.

215. The use of any one of embodiments 144-214, wherein the subject is a human.

216. The use of any one of embodiments 144-215, wherein the antibody-drug conjugate is in a pharmaceutical composition comprising the antibody-drug conjugate and a pharmaceutical acceptable carrier.

217. The use of any one of embodiments 144-216, wherein the anti-PD-1 antibody or antigen-binding fragment thereof is in a pharmaceutical composition comprising the anti-PD-1 antibody or antigen-binding fragment thereof and a pharmaceutical acceptable carrier.

218. A kit comprising:
(a) a dosage ranging from about 50 mg to about 500 mg of an antibody or an antigen-binding fragment thereof, wherein the antibody binds to Programmed Death-1 (PD-1) and inhibits PD-1 activity, wherein the anti-PD-1 antibody or antigen-binding fragment thereof comprises a heavy chain variable region and a light chain variable region, wherein the heavy chain variable region comprises:
  (i) a CDR-H1 comprising the amino acid sequence of SEQ ID NO:17;
  (ii) a CDR-H2 comprising the amino acid sequence of SEQ ID NO:18; and
  (iii) a CDR-H3 comprising the amino acid sequence of SEQ ID NO:19; and
wherein the light chain variable region comprises:
  (i) a CDR-L1 comprising the amino acid sequence of SEQ ID NO:20;
  (ii) a CDR-L2 comprising the amino acid sequence of SEQ ID NO:21; and
  (iii) a CDR-L3 comprising the amino acid sequence of SEQ ID NO:22;
(b) a dosage ranging from about 0.9 mg/kg to about 2.1 mg/kg of an antibody-drug conjugate that binds to tissue factor (TF), wherein the antibody-drug conjugate comprises an anti-TF antibody or an antigen-binding fragment thereof conjugated to monomethyl auristatin E, wherein the anti-TF antibody or antigen-binding fragment thereof comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6, wherein the CDRs of the anti-TF antibody or antigen-binding fragment thereof are defined by the IMGT numbering scheme; and
(c) instructions for use of the anti-PD-1 antibody or antigen-binding fragment thereof and the antibody-drug conjugate according to the method of any one of embodiments 1-69 or the antibody-drug conjugate in combination with the anti-PD-1 antibody or the antigen-binding fragment thereof for use of any one of embodiments 70-143 in a method for treating cancer in the subject.

219. The kit of embodiment 218, wherein the anti-PD-1 antibody or antigen-binding fragment thereof is pembrolizumab.

220. The kit of embodiment 219, wherein the dose of the pembrolizumab is 200 mg.

221. The kit of any one of embodiments 218-220, wherein the antibody-drug conjugate is tisotumab vedotin.

222. The kit of embodiment 221, wherein the dose of the tisotumab vedotin is 1.3 mg/kg.

223. The kit of embodiment 221, wherein the dose of the tisotumab vedotin is 2.0 mg/kg.

224. An anti-PD-1 antibody or an antigen-binding fragment thereof for use in the treatment of cancer in a subject, wherein the anti-PD-1 antibody is for administration, or to be administered in combination with an antibody-drug conjugate that binds to TF wherein the antibody-drug conjugate comprises an anti-TF antibody or an antigen-binding fragment thereof conjugated to monomethyl auristatin E, wherein the anti-PD-1 antibody or the antigen-binding fragment thereof inhibits PD-1 activity, wherein the anti-PD-1 antibody or antigen-binding fragment thereof comprises a heavy chain variable region and a light chain variable region, wherein the heavy chain variable region comprises:
  (i) a CDR-H1 comprising the amino acid sequence of SEQ ID NO:17;
  (ii) a CDR-H2 comprising the amino acid sequence of SEQ ID NO:18; and
  (iii) a CDR-H3 comprising the amino acid sequence of SEQ ID NO:19; and
wherein the light chain variable region comprises:
  (i) a CDR-L1 comprising the amino acid sequence of SEQ ID NO:20;
  (ii) a CDR-L2 comprising the amino acid sequence of SEQ ID NO:21; and
  (iii) a CDR-L3 comprising the amino acid sequence of SEQ ID NO:22;
and wherein the anti-TF antibody or antigen-binding fragment thereof comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6, wherein the CDRs of the anti-TF antibody or antigen-binding fragment thereof are defined by the IMGT numbering scheme.

225. The anti-PD-1 antibody or an antigen-binding fragment thereof for use of embodiment 224, wherein the antibody-drug conjugate is administered at a dose ranging from about 0.9 mg/kg to about 2.1 mg/kg, such as about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg or about 2.1 mg/kg.

226. The anti-PD-1 antibody or an antigen-binding fragment thereof for use of any one of embodiments 224-225, wherein the antibody-drug conjugate is administered at a dose of about 1.3 mg/kg.

227. The anti-PD-1 antibody or an antigen-binding fragment thereof for use of any one of embodiments 224-225, wherein the antibody-drug conjugate is administered at a dose of 1.3 mg/kg.

228. The anti-PD-1 antibody or an antigen-binding fragment thereof for use of any one of embodiments 224-225, wherein the antibody-drug conjugate is administered at a dose of about 2.0 mg/kg.

229. The anti-PD-1 antibody or an antigen-binding fragment thereof for use of any one of embodiments 224-225, wherein the antibody-drug conjugate is administered at a dose of 2.0 mg/kg.

230. The anti-PD-1 antibody or an antigen-binding fragment thereof for use of any one of embodiments 224-229, wherein the antibody-drug conjugate is administered once about every 1 week, once about every 2 weeks, once about every 3 weeks or once about every 4 weeks.

231. The anti-PD-1 antibody or an antigen-binding fragment thereof for use of embodiment 230, wherein the antibody-drug conjugate is administered once about every 3 weeks.

232. The anti-PD-1 antibody or an antigen-binding fragment thereof for use of embodiment 230, wherein the antibody-drug conjugate is administered once every 3 weeks.

233. The anti-PD-1 antibody or an antigen-binding fragment thereof for use of any one of embodiments 224-232, wherein the anti-PD-1 antibody or antigen-binding fragment thereof is administered at a flat dose ranging from about 50 mg to about 500 mg.

234. The anti-PD-1 antibody or an antigen-binding fragment thereof for use of any one of embodiments 224-232, wherein the anti-PD-1 antibody or antigen-binding fragment thereof is administered at a flat dose of about 200 mg.

235. The anti-PD-1 antibody or an antigen-binding fragment thereof for use of any one of embodiments 224-232, wherein the anti-PD-1 antibody or antigen-binding fragment thereof is administered at a flat dose of 200 mg.

236. The anti-PD-1 antibody or an antigen-binding fragment thereof for use of any one of embodiments 224-232, wherein the anti-PD-1 antibody or antigen-binding fragment thereof is administered at a flat dose of about 400 mg.

237. The anti-PD-1 antibody or an antigen-binding fragment thereof for use of any one of embodiments 224-232, wherein the anti-PD-1 antibody or antigen-binding fragment thereof is administered at a flat dose of 400 mg.

238. The anti-PD-1 antibody or an antigen-binding fragment thereof for use of any one of embodiments 224-237, wherein the anti-PD-1 antibody or antigen-binding fragment thereof is administered once about every 1 week, once about every 2 weeks, once about every 3 weeks, once about every 4 weeks, once about every 5 weeks, or once about every 6 weeks.

239. The anti-PD-1 antibody or an antigen-binding fragment thereof for use of embodiment 238, wherein the anti-PD-1 antibody or antigen-binding fragment thereof is administered once about every 3 weeks.

240. The anti-PD-1 antibody or an antigen-binding fragment thereof for use of embodiment 238, wherein the anti-PD-1 antibody or antigen-binding fragment thereof is administered once every 3 weeks.

241. The anti-PD-1 antibody or an antigen-binding fragment thereof for use of embodiment 238, wherein the anti-PD-1 antibody or antigen-binding fragment thereof is administered once about every 6 weeks.

242. The anti-PD-1 antibody or an antigen-binding fragment thereof for use of embodiment 238, wherein the anti-PD-1 antibody or antigen-binding fragment thereof is administered once every 6 weeks.

243. The anti-PD-1 antibody or an antigen-binding fragment thereof for use of any one of embodiments 224-242, wherein the cancer is breast cancer.

244. The anti-PD-1 antibody or an antigen-binding fragment thereof for use of embodiment 243, wherein the breast cancer is ER+/HER2− breast cancer or triple negative breast cancer.

245. The anti-PD-1 antibody or an antigen-binding fragment thereof for use of any one of embodiments 224-242, wherein the cancer is cervical cancer.

246. The anti-PD-1 antibody or an antigen-binding fragment thereof for use of embodiment 245, wherein the subject is not a candidate for curative therapy.

247. The anti-PD-1 antibody or an antigen-binding fragment thereof for use of embodiment 246, wherein curative therapy comprises radiotherapy and/or exenterative surgery.

248. The anti-PD-1 antibody or an antigen-binding fragment thereof for use of embodiment 245, wherein the subject has not received prior systemic therapy for the cervical cancer.

249. The anti-PD-1 antibody or an antigen-binding fragment thereof for use of any one of embodiments 245-248, wherein the cervical cancer is an adenocarcinoma, an adenosquamous carcinoma or a squamous cell carcinoma.

250. The anti-PD-1 antibody or an antigen-binding fragment thereof for use of any one of embodiments 245-249, wherein the cervical cancer is an advanced stage cervical cancer.

251. The anti-PD-1 antibody or an antigen-binding fragment thereof for use of embodiment 250, wherein the advanced stage cervical cancer is a stage 3 or stage 4 cervical cancer.

252. The anti-PD-1 antibody or an antigen-binding fragment thereof for use of embodiment 250 or 251, wherein the advanced stage cervical cancer is metastatic cervical cancer.

253. The anti-PD-1 antibody or an antigen-binding fragment thereof for use of any one of embodiments 245-252, wherein the cervical cancer is recurrent cervical cancer.

254. The anti-PD-1 antibody or an antigen-binding fragment thereof for use of any one of embodiments 224-253, wherein the anti-TF antibody or antigen-binding fragment thereof of the antibody-drug conjugate is a monoclonal antibody or a monoclonal antigen-binding fragment thereof.

255. The anti-PD-1 antibody or an antigen-binding fragment thereof for use of any one of embodiments 224-254, wherein the anti-TF antibody or antigen-binding fragment thereof of the antibody-drug conjugate comprises a heavy chain variable region comprising an amino acid sequence having at least 85% sequence identity to the amino acid sequence of SEQ ID NO:7 and a light chain variable region comprising an amino acid sequence having at least 85% sequence identity to the amino acid sequence of SEQ ID NO:8.

256. The anti-PD-1 antibody or an antigen-binding fragment thereof for use of any one of embodiments 224-255, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

257. The anti-PD-1 antibody or an antigen-binding fragment thereof for use of any one of embodiments 224-256, wherein the anti-TF antibody of the antibody-drug conjugate is tisotumab.

258. The anti-PD-1 antibody or an antigen-binding fragment thereof for use of any one of embodiments 224-257, wherein the antibody-drug conjugate further comprises a linker between the anti-TF antibody or antigen-binding fragment thereof and the monomethyl auristatin E.

259. The anti-PD-1 antibody or an antigen-binding fragment thereof for use of embodiment 258, wherein the linker is a cleavable peptide linker.

260. The anti-PD-1 antibody or an antigen-binding fragment thereof for use of embodiment 259, wherein the cleavable peptide linker has a formula: -MC-vc-PAB-, wherein:

a) MC is:

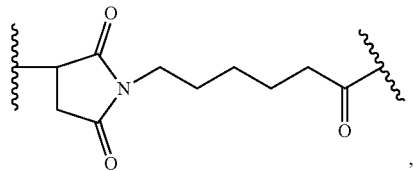 [SMILES: *C(=O)CCCCCN1C(=O)CC(*)C1=O]

b) vc is the dipeptide valine-citrulline, and
c) PAB is:

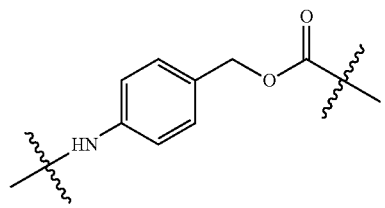

261. The anti-PD-1 antibody or an antigen-binding fragment thereof for use of any one of embodiments 258-260, wherein the linker is attached to sulphydryl residues of the anti-TF antibody or antigen-binding fragment thereof obtained by partial reduction or full reduction of the anti-TF antibody or antigen-binding fragment thereof.

262. The anti-PD-1 antibody or an antigen-binding fragment thereof for use of embodiment 261, wherein the linker is attached to MMAE, wherein the antibody-drug conjugate has the following structure:

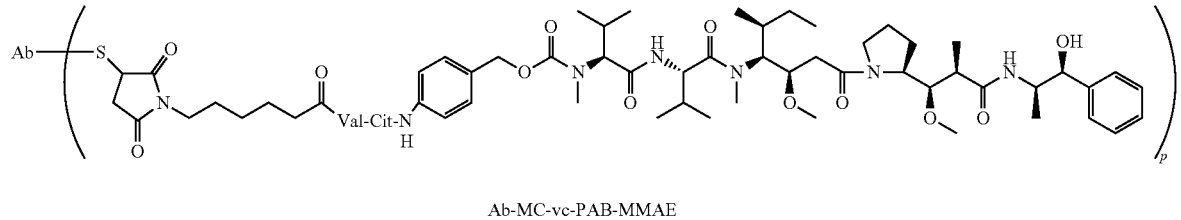

Ab-MC-vc-PAB-MMAE wherein p denotes a number from 1 to 8, S represents a sulphydryl residue of the anti-TF antibody, and Ab designates the anti-TF antibody or antigen-binding fragment thereof.

263. The anti-PD-1 antibody or an antigen-binding fragment thereof for use of embodiment 262, wherein the average value of p in a population of the antibody-drug conjugates is about 4.

264. The anti-PD-1 antibody or an antigen-binding fragment thereof for use of any one of embodiments 224-263, wherein the antibody-drug conjugate is tisotumab vedotin.

265. The anti-PD-1 antibody or an antigen-binding fragment thereof for use of any one of embodiments 224-264, wherein the route of administration for the antibody-drug conjugate is intravenous.

266. The anti-PD-1 antibody or an antigen-binding fragment thereof for use of any one of embodiments 224-265, wherein the anti-PD-1 antibody or antigen-binding fragment thereof comprises a heavy chain variable region comprising an amino acid sequence having at least 85% sequence identity to the amino acid sequence of SEQ ID NO:31 and a light chain variable region comprising an amino acid sequence having at least 85% sequence identity to the amino acid sequence of SEQ ID NO:32.

267. The anti-PD-1 antibody or an antigen-binding fragment thereof for use of any one of embodiments 224-266, wherein the anti-PD-1 antibody comprises a heavy chain variable region comprising the amino acid sequence of SEQ ID NO:31 and a light chain variable region comprising the amino acid sequence of SEQ ID NO:32.

268. The anti-PD-1 antibody or an antigen-binding fragment thereof for use of any one of embodiments 224-267, wherein the anti-PD-1 antibody comprises a heavy chain comprising the amino acid sequence of SEQ ID NO:33 and a light chain comprising the amino acid sequence of SEQ ID NO:34.

269. The anti-PD-1 antibody or an antigen-binding fragment thereof for use of any one of embodiments 224-268, wherein the anti-PD-1 antibody is pembrolizumab.

270. The anti-PD-1 antibody or an antigen-binding fragment thereof for use of any one of embodiments 224-269, wherein the route of administration for the anti-PD-1 antibody or antigen-binding fragment thereof is intravenous or subcutaneous.

271. The anti-PD-1 antibody or an antigen-binding fragment thereof for use of any one of embodiments 224-269, wherein the route of administration for the anti-PD-1 antibody or antigen-binding fragment thereof is intravenous.

272. The anti-PD-1 antibody or an antigen-binding fragment thereof for use of any one of embodiments 224-269, wherein the route of administration for the anti-PD-1 antibody or antigen-binding fragment thereof is subcutaneous.

273. The anti-PD-1 antibody or an antigen-binding fragment thereof for use of any one of embodiments 224-272, wherein the anti-PD-1 antibody or antigen-binding fragment thereof and the antibody-drug conjugate are administered sequentially.

274. The anti-PD-1 antibody or an antigen-binding fragment thereof for use of any one of embodiments 224-272, wherein the anti-PD-1 antibody or antigen-binding fragment thereof and the antibody-drug conjugate are administered simultaneously.

275. The anti-PD-1 antibody or an antigen-binding fragment thereof for use of any one of embodiments 224-274, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express TF.

276. The anti-PD-1 antibody or an antigen-binding fragment thereof for use of any one of embodiments 224-275, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express PD-L1.

277. The anti-PD-1 antibody or an antigen-binding fragment thereof for use of any one of embodiments 224-276, wherein the subject has a tumor that expresses PD-L1 (TPS≥1).

278. The anti-PD-1 antibody or an antigen-binding fragment thereof for use of any one of embodiments 224-276, wherein the subject has a tumor that has high PD-L1 expression (TPS≥50).

279. The anti-PD-1 antibody or an antigen-binding fragment thereof for use of any one of embodiments 224-276, wherein the subject has a tumor that expresses PD-L1 (CPS≥1).

280. The anti-PD-1 antibody or an antigen-binding fragment thereof for use of any one of embodiments 224-279, wherein a tumor derived from the cancer comprises one or more cells that express PD-L1, PD-L2, or both PD-L1 and PD-L2.

281. The anti-PD-1 antibody or an antigen-binding fragment thereof for use of any one of embodiments 224-280, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1.

282. The anti-PD-1 antibody or an antigen-binding fragment thereof for use of any one of embodiments 224-281, wherein one or more therapeutic effects in the subject is improved after administration of the antibody-drug conjugate and the anti-PD-1 antibody or antigen-binding fragment thereof relative to a baseline.

283. The anti-PD-1 antibody or an antigen-binding fragment thereof for use of embodiment 282, wherein the one or more therapeutic effects is selected from the group consisting of: size of a tumor derived from the cancer, objective response rate, duration of response, time to response, progression free survival, and overall survival.

284. The anti-PD-1 antibody or an antigen-binding fragment thereof for use of any one of embodiments 224-283, wherein the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the antibody-drug conjugate and the anti-PD-1 antibody or antigen-binding fragment thereof.

285. The anti-PD-1 antibody or an antigen-binding fragment thereof for use of any one of embodiments 224-284, wherein the objective response rate is at least about 20%, at least about 25%, at least about 30%, at least about 35%, at least about 40%, at least about 45%, at least about 50%, at least about 60%, at least about 70%, or at least about 80%.

286. The anti-PD-1 antibody or an antigen-binding fragment thereof for use of any one of embodiments 224-285, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

287. The anti-PD-1 antibody or an antigen-binding fragment thereof for use of any one of embodiments 224-286, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

288. The anti-PD-1 antibody or an antigen-binding fragment thereof for use of any one of embodiments 224-287, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

289. The anti-PD-1 antibody or an antigen-binding fragment thereof for use of any one of embodiments 224-288, wherein the subject has one or more adverse events and is further administered an additional therapeutic agent to eliminate or reduce the severity of the one or more adverse events.

290. The anti-PD-1 antibody or an antigen-binding fragment thereof for use of any one of embodiments 224-289, wherein the subject is at risk of developing one or more adverse events and is further administered an additional therapeutic agent to prevent or reduce the severity of the one or more adverse events.

291. The anti-PD-1 antibody or an antigen-binding fragment thereof for use of embodiment 289 or embodiment 290, wherein the one or more adverse events is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration.

292. The anti-PD-1 antibody or an antigen-binding fragment thereof for use of any one of embodiments 289-291, wherein the one or more adverse events is a grade 3 or greater adverse event.

293. The anti-PD-1 antibody or an antigen-binding fragment thereof for use of any one of embodiments 289-291, wherein the one or more adverse events is a serious adverse event.

294. The anti-PD-1 antibody or an antigen-binding fragment thereof for use of embodiment 289 or embodiment 290, wherein the one or more adverse events is conjunctivitis, conjunctival ulceration, and/or keratitis and the additional agent is a preservative-free lubricating eye drop, an ocular vasoconstrictor, antibiotic, and/or a steroid eye drop.

295. The anti-PD-1 antibody or an antigen-binding fragment thereof for use of any one of embodiments 224-294, wherein the subject is a human.

296. The anti-PD-1 antibody or an antigen-binding fragment thereof for use of any one of embodiments 224-295, wherein the antibody-drug conjugate is in a pharmaceutical composition comprising the antibody-drug conjugate and a pharmaceutical acceptable carrier.

297. The anti-PD-1 antibody or an antigen-binding fragment thereof for use of any one of embodiments 224-296, wherein the anti-PD-1 antibody or antigen-binding fragment thereof is in a pharmaceutical composition comprising the anti-PD-1 antibody or antigen-binding fragment thereof and a pharmaceutical acceptable carrier.

298. Use of an anti-PD-1 antibody or an antigen-binding fragment thereof for the manufacture of a medicament for treating cancer in a subject, wherein the medicament is for use in combination with an antibody-drug conjugate that binds to TF, wherein the antibody-drug conjugate comprises an anti-TF antibody or an antigen-binding fragment thereof conjugated to monomethyl auristatin E, wherein the anti-PD-1 antibody or the antigen-binding fragment thereof inhibits PD-1 activity, wherein the anti-PD-1 antibody or antigen-binding fragment thereof comprises a heavy chain variable region and a light chain variable region, wherein the heavy chain variable region comprises:
  (i) a CDR-H1 comprising the amino acid sequence of SEQ ID NO:17;
  (ii) a CDR-H2 comprising the amino acid sequence of SEQ ID NO:18; and
  (iii) a CDR-H3 comprising the amino acid sequence of SEQ ID NO:19; and
wherein the light chain variable region comprises:
  (i) a CDR-L1 comprising the amino acid sequence of SEQ ID NO:20;
  (ii) a CDR-L2 comprising the amino acid sequence of SEQ ID NO:21; and
  (iii) a CDR-L3 comprising the amino acid sequence of SEQ ID NO:22;
and wherein the anti-TF antibody or antigen-binding fragment thereof comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6, wherein the CDRs of the anti-TF antibody or antigen-binding fragment thereof are defined by the IMGT numbering scheme.

299. The use of embodiment 298, wherein the antibody-drug conjugate is administered at a dose ranging from about 0.9 mg/kg to about 2.1 mg/kg, such as about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg or about 2.1 mg/kg.

300. The use of any one of embodiments 298-299, wherein the antibody-drug conjugate is administered at a dose of about 1.3 mg/kg.

301. The use of any one of embodiments 298-299, wherein the antibody-drug conjugate is administered at a dose of 1.3 mg/kg.

302. The use of any one of embodiments 298-299, wherein the antibody-drug conjugate is administered at a dose of about 2.0 mg/kg.

303. The use of any one of embodiments 298-299, wherein the antibody-drug conjugate is administered at a dose of 2.0 mg/kg.

304. The use of any one of embodiments 298-303, wherein the antibody-drug conjugate is administered once about every 1 week, once about every 2 weeks, once about every 3 weeks or once about every 4 weeks.

305. The use of embodiment 304, wherein the antibody-drug conjugate is administered once about every 3 weeks.

306. The use of embodiment 304, wherein the antibody-drug conjugate is administered once every 3 weeks.

307. The use of any one of embodiments 298-306, wherein the anti-PD-1 antibody or antigen-binding fragment thereof is administered at a flat dose ranging from about 50 mg to about 500 mg.

308. The use of any one of embodiments 298-307, wherein the anti-PD-1 antibody or antigen-binding fragment thereof is administered at a flat dose of about 200 mg.

309. The use of any one of embodiments 298-307, wherein the anti-PD-1 antibody or antigen-binding fragment thereof is administered at a flat dose of 200 mg.

310. The use of any one of embodiments 298-307, wherein the anti-PD-1 antibody or antigen-binding fragment thereof is administered at a flat dose of about 400 mg.

311. The use of any one of embodiments 298-307, wherein the anti-PD-1 antibody or antigen-binding fragment thereof is administered at a flat dose of 400 mg.

312. The use of any one of embodiments 298-311, wherein the anti-PD-1 antibody or antigen-binding fragment thereof is administered once about every 1 week, once about every 2 weeks, once about every 3 weeks, once about every 4 weeks, once about every 5 weeks, or once about every 6 weeks.

313. The use of embodiment 312, wherein the anti-PD-1 antibody or antigen-binding fragment thereof is administered once about every 3 weeks.

314. The use of embodiment 312, wherein the anti-PD-1 antibody or antigen-binding fragment thereof is administered once every 3 weeks.

315. The use of embodiment 312, wherein the anti-PD-1 antibody or antigen-binding fragment thereof is administered once about every 6 weeks.

316. The use of embodiment 312, wherein the anti-PD-1 antibody or antigen-binding fragment thereof is administered once every 6 weeks.

317. The use of any one of embodiments 298-316, wherein the cancer is breast cancer.

318. The use of embodiment 317, wherein the breast cancer is ER+/HER2− breast cancer or triple negative breast cancer.

319. The use of any one of embodiments 298-316, wherein the cancer is cervical cancer.

320. The use of embodiment 319, wherein the subject is not a candidate for curative therapy.

321. The use of embodiment 320, wherein curative therapy comprises radiotherapy and/or exenterative surgery.

322. The use of embodiment 319, wherein the subject has not received prior systemic therapy for the cervical cancer.

323. The use of any one of embodiments 319-322, wherein the cervical cancer is an adenocarcinoma, an adenosquamous carcinoma or a squamous cell carcinoma.

324. The use of any one of embodiments 319-323, wherein the cervical cancer is an advanced stage cervical cancer.

325. The use of embodiment 324, wherein the advanced stage cervical cancer is a stage 3 or stage 4 cervical cancer.

326. The use of embodiment 324 or 325, wherein the advanced stage cervical cancer is metastatic cervical cancer.

327. The use of any one of embodiments 319-326, wherein the cervical cancer is recurrent cervical cancer.

328. The use of any one of embodiments 298-327, wherein the anti-TF antibody or antigen-binding fragment thereof of the antibody-drug conjugate is a monoclonal antibody or a monoclonal antigen-binding fragment thereof.

329. The use of any one of embodiments 298-328, wherein the anti-TF antibody or antigen-binding fragment thereof of the antibody-drug conjugate comprises a heavy chain variable region comprising an amino acid sequence having at least 85% sequence identity to the amino acid sequence of SEQ ID NO:7 and a light chain variable region comprising an amino acid sequence having at least 85% sequence identity to the amino acid sequence of SEQ ID NO:8.

330. The use of any one of embodiments 298-329, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

331. The use of any one of embodiments 298-330, wherein the anti-TF antibody of the antibody-drug conjugate is tisotumab.

332. The use of any one of embodiments 298-331, wherein the antibody-drug conjugate further comprises a linker between the anti-TF antibody or antigen-binding fragment thereof and the monomethyl auristatin E.

333. The use of embodiment 332, wherein the linker is a cleavable peptide linker.

334. The use of embodiment 333, wherein the cleavable peptide linker has a formula: -MC-vc-PAB-, wherein:

a) MC is:

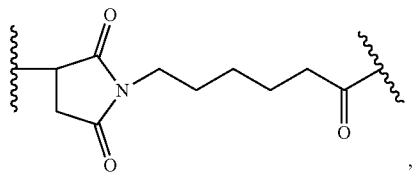 [SMILES: *C(=O)CCCCCN1C(=O)CC(*)C1=O]

b) vc is the dipeptide valine-citrulline, and c) PAB is:

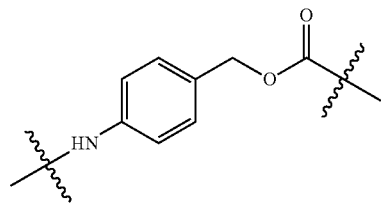

335. The use of any one of embodiments 322-334, wherein the linker is attached to sulphydryl residues of the anti-TF antibody or antigen-binding fragment thereof obtained by partial reduction or full reduction of the anti-TF antibody or antigen-binding fragment thereof.

336. The use of embodiment 335, wherein the linker is attached to MMAE, wherein the antibody-drug conjugate has the following structure:

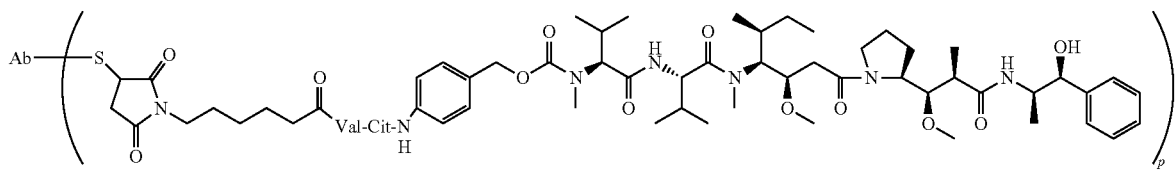

Ab-MC-vc-PAB-MMAE wherein p denotes a number from 1 to 8, S represents a sulphydryl residue of the anti-TF antibody, and Ab designates the anti-TF antibody or antigen-binding fragment thereof.

337. The use of embodiment 336, wherein the average value of p in a population of the antibody-drug conjugates is about 4.

338. The use of any one of embodiments 298-337, wherein the antibody-drug conjugate is tisotumab vedotin.

339. The use of any one of embodiments 298-338, wherein the route of administration for the antibody-drug conjugate is intravenous.

340. The use of any one of embodiments 298-339, wherein the anti-PD-1 antibody or antigen-binding fragment thereof comprises a heavy chain variable region comprising an amino acid sequence having at least 85% sequence identity to the amino acid sequence of SEQ ID NO:31 and a light chain variable region comprising an amino acid sequence having at least 85% sequence identity to the amino acid sequence of SEQ ID NO:32.

341. The use of any one of embodiments 298-340, wherein the anti-PD-1 antibody comprises a heavy chain variable region comprising the amino acid sequence of SEQ ID NO:31 and a light chain variable region comprising the amino acid sequence of SEQ ID NO:32.

342. The use of any one of embodiments 298-341, wherein the anti-PD-1 antibody comprises a heavy chain comprising the amino acid sequence of SEQ ID NO:33 and a light chain comprising the amino acid sequence of SEQ ID NO:34.

343. The use of any one of embodiments 298-342, wherein the anti-PD-1 antibody is pembrolizumab.

344. The use of any one of embodiments 298-343, wherein the route of administration for the anti-PD-1 antibody or antigen-binding fragment thereof is intravenous or subcutaneous.

345. The use of any one of embodiments 298-343, wherein the route of administration for the anti-PD-1 antibody or antigen-binding fragment thereof is intravenous.

346. The use of any one of embodiments 298-343, wherein the route of administration for the anti-PD-1 antibody or antigen-binding fragment thereof is subcutaneous.

347. The use of any one of embodiments 298-346, wherein the anti-PD-1 antibody or antigen-binding fragment thereof and the antibody-drug conjugate are administered sequentially.

348. The use of any one of embodiments 298-346, wherein the anti-PD-1 antibody or antigen-binding fragment thereof and the antibody-drug conjugate are administered simultaneously.

349. The use of any one of embodiments 298-348, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express TF.

350. The use of any one of embodiments 298-349, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of cancer cells from the subject express PD-L1.

351. The use of any one of embodiments 298-350, wherein the subject has a tumor that expresses PD-L1 (TPS≥1).

352. The method of any one of embodiments 298-350, wherein the subject has a tumor that has high PD-L1 expression (TPS≥50).

353. The method of any one of embodiments 298-350, wherein the subject has a tumor that expresses PD-L1 (CPS≥1).

354. The use of any one of embodiments 298-353, wherein a tumor derived from the cancer comprises one or more cells that express PD-L1, PD-L2, or both PD-L1 and PD-L2.

355. The use of any one of embodiments 298-354, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of T-cells from the subject express PD-1.

356. The use of any one of embodiments 298-355, wherein one or more therapeutic effects in the subject is improved after administration of the antibody-drug conjugate and the anti-PD-1 antibody or antigen-binding fragment thereof relative to a baseline.

357. The use of embodiment 356, wherein the one or more therapeutic effects is selected from the group consisting of: size of a tumor derived from the cancer, objective response rate, duration of response, time to response, progression free survival, and overall survival.

358. The use of any one of embodiments 298-357, wherein the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the antibody-drug conjugate and the anti-PD-1 antibody or antigen-binding fragment thereof.

359. The use of any one of embodiments 298-358, wherein the objective response rate is at least about 20%, at least about 25%, at least about 30%, at least about 35%, at least about 40%, at least about 45%, at least about 50%, at least about 60%, at least about 70%, or at least about 80%.

360. The use of any one of embodiments 298-359, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

361. The use of any one of embodiments 298-360, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

362. The use of any one of embodiments 298-361, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and the anti-PD-1 antibody or antigen-binding fragment thereof.

363. The use of any one of embodiments 298-362, wherein the subject has one or more adverse events and is further administered an additional therapeutic agent to eliminate or reduce the severity of the one or more adverse events.

364. The use of any one of embodiments 298-363, wherein the subject is at risk of developing one or more adverse events and is further administered an additional therapeutic agent to prevent or reduce the severity of the one or more adverse events.

365. The use of embodiment 363 or embodiment 364, wherein the one or more adverse events is anemia, abdominal pain, hemorrhage, hyperthyroidism, hypothyroidism, hypokalemia, hyponatremia, epistaxis, fatigue, nausea, alopecia, conjunctivitis, keratitis, conjunctival ulceration, constipation, decreased appetite, diarrhea, vomiting, peripheral neuropathy, or general physical health deterioration.

366. The use of any one of embodiments 363-365, wherein the one or more adverse events is a grade 3 or greater adverse event.

367. The use of any one of embodiments 363-365, wherein the one or more adverse events is a serious adverse event.

368. The use of embodiment 363 or embodiment 364, wherein the one or more adverse events is conjunctivitis, conjunctival ulceration, and/or keratitis and the additional agent is a preservative-free lubricating eye drop, an ocular vasoconstrictor, antibiotic, and/or a steroid eye drop.

369. The use of any one of embodiments 298-368, wherein the subject is a human.

370. The use of any one of embodiments 298-369, wherein the antibody-drug conjugate is in a pharmaceutical composition comprising the antibody-drug conjugate and a pharmaceutical acceptable carrier.

371. The use of any one of embodiments 298-370, wherein the anti-PD-1 antibody or antigen-binding fragment thereof is in a pharmaceutical composition comprising the anti-PD-1 antibody or antigen-binding fragment thereof and a pharmaceutical acceptable carrier.

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: MMAE Elicits Hallmark Characteristics Associated with Immunogenic Cell Death in a Cervical Cancer Cell Line Immunogenic cell death (ICD) is a regulated cell death program that is highlighted by the production and exposure of pro-inflammatory signals that leads to the generation of immune responses against the apoptotic tumor cells. ICD is characterized by: 1) exposure of endoplasmic reticulum (ER)-resident chaperone proteins on the surface of tumor cells; 2) secretion of ATP; and 3) secretion of HMGB1. Induction of ER stress is critical for regulating these 3 processes and has been shown to be elicited by antibody-drug conjugates (ADCs) wherein the conjugated drug is MMAE.

HeLa cells, a cervical cancer cell line, were cultured in Minimum Essential Medium (MEM) with 10% FBS, 10 mM HEPES, 1 mM sodium pyruvate, 2 mM L-glutamine, penicillin (100U/ml), and streptomycin (100 µg/ml). HeLa cells were treated with 100 nM MMAE for 16 hours and harvested in radioimmunoprecipitation assay buffer (RIPA) buffer for western blot analysis. Treatment with MMAE led to phosphorylation of the serine threonine kinase IRE1, indicating activation of ER stress. Severe ER stress is a prerequisite to the exposure of pro-phagocytic signals on the surface of tumor cells, and can be indicated by activation of JNK signaling by phosphorylated IRE1. As demonstrated herein, treatment with MMAE elicited severe ER stress by phosphorylation of IRE1 and JNK (FIG. 1).

Treatment of HeLa cells with MMAE led to disassembly of the microtubule network and subsequent ER mislocalization. HeLa cells were transduced with a baculovirus encoding RFP-labeled Tubulin (CellLight Tubulin-RFP, ThermoFisher Scientific) and an ER-binding dye (ER-ID Green, Enzo Life Sciences). Cells were treated with 100 nM MMAE and imaged over time in the present of MMAE. Within 2 hours, fragmentation and disassembly of the microtubule network became evident, concurrent with the breakdown of the perinuclear organized ER lattice (FIGS. 2A and 2B). The condensed and mislocalized ER skeleton indicated severe ER stress within 8 hours.

Figure 3A:
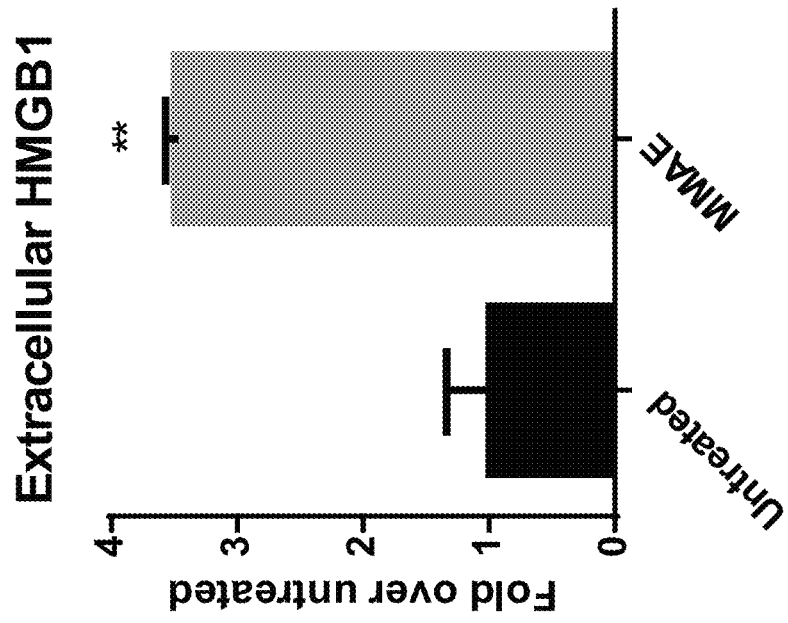
FIGS. 3A and 3B is a series of graphs showing A) ATP secretion and B) HMGB1 secretion from HeLa cells treated with 100 nM MMAE as compared to HeLa cells not treated with MMAE. Measurements were treated HeLa cells are shown as the fold change over the signal produced by untreated HeLa cells. p<0.01 and **p<0.0001.
Figure 3B:
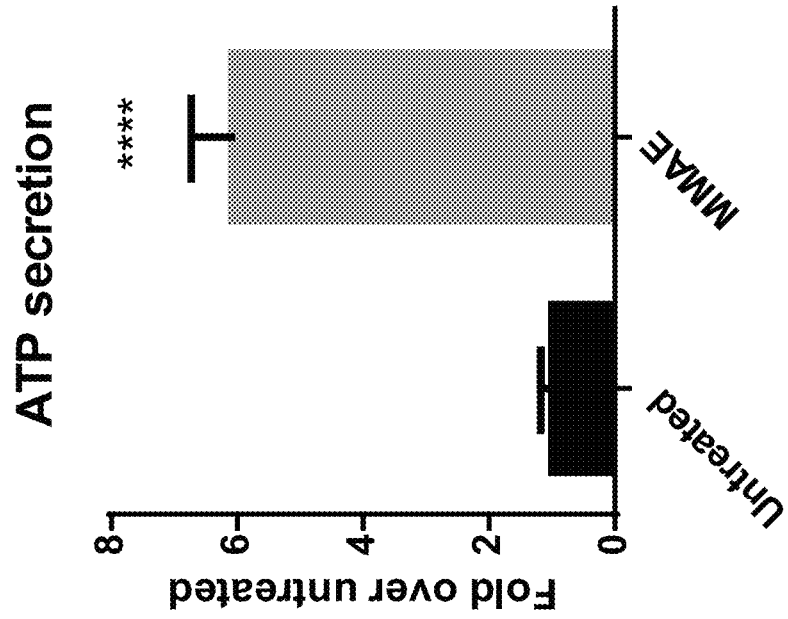

Induction of ICD is also characterized by the secretion of ATP and HMGB1. Extracellular ATP serves as a strong chemotactic signal, promoting immune cell migration to the tumor site. Upon arrival, extracellular HMGB1 signals through various pro-inflammatory receptors (TLR2, TLR4, RAGE) to activate antigen-presenting cells, thereby promoting immune activity within the tumor. As demonstrated herein, treatment of HeLa cells with 100 nM MMAE led to increased secretion of ATP and HMGB1 over a period of 24 hours (FIGS. 3A and 3B; p<0.01, **p<0.0001).

While the sequence of events of ADC binding to antigen positive cells, cleavage and release of the MMAE payload, and subsequent cell death is the primary mechanism of tisotumab vedotin functionality, each step in this process can evoke additional and distinct modalities that may contribute to overall antitumor activity. The MMAE cytotoxic payload connected to tisotumab vedotin disrupts microtubules which results in subsequent endoplasmic reticulum (ER) stress that drives exposure of immune activating molecules that can promote a T-cell response. The effect of MMAE on a cervical cancer cell line as shown in this example, demonstrates induction of the ER stress pathway and exposure of immune activating molecules. Accordingly, the T-cell response that may occur following tumor cell death with tisotumab vedotin could amplify the effect of treatment with a checkpoint inhibitor.

Example 2: Anti-Tumor Activity of Tisotumab Vedotin in Combination with an Anti-PD-1 Monoclonal Antibody in a Xenograft Model in Humanized Mice Tisotumab vedotin is an antibody-drug conjugate comprising an antibody that binds to tissue factor (TF), a protease-cleavable linker, and the microtubule disrupting agent MMAE. TF is a protein aberrantly expressed in a wide number of tumors including cervical cancer and is associated with poor prognosis. See Förster Y et al. *Clin Chim Acta.* 2006; 364(1-2):12-21 and Cocco E et al. *BMC Cancer.* 2011; 11:263. Tisotumab vedotin selectively targets TF to deliver a clinically validated toxic payload to tumor cells. See Breij E C et al. *Cancer Res.* 2014; 74(4):1214-1226 and Chu A J. *Int J Inflam.* 2011; 2011. doi: 10.4061/2011/367284.

The anti-PD-1 antibody, pembrolizumab (KEYTRUDA®), is a checkpoint inhibitor that is a standard of care therapy alone or in combination with chemotherapies in multiple tumor indications. The combination of tisotumab vedotin with an anti-PD-1 antibody such as pembrolizumab was evaluated herein for the treatment of cancer.

Materials and Methods

The in vivo anti-tumor efficacy of tisotumab vedotin in combination with an anti-PD-1 monoclonal antibody was evaluated in NOD.Cg-Prkdc$^{scid}$ Il2rg$^{tm1Wjl}$/SzJ (NSG) immunodeficient mice (The Jackson Laboratory, Stock No. 005557), humanized by engraftment with human CD34$^+$ hematopoietic stem cells (Jackson Laboratories, Sacramento). Mice were subcutaneously inoculated with 5×10$^6$ MDA-MB-231 cells (breast adenocarcinoma; American Tissue Culture Collection (ATCC), cat. no. HTB-26), in 100 µL phosphate-buffered saline (PBS). Before inoculation, cells were cultured in DMEM with high glucose and HEPES without L-glutamine (Lonza, cat. no. BE12-709F), 10% (v/v) donor bovine serum with iron New Zealand Origin (Thermo Fisher Scientific, DBSI, cat. no. 10371-029), 2 mM L-glutamine (Lonza, cat. no. BE17-605E), 1 mM Na-pyruvate (Lonza, cat. no. BE13-115E), MEM non-essential amino acids (Life Technologies, cat. no. 11140) and 1% (v/v) penicillin/streptomycin (Lonza, cat. no. DE17-603E), in CellSTACK culture chambers (Corning, cat. no. 3313).

Tumor size was determined by caliper measurement at least two times a week and tumor volume was calculated as 0.52×length×width$^2$. When tumors reached the size of 100 mm$^3$ mice were randomized in 7 groups (8 mice per treatment group) based on mouse cohort and tumor size (Table 1). Mice were treated with tisotumab vedotin alone (1 mg/kg or 0.5 mg/kg), intravenously, weekly for a maximum of five treatments, or in combination with an anti-PD-1 antibody (i.e., pembrolizumab, KEYTRUDA®, 50 mg concentrate, Merck & Co., Inc., Kenilworth, NJ USA) or with anti-PD-1 antibody alone. The first dose of the anti-PD-1 antibody (i.e., pembrolizumab) was 10 mg/kg, followed by 5 mg/kg every five days for a maximum of six treatments. Mice in control groups were administered 1 mg/kg of IgG1 isotype control antibody or IgG1 isotype control antibody conjugated to MMAE intravenously, weekly for a maximum of five treatments (Table 1). The IgG1 isotype control antibody is the b12 antibody which is known to bind to HIV-1 gp120. Mice were observed for clinical signs of illness at least twice a week. Mice were housed in individually ventilated (IVC) cages, five mice per cage and identified by ear tags.

TABLE 1

Trial design

| Group | Treatment | Dosing (mg/kg) | Day of treatment | Route of administration | Number of mice |
|---|---|---|---|---|---|
| 1 | IgG1 control | 1 mg/kg | Approximately d14, d21, d28, d35, optionally d42 | IV | 8 |
| 2 | IgG1-MMAE control | 1 mg/kg | Approximately d14, d21, d28, d35, optionally d42 | IV | 8 |
| 3 | ADC | 1 mg/kg | Approximately d14, d21, d28, d35, optionally d42 | IV | 8 |
| 4 | PD-1 | First dose 10 mg/kg, followed by 5 mg/kg | Q5D × 6 (Approximately d14, d19, d24, d29, d34, optionally d39) | IP | 8 |
| 5 | ADC + PD-1 | 1 mg/kg + First dose 10 mg/kg, followed by 5 mg/kg | Approximately d14, d21, d28, d35, optionally d42 + Q5D × 6 (Approximately d14, d19, d24, d29, d34, optionally d39) | IV IP | 8 |
| 6 | ADC | 0.5 mg/kg | Approximately d14, d21, d28, d35, optionally d42 | IV | 8 |
| 7 | ADC + PD-1 | 0.5 mg/kg + First dose 10 mg/kg, followed by 5 mg/kg | Approximately d14, d21, d28, d35, optionally d42 + Q5D × 6 (Approximately d14, d19, d24, d29, d34, optionally d39) | IV IP | 8 |

IgG1 control indicates the IgG1 b12 antibody that binds to HIV-1 gp120 and was used as an IgG1 isotype control;
IgG1-MMAE control indicates the IgG1 b12 antibody conjugated to MMAE;
ADC indicates anti-TF antibody conjugated to MMAE; and
PD-1 indicates anti-PD-1 antibody;
IV indicates intravenous administration; and
IP indicates intraperitoneal administration.

To determine whether there were statistically significant differences between tumor burden in control and treatment groups, tumor burden in the treatment groups were compared with those in the control groups (e.g., control antibody (e.g., IgG1 control or anti-PD-1 antibody) or control antibody-drug conjugate (e.g., tisotumab vedotin or IgG1-MMAE)). Statistical comparison of tumor burden was performed using Mann-Whitney analysis on the last day that all treatment groups were intact. Kaplan-Meier analysis was performed based on tumor volume (>500 mm$^3$).

Results

Treatment with pembrolizumab alone hardly reduced tumor burden as assessed by tumor volume (FIGS. 4A and 4B). Treatment with tisotumab vedotin efficiently reduced tumor burden at a dose of 0.5 mg/kg and at a dose of 1.0 mg/kg (FIGS. 4A and 4B). Combination treatment with tisotumab vedotin and pembrolizumab enhanced the induction of tumor regression (FIGS. 4A and 4B).

Example 3: Anti-Tumor Activity of Tisotumab Vedotin in Combination with an Anti-PD-1 Monoclonal Antibody in a Patient-Derived Xenograft Model in Humanized Mice Pembrolizumab has been tested in patients with cervical cancer. Pembrolizumab 200 mg Q3W was administered to 82 patients with previously treated, advanced cervical cancer. The objective response rate was 12%. See Schellens J. H. M, et al., *J Clin Oncol,* 2017, 35. (Suppl.): abstr 5514.

The combination of tisotumab vedotin with an anti-PD-1 antibody such as pembrolizumab is evaluated herein for the treatment of cervical cancer.

Materials and Methods

The in vivo anti-tumor efficacy of tisotumab vedotin in combination with an anti-PD-1 monoclonal antibody is evaluated in an animal model such as in NOD.Cg-Prkdc$^{scid}$ Il2rg$^{tm1Wjl}$ (NSG) immunodeficient mice or NOD-Prkdc$^{em26Cd52}$Il2rg$^{em26Cd22}$ (NCG) immunodeficient mice humanized by engraftment with human CD34$^+$ hematopoietic stem cells. Patient-derived xenografts (PDX) are derived from tumor specimens from cancer patients. Establishment and characterization of the PDX model is performed following the primary implantation into nude mice. Tumor xenografts are passaged approximately three to five times until establishment of stable growth patterns. Tumor fragments are obtained from xenografts in serial passage in nude mice. Tumors are cut into fragments of 4-5 mm diameter and placed in phosphate-buffered saline (PBS) until subcutaneous implantation. Cervical cancer PDX models (HUPRIME® cervical xenograft model CV1802 and CV2302; Crown Bioscience Inc.) are used in this experiment. Tumor size is determined by caliper measurement at least two times a week and tumor volume is calculated as 0.52×length×width$^2$. When tumors reach the volume of 150-250 mm$^3$, mice are randomized in 7 groups per model (10 mice per treatment group), based on tumor volume. Mice are treated with intravenous injections of tisotumab vedotin alone (e.g., at two dose levels between 0.5 mg/kg and 4 mg/kg, weekly) or in combination with an anti-PD-1 monoclonal antibody (e.g., pembrolizumab, KEYTRUDA®; at a dose between 5 and 15 mg/kg, every 5-7 days) or with anti-PD-1 antibody alone (e.g., pembrolizumab, KEYTRUDA®; at a dose between 5 and 15 mg/kg, every 5-7 days). In one example, when the HUPRIME® cervical xenograft model CV2320 is used, mice are treated with intravenous injections of tisotumab vedotin alone at a dose of 4 mg/kg or 2 mg/kg, or in combination with an anti-PD-1 monoclonal antibody (e.g., pembrolizumab) at a first dose of 10 mg/kg, followed by a 5 mg/kg dose every 5 days until a maximum amount of treatment is reached (e.g., five treatments). HUPRIME® cervical xenograft model CV2320 treated with anti-PD-1 monoclonal antibody alone (e.g., pembrolizumab) are provided at a first dose of 10 mg/kg, followed by a 5 mg/kg dose every 5 days until a maximum amount of treatment is reached (e.g., five treatments). In another example, when the HUPRIME® cervical xenograft model CV1802 is used, mice are treated with intravenous injections of tisotumab vedotin alone at a dose of 1 mg/kg or 0.5 mg/kg, or in combination with an anti-PD-1 monoclonal antibody (e.g., pembrolizumab) at a first dose of 10 mg/kg, followed by a 5 mg/kg dose every 5 days until a maximum amount of treatment is reached (e.g., five treatments). HUPRIME® cervical xenograft model CV1802 treated with anti-PD-1 monoclonal antibody alone (e.g., pembrolizumab) are provided aa first dose of 10 mg/kg, followed by a 5 mg/kg dose every 5 days until a maximum amount of treatment is reached (e.g., five treatments). Mice are observed for clinical signs of illness at least twice a week. Mice are housed in individually ventilated (IVC) cages, five mice per cage and identified by ear tags.

To determine whether there are statistically significant differences between tumor volumes in control and treatment groups, tumor volumes in the treatment groups are compared with those in the control groups (e.g., control antibody (e.g., IgG1 control or anti-PD-1 antibody) or control antibody-drug conjugate (e.g., tisotumab vedotin or IgG1-MMAE)), using Mann-Whitney analysis at the last day that all groups are intact. Tumor volumes in mice treated with both tisotumab vedotin and anti-PD-1 antibody are compared with those in mice treated with either control antibody alone (e.g., IgG1 control or anti-PD-1 antibody) or control antibody-drug conjugate alone (e.g., tisotumab vedotin or IgG1-MMAE) and analyzed such as by using Mantel-Cox analysis on Kaplan-Meier plots.

Example 4: Anti-Tumor Activity of Tisotumab Vedotin in Combination with an Anti-PD-1 Monoclonal Antibody in a Syngeneic Tumor Model Mouse tumor cells are transfected with plasmid constructs encoding human tissue factor (TF) and sgRNA-guided Cas9 nuclease (sgRNA/Cas9) to generate a murine cell line that expresses the human TF. Fluorescence activated cell sorting (FACS) yields a clonal population of murine tumor cells that stably express human TF, these cells are then treated with 1 μg to 5 μg per ml of tisotumab vedotin or 100 nM of MMAE for 4 days. In order to prepare dying cells for immunization, treated murine tumor cells are overlaid atop Histopaque, and centrifuged at 2000 g for 30 minutes. Dead and dying cells are pelleted underneath the Histopaque layer, and viability assessed by trypan blue exclusion. A sample with approximately <20% live cells as measured by trypan blue exclusion is obtained. Flash-frozen tumor cells are prepared by submerging the cells in liquid nitrogen for 10 seconds, followed by immersion in 37° C. water until completely thawed. The liquid nitrogen freeze-thaw process is repeated 5 times. Dead and dying human TF positive tumor cells are resuspended in phosphate buffered saline (PBS) and 2×10$^6$ cells are injected into the peritoneum of immune-competent Balb/c mice. Seven days later, mice receive a second immunization with dead and dying cells prepared in the same manner.

Fourteen days after initial immunization with the dead and dying human TF positive tumor cells, mice are subcutaneously implanted with 5×10$^6$ wild-type tumor cells and monitored for tumor growth. Mice that are immunized with tisotumab vedotin-killed tumor cells or MMAE-killed tumor cells experience delayed tumor growth and increased survival. As these effects occur in the absence of any administered therapeutic agent, the administration of cells killed by tisotumab vedotin or MMAE is sufficient to generate long-lasting protective immune memory against subsequent tumor cell challenge. Protective immune memory is amplified by treating these mice with tisotumab vedotin in combination with an antibody that binds to murine PD-1. This combination treatment increases the number of mice that are cured by subsequent tumor challenge.

Example 5: A Phase II Trial of Tisotumab Vedotin Alone or in Combination with a Monoclonal Anti-PD-1 Antibody in First Line Recurrent or Stage IVB Cervical Cancer A Phase I/II trial demonstrated a robust efficacy and manageable safety profile for 2.0 mg/kg tisotumab vedotin administered to subjects with relapsed, recurrent, and/or metastatic cervical cancer (NCT02001623). That preliminary data suggests a positive benefit risk profile for that population of high unmet need. Further investigation of tisotumab vedotin as a monotherapy and in combination with immunotherapy (e.g., an anti-PD-1 antibody) in a larger cohort of patients with cervical cancer is needed.

The efficacy, safety and tolerability of 1.3 mg/kg or 2.0 mg/kg tisotumab vedotin alone or in combination with pembrolizumab, a monoclonal anti-PD-1 antibody, in subjects with first line recurrent or Stage IVB cervical cancer is evaluated herein.

Methods

This phase II, open-label, multi-center trial evaluates the efficacy, safety and tolerability of tisotumab vedotin alone or in combination with the anti-PD-1 antibody, pembrolizumab, in subjects with first line recurrent or Stage IVB squamous, adenosquamous, or adenocarcinoma of the cervix who are not amenable to curative treatment with surgery and/or radiation therapy and who have not received prior systemic therapy for their recurrent or Stage IVB disease. Subjects with recurrent disease who are candidates for curative therapy by means of pelvic exenteration are not eligible to participate in the trial.

Subjects are symmetrically allocated to one of four treatment groups. The allocation is done in a way that minimizes imbalance on disease status (metastatic/recurrent) and histology (squamous/non-squamous). Eligible subjects are treated with tisotumab vedotin 1.3 mg/kg Q3W, tisotumab vedotin 2.0 mg/kg Q3W, tisotumab vedotin 1.3 mg/kg Q3W+pembrolizumab 200 mg Q3W or tisotumab vedotin 2.0 mg/kg Q3W+pembrolizumab 200 mg Q3W. Treatment cycles occur every 21 days (3 days). All treatment components are administered intravenously (IV). Approximately 60 subjects, age r18 years, are enrolled in the trial. The duration of the trial is approximately 7 years. Inclusion criteria and exclusion criteria for subjects enrolled in the trial are shown in Table 2.

TABLE 2

List of inclusion and exclusion criteria

| Inclusion Criteria | Must have recurrent or Stage IVB squamous, adenosquamous, or adenocarcinoma histologies of the cervix which are not amenable to curative treatment with surgery and/or radiation therapy.<br>Must have not received prior systemic therapy for recurrent or Stage IVB disease.<br>Note: Subjects are excluded if they are candidates for curative therapy by means of pelvic exenteration.<br>Note: Chemotherapy administered in the adjuvant or neoadjuvant setting, or in combination with radiation therapy is not counted as a prior systemic therapy.<br>Must have baseline measurable disease per RECIST v1.1.<br>Note: Lesions situated in a previously irradiated area are considered measurable if progression has been demonstrated in such lesions.<br>Age ≥ 18 years of age on day of signing informed consent.<br>Acceptable renal function: Calculated (Cockcroft-Gault) Glomerular Filtration Rate (GFR) > 50 mL/min.<br>Acceptable liver function:<br>Alanine aminotransferase (ALT) and aspartate aminotransferase (AST) ≤ 2.5 × Upper Limit of Normal (ULN) (if liver tumor/metastases are present, then ≤ 5 × ULN is allowed);<br>Bilirubin ≤ 1.5 × ULN unless direct bilirubin ≤ institutional ULN, except in subjects diagnosed with Gilbert's syndrome, direct bilirubin ≤ 2 × ULN.<br>Acceptable hematological status:<br>Hemoglobin ≥ 5.6 mmol/L (9.0 g/dL).*<br>Absolute neutrophil count (ANC) ≥ 1500/μL (1.5 × 10$^9$/L).<br>Platelet count ≥ 100 × 10$^9$/L.<br>*Acceptable hematologic status must be met without erythropoietin dependency and without packed red blood cell (pRBC) transfusion within the last 2 weeks. |
|---|---|

TABLE 2-continued

List of inclusion and exclusion criteria

| | Acceptable coagulation status:<br>For subjects not on anti-coagulation therapy:<br>Activated partial thromboplastin time (aPTT) ≤ 1.25 × ULN.<br>International normalized ratio (INR) ≤ 1.2.<br>For subjects on anti-coagulation therapy:<br>aPTT ≤ 1.25 × ULN<br>INR: (1) Subjects on anti-coagulation therapy requiring laboratory assessments for dose titration (warfarin or other Vitamin K dependent anticoagulant agents) must be on a steady dose (no active titration) for at least 4 weeks prior to first planned dose of tisotumab vedotin and must have an INR ≤ 2.5 for eligibility. (2) Subjects on anti-coagulants that do not require laboratory assessments for dose titration must have an INR of ≤ 1.2 and do not need to be on a stable dose for ≥ 4 weeks prior to first planned dose of IMP.<br>Concurrent use of prophylactic AcetylSalicylic Acid (ASA, e.g., aspirin) is prohibited for subjects on any type of anti-coagulation therapy.<br>Eastern Cooperative Oncology Group (ECOG) performance status of 0 or 1.<br>Life expectancy of ≥ 3 months<br>A female subject is eligible to participate if she is not pregnant, breastfeeding, or expecting to conceive children, or expecting to donate eggs for the purposes of assisted reproduction within the projected duration of the trial and for at least 6 months after the last trial administration and at least one of the following conditions applies:<br>Not a woman of childbearing potential (WOCBP)<br>A WOCBP must agree to use adequate contraception during and for 6 months after the last dose of trial treatment administration. Adequate contraception for women is defined as highly effective methods of contraception. In countries where two highly effective methods of contraception are required this will be an inclusion criterion.<br>Must provide a fresh specimen from a lesion not previously irradiated. Subjects for whom fresh samples cannot be obtained (e.g., inaccessible tumor or for safety concerns) may submit an archived specimen in place of the fresh tissue.<br>Note: Aspirates are not acceptable.<br>Must have recovered from all AEs due to previous therapies to ≤ grade 1. Subjects with ≤ grade 2 neuropathy or alopecia are eligible.<br>Must be willing and able to adhere to the prohibitions and restrictions specified in this protocol.<br>Following receipt of verbal and written information about the trial, subjects must provide signed informed consent before any trial-related activity is carried out. |
|---|---|
| Exclusion Criteria | Clinically relevant bilateral hydronephrosis which cannot be alleviated by ureteral stents or percutaneous drainage.<br>Have clinical signs or symptoms of gastrointestinal obstruction and requires parenteral hydration and/or nutrition.<br>Hematological: Known past or current coagulation defects leading to an increased risk of bleeding; diffuse alveolar hemorrhage from vasculitis; known bleeding diathesis; ongoing major bleeding; trauma with increased risk of life-threatening bleeding or history of severe head trauma or intracranial surgery within 8 weeks of trial entry.<br>Ophthalmological: Active ocular surface disease at baseline. Subjects with prior history of cicatricial conjunctivitis or Steven Johnson Syndrome are not eligible to participate.<br>Has an active autoimmune disease that has required systemic treatment in past 2 years (i.e., with use of disease modifying agents, corticosteroids or immunosuppressive drugs).<br>Replacement therapy (e.g., thyroxine, insulin, or physiologic corticosteroid replacement therapy for adrenal or pituitary insufficiency) is not considered a form of systemic treatment and is allowed.<br>Cardiovascular: Clinically significant cardiac disease including unstable angina, acute myocardial infarction within 6 months prior to screening; any medical history of congestive heart failure (Grade III or IV as classified by the New York Heart Association), any medical history of decreased cardiac ejection fraction of < 45%; a marked baseline prolongation of QT/QTc interval (e.g., repeated demonstration of a QTc interval > 450 msec), a complete left bundle branch block (defined as a QRS interval ≥ 120 msec in left bundle branch block form) or an incomplete left bundle branch block. |

TABLE 2-continued

List of inclusion and exclusion criteria

Current or a prior history of (non-infectious) pneumonitis that required steroids or has current pneumonitis.
Other cancers: Known past or current malignancy other than inclusion diagnosis, except for: Non-invasive basal cell or squamous cell skin carcinoma; noninvasive, superficial bladder cancer; any cancer with a complete response (CR) of > 5 years duration.
Known active CNS metastases and/or carcinomatous meningitis. Subjects with previously treated brain metastases may participate provided they are radiologically stable, (i.e., without evidence of progression) for at least 28 days by repeat imaging (note that the repeat imaging should be performed during trial screening), subjects should be clinically stable, and should not require steroid treatment for at least 14 days prior to first dose of trial treatment.
Prior therapy:
Any prior treatment with MMAE-derived drugs.
Has received prior para-aortic radiation.
Prior radiotherapy (with the exception of para-aortic radiation) within 2 weeks (14 days) of start of trial treatment. Subjects must have recovered from all radiation-related toxicities, not require corticosteroids, and not have had radiation pneumonitis. A 1-week washout is permitted for palliative radiation (≤2 weeks of radiotherapy) to non-CNS disease.
Has received prior systemic anti-cancer therapy including investigational agents within 4 weeks (28 days) prior to the first dose of trial treatment.
Has received prior therapy with an anti-PD-1, anti-PD-L1, or anti PD-L2 agent or with an agent directed to another stimulatory or co-inhibitory T-cell receptor (e.g., CTLA-4, OX40, CD137) and was discontinued from treatment due to a grade 3 or higher AE of special interest (AESI).
Surgery/procedures: major surgery within 4 weeks (28 days) or minor surgery within 7 days prior to the first dose of trial treatment. Subjects must have recovered adequately from the toxicity and/or complications from the intervention prior to starting trial treatment. Subjects who have planned major surgery during the treatment period must also be excluded from the trial.
Has a diagnosis of immunodeficiency or is receiving systemic steroid therapy (in dosing exceeding 10 mg daily of prednisone or equivalent) or any other form of immunosuppressive therapywithin 7 days prior to the first dose of trial treatment.
Received a live vaccine within 30 days prior to the first dose of trial treatment. Examples of live vaccines include, but are not limited to, the following: measles, mumps, rubella, varicella/zoster (chicken pox), yellow fever, rabies, Bacillus Calmette-Guérin, and typhoid vaccine. Seasonal influenza vaccines for injection are generally killed virus vaccines and are allowed; however, intranasal influenza vaccines (e.g., FluMist ®) are live attenuated vaccines and are not allowed.
Is currently participating in or has participated in a trial of an investigational agent or has used an investigational device within 4 weeks prior to the first dose of trial treatment.
Note: Subjects who have entered the follow-up phase of an investigational trial may participate as long as it has been 4 weeks after the last dose of the previous investigational agent.
Other: Ongoing significant, uncontrolled medical condition; clinically significant active viral, bacterial or fungal infection requiring IV or oral (PO) treatment with antimicrobial therapy ending less than 7 days prior to first trial treatment administration;
Known history of human immunodeficiency virus (HIV) infection. No HIV testing is required unless mandated by local health authority.
Known history of Hepatitis B (defined as Hepatitis B surface [HBsAg] reactive) or known active Hepatitis C virus (defined as HCV RNA [qualitative] is detected) infection.
Note: No testing for Hepatitis B and Hepatitis C is required unless mandated by local health authority.
Has known allergies, severe hypersensitivity (Grade 3), or intolerance to tisotumab vedotin, pembrolizumab, or their excipients.

TABLE 2-continued

List of inclusion and exclusion criteria

Has a history or current evidence of any condition, therapy, or laboratory abnormality that might confound the results of the trial, interfere with the subject's participation for the full duration of the trial, or is not in the best interest of the subject to participate, in the opinion of the treating investigator.
Has known psychiatric or substance abuse disorders that would interfere with cooperating with the requirements of the trial.
A WOCBP who has a positive pregnancy test (e.g., within 72 hours) prior to treatment. If the urine test is positive or cannot be confirmed as negative, a serum pregnancy test will be required. Subjects that are postmenopausal or permanently sterilized can be considered as not having reproductive potential.

Lyophilized vials containing 40 mg of tisotumab vedotin are stored in a refrigerator at 2° C. to V° C. Tisotumab vedotin is reconstituted in 4 ml of water leading to a reconstituted solution comprising 10 mg/mL tisotumab vedotin, 30 mM histidine, 88 mM sucrose, and 165 mM D-mannitol. The reconstituted antibody drug-conjugate solution has a pH of 6.0. The reconstituted tisotumab vedotin is diluted into a 0.9% NaCl 100 mL infusion bag according to the dose calculated for the subject. Intravenous infusion is completed within 24 hours after the tisotumab vedotin vial has been reconstituted. A 0.2 µm in-line filter is used for the intravenous infusion. The entire 100 mL volume from the prepared infusion bag is administered. No dead volume is provided. Pembrolizumab (KEYTRUDA®) injection is a sterile, preservative-free, clear to slightly opalescent, colorless to slightly yellow solution that requires dilution for intravenous infusion. Each vial contains 100 mg of pembrolizumab in 4 mL of solution. Each 1 mL of solution contains 25 mg of pembrolizumab and is formulated in: L-histidine (1.55 mg), polysorbate 80 (0.2 mg), sucrose (70 mg), and Water for Injection, USP. The dose of pembrolizumab for administration to the subject is calculated at the trial site.

Objectives and endpoints are described in Table 3. Subjects are treated until disease progression, toxicity, or withdrawal of consent. For subjects participating in the tisotumab vedotin in combination with pembrolizumab treatment group, treatment with pembrolizumab is discontinued after the subject has completed 35 treatments (approximately 2 years) with pembrolizumab. Treatment with pembrolizumab may also be discontinued if the subject achieves a confirmed complete response (CR) and has been treated for at least 8 cycles (≥24 weeks) and the subject has received at least 2 doses of pembrolizumab beyond the date when the initial CR was declared. Subjects may continue to receive tisotumab vedotin monotherapy after the discontinuation of pembrolizumab if the subject has achieved stable disease (SD) or better.

Imaging is obtained every 6 weeks for 32 weeks and then every 12 weeks thereafter, calculated from the date of first dose. On-trial imaging is continued until the subject experiences radiographic disease progression, begins a new anti-cancer therapy, withdraws consent or subject death. Tumor response is analyzed at three time points; futility assessment, early efficacy assessment, and primary efficacy assessment, respectively.

TABLE 3

Objectives and endpoints

| OBJECTIVES | ENDPOINTS |
|---|---|
| Primary | |
| Evaluate anti-tumor efficacy of tisotumab vedotin alone or in combination with pembrolizumab. | Objective Response Rate (ORR) as determined per Response Evaluation Criteria in Solid Tumors (RECIST) v1.1. |
| Secondary | |
| Assess safety and tolerability of tisotumab vedotin alone or in combination with pembrolizumab. | Frequency, duration, and severity of adverse events (AEs) and evaluation of safety laboratory parameters. |
| Evaluate durability of tisotumab vedotin alone or in combination with pembrolizumab. | Duration of Response (DOR) per RECIST v1.1. Time to Response (TTR) per RECIST v1.1. |
| Evaluate clinical response with tisotumab alone or in combination with pembrolizumab. | Progression free survival (PFS) per RECIST v 1.1. Overall Survival (OS). |
| To evaluate the pharmacokinetics (PK) and immunogenicity of tisotumab vedotin alone and in combination with pembrolizumab. | TPK and anti-drug antibodies (ADA) associated with tisotumab vedotin alone and in combination with pembrolizumab. |
| Exploratory | |
| Explore relationship between biomarkers and clinical response. Assess potential pharmacodynamic biomarkers. | TF and PD-L1 expression in tumor biopsies, circulating TF, proteomic analyses and genomic signatures. Circulating tissue factor (TF) and proteomic analyses. |

For subjects that do not tolerate the protocol-specified dosing schedule, dose reductions are permitted for tisotumab vedotin in order to allow the subject to continue treatment with tisotumab vedotin alone or in combination with pembrolizumab (Table 4).

TABLE 4

Dose modification scheme for tisotumab vedotin

| Current Dose of Tisotumab Vedotin | Reduced Dose of Tisotumab Vedotin |
|---|---|
| 2.0 mg/kg | 1.3 mg/kg |
| 1.3 mg/kg | 0.9 mg/kg* |

*No more than 2 dose reductions of tisotumab vedotin will be permitted. If an AE recurs after the second dose reduction of tisotumab vedotin, then the subject must be permanently discontinued from trial treatment.

The dose of pembrolizumab cannot be reduced but may be held. AEs associated with pembrolizumab exposure may represent an immunologic etiology. These immune-related AEs (irAEs) may occur shortly after the first dose or several months after the last dose of pembrolizumab treatment and may affect more than one body system simultaneously. Based on existing clinical trial data, most irAEs were reversible and could be managed with interruptions of pembrolizumab, administration of corticosteroids and/or other supportive care. Based on the severity of irAEs, withhold or permanently discontinue pembrolizumab and administer corticosteroids. Dose modification and toxicity management guidelines for irAEs associated with pembrolizumab are provided in Table 5. Corticosteroid taper should be initiated upon AE improving to Grade 1 or less and continue to taper over at least 4 weeks. For situations where pembrolizumab and tisotumab vedotin are withheld, pembrolizumab can be resumed after AE has been reduced to Grade 1 or 0 and corticosteroid has been tapered. Tisotumab vedotin can be resumed after the AE has been reduced to Grade 1 or 0. Pembrolizumab and tisotumab vedotin should be permanently discontinued if AE does not resolve within 12 weeks of last dose or corticosteroids cannot be reduced to ≤10 mg prednisone or equivalent per day within 12 weeks. Pembrolizumab should be discontinued for any recurrent ≥grade 3 irAE that recurs. For severe and life-threatening immune-related adverse events (irAEs), IV corticosteroid should be initiated first followed by oral steroid. Other immunosuppressive treatment should be initiated if irAEs cannot be controlled by corticosteroids.

TABLE 5

Dose modification and toxicity management guidelines for irAEs associated with the pembrolizumab in combination with tisotumab vedotin treatment group

| Immune-related AEs | Toxicity grade or conditions (CTCAE v4.0) | Action taken to pembrolizumab | Action taken to tisotumab vedotin | irAE management with corticosteroid and/or other therapies | Monitor and follow-up |
|---|---|---|---|---|---|
| Pneumonitis | Grade 2 Grade 3 or 4, or recurrent ≥ Grade 2 | Withhold Permanently discontinue | Withhold Withhold[1] | Administer corticosteroids (initial dose of 1-2 mg/kg prednisone or equivalent) followed by taper | Monitor subjects for signs and symptoms of pneumonitis Evaluate subjects with suspected pneumonitis with radiogrnphic imaging and initiate corticosteroid treatment Add prophylactic antibiotics for opportunistic infections |

TABLE 5-continued

Dose modification and toxicity management guidelines for irAEs associated with the pembrolizumab in combination with tisotumab vedotin treatment group

| Immune-related AEs | Toxicity grade or conditions (CTCAE v4.0) | Action taken to pembrolizumab | Action taken to tisotumab vedotin | irAE management with corticosteroid and/or other therapies | Monitor and follow-up |
|---|---|---|---|---|---|
| Diarrhea/Colitis | Grade 2 or 3 Grade 4 | Withhold Permanently discontinue | Withhold Withhold[2] | Administer corticosteroids (initial dose of 1-2 mg/kg prednisone or equivalent) followed by taper | Monitor subjects for signs and symptoms of enterocolitis (i.e., diarrhea, abdominal pain, blood or mucus in stool with or without fever) and of bowel perforation (i.e., peritoneal signs and ileus). Subjects with Grade 2 diarrhea suspecting colitis should consider GI consultation and performing endoscopy to rule out colitis. Subjects with ≥ diarrhea/colitis should be advised to drink liberal quantities of clear fluids. If sufficient oral fluid intake is not feasible, fluid and electrolytes should be substituted via IV infusion. |
| AST/ALT elevation or Increased bilirubin | Grade 2 | Withhold | Withhold | Administer corticosteroids (initial dose of 0.5-1 mg/kg prednisone or equivalent) followed by taper | Monitor with liver function tests (consider weekly or more frequently until liver enzyme value returned to baseline or is stable |
|  | Grade 3 or 4 | Permanently discontinue | Withhold[2] | Administer corticosteroids (initial dose of 1-2 mg/kg prednisone or equivalent) followed by taper |  |
| Type 1 diabetes mellitus (T1DM) or Hyperglycemia | Newly onset T1DM or Grade 3 or 4 hyperglycemia associated with evidence of β-cell failure | Withhold[3] | Withhold | Initiate insulin replacement therapy for subjects with T1DM Administer anti-hyperglycemic in subjects with hyperglycemia | Monitor subjects for hyperglycemia or other signs and symptoms of diabetes. |
| Hypophysitis | Grade 2 Grade 3 or 4 | Withhold Withhold or permanently discontinue[3] | Withhold Withhold[3] | Administer corticosteroids and initiate hormonal replacements as clinically indicated. | Monitor for signs and symptoms of hypophysitis (including hypopituitarism and adrenal insufficiency). |
| Hyperthyroidism | Grade 2 Grade 3 or 4 | Continue Withhold or permanently discontinue[3] | Continue Withhold[3] | Treat with non-selective beta-blockers (e.g., propranolol) or thionamides as appropriate | Monitor for signs and symptoms of thyroid disorders. |

TABLE 5-continued

Dose modification and toxicity management guidelines for irAEs associated with the pembrolizumab in combination with tisotumab vedotin treatment group

| Immune-related AEs | Toxicity grade or conditions (CTCAE v4.0) | Action taken to pembrolizumab | Action taken to tisotumab vedotin | irAE management with corticosteroid and/or other therapies | Monitor and follow-up |
|---|---|---|---|---|---|
| Hypothyroidism | Grade 2-4 | Continue | Continue | Initiate thyroid replacement hormones (e.g., levothyroxine or liothyroinine) per standard of care | Monitor for signs and symptoms of thyroid disorders. |
| Nephritis and Renal dysfunction | Grade 2<br>Grade 3 or 4 | Withhold<br>Permanently discontinue | Withhold<br>Withhold[2] | Administer corticosteroids (prednisone 1-2 mg/kg or equivalent) followed by taper. | Monitor changes of renal function |
| Myocarditis | Grade 1 or 2<br>Grade 3 or 4 | Withhold<br>Permanently discontinue | Withhold<br>Withhold[2] | Based on severity of AE administer corticosteroids | Ensure adequate evaluation to confirm etiology and/or exclude other causes |
| All other immune-related AEs | Intolerable/persistent Grade 2 | Withhold | Withhold | Based on type and severity of AE administer corticosteroids | Ensure adequate evaluation to confirm etiology and/or exclude other causes |
|  | Grade 3 | Withhold or discontinue based on the type of event. Events that require discontinuation include and not limited to: Gullain-Barre Syndrome, encephalitis | Withhold[2] |  |  |
|  | Grade 4 or recurrent Grade 3 | Permanently discontinue | Permanently discontinue |  |  |

Note:
Withhold or permanently discontinue pembrolizumab and tisotumab vedotin is at the discretion of the investigator or treating physician.
[1]For grade 3 pneumonitis, tisotumab vedotin monotherapy can continue after consultation with the sponsor if the event resolves to grade 1 or 0 within 12 weeks from the last dose. If pneumonitis recurs, tisotumab vedotin must be discontinued immediately. For grade 4 pneumonitis, tisotumab vedotin must be discontinued immediately.
[2]Tisotumab vedotin should be withheld until etiology has been established. If the grade 3 event is clearly not related to tisotumab vedotin and if the event resolves to grade 1 or 0 within 12 weeks from the last dose, monotherapy tisotumab may continue after consultation with the sponsor. If the ≥ grade 3 event recurs, tisotumab vedotin must be discontinued immediately. For grade 4 events, discontinue tisotumab vedotin immediately.
[3]For subjects with grade 3 or 4 immune-related endocrinopathy where withhold of pembrolizumab and tisotumab vedotin is required, pembrolizumab and tisotumab vedotin may be resumed when AE resolves to ≤ grade 2 and is controlled with hormonal replacement therapy or achieved metabolic control (in case of Type 1 diabetes mellitus [T1DM]).

Three adverse events of special interest were identified during treatment with tisotumab vedotin alone in the Phase IIa trial discussed above: 1) ocular adverse events; 2) adverse events of peripheral neuropathy; and 3) adverse events of bleeding. For ocular AEs: AEs of grade 1-2 conjunctivitis were frequently reported in relation to treatment with tisotumab vedotin. Implementation of a comprehensive mitigation plan and preventive measures substantially reduced both the frequency and severity of ocular adverse events. In the present trial, in order to prevent ocular AEs, all subjects in both treatment groups (i.e., tisotumab vedotin alone or in combination with pembrolizumab) must adhere to the following ocular pre-medication guidelines: 1) use of preservative-free lubricating eye drops during the whole treatment phase of the trial (i.e., from first dose of tisotumab vedotin until the safety follow-up visit). Lubricating eye drops should be administered according to the product prescribing information; 2) it is recommended not to wear contact lenses while treated with tisotumab vedotin from the first dose until a safety follow-up visit; 3) use of refrigerator-based eye cooling pads during infusion, e.g. THERA PEARL Eye Mask or similar, to be applied immediately before infusion in accordance with the instructions provided with the eye cooling pads; 4) administration of local ocular vasoconstrictor before infusion (brimonidine tartrate 0.2% eye drops or similar, 3 drops in each eye immediately prior to start of infusion; otherwise to be used in accordance with the product prescribing information). If the subject does not tolerate ocular vasoconstrictors due to adverse reactions, continued treatment with these may be stopped; and 5) application of steroid eye drops (dexamethasone 0.1% eye drops or equivalent) during the first 3 days of each treatment cycle (i.e., first drop to be given before start of tisotumab vedotin infusion; continue treatment for 72 hours thereafter). Steroid eye drops should be administered as 1 drop in each eye, 3 times daily, for 3 days, or used in accordance with the product prescribing information. The guidelines for ocular AEs are shown in Table 6.

TABLE 6

Dose modification and toxicity management guidelines for ocular adverse events.

| Adverse Event & Toxicity Grade (CTCAE v4.0) | Action Taken with Tisotumab Vedotin | Action Taken with pembrolizumab | Guidelines for Treatment Prescribed by the Ophthalmologist |
|---|---|---|---|
| Conjunctivitis | | | |
| Conjunctivitis gr 1 | Hold dosing until event is managed effectively Continue tisotumab vedotin at the same dose level | Continue | Local ophthalmologist must prescribe frequent dosing of preservative-free topical steroid drops. |
| Conjunctivitis gr 2 $1^{st}$ occurrence | Hold dosing until event has improved to ≤ gr 1 Continue tisotumab vedotin at the same dose level | Continue | Local ophthalmologist must prescribe frequent dosing (every second hour) of preservative free topical steroid drops in conjunction with preservative free antibiotic prophylaxis such as chloramphenicol until the local ophthalmologist deems necessary. |
| Conjunctivitis gr 2 ≥ $2^{nd}$ occurrence | Hold dose of tisotumab vedotin: If the event improves to baseline within 6 weeks (calculated from the onset date of the $2^{nd}$ grade 2 event), reduce next dose of tisotumab vedotin according to Table 4. If the event does not improve to baseline within 6 weeks, permanently discontinue tisotumab vedotin. | Continue | |
| Conjunctivitis ≥ gr 2 $3^{rd}$ occurrence | Permanently discontinue tisotumab vedotin. | Continue | |
| Conjunctivitis ≥ gr 3 | Permanently discontinue tisotumab vedotin | Hold dosing until event has improved to ≤ gr 1. Contact sponsor to determine if pembrolizumab may be continued. | |
| Keratitis | | | |
| Keratitis ≤ gr 2 $1^{st}$ occurrence | Hold tisotumab vedotin until event has improved to ≤ gr 1 Reduce tisotumab vedotin according to Table 4. | Continue | The local ophthalmologist must prescribe frequent dosing (every second hour) of preservative free topical steroid drops in conjunction with preservative free antibiotic prophylaxis such as chloramphenicol until the local ophthalmologist deems necessary. |
| Keratitis ≤ gr 2 $2^{nd}$ occurrence | Hold tisotumab vedotin until event has improved to ≤ gr 1 Reduce tisotumab vedotin again according to Table 4. | Continue | |
| Keratitis ≤ gr 2 $3^{rd}$ occurrence | Permanently discontinue tisotumab vedotin | Continue | |
| Keratitis ≥ gr 3 | Permanently discontinue tisotumab vedotin | Hold dosing until event has improved to ≤ gr 1 | |
| Conjunctival ulceration and ophthalmological findings of fluorescent patches must be handled as below | | | |
| Any grade $1^{st}$ occurrence | Hold tisotumab vedotin until event is managed effectively Reduce tisotumab vedotin according to Table 4. | Continue | The local ophthalmologist must prescribe frequent dosing (every second hour) of preservative free topical steroid drops in conjunction with preservative free antibiotic prophylaxis such as chloramphenicol until the local ophthalmologist deems necessary. |
| Any grade ≥ $2^{nd}$ occurrence | If symptoms do not stabilize/improve after dose reduction, the subject must permanently discontinue tisotumab vedotin. | Hold dosing until event has improved to ≤ gr 1. Contact sponsor to determine if pembrolizumab may be continued. | |
| Symblepharon must be handled as below | | | |
| All other ocular toxicities grade 1 | Hold dosing until event is managed effectively, Continue tisotumab vedotin at the same dose level. | Continue. | Local ophthalmologist must prescribe frequent dosing (every second hour) of preservative free topical steroid drops in conjunction with preservative free antibiotic prophylaxis such as chloramphenicol until the local ophthalmologist deems necessary. |

TABLE 6-continued

Dose modification and toxicity management guidelines for ocular adverse events.

| Adverse Event & Toxicity Grade (CTCAE v4.0) | Action Taken with Tisotumab Vedotin | Action Taken with pembrolizumab | Guidelines for Treatment Prescribed by the Ophthalmologist |
|---|---|---|---|
| All other ocular toxicities grade 2 1$^{st}$ occurrence | Hold tisotumab vedotin until event is managed effectively. Reduce tisotumab vedotin according to Table 4. | Continue. | |
| All other ocular toxicities grade 2 2$^{nd}$ occurrence | Hold dose of tisotumab vedotin: If the event has improved to baseline within 6 weeks, reduce next dose of tisotumab vedotin according to Table 4. If the event does not improve to baseline within 6 weeks, permanently discontinue tisotumab vedotin. | Continue. | |
| All other ocular toxicities grade 2 3$^{rd}$ occurrence | Permanently discontinue tisotumab vedotin. | Continue. | Consult local ophthalmologist immediately. | gr = grade

For AEs of peripheral neuropathy (including neuropathy peripheral; peripheral sensory neuropathy; peripheral motor neuropathy; polyneuropathy): Peripheral neuropathy is a well-known adverse reaction to treatment with platinum and taxane based chemotherapies as well as MMAE-based ADCs and is reported in approximately 35% of subjects who received treatment with tisotumab vedotin. The majority of the reported cases are grade 1-2; however peripheral neuropathy is the leading cause of permanently discontinuation of tisotumab vedotin treatment. A mitigation plan, including dose reduction (See Table 4) and dose delays, is in place to control the rates and severity of peripheral neuropathy observed in subjects treated with tisotumab vedotin. For Grade 2 and 3, or initial or worsening of pre-existing condition, hold tisotumab vedotin until event has improved to ≤grade 1 then reduce next dose according to dose reduction shown in Table 4. No action is required to be taken with pembrolizumab. For ≥Grade 4, permanently discontinue tisotumab vedotin. Contact sponsor to discuss continuation of pembrolizumab alone.

For AEs of bleeding: Bleeding events are considered of special interest due to the mode of action of tisotumab vedotin. Epistaxis is the most common reported AE, however, nearly all of the cases are grade 1. Furthermore, clinically relevant perturbations in activated partial thromboplastin time (aPTT) or prothrombin time (PT) have not been observed. Dose modification and toxicity management guidelines are in place (Table 7).

TABLE 7

Dose modification and toxicity management guidelines for adverse events (Bleeding, Mucositis, Neutropenia, and Neuropathy) associated with the pembrolizumab in combination with tisotumab vedotin treatment group.

| Adverse Event (CTCAE v4.0) | Action Taken with Tisotumab Vedotin | Action Taken with Pembrolizumab |
|---|---|---|
| Bleeding Events | | |
| Control vital signs and ensure stabilization of the subject according to local standards. Prompt evaluation to identify the underlying etiology of the bleeding event. Management should ultimately be dictated by the underlying diagnosis. Control laboratory coagulation and hematologic parameters including PT, aPTT, fibrinogen, platelets, INR and hemoglobin as soon as possible. | | |
| All Subjects | | |
| Any grade pulmonary or CNS hemorrhage ≥ grade 2 | Permanently discontinue tisotumab vedotin treatment. | Withhold until event resolves to grade 0 or 1 |
| Subjects not on anti-coagulation therapy | | |
| 1$^{st}$ occurrence Hemorrhage (other)[1] ≥ grade 3 | Hold dosing until: a) Bleeding has resolved. b) Blood hemoglobin level is stable. c) There is no bleeding diathesis that could increase the risk of continuing therapy. d) There is no anatomical or pathologic condition that can increase the risk of hemorrhage recurrence. | Withhold until event resolves to grade 0 or 1 |

TABLE 7-continued

Dose modification and toxicity management guidelines for adverse events (Bleeding, Mucositis, Neutropenia, and Neuropathy) associated with the pembrolizumab in combination with tisotumab vedotin treatment group.

| Adverse Event (CTCAE v4.0) | Action Taken with Tisotumab Vedotin | Action Taken with Pembrolizumab |
|---|---|---|
| ≥2$^{nd}$ occurrence Hemorrhage (other)[1] ≥ grade 3 | When the above criteria are fulfilled the subject can resume treatment with tisotumab vedotin at the same dose as prior to the event. Contact sponsor in order to discuss whether the subject may continue or must permanently discontinue tisotumab vedotin treatment. | Withhold until event resolves to grade 0 or 1 |
| | Subjects on anti-coagulation therapy | |
| INR > 3.0 | Subjects on therapeutic anticoagulation whose INR is > 3.0 prior to infusion of tisotumab vedotin must hold tisotumab vedotin until INR is 3.0. Subjects may resume tisotumab vedotin administration immediately after the INR is 3.0. Strongly consider holding anticoagulation until the above parameters are met. | None |
| Hemorrhage (other)[1] ≥ grade 3 | Hold anti-coagulation therapy. Contact sponsor in order to discuss whether the subject may continue or must permanently discontinue tisotumab vedotin treatment. | Withhold until event resolves to grade 0 or 1 |

[1]Any other hemorrhage with the exception of pulmonary or CNS hemorrhage.

Example 6: Cells from Multiple Tissues Exposed to Tisotumab Vedotin ADC and MMAE Undergo Cell Death and Release ATP and HMGB1

Immunogenic cell death (ICD) is a mode of apoptosis that generates immune responses against the apoptotic cancerous cells. Proteins normally found within the endoplasmic reticulum (ER) become exposed on the cell surface, leading to increased phagocytic uptake and presentation of tumor antigens to T cells in order to prime the adaptive immune system. As such, ICD induction enables the immune system to recognize and mount cytotoxic activity against tumors.

Figure 5A:
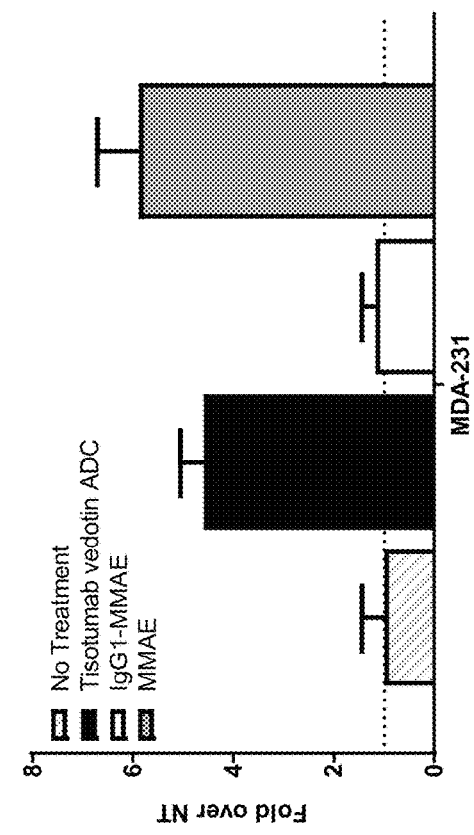
FIG. 5A-5C is a series of graphs showing that tisotumab vedotin antibody-drug conjugate and MMAE free drug both drove robust A) ATP secretion and C) HMGB1 release. Activity was specific to the targeted agent (tisotumab vedotin) and free drug (MMAE). The non-targeted isotype ADC (IgG1-MMAE) did not elicit A) ATP or C) HMGB1 secretion. B) Tisotumab vedotin was active on multiple Tissue Factor positive cell lines.
Figure 5B:
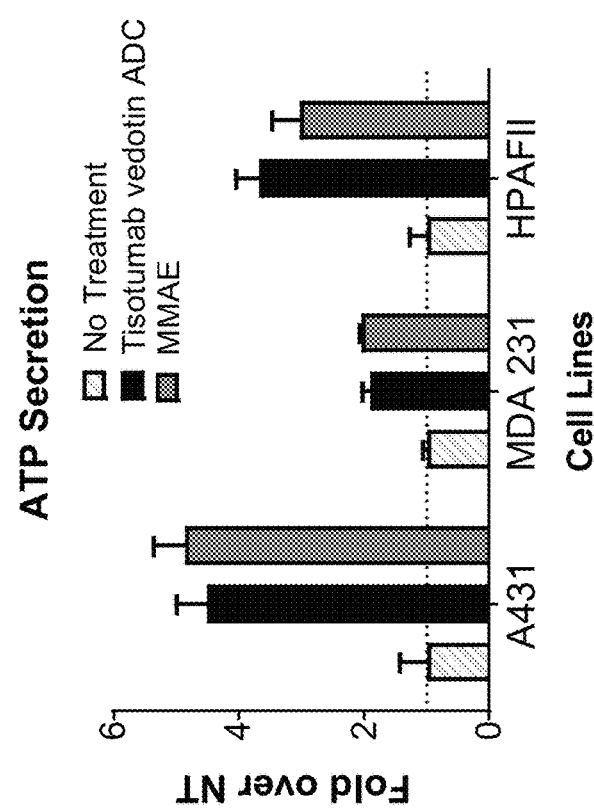
Figure 5C:
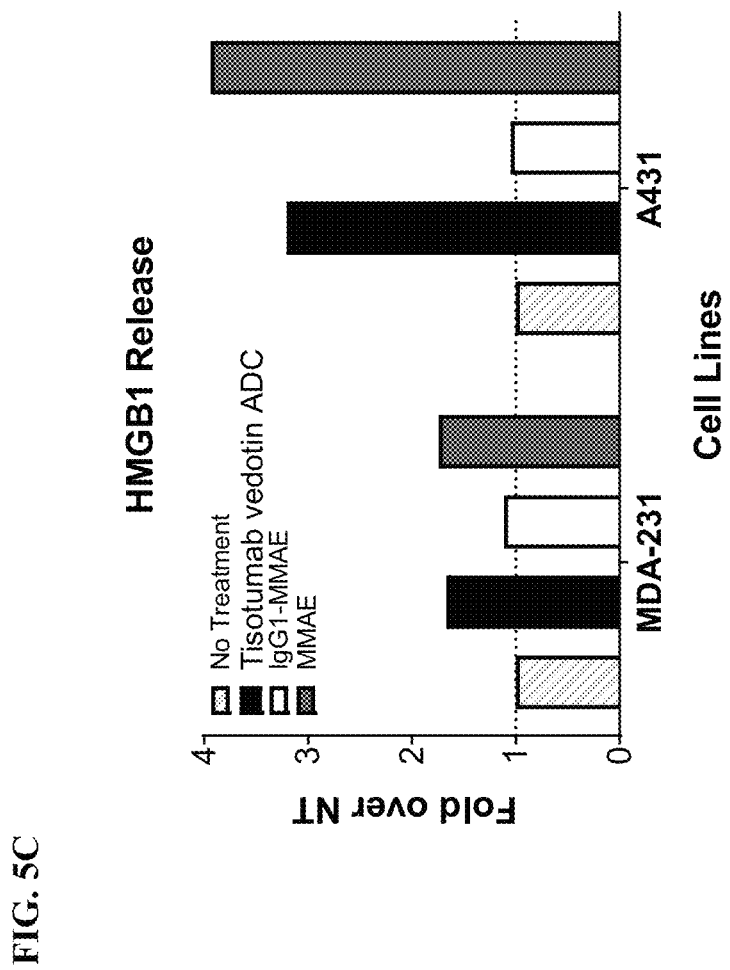

Auristatin ADC payloads disrupt the microtubule networks resulting in altered ER localization and function, which ultimately results in ER stress. Cells exposed to Tissue Factor directed antibody linked to the monomethyl auristatin E payload (MMAE), i.e., tisotumab vedotin (an antibody drug conjugate or ADC), undergo cell death and as they do release the ICD related molecules ATP (FIG. 5A) and HMGβ1 (FIG. 5C). The release of these molecules is specific to tisotumab vedotin ADC and MMAE treatment and occurs across multiple Tissue Factor positive cell lines (FIG. 5B).

Figure 6:
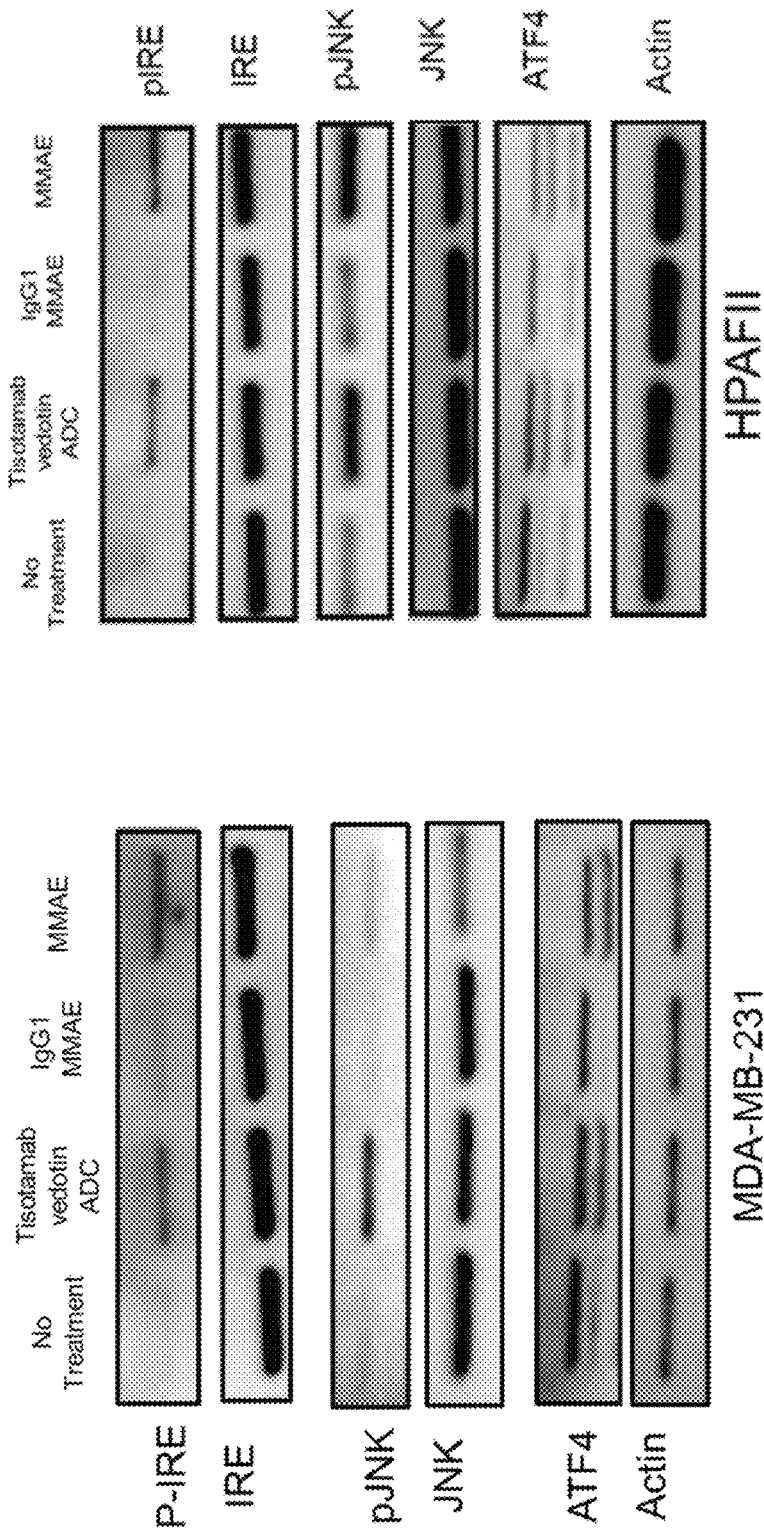
FIG. 6 is images of a Western blots showing treatment of HPAFII (pancreatic carcinoma) or MDA-MB-231 (breast carcinoma) cells for 16 hours with tisotumab vedotin ADC or MMAE payloads trigger multiple ER stress pathways including phosphorylation of IRE and its down-stream target JNK as well as cleavage of ATF4. Treatment with the non-targeting H00-MMAE ADC (IgG1 MMAE) did not trigger activation of these ER stress pathways.

Example 7: Auristatins, Both Free and ADC-Loaded, are Able to Induce ER Stress Pathways that are Critical for Immunogenic Cell Death Induction of cell death and release of ICD danger signals occurs concomitant with initiation of an ER stress response. Two Tissue Factor positive cell lines, HPAFII (pancreatic carcinoma) and MDA-MB-231 (breast cell carcinoma) were exposed to tisotumab vedotin ADC, an Isotype-MMAE ADC (H00-MMAE, IgG1 MMAE), or free MMAE for 18 hours and induction of ER stress monitored by western blot analysis. Phosphorylation of inositol-requiring transmembrane kinase/endonuclease 1 (IRE1) was detected after treatment with tisotumab vedotin ADC or MMAE free drug (FIG. 6). Activation of the IRE1 downstream effector Jun N-terminal kinase (JNK) also occurred as monitored by increased phosphorylation. Furthermore, activation of the PKR-like ER kinase (PERK) secondary ER stress pathway was detected via upregulation of ATF4 cleavage. These data indicate that auristatins, both free and ADC-loaded, are able to induce ER stress pathways that are critical for ICD and the expression of tumor antigens on apoptotic cell surfaces. The ability for auristatins to prime the immune system to recognize tumor antigens opens the door for a myriad of combinatorial therapeutic options.

Figure 7A:
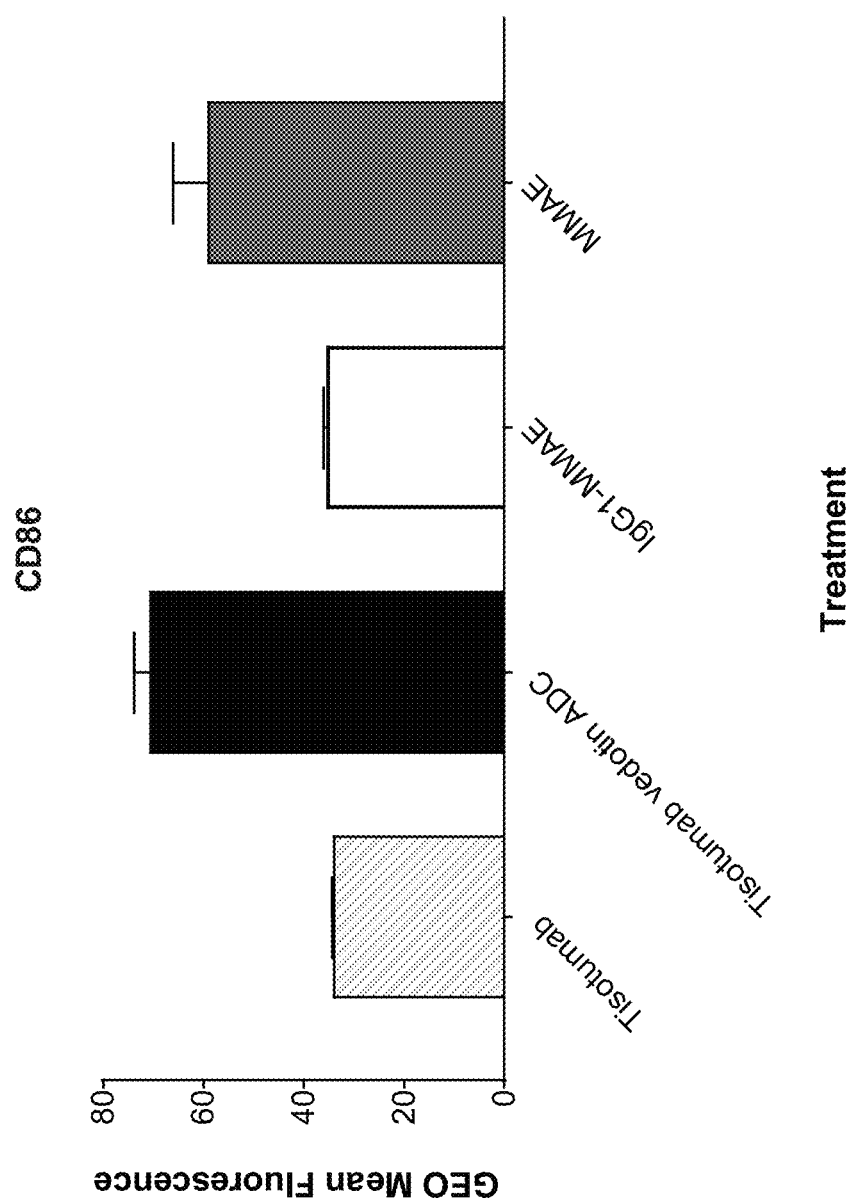
FIGS. 7A and 7B is a series of graphs in which Tissue Factor positive MDA-MB-231 cells killed with various agents were fed to human peripheral blood mononuclear cells (PBMCs) and immune activation assessed by increased expression of activations markers on innate CD14+ monocyte/macrophages and induction of chemokine and cytokine production. Treatment with tisotumab vedotin ADC or MMAE free drug drove monocyte/macrophage activations as monitored by A) CD86 expression by flow cytometry and B) induced release of innate chemokines including MIP 1β compared to non-targeting IgG1-MMAE ADC or targeting antibody (tisotumab) alone.
Figure 7B:
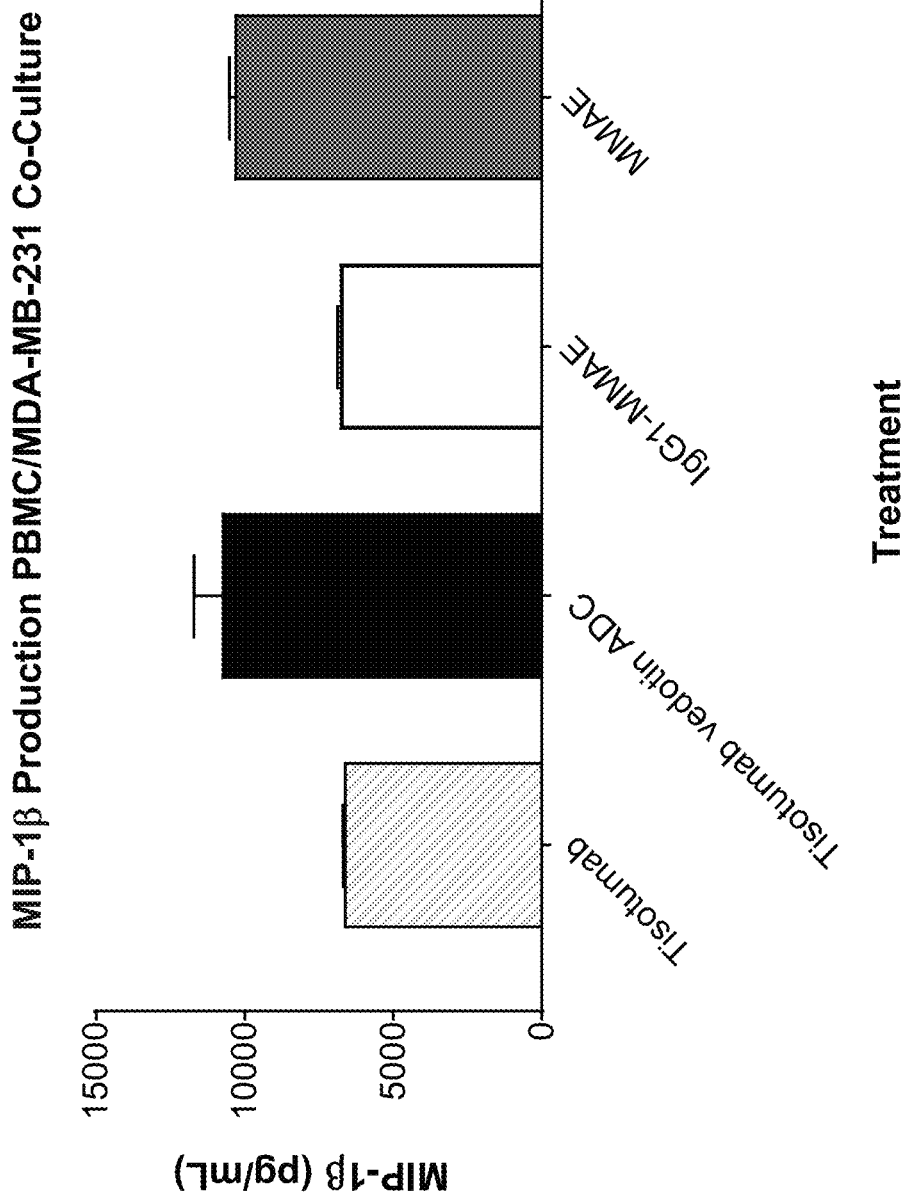

Example 8: Tisotumab Vedotin ADC and MMAE Killed Tissue Factor Positive Cells Elicit Strong Chemotactic and Inflammatory Mediators from Monocyte/Macrophages after Uptake of Dead Cells Investigations into the mechanisms of action of therapeutics for oncology extend long past cytolysis of tumor cells. The growing focus on immunotherapy highlights the processes involved in clearing dying tumor cells, as well as engaging the patient's immune system to provoke antitumor responses. The method of cell death and subsequent clearance of cell debris speaks volumes to the level of engagement and stimulation of the immune system to generate targeted responses against the tumor cells Immunogenic cell death, as mediated by MMAE, is regulated cell death that activates adaptive immune responses against antigens from dead and dying tumor cells, and allows for the generation of robust innate immune cell activation and subsequent cytotoxic T cell responses targeted towards specific tumor cell antigens. Here, we demonstrated that tisotumab vedotin ADC and MMAE killed Tissue Factor positive cells elicit strong chemotactic and inflammatory mediators from monocyte/macrophages after uptake of dead cells (FIGS. 7A and 7B). Furthermore, these monocyte/macrophages conditioned by ICD-killed cells promote activation of T cells, as evidenced by production of signature inflammatory cytokines associated with cytotoxic T cell responses.

Figure 8A:
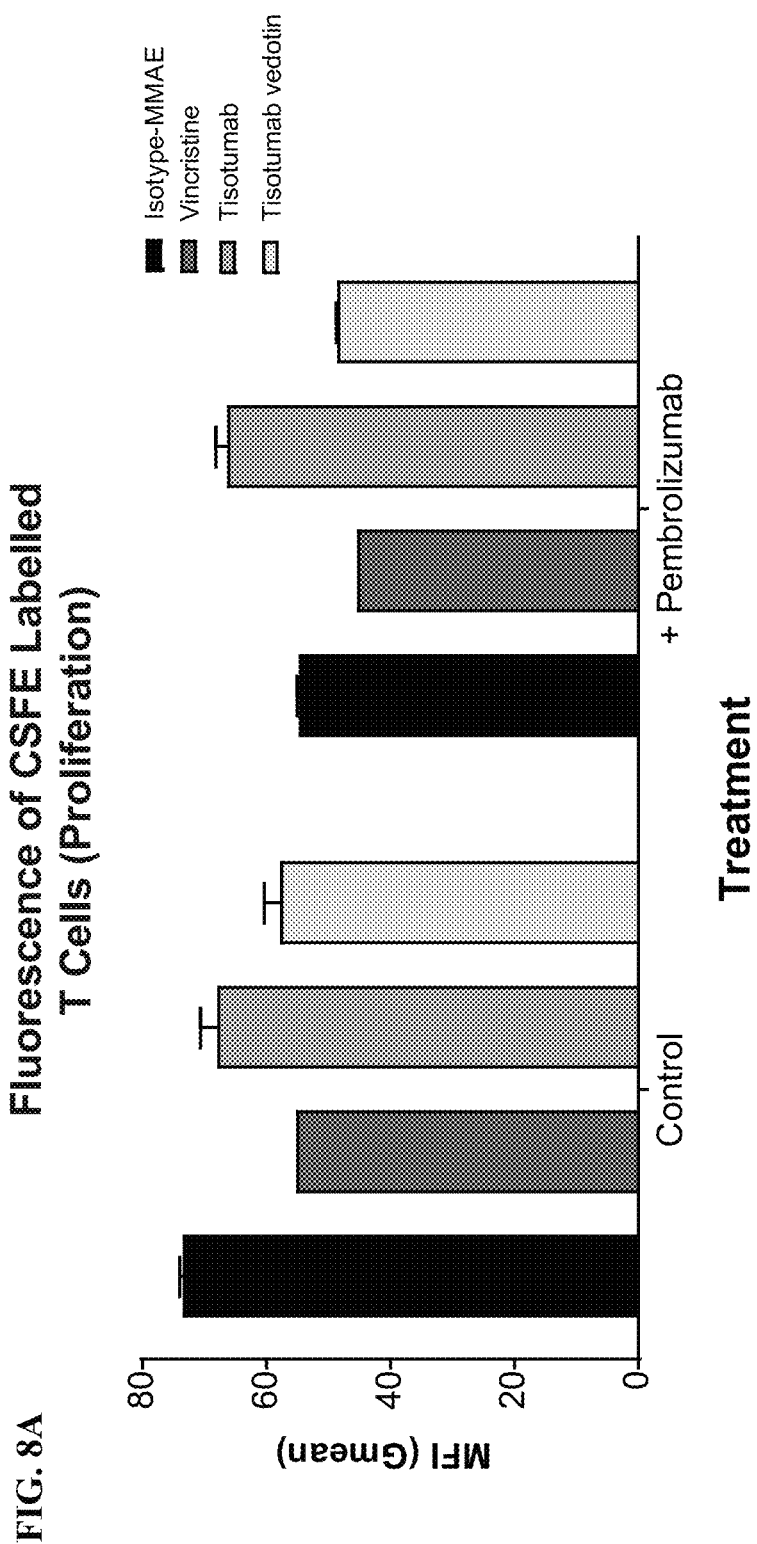
FIG. 8A-8C is a series of graphs in which Tissue Factor positive MDA-MB-231 cells killed with various agents were fed to CSFE labeled human peripheral blood mononuclear cells (PBMCs) in the presence or absence of the PD1 targeting antibody pembrolizumab for 48 hours and T cells activation assessed by A) decreased CSFE fluorescent indicative of T cell proliferation and B) and C) cytokine production. Treatment with tisotumab vedotin or MMAE free drug drove T cell proliferation, which was enhanced with 2 mg/ml of pembrolizumab treatment. Production of B) IL12p70 and C) IFNγ was also increased following exposure to tisotumab vedotin and MMAE killed cell and cytokine production was increased by concomitant pembrolizumab treatment.
Figure 8B:
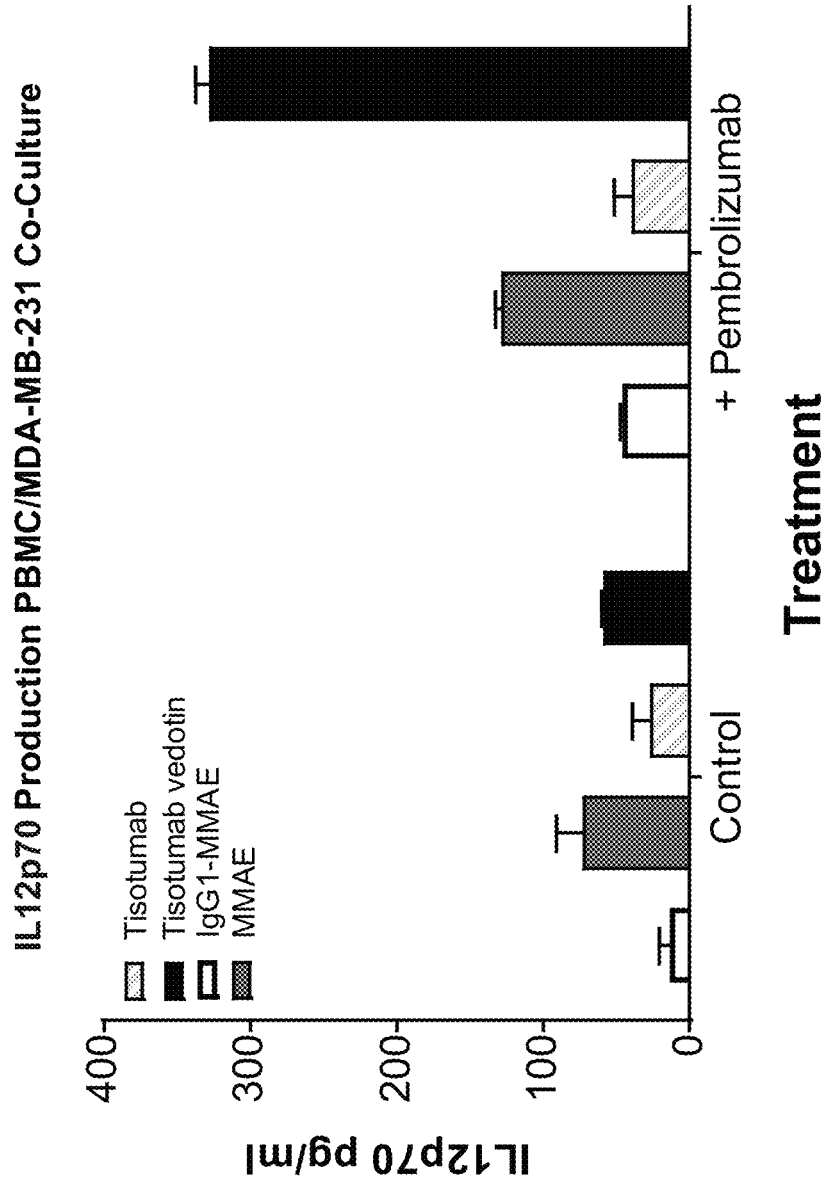
Figure 8C:
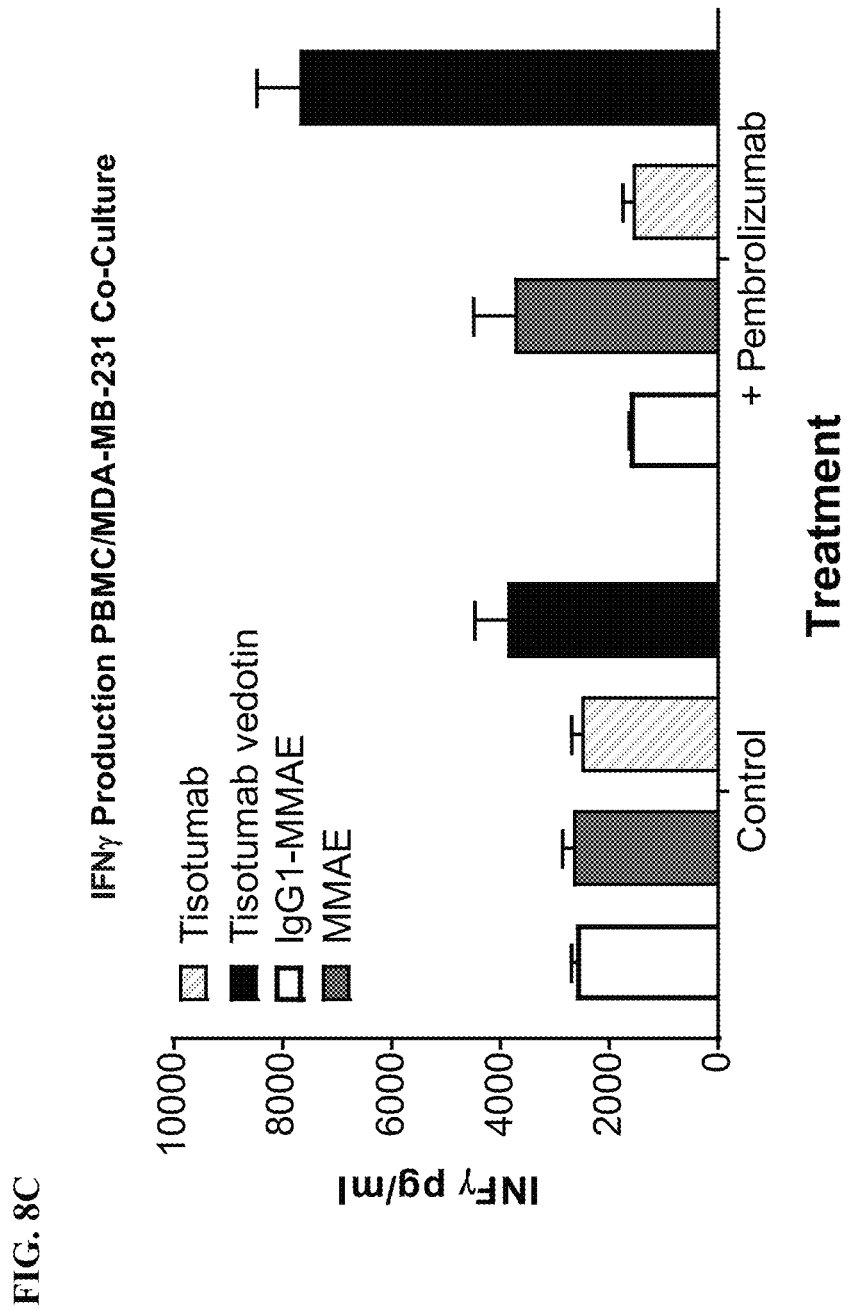

Example 9: Tisotumab Vedotin Induces ICD which Results in Innate Immune Cells Activation and Secondary T Cell Responses that can be Amplified with the PD1 Targeted Agent Pembrolizumab Induction of the innate immune response following exposure to cancer cells undergoing ICD sets up secondary T cell activation, which can be enhanced by concomitant pembrolizumab treatment. Tissue Factor positive MDA-MB-231 cells exposed to tisotumab vedotin or MMAE when fed to CSFE labeled human PBMCs for 48 hours drove T cell proliferation as monitored by CSFE dilution (FIG. 8A) and production of T cell specific cytokines such as $IL12_p70$ and IFNγ (FIGS. 8B and 8C). Tissue Factor targeting antibody alone or an isotype-MMAE ADC (Isotype-MMAE, IgG1-MMAE) did not elicit these responses. These data support that tisotumab vedotin induces ICD which results in innate immune cells activation and secondary T cell responses that can be amplified with pembrolizumab.

What is claimed is:

1. A method of treating breast or cervical cancer that expresses tissue factor (TF) and programmed death-ligand 1 (PD-L1) in a subject, the method comprising administering to the subject an antibody or an antigen-binding fragment thereof, wherein the antibody binds to Programmed Death-1 (PD-1) and inhibits PD-1 activity, and an antibody-drug conjugate that binds to tissue factor TF, wherein the antibody-drug conjugate comprises an anti-TF antibody or an antigen-binding fragment thereof conjugated to monomethyl auristatin E, wherein the antibody-drug conjugate further comprises a linker between the anti-TF antibody or antigen-binding fragment thereof and the monomethyl auristatin E, wherein the anti-PD-1 antibody or antigen-binding fragment thereof comprises a heavy chain variable region and a light chain variable region, wherein the heavy chain variable region comprises:

(i) a CDR-H1 comprising the amino acid sequence of SEQ ID NO:17;
(ii) a CDR-H2 comprising the amino acid sequence of SEQ ID NO:18; and
(iii) a CDR-H3 comprising the amino acid sequence of SEQ ID NO:19; and wherein the light chain variable region comprises:

(i) a CDR-L1 comprising the amino acid sequence of SEQ ID NO:20;
(ii) a CDR-L2 comprising the amino acid sequence of SEQ ID NO:21; and
(iii) a CDR-L3 comprising the amino acid sequence of SEQ ID NO:22, and wherein the anti-TF antibody or antigen-binding fragment thereof comprises a heavy chain variable region and a light chain variable region, wherein the heavy chain variable region comprises:

(i) a CDR-H1 comprising the amino acid sequence of SEQ ID NO:1;
(ii) a CDR-H2 comprising the amino acid sequence of SEQ ID NO:2; and
(iii) a CDR-H3 comprising the amino acid sequence of SEQ ID NO:3; and 13. The method of claim 1, wherein the anti-TF antibody of the antibody-drug conjugate is tisotumab.

14. The method of claim 1, wherein the linker is attached to MMAE, wherein the antibody-drug conjugate has the following structure:

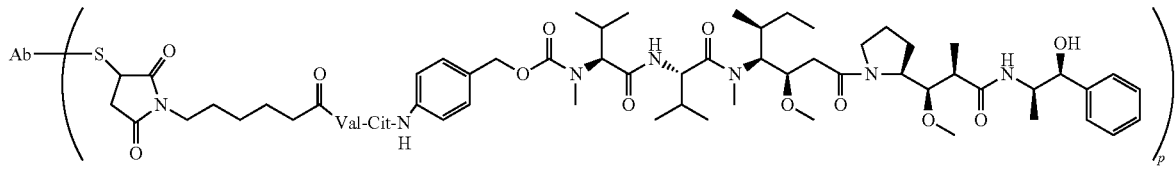

Ab-MC-vc-PAB-MMAE wherein the light chain variable region comprises:
(i) a CDR-L1 comprising the amino acid sequence of SEQ ID NO:4;
(ii) a CDR-L2 comprising the amino acid sequence of SEQ ID NO:5; and
(iii) a CDR-L3 comprising the amino acid sequence of SEQ ID NO:6.

2. The method of claim 1, wherein the antibody-drug conjugate is administered at a dose ranging from about 0.9 mg/kg to about 2.1 mg/kg.

3. The method of claim 2, wherein the antibody-drug conjugate is administered at a dose of about 2.0 mg/kg.

4. The method of claim 1, wherein the antibody-drug conjugate is administered once about every 1 week, once about every 2 weeks, once about every 3 weeks or once about every 4 weeks.

5. The method of claim 4, wherein the antibody-drug conjugate is administered once every 3 weeks.

6. The method of claim 1, wherein the anti-PD-1 antibody or antigen-binding fragment thereof is administered at a flat dose ranging from about 50 mg to about 500 mg.

7. The method of claim 1, wherein the anti-PD-1 antibody or antigen-binding fragment thereof is administered at a flat dose of 200 mg.

8. The method of claim 1, wherein the anti-PD-1 antibody or antigen-binding fragment thereof is administered at a flat dose of 400 mg.

9. The method of claim 8, wherein the anti-PD-1 antibody or antigen-binding fragment thereof is administered once about every 6 weeks.

10. The method of claim 7, wherein the anti-PD-1 antibody or antigen-binding fragment thereof is administered once every 3 weeks.

11. The method of claim 1, wherein the anti-TF antibody or antigen-binding fragment thereof of the antibody-drug conjugate is a monoclonal antibody or a monoclonal antigen-binding fragment thereof.

12. The method of claim 1, wherein the anti-TF antibody or antigen-binding fragment thereof of the antibody-drug conjugate comprises a heavy chain variable region comprising an amino acid sequence having at least 85% sequence identity to the amino acid sequence of SEQ ID NO:7 and a light chain variable region comprising an amino acid sequence having at least 85% sequence identity to the amino acid sequence of SEQ ID NO:8.

wherein p denotes a number from 1 to 8, S represents a sulphydryl residue of the anti-TF antibody, and Ab designates the anti-TF antibody or antigen-binding fragment thereof.

15. The method of claim 14, wherein the average value of p in a population of the antibody-drug conjugates is about 4.

16. The method of claim 1, wherein the antibody-drug conjugate is tisotumab vedotin.

17. The method of claim 1, wherein the anti-PD-1 antibody or antigen-binding fragment thereof comprises a heavy chain variable region comprising an amino acid sequence having at least 85% sequence identity to the amino acid sequence of SEQ ID NO:31 and a light chain variable region comprising an amino acid sequence having at least 85% sequence identity to the amino acid sequence of SEQ ID NO:32.

18. The method of claim 1, wherein the anti-PD-1 antibody is pembrolizumab.

19. The method of claim 1, wherein the anti-PD-1 antibody or antigen-binding fragment thereof and the antibody-drug conjugate are administered sequentially.

20. The method of claim 1, wherein the anti-PD-1 antibody or antigen-binding fragment thereof and the antibody-drug conjugate are administered simultaneously.

21. The method of claim 1, wherein one or more therapeutic effects in the subject is improved after administration of the antibody-drug conjugate and the anti-PD-1 antibody or antigen-binding fragment thereof relative to a baseline.

22. The method of claim 21, wherein the one or more therapeutic effects is selected from the group consisting of: size of a tumor derived from the cancer, objective response rate, duration of response, time to response, progression free survival, and overall survival.

23. The method of claim 1, wherein the subject has one or more adverse events and is further administered an additional therapeutic agent to eliminate or reduce the severity of the one or more adverse events.

24. The method of claim 1, wherein the subject is at risk of developing one or more adverse events and is further administered an additional therapeutic agent to prevent or reduce the severity of the one or more adverse events.

25. The method of claim 23, wherein the one or more adverse events is conjunctivitis, conjunctival ulceration, and/or keratitis and the additional agent is a preservative-free lubricating eye drop, an ocular vasoconstrictor, antibiotic, and/or a steroid eye drop.

26. The method of claim 1, wherein the subject is a human.

27. A kit comprising:
(a) an antibody or an antigen-binding fragment thereof, wherein the antibody binds to Programmed Death-1 (PD-1) and inhibits PD-1 activity, wherein the anti-PD-1 antibody or antigen-binding fragment thereof comprises a heavy chain variable region and a light chain variable region, wherein the heavy chain variable region comprises:
 (i) a CDR-H1 comprising the amino acid sequence of SEQ ID NO:17;
 (ii) a CDR-H2 comprising the amino acid sequence of SEQ ID NO:18; and
 (iii) a CDR-H3 comprising the amino acid sequence of SEQ ID NO:19; and
wherein the light chain variable region comprises:
 (i) a CDR-L1 comprising the amino acid sequence of SEQ ID NO:20;
 (ii) a CDR-L2 comprising the amino acid sequence of SEQ ID NO:21; and
 (iii) a CDR-L3 comprising the amino acid sequence of SEQ ID NO:22;
(b) an antibody-drug conjugate that binds to tissue factor (TF), wherein the antibody-drug conjugate comprises an anti-TF antibody or an antigen-binding fragment thereof conjugated to monomethyl auristatin E, wherein the antibody-drug conjugate further comprises a linker between the anti-TF antibody or antigen-binding fragment thereof and the monomethyl auristatin E, wherein the anti-TF antibody or antigen-binding fragment thereof comprises a heavy chain variable region and a light chain variable region, wherein the heavy chain variable region comprises:
 (i) a CDR-H1 comprising the amino acid sequence of SEQ ID NO:1;
 (ii) a CDR-H2 comprising the amino acid sequence of SEQ ID NO:2; and
 (iii) a CDR-H3 comprising the amino acid sequence of SEQ ID NO:3; and
wherein the light chain variable region comprises:
 (i) a CDR-L1 comprising the amino acid sequence of SEQ ID NO:4;
 (ii) a CDR-L2 comprising the amino acid sequence of SEQ ID NO:5; and
 (iii) a CDR-L3 comprising the amino acid sequence of SEQ ID NO:6; and
(c) instructions for use of the anti-PD-1 antibody or antigen-binding fragment thereof and the antibody drug conjugate for the treatment of breast or cervical cancer.

28. The method of claim 9, wherein the anti-PD-1 antibody or antigen-binding fragment thereof is administered once every 6 weeks.

* * * * *

```
SEQUENCE LISTING

<160> NUMBER OF SEQ ID NOS: 34

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Asn Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Ser Gly Ser Gly Asp Tyr Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Ala Arg Ser Pro Trp Gly Tyr Tyr Leu Asp Ser
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gln Gly Ile Ser Ser Arg
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Ala Ala Ser
1
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Tyr Asn Ser Tyr Pro Tyr Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Met Ser Trp Val Arg Gln Ala Pro Gly Lys Gly Leu Glu Trp Val Ser
1               5                   10                  15

Ser

<210> SEQ ID NO 11
<211> LENGTH: 38
<212> TYPE: PRT
<213> ORGANISM: Artificial Sequence
<220> FEATURE:
<223> OTHER INFORMATION: Synthetic Construct

<400> SEQUENCE: 11

Tyr Tyr Thr Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Gly Gln Gly Thr Leu Val Thr Val Ser Ser
1               5                   10

<210> SEQ ID NO 13
<211> LENGTH: 26
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Ser Pro Pro Ser Leu Ser Ala Ser Ala Gly
1               5                   10                  15

Asp Arg Val Thr Ile Thr Cys Arg Ala Ser
            20                  25

```
<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Leu Ala Trp Tyr Gln Gln Lys Pro Glu Lys Ala Pro Lys Ser Leu Ile
1               5                   10                  15

Tyr

<210> SEQ ID NO 15
<211> LENGTH: 36
<212> TYPE: PRT
<213> ORGANISM: Artificial Sequence
<220> FEATURE:
<223> OTHER INFORMATION: Synthetic Construct

<400> SEQUENCE: 15

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Phe Gly Gln Gly Thr Lys Leu Glu Ile Lys
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Asn Tyr Tyr Met Tyr
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Gly Ile Asn Pro Ser Asn Gly Gly Thr Asn Phe Asn Glu Lys Phe Lys
1               5                   10                  15

Asn

<210> SEQ ID NO 19
<211> LENGTH: 11
<212> TYPE: PRT
```

<213> ORGANISM: Artificial Sequence
<220> FEATURE:
<223> OTHER INFORMATION: Synthetic Construct

<400> SEQUENCE: 19

Arg Asp Tyr Arg Phe Asp Met Gly Phe Asp Tyr
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Arg Ala Ser Lys Gly Val Ser Thr Ser Gly Tyr Ser Tyr Leu His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Leu Ala Ser Tyr Leu Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln His Ser Arg Asp Leu Pro Leu Thr
1               5

<210> SEQ ID NO 23
<211> LENGTH: 30
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Trp Val Arg Gln Ala Pro Gly Gln Gly Leu Glu Trp Met Gly
1               5                   10

<210> SEQ ID NO 25

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 25

Arg Val Thr Leu Thr Thr Asp Ser Ser Thr Thr Ala Tyr Met Glu
1               5                   10                  15

Leu Lys Ser Leu Gln Phe Asp Asp Thr Ala Val Tyr Tyr Cys Ala Arg
            20                  25                  30

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Trp Gly Gln Gly Thr Thr Val Thr Val Ser Ser
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Synthetic Construct

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

Trp Tyr Gln Gln Lys Pro Gly Gln Ala Pro Arg Leu Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 30

Phe Gly Gly Gly Thr Lys Val Glu Ile Lys
1               5                   10

<210> SEQ ID NO 31
<211> LENGTH: 120
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 32
<211> LENGTH: 111
<212> TYPE: PRT
<213> ORGANISM: Artificial Sequence
<220> FEATURE:
<223> OTHER INFORMATION: Synthetic Construct

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 33
<211> LENGTH: 446
<212> TYPE: PRT
<213> ORGANISM: Artificial Sequence
<220> FEATURE:
<223> OTHER INFORMATION: Synthetic Construct -continued

```
<400> SEQUENCE: 33

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

-continued

```
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly
            435                 440                 445

<210> SEQ ID NO 34
<211> LENGTH: 218
<212> TYPE: PRT
<213> ORGANISM: Artificial Sequence
<220> FEATURE:
<223> OTHER INFORMATION: Synthetic Construct

<400> SEQUENCE: 34

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
                20                  25                  30
Gly Tyr Ser Tyr Leu His Trp Tyr Gln Gln Lys Pro Gly Gln Ala Pro
            35                  40                  45
Arg Leu Leu Ile Tyr Leu Ala Ser Tyr Leu Glu Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```